US011128804B2

(12) United States Patent
Haggerty et al.

(10) Patent No.: US 11,128,804 B2
(45) Date of Patent: Sep. 21, 2021

(54) ENDOSCOPE WITH PANNABLE CAMERA AND RELATED METHOD

(71) Applicant: DEKA Products Limited Partnership, Manchester, NH (US)

(72) Inventors: Andrew M. Haggerty, Lake Mary, FL (US); Kevin L. Grant, Litchfield, NH (US); Peter K. Vondras, Somerville, MA (US); Timothy D. Moreau, Manchester, NH (US); Jason A. Demers, Manchester, NH (US); Daniel B. Davis, Nashua, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 16/838,308

(22) Filed: Apr. 2, 2020

(65) Prior Publication Data

US 2020/0322538 A1    Oct. 8, 2020

Related U.S. Application Data

(60) Division of application No. 15/253,399, filed on Aug. 31, 2016, now Pat. No. 10,616,491, which is a
(Continued)

(51) Int. Cl.
*A61B 1/00* (2006.01)
*H04N 5/232* (2006.01)
(Continued)

(52) U.S. Cl.
CPC ....... *H04N 5/23296* (2013.01); *A61B 1/0011* (2013.01); *A61B 1/00071* (2013.01);
(Continued)

(58) Field of Classification Search
None
See application file for complete search history.

(56) References Cited

U.S. PATENT DOCUMENTS 5,712,543 A * 1/1998 Sjostrom ............ A61B 17/1626
                                                    318/71
5,836,867 A * 11/1998 Speier ................ A61B 1/00126
                                                    600/112
(Continued)

OTHER PUBLICATIONS

European Search Report dated May 3, 2021, received in European patent application No. 21151017.7, 7 pgs.
(Continued)

*Primary Examiner* — Timothy J Neal
(74) *Attorney, Agent, or Firm* — Michael George Norris

(57) ABSTRACT

An endoscope and related method comprise a proximal handle and a distal shaft having an insertion end. A housing comprising a camera assembly may be mounted on an insertion end of the shaft and include at least one lens and an image sensor. The camera assembly housing is rotatable about an axis perpendicular to the long axis of the shaft, giving the camera assembly a variable field of view. The rotatable camera assembly housing may be mounted to the insertion end of the shaft so that the rotatable housing of the camera assembly comprises the distal-most element of the endoscope shaft or insertion end. The endoscope may include a circuit board having a first portion disposed within the proximal handle and one or more extension portions that extend within the shaft to the camera assembly and/or to a light source near the distal end of the shaft. At least one light emitter may be mounted on the insertion end of the shaft and configured to project light in a direction either toward or away from the field of view of the camera assembly. The light emitter may also be mounted on the camera assembly housing to direct light toward the field of view of the camera
(Continued)

assembly. Power and communication lines can be co-located within a lumen of the shaft of the endoscope used for fluid irrigation or suction.

9 Claims, 66 Drawing Sheets

Related U.S. Application Data continuation-in-part of application No. 14/170,080, filed on Jan. 31, 2014, now Pat. No. 9,907,457, and a continuation-in-part of application No. PCT/US2014/014243, filed on Jan. 31, 2014.

(60) Provisional application No. 62/306,288, filed on Mar. 10, 2016, provisional application No. 62/212,871, filed on Sep. 1, 2015, provisional application No. 61/826,303, filed on May 22, 2013, provisional application No. 61/759,784, filed on Feb. 1, 2013.

(51) Int. Cl.
| | | |
|---|---|---|
| *H04N 5/225* | (2006.01) | |
| *A61B 1/05* | (2006.01) | |
| *A61B 1/045* | (2006.01) | |
| *A61B 1/12* | (2006.01) | |
| *A61B 90/30* | (2016.01) | |
| *A61B 17/34* | (2006.01) | |
| *A61B 90/00* | (2016.01) | |

(52) U.S. Cl.
CPC ...... *A61B 1/00096* (2013.01); *A61B 1/00183* (2013.01); *A61B 1/045* (2013.01); *A61B 1/051* (2013.01); *A61B 1/126* (2013.01); *H04N 5/2252* (2013.01); *H04N 5/2253* (2013.01); *H04N 5/2254* (2013.01); *H04N 5/2256* (2013.01); *A61B 1/05* (2013.01); *A61B 2017/3456* (2013.01); *A61B 2090/306* (2016.02); *A61B 2090/3616* (2016.02); *H04N 5/23293* (2013.01); *H04N 2005/2255* (2013.01)

(56) References Cited

U.S. PATENT DOCUMENTS

| | | | | |
|---|---|---|---|---|
| 2004/0203608 | A1* | 10/2004 | Osann, Jr. | H04N 21/4788 455/412.1 |
| 2005/0059858 | A1* | 3/2005 | Frith | H01H 36/0006 600/118 |
| 2009/0076328 | A1* | 3/2009 | Root | A61B 1/0669 600/131 |
| 2011/0144576 | A1* | 6/2011 | Rothe | A61M 25/0136 604/95.04 |
| 2012/0289858 | A1* | 11/2012 | Ouyang | A61B 1/00124 600/562 |
| 2013/0341127 | A1* | 12/2013 | Mann | A63C 7/1086 188/6 |
| 2014/0270688 | A1* | 9/2014 | Han | H04N 5/772 386/225 |

OTHER PUBLICATIONS

U.S. Appl. No. 61/759,784, filed Feb. 1, 2013, Provisional.
U.S. Appl. No. 61/826,303, filed May 22, 2013, Provisional.
U.S. Appl. No. 14/170,080, filed Jan. 31, 2014, U.S. Pub. No. 9,907,457.
PCT/US14/14243, filed Jan. 31, 2014, U.S. Pub. No. WO 2014/121116.
U.S. Appl. No. 29/481,097, filed Jan. 31, 2014, U.S. Pub. No. D753,296.
U.S. Appl. No. 62/212,871, filed Sep. 1, 2015, Provisional.
U.S. Appl. No. 29/538,153, filed Sep. 1, 2015, U.S. Pub. No. D795,424.
U.S. Appl. No. 62/306,288, filed Mar. 10, 2016, Provisional.
U.S. Appl. No. 29/559,980, filed Apr. 1, 2016, U.S. Pub. No. D841,160.
U.S. Appl. No. 15/253,399, filed Aug. 31, 2016, U.S. Pub. No. 10,616,491.
PCT/US16/49743, filed Aug. 31, 2016, WO 2017/040692.
U.S. Appl. No. 15/910,495, filed Mar. 2, 2018, U.S. Pub. No. 10,362,927.
U.S. Appl. No. 16/396,282, filed Apr. 26, 2019, U.S. Pat. No. 2019-0328217-A1
PCT/US19/29436, filed Apr. 26, 2019, U.S. Pub. No. WO/2019/210227.
U.S. Appl. No. 16/460,545, Jul. 2, 2019, U.S. Pub. No. 10,863,888.
U.S. Appl. No. 17/120,614, filed Dec. 14, 2020, U.S. Pat. No. US-2021-0093171-A1.

\* cited by examiner

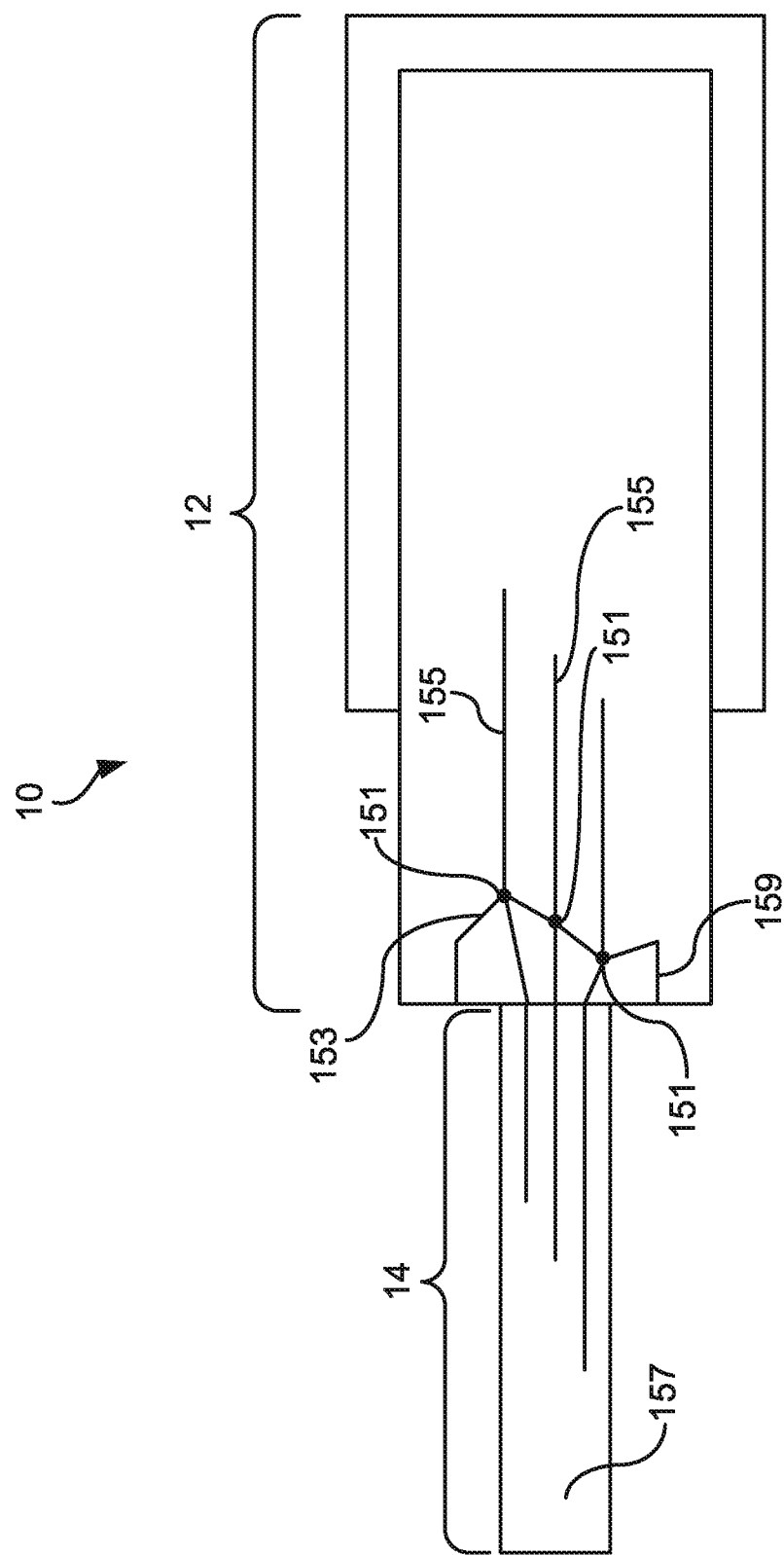

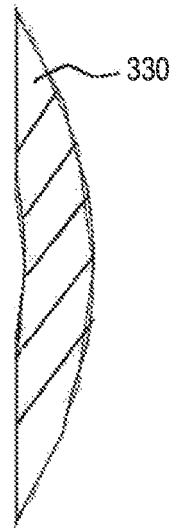
FIG. 20

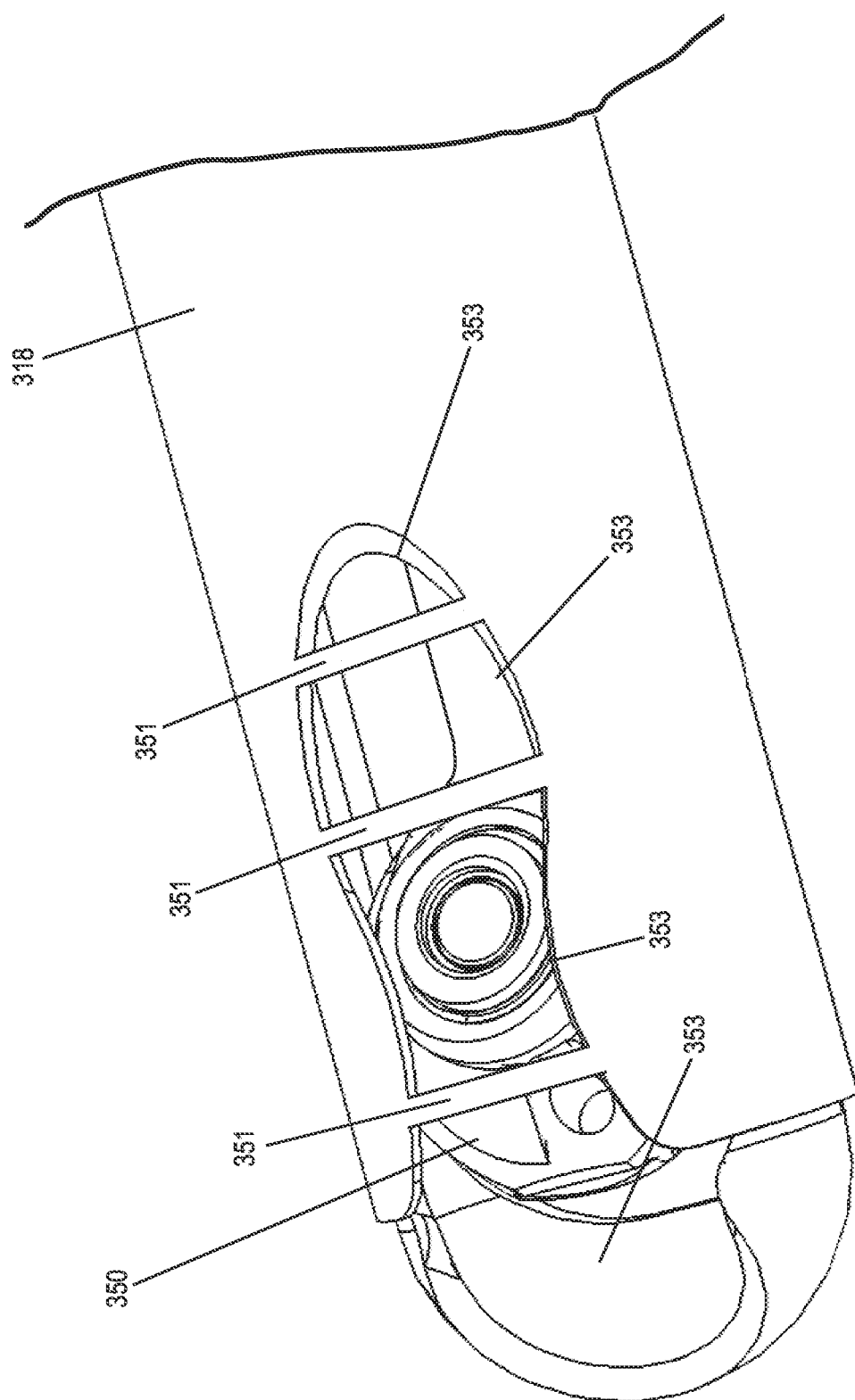

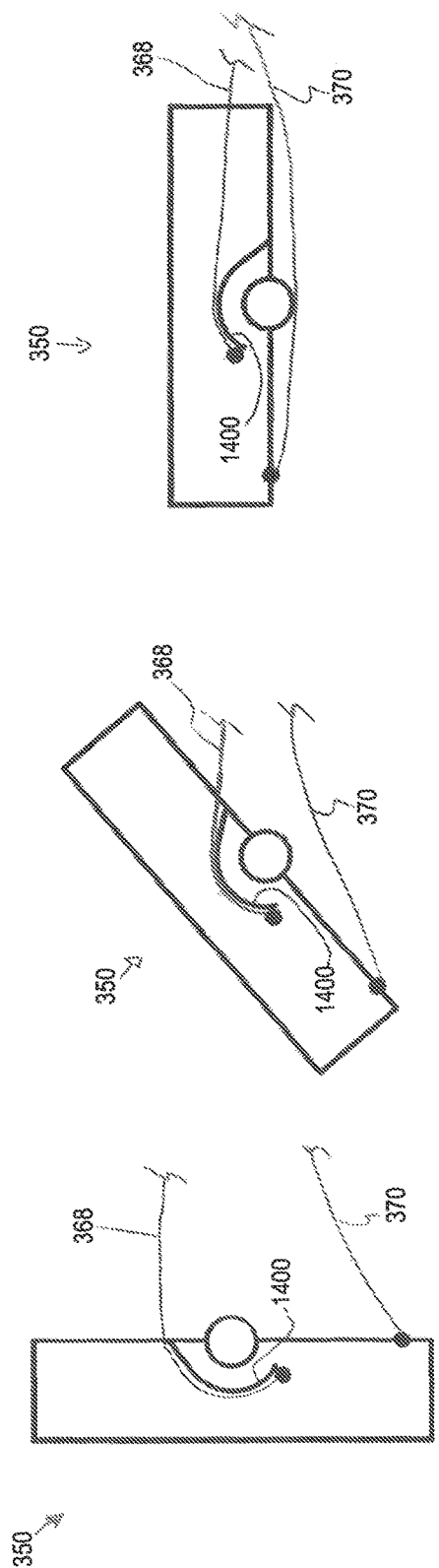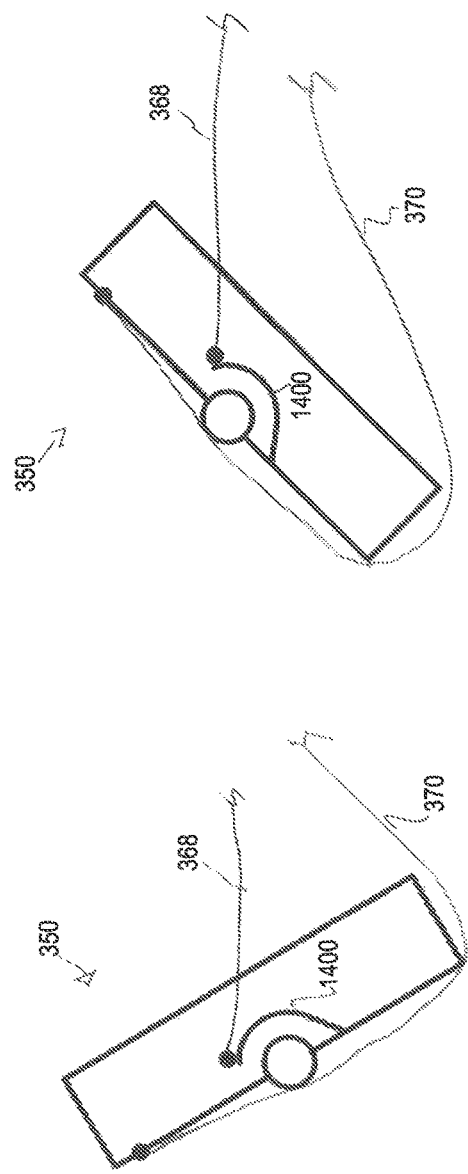
FIG. 28
FIG. 29
FIG. 30
FIG. 31
FIG. 32

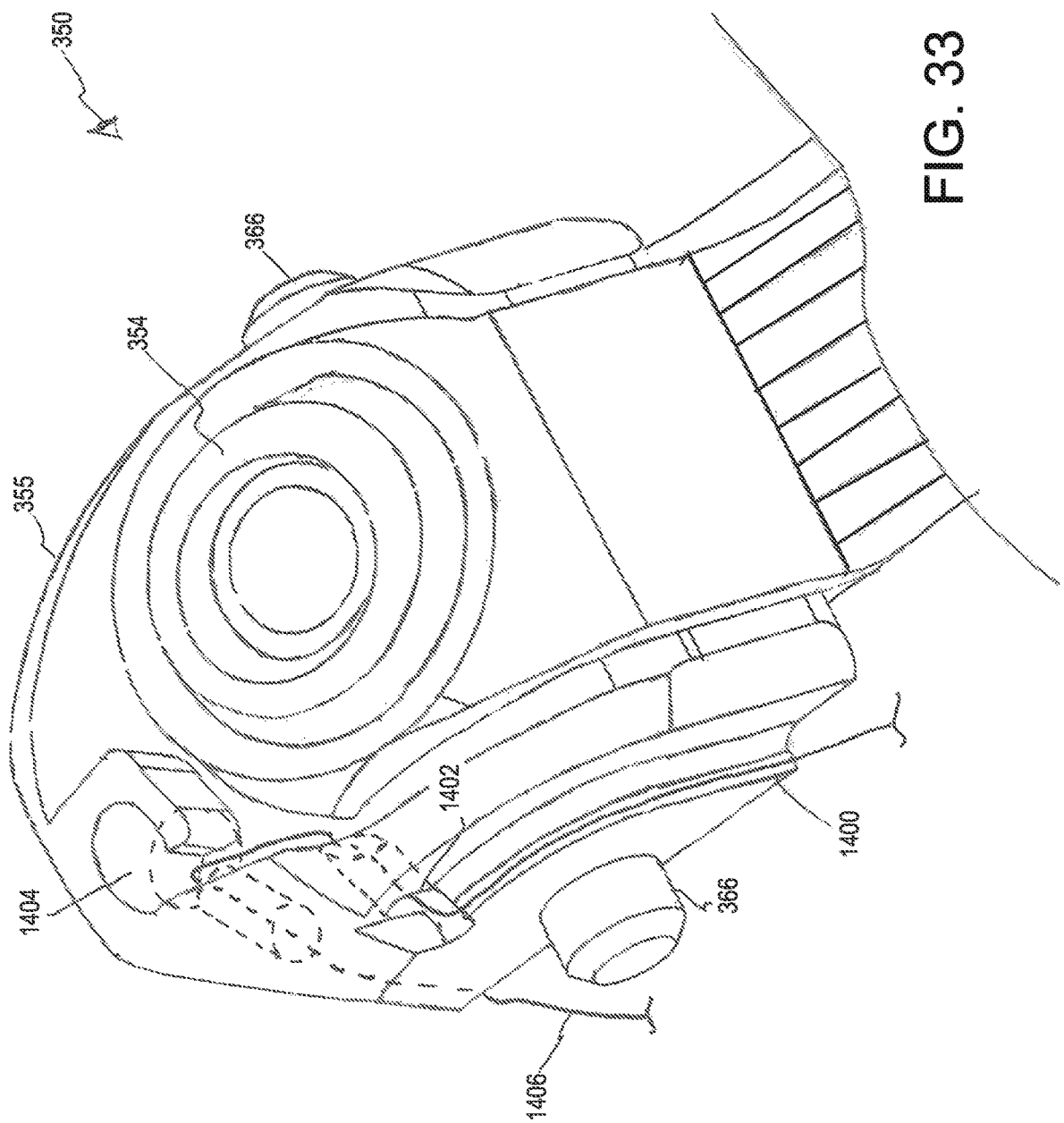

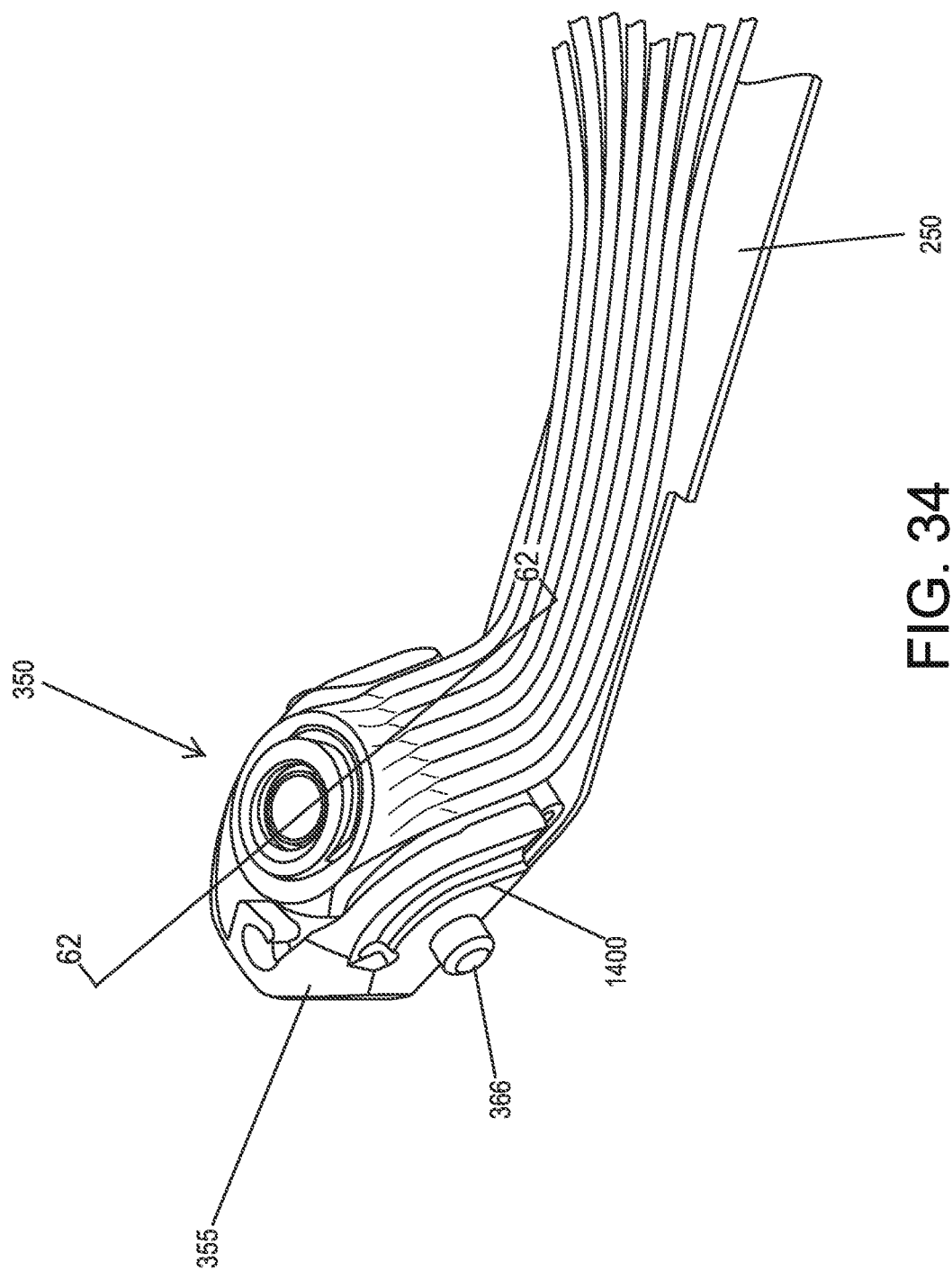

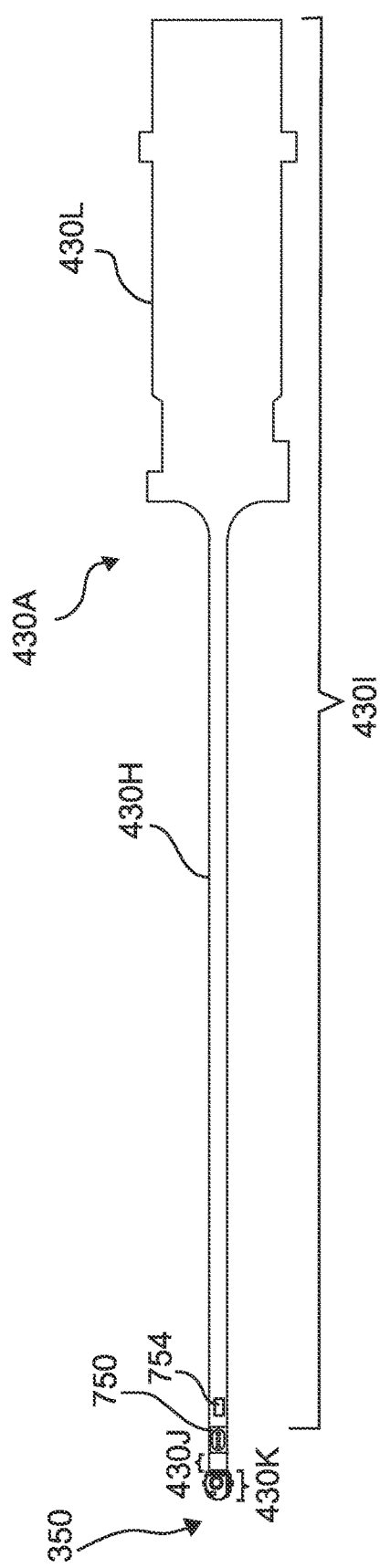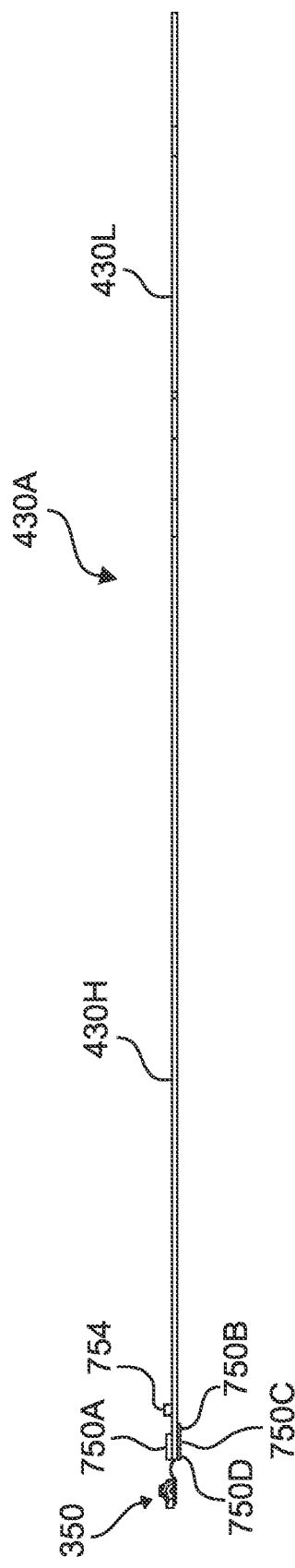
FIG. 53
FIG. 54

ENDOSCOPE WITH PANNABLE CAMERA AND RELATED METHOD

CROSS-REFERENCES TO RELATED APPLICATIONS

This application is a divisional application of U.S. patent application Ser. No. 15/253,399, filed Aug. 31, 2016, entitled Endoscope with Pannable Camera and Related Method and will be U.S. Pat. No. 10,616,491, issuing on Apr. 7, 2020, claiming the benefit of U.S. Provisional Patent Application Ser. No. 62/306,288, filed Mar. 10, 2016 entitled Endoscope with Pannable Camera and Related Method, and U.S. Provisional Patent Application Ser. No. 62/212,871, filed Sep. 1, 2015 entitled Endoscope with Pannable Camera and Related Method, which are hereby incorporated herein by reference in their entireties.

U.S. patent application Ser. No. 15/253,399, filed Aug. 31, 2016, entitled Endoscope with Pannable Camera and Related Method and will be U.S. Pat. No. 10,616,491, issuing on Apr. 7, 2020 is also a Continuation In Part Application of U.S. patent application Ser. No. 14/170,080, filed Jan. 31, 2014 entitled Endoscope with Pannable Camera, now U.S. Pat. No. 9,907,457, issued Mar. 6, 2018 and International Patent Application Serial No. PCT/US14/014243, filed Jan. 31, 2014, now Publication No. WO2014/121116, published Aug. 7, 2014 entitled Endoscope with Pannable Camera.

U.S. patent application Ser. No. 14/170,080, filed Jan. 31, 2014 entitled Endoscope with Pannable Camera claims the benefit of U.S. Provisional Patent Application Ser. No. 61/826,303, filed May 22, 2013 entitled Endoscope with Pannable Camera and U.S. Provisional Patent Application Ser. No. 61/759,784, filed Feb. 1, 2013 entitled Pannable Endoscope each of which is hereby incorporated herein by reference in its entirety.

BACKGROUND

Field of Disclosure

The present disclosure relates to endoscopic instruments for viewing and working in relatively inaccessible spaces; and in some aspects for operating in tight anatomical spaces within a body using an endoscope or arthroscope, or the like.

Background Information

The use of endoscopic instruments in medicine, allowing for remote viewing and operating in difficult-to-access spaces has become well-established. These instruments have also been useful in automotive, aviation, plumbing, electronics, and many other industries. In the field of medicine or veterinary practice, endoscopy or arthroscopy is often used to view or treat an anatomical region when minimal or no incisions are desired, or to avoid disturbing nearby tissues. In orthopedics, for example, the condition of a joint such as a knee or shoulder may be accessed using one or more arthroscopic instruments introduced into the joint through one or more small skin incisions. These instruments may also be used to repair various intra-articular tissues. Standard techniques of open surgery to view and repair these anatomical areas can be comparatively more time consuming, associated with greater risk and trauma to a patient, and can be associated with longer recovery time. Furthermore, anesthesia associated with open surgery may be more complicated, risky and costly. For improved field of view, an endoscope may be equipped with an actively flexible distal segment, controllable by the user at the handle end of the instrument. This may not be an effective option when the tip of the instrument is positioned in a confined space that may not accommodate the range of motion required for flexing the distal segment of an endoscope. In medical applications, one such example would include intra-articular surgery. Generally, using an instrument with a rigid insertion shaft may be preferred if the use of an instrument with an actively flexible distal segment is impractical. A non-flexible shaft may provide improved optics or image reproduction, increased space within the instrument for additional functionality, and greater durability. However, rigid endoscopes or arthroscopes have a limited field of view and may need to be repositioned or rotated frequently to increase the field of view. Some endoscopes or arthroscopes must be physically removed from the patient to have parts swapped out in order to change the field of view. Cannula systems may facilitate this approach, but may also increase the complexity of the procedure and the size of an incision. These limitations may reduce operator efficiency, increase surgery time, and may increase the risk of iatrogenic injury. In medical and other applications, it would be advantageous for an endoscope to have an increased or variable field of view without the use of an actively flexible distal segment. It may also be advantageous to combine functions within a single conduit in order to decrease the overall diameter of the shaft of an endoscope. Additionally, current instruments are prone to degradation in function and optical quality over repeated use, cleaning and/or sterilization. An endoscope design whose manufacturing and assembly cost is low enough to economically justify its non-re-use would also be advantageous. The costs of repeated cleaning or sterilization and re-packaging would be eliminated, and it may also be easier to standardize the sterility, quality and reliability of a single-use device.

SUMMARY

An endoscope may comprise a proximal handle and a shaft having a distal insertion end at which a camera assembly is mounted in a rotatable housing. The rotatable housing is configured to rotate about an axis generally perpendicular to a long axis of the insertion end, with the rotatable housing being the distal-most element of the endoscope at the insertion end. The camera assembly may include a lens adjacent to an image sensor, which can be a CMOS or CCD device. A pull wire may extend from the handle to the insertion end of the shaft, the pull wire wrapping around a portion of the rotatable housing, and configured to rotate the housing upon for and aft movement of the pull wire in the endoscope shaft. The housing may have a range of motion that provides the camera assembly a field of view that includes a region in line with the long axis of the insertion end and a region at least perpendicular to the long axis of the insertion end. In some cases this may comprise a range of about 0 degrees to about 120 degrees with respect to the long axis of the insertion end, or between about 35 degrees and about 115 degrees. The housing may be a spheroid shell constructed from two half-shells in which a cutout of one or both shells is configured to accommodate an image sensor or camera assembly (e.g. lens plus image sensor). The light source may be mounted on the rotatable housing so that it can illuminate the field of view to which the camera assembly is pointing.

In another aspect, an endoscope may comprise a proximal handle and a shaft having a distal insertion end, the camera assembly configured to rotate about an axis generally perpendicular to a long axis of the insertion end. A light source may be located on the insertion end of the shaft, and oriented to project light in a direction generally perpendicular to the long axis of the insertion end. The rotation range of the field of view of the camera assembly may include the area illuminated by the light source, or alternatively it may exclude the area illuminated by the light source. In this case, the illumination by the light source provided to the image sensor or camera is indirect, reflected or ambient light. The light source may comprise one or more LED's.

In another aspect, an endoscope may include a printed circuit board (PCB) that comprises a base portion residing within a handle of the endoscope, and one or more elongate extension portions of the PCB configured to extend from the base portion of the PCB in the handle through a shaft of the endoscope, and terminating at a distal insertion end of the shaft. The base portion of the PCB may be a composite of a flexible board mated to or sandwiched with a rigid board, at least one of the extension portions comprising a flexible board extension, or at least one of the extension portions comprising a rigid board extension, or at least two of the extension portions comprising a flexible board extension and a rigid board extension. A proximal leg of the flexible board extension may be angled at about 90 degrees to a proximal end of the rigid board extension, and a distal leg of the flexible board extension may curve back to be parallel to the rigid board extension. The proximal leg of the flexible board extension can then be folded so as to bring the distal leg of the flexible board extension into alignment adjacent to the rigid board extension. Both the rigid board extension and the flexible board extension may extend through a lumen of the shaft of the endoscope. The PCB and its extensions may be coated with a water resistant coating or membrane, so that the extensions can run through a fluid carrying lumen of the endoscope shaft. The flexible board extension can be connected to a rotatable image sensor (such as a CMOS or a CCD) in the distal insertion end of the endoscope shaft, while the rigid board extension can be connected to one or more stationary light sources at the insertion end of the shaft. The flexible board extension is configured to have sufficient slack to allow free rotation of the image sensor within a pre-determined rotational range.

In another aspect an endoscope may comprise a proximal handle housing configured to house an electronic processing board for processing signals from an image sensor located at a distal end of a shaft of the endoscope. A distal handle housing is configured to hold the electronic processing board in a position fixed with respect to the distal handle section. One or more magnets are attached to an internal wall of the proximal handle housing, said magnets being located next to a Hall effect sensor on the electronic processing board. Thus the proximal handle housing is rotatable with respect to the distal handle housing, and the Hall effect sensor is configured to provide a signal to an electronic processor representing the relative rotation of the proximal handle housing with respect to the distal handle housing. The electronic processor may be connected to a user interface displaying an image generated by the image sensor, and a rotational orientation of the image can thus altered by a change in the relative rotation of the proximal handle housing with respect to the distal handle housing.

In another aspect, an endoscope comprises a handle enclosing an electronic processing board for processing signals from an image sensor located at a distal end of a shaft of the endoscope. A button on the handle includes a member that encloses a magnet positioned above or adjacent to a portion of the electronic processing board on which a Hall effect sensor is located. Thus depression, release or movement of the button alters a magnetic field near the Hall effect sensor sufficiently to alter a signal produced by the Hall effect sensor. The button can be configured to cause an electronic controller connected to the electronic processing board to start a recording of an image generated by the image sensor, to stop a recording of an image generated by the image sensor, or to take a photograph of an image generated by the image sensor, based on a movement or release of the button by a user. The button can also be configured to cause an electronic controller connected to the electronic processing board to turn on, turn off, or adjust a light source located at a distal insertion end of a shaft of the endoscope, based on a movement or release of the button by a user. The movement or release of the button may comprise a short or longer duration depression of the button, a pre-determined series of two or more depressions and releases of the button, or a release of the button between two depressions having two or more variable durations.

BRIEF DESCRIPTION OF THE DRAWINGS

These and other aspects will become more apparent from the following detailed description of the various embodiments of the present disclosure with reference to the drawings wherein:

FIG. 10B shows a representational illustration of a pass-through barrier with a flexible component;

FIG. 20 depicts a cross-sectional view of example camera assembly mount and inner sheath of FIG. 19 taken at line 20-20 of FIG. 19;

FIG. 23 shows an alternate example of a camera assembly, part of an outer sheath, and part of a camera assembly mount;

FIGS. 28-32 depict some of the possible rotational positions of an alternate camera assembly;

FIG. 33 shows an example camera assembly;

FIG. 34 shows an example camera assembly with attached optical fiber bundle and electronic flex cable;

FIG. 53 depicts a top down view of an example printed circuit board which includes an extension portion for projection into an endoscope shaft;

FIG. 54 depicts a side view of an example printed circuit board including a projecting portion;

DETAILED DESCRIPTION

The terms 'endoscope' and 'arthroscope' as used herein are meant to be used interchangeably and are to be given their broadest interpretation, each term denoting an instrument having an elongate section for insertion into a space that is otherwise difficult to access, for the purpose of visual inspection, diagnosis and/or treatment or repair. In the field of medicine or veterinary practice, such a space may include a body or organ cavity, joint space, tissue plane or other body structure. The instrument may also be used in a number of non-medical (e.g., industrial) applications, in which the diameter of the insertion portion of an endoscope needs to be minimized, or in which the space within which an endoscope must operate is too confined to permit the use of an actively flexible distal segment.

Figure 1:
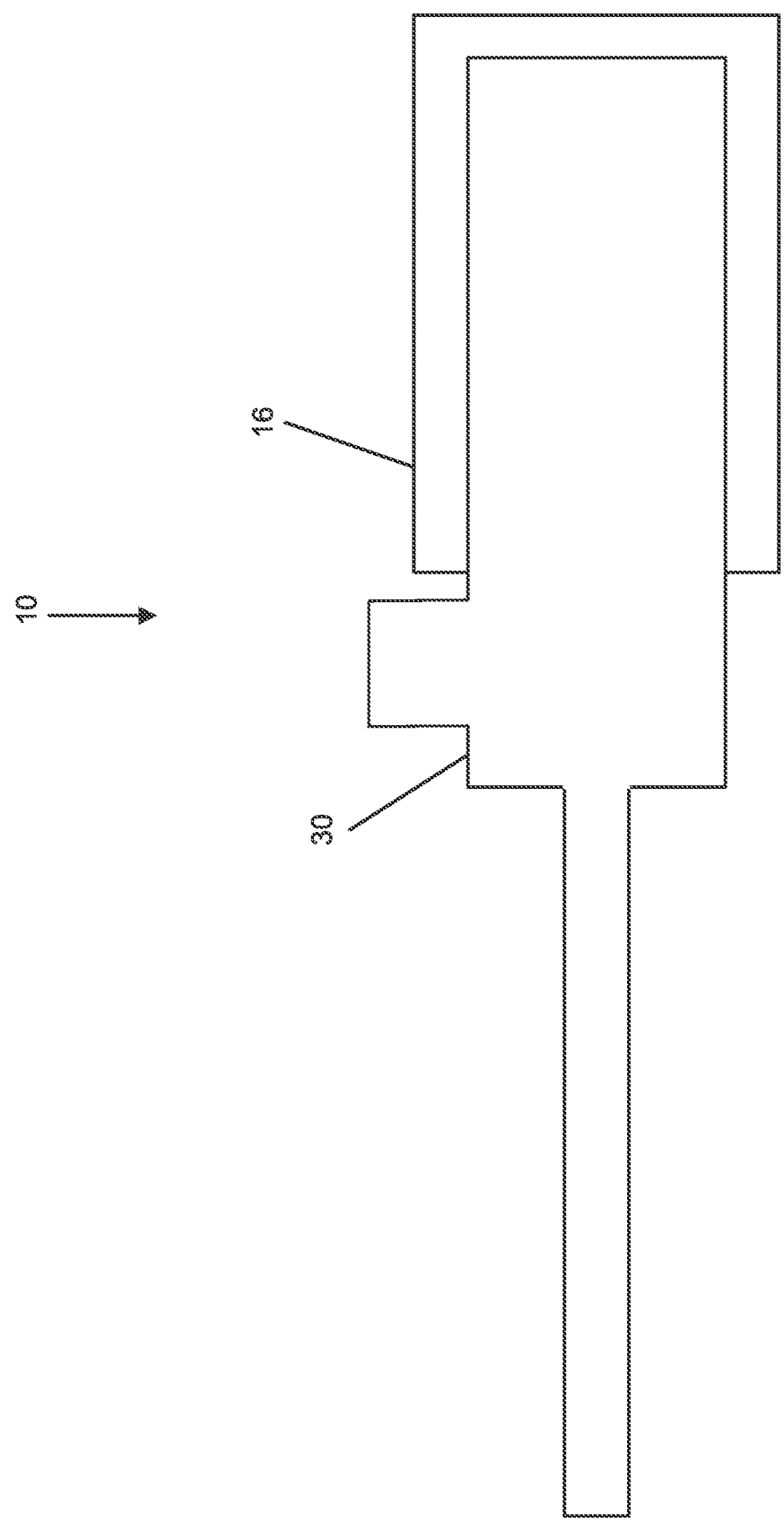
FIG. 1 is a representational illustration of a two-component handle design for an endoscope.

A two-component handle design of an endoscope 10 is shown in FIG. 1. The example endoscope 10 includes a handle proximal section 16 and a handle distal section 30. The handle proximal section 16 may be a housing. As shown, the handle distal section 30 may extend at least partially into the handle proximal section 16. The handle distal section 30 and the handle proximal section 16 may be rotatable relative to each other. In some embodiments, a user may hold the handle proximal section 16 immobile while rotating the handle distal section 30 with a thumb or finger. The endoscope 10 may have a number of features such as, but not limited to, a rotation sensing assembly, fluid conduits, lighting, an imager or camera assembly, pivot control for the imager etc.

Figure 2:
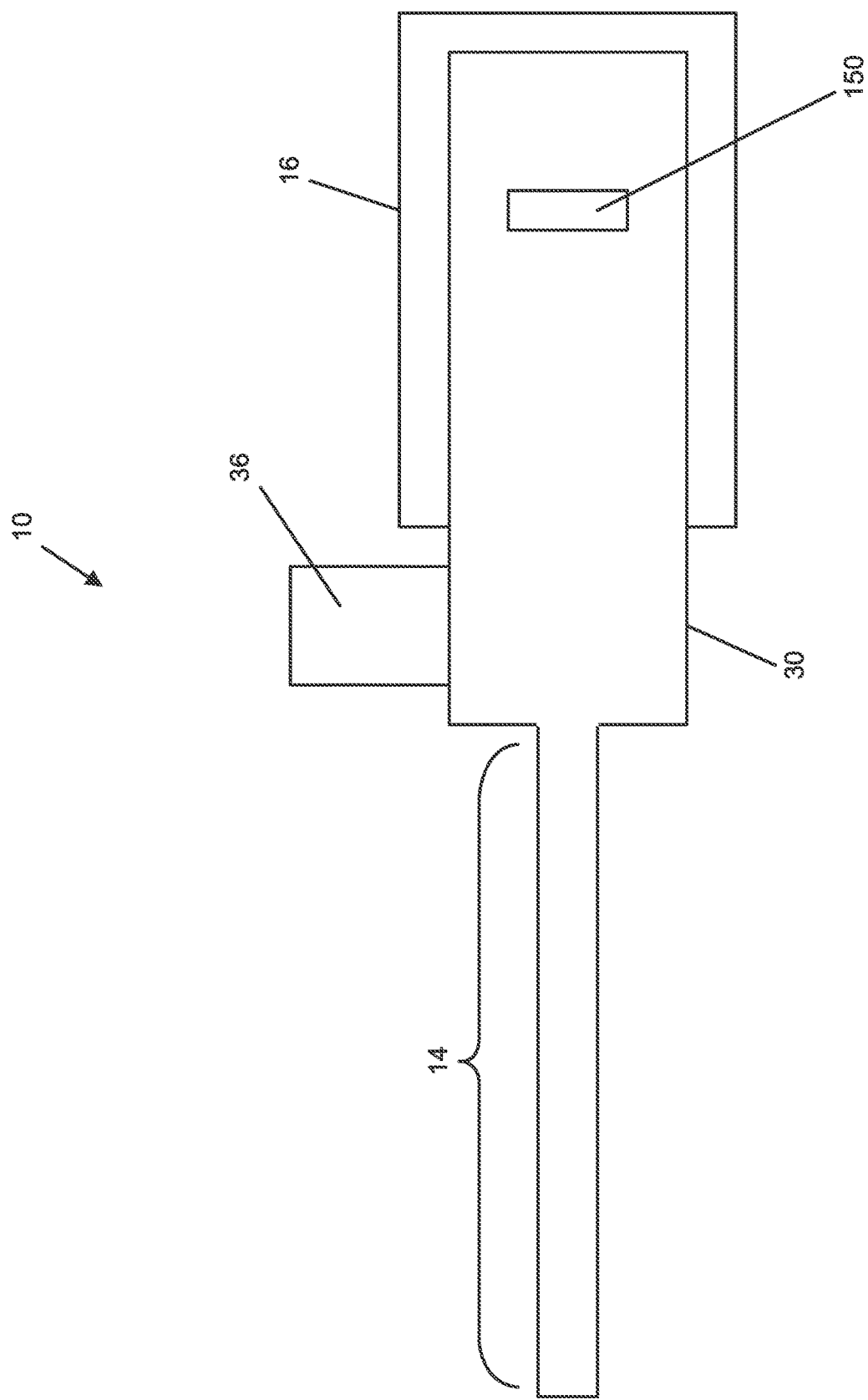
FIG. 2 shows additional features of the illustration of FIG. 1.

Additional features of the endoscope 10 are represented in FIG. 2. The endoscope 10 includes a handle proximal section 16 and a handle distal section 30. In this example, at least a part of an insertion shaft or section 14 is fixed to the handle distal section 30 and moves with the handle distal section 30. The handle distal section 30 includes a handle protuberance or fin 36 which provides a surface for a user to press against to facilitate rotating the handle distal section 30 relative to the handle proximal section 16. In some embodiments, a user's hand may hold the handle proximal section 16 immobile while the handle distal section 30 is rotated using one of the user's fingers or thumb.

In some embodiments, one or both the handle proximal section 16 and the handle distal section 30 may function as a housing or provide a support structure for other components of the endoscope 10. The endoscope 10 shown in FIG. 2 may include a rotation sensing assembly 150. The rotation sensing assembly 150 may track the rotation of handle distal section 30 relative to the handle proximal section 16. In some embodiments, the rotation sensing assembly 150 may include a component which is stationary with respect to the handle proximal section 16 and a component that is stationary with respect to the handle distal section 30. For example, the rotation sensing assembly 150 may include a potentiometer and a keyed shaft. The potentiometer may be mounted, for example to a support member comprising the internal housing of the handle proximal section 16. Alternatively, the handle distal section 30 may also comprise a support member for mounting one or more components of the rotation sensing assembly 150 (see for example the rotational sensor holder in FIG. 8). In either case, a rotational or translational component of the rotation sensing assembly is arranged to move in proportion to the degree of rotation of the handle distal section 30 relative to the handle proximal section 16.

Figure 3A:
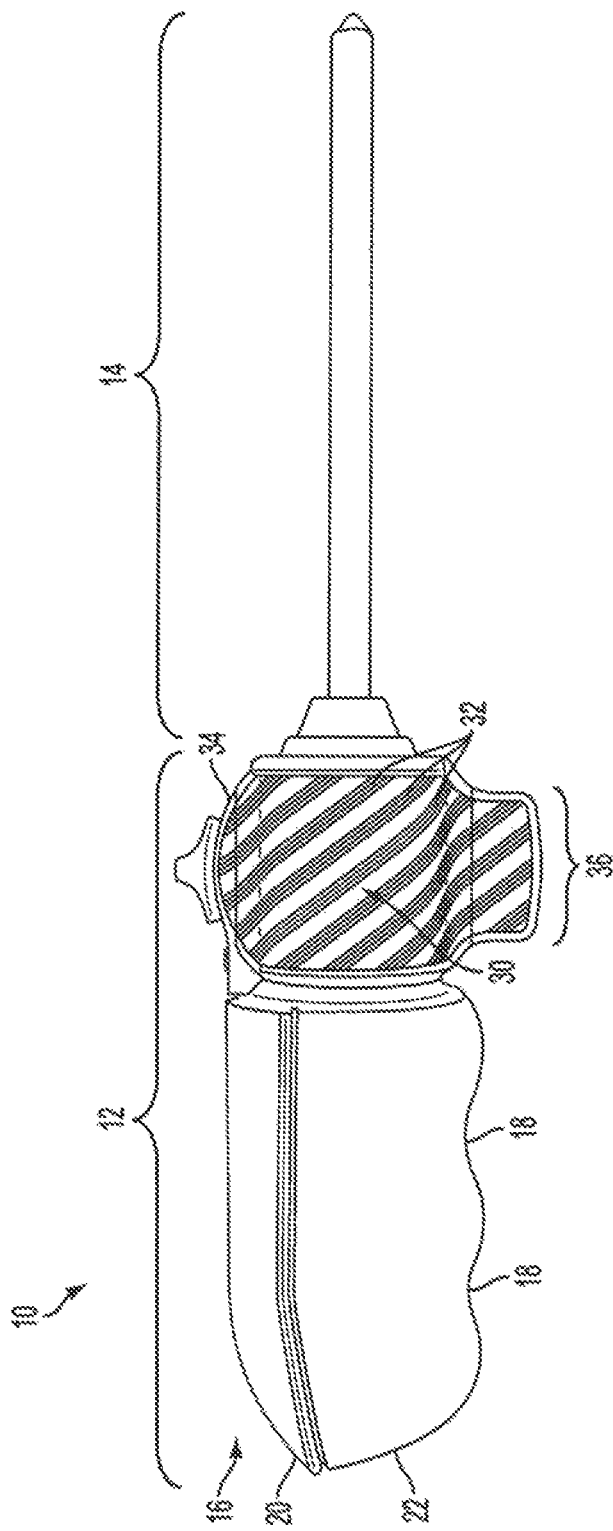
FIG. 3A shows an exemplary side view of an endoscope.

An exemplary embodiment of an endoscope (or, e.g., arthroscope) 10 is shown in FIG. 3A. The endoscope 10 may be used in various endoscopic procedures, including arthroscopy, among others. As shown, the endoscope 10 includes a handle 12 and an insertion section or shaft 14, which may comprise an elongate hollow shaft within which one or more actuation members, electrical/communications wires, lighting or light-transmitting cables and/or fluid channels may be located. As shown, in an embodiment the handle 12 may be roughly cylindrical and rounded in shape. The insertion section 14 may also be roughly cylindrical in shape and extend along a longitudinal axis. In an embodiment, the insertion section 14 may be rigid and relatively straight. In other embodiments, the insertion section 14 may be curved or angled along at least a portion of its length. In yet other embodiments, the insertion section 14 may comprise semirigid, malleable material permitting it to be bent and held to a desired shape. The diameter of the insertion section 14 is significantly smaller than that of the handle 12. In some embodiments, the diameter of the insertion section 14 may be approximately 5.5 mm or smaller. The insertion section 14 of the endoscope 10 may be roughly the same length as that of the handle 12. In alternative embodiments, the lengths and shapes of the handle 12 and insertion section 14 may differ substantially.

At least a portion of the insertion section 14 may be detachable from the handle 12. In such embodiments, the insertion section 14 or detachable portion of the insertion section 14 may be coupled to the handle 12 by any of a variety of means including, but not limited to friction fit, snap fit, threaded coupling, bayonet mount, etc. In some embodiments, the insertion section 14 may be a disposable component and the handle 12 may be a reusable component. In embodiments in which the insertion section 14 is disposable, the insertion section 14 may be discarded after use. In other embodiments, the insertion section 14 may be sterilized after use via an autoclave, solution soaking, or other suitable sterilization procedure. In a preferred embodiment, both the handle 12 and the insertion section 14 are disposable and may be discarded after use, obviating the need for and cost of sterilization procedures and equipment (aside from a pre-usage sterilization with ethylene oxide, radiation, or the like, during, for example, manufacture, assembly or packaging of the device). Additionally, by making both the handle 12 and insertion section 14 of the endoscope 10 disposable, there is no degradation in function or reliability resulting from repeated use and repeated cleaning. Making the entire endoscope 10 disposable has other benefits, some which will be discussed below.

Preferably, a disposable endoscope 10 may be equipped with a means to prevent its reuse, particularly if sterilization of a used instrument is likely to degrade its function. For example, the endoscope 10 may include a memory chip storing an identification code that can be recognized by an electronic processor in a base unit to which the endoscope 10 must be connected for operability and display of images. The connection may include wired communications between a controller in the base unit and a memory chip in the endoscope 10, or, for example wireless communications using an RFID device mounted in the endoscope 10. (Other types of wireless transmission, such as, e.g. Bluetooth or Wi-Fi, may also be used). In an embodiment, the base unit may be programmed to encode a memory device on the endoscope 10 upon first use, and may be programmed to read and identify a code signifying that the endoscope 10 has been previously used whenever the endoscope 10 is subsequently re-connected to any base unit. Upon identification of a 'used' endoscope 10, the controller may be programmed to prevent electronic and imaging communications between the endoscope 10 and the base unit. The code and its communication may be encrypted to enhance system security. Alternatively, the endoscope 10 may include a disablement feature in its software which renders the endoscope 10 inoperable after usage.

As shown in FIG. 3A, the handle 12 of the endoscope 10 may include a number of different features. The handle 12 may include a handle proximal section 16. The handle proximal section 16 may be relatively smooth as shown in FIG. 3A. The handle proximal section 16 may comprise one or more hollow sections. The handle proximal section 16 may also be contoured such that it includes a number of ergonomic attributes. In some embodiments, at least a portion of the handle proximal section 16 may not have a smooth surface and may include a knurled, ribbed, roughened, honeycombed, etc. type texture, and/or a rubberized or elastomeric surface layer to facilitate gripping the endoscope 10 during its operation. In the example embodiment, the handle proximal section 16 is formed with a number of finger grooves 18. In some embodiments, the handle proximal section 16 may be made of a material (e.g. rubber or other elastomer) that has a soft feel or is otherwise comfortable to hold. In some embodiments, a pistol grip-like feature (not shown) may be included as part of the handle proximal section 16.

As shown in FIG. 3A, the handle proximal section 16 may be divided into two separate parts. The handle proximal section 16 in FIG. 3A includes a handle top section 20 and a handle bottom section 22. The handle top section 20 and handle bottom section 22 of the handle proximal section 16 may be manufactured as two separate parts and coupled together by any suitable means, such as, e.g., adhesive, screws, snap-fit, etc. As shown, the handle top section 20 is smooth and contoured differently from the handle bottom section 22. This may help a user quickly and easily determine orientation of the endoscope 10 by feel. In some embodiments the handle top section 20 and handle bottom section 22 may comprise surface materials that have a different feel (e.g., metallic vs. plastic, metallic vs. elastomeric, smooth vs. textured, etc.).

The handle 12 of the endoscope 10 may also include a handle distal section 30. As shown in FIG. 3A, the handle distal section 30 extends from the handle proximal section 16 toward the insertion section 14. The handle distal section 30 may be smaller in diameter than the handle proximal section 16. As shown, the handle distal section 30 may be longer in length than the handle proximal section 16, but in alternate embodiments, the relative dimensions of the handle distal section 30 and handle proximal section 16 may differ.

On at least a portion of the handle distal section 30 there may be a gripping texture as shown in FIG. 3A. In the example embodiment shown in FIG. 3A, the grip texture is a series of spiraling ribs 32. In other embodiments, other gripping textures, such as non-spiraling ribs, nubs, bumps, grooves, honeycomb patterning or other form of knurling or checkering, etc. may also be used. As shown, the spiraling ribs 32 in the example embodiment encircle most of the outer diameter of the handle distal section 30. In some embodiments including a gripping texture on the handle distal section 30, the gripping texture may not be formed as a continuous part of the handle distal section 30. In such embodiments, the gripping texture may be a 'skin' or sleeve applied onto the handle distal section 30. The gripping texture skin may be coupled to the handle distal section 30 by any suitable means such as, but not limited to, adhesive, snap fit, various fasteners, over-mold, etc. In some embodiments, the gripping texture skin may be made of a material different from the handle distal section 30. The gripping texture skin, for example, may be a softer, elastomeric or rubbery, material which is more comfortable to grip/less slippery than the handle distal section 30 material.

In the example embodiment of FIG. 3A, the handle distal section 30 includes a handle raised portion 34 projecting from the top of the handle distal section 30. In this example, the handle raised portion 34 does not project sharply up from the rest of the handle distal section 30. Instead, the handle raised portion 34 may be constructed to gently curve up from the rest of the handle distal section 30. In this example, the spiraling ribs 32 do not extend over and onto the top of the handle raised portion 34. Additional features of the handle raised portion 34 will be further described below.

In one aspect, projecting from the bottom of the handle distal section 30 may be a handle fin or paddle 36. In this example, the handle fin 36 may be constructed to gently curve away from the rest of the handle distal section 30 toward an inferior or dependent position of the endoscope 10. The spiraling ribs 32 may or may not extend over and onto the bottom of the handle fin 36. In other embodiments, a handle fin 36 may be configured to project from the top of the handle distal section 30, while the handle raised portion 34 may be configured to project from another aspect of the handle distal section 30. The handle fin 36 may be disposed so as to correspond to the location of an entry point for various cables, irrigation, etc. in endoscopes which may already be familiar to a physician. This may be desirable since such an entry point is often used as a surface to press against to facilitate rotation and as an orientation marker. Additional features of the handle fin 36 will be further described below.

Figure 3B:
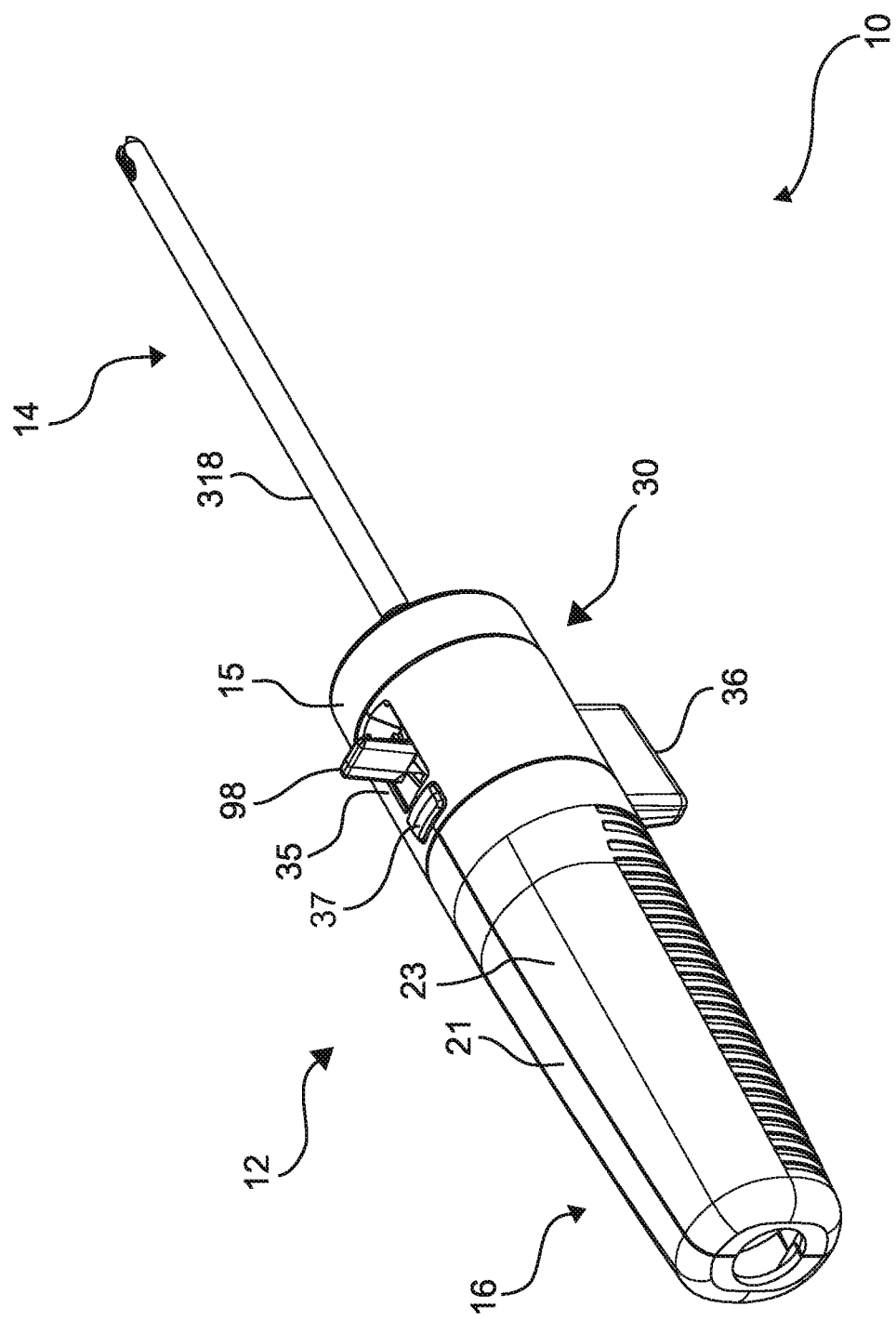
FIG. 3B shows an exemplary perspective view of another endoscope.

An alternative embodiment of an endoscope (or, e.g., arthroscope) 10 is shown in FIG. 3B. As shown, the endoscope 10 includes a handle 12 and an insertion section or shaft 14, which may comprise an elongate hollow shaft within which one or more actuation members, electrical/ communications wires, lighting or light-transmitting cables and/or fluid channels may be located. At least a portion of the shaft 14 may be detachable from the handle 12. In the example embodiment, the shaft 14 of the endoscope comprises an outer sheath or cannula 318 attached to a mounting structure 15 which may facilitate attachment of the cannula to and detachment of the cannula from the handle 12 by any of a variety of means including, but not limited to friction fit, snap fit, threaded coupling, bayonet mount, etc.

As shown in FIG. 3B, the handle 12 of the endoscope 10 may include a handle proximal section 16 which encloses (among other components) a printed circuit board (PCB) for controlling or processing image data detected by a sensor at the distal end of the shaft, and/or for providing power to light sources (e.g. LED's) at the end of the shaft. It may also house a fluid conduit for connecting to a fluid carrying lumen within the shaft 14. A handle proximal section 16 may be divided into two separate parts. The handle proximal section 16 in FIG. 3B includes a handle first half-shell 21 and a handle second half-shell 23. The handle first half-shell 21 and handle second half-shell 23 of the handle proximal section 16 may be manufactured as two separate parts and coupled together during assembly by any suitable means, such as, e.g., adhesive, screws, snap-fit, etc and may be symmetrical. For example, the handle first half-shell 21 may be ultrasonically welded to the handle second half-shell 23 using any ultrasonic welding techniques. Additionally, alternatively, or optionally, the hand half-shells 21, 23 may be manufactured using injection molding techniques know in the art.

The handle 12 of the endoscope 10 may also include a handle distal section 30. As shown in FIG. 3B, the handle distal section 30 extends from the handle proximal section 16 toward the shaft 14. Projecting from the bottom of the handle distal section 30 may be a handle fin or paddle 36. The handle distal section 30 also includes a recess 35 which is sized to accommodate a finger contact 98 of a pivot control structure 100 (see, e.g. FIG. 14). Examples of pivot control structures 100 are also described below, and are used to rotate a pivotable sensor housing at the distal end of the shaft 14.

Also shown in FIG. 3B is a display or camera control button 37. It may be used to capture images produced by the image sensor at the distal end of the shaft 14. In some embodiments, a user can depress the button 37 using a pre-determined pattern or sequence to, for example, turn on or off a video recording of images shown on a display of the field of view of the image sensor at the distal end of the shaft 14, record a snapshot of the image shown on a display of the field of view of the image sensor at the distal end of the shaft 14, alter the brightness of the light elements (e.g. LED's) at the end of the endoscope shaft 14, or adjust other characteristics of the sensor or displayed image (such as, e.g., white balance, color saturation, digital magnification, etc.). It may be preferable to have the sensor characteristics and LED illumination controlled by a processor associated with a graphical user interface connected to the endoscope, rather than by the endoscope PCB itself in order to reduce the amount and cost of on-board processing power of the endoscope PCB.

Figure 33A:
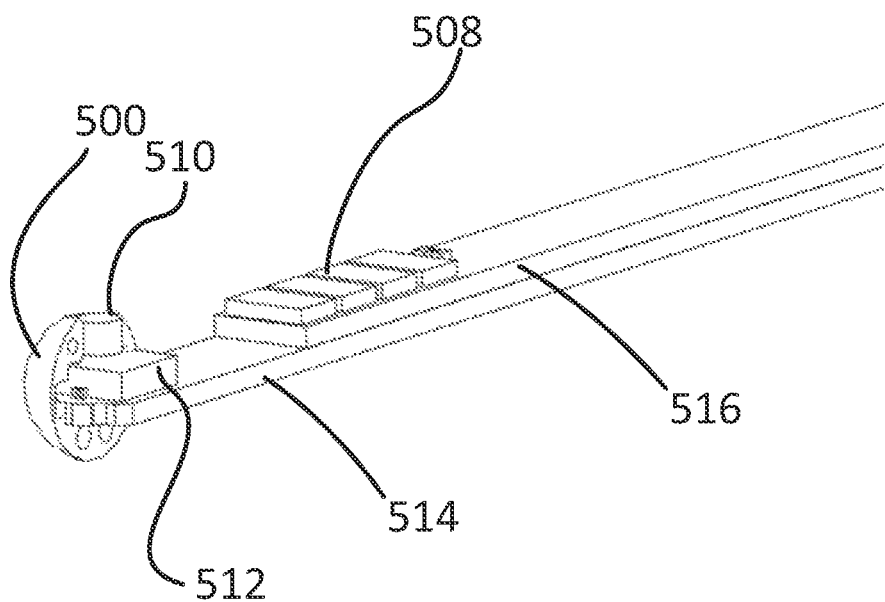
FIG. 33A shows a relationship between a camera assembly and LED's and their respective power and communications PCB extensions.

The button 37 may operate an electromechanical switch located on the main PCB within the endoscope handle distal section 30. To ensure maximum moisture resistance of the PCB electronic components, it may be preferable to employ a magnetic or optical sensor assembly to detect the movements of button 37. As shown in FIG. 33E (showing relative positions of some of the components within handle 12), in one embodiment a Hall effect sensor on the endoscope PCB 518 may be positioned below and near the location of a shaft 38 connected to button 37. The button 37 may be spring loaded, and the end of the shaft 38 closest to the PCB 518 can be made to include an embedded magnet. As the button shaft 38 is moved closer to or away from the PCB-based Hall effect sensor, the sensor can generate the appropriate signal corresponding to the position of the button shaft 38 and its duration in that position.

Figure 4:
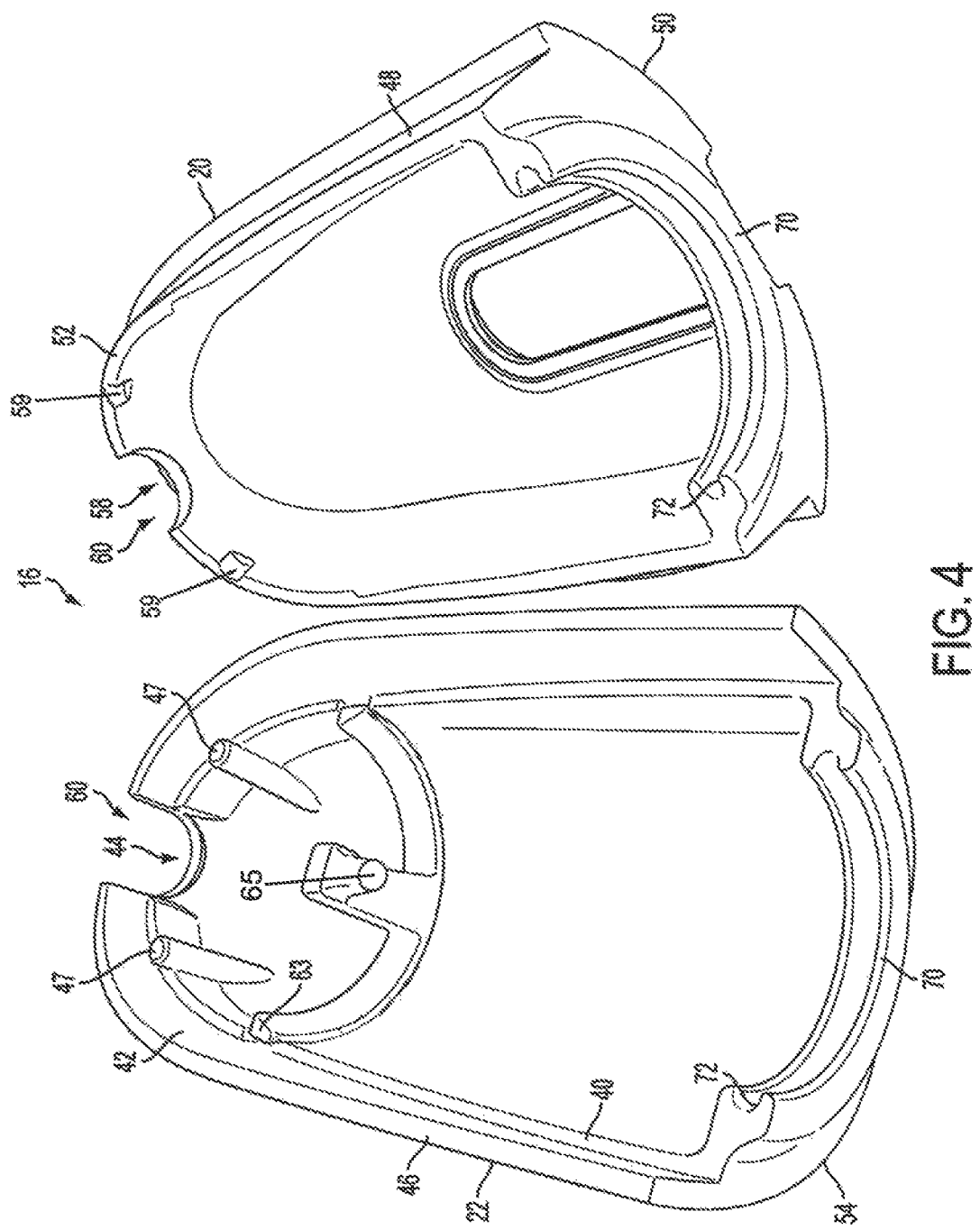
FIG. 4 shows a disassembled view of an example of a handle proximal section of an endoscope.
Figure 5:
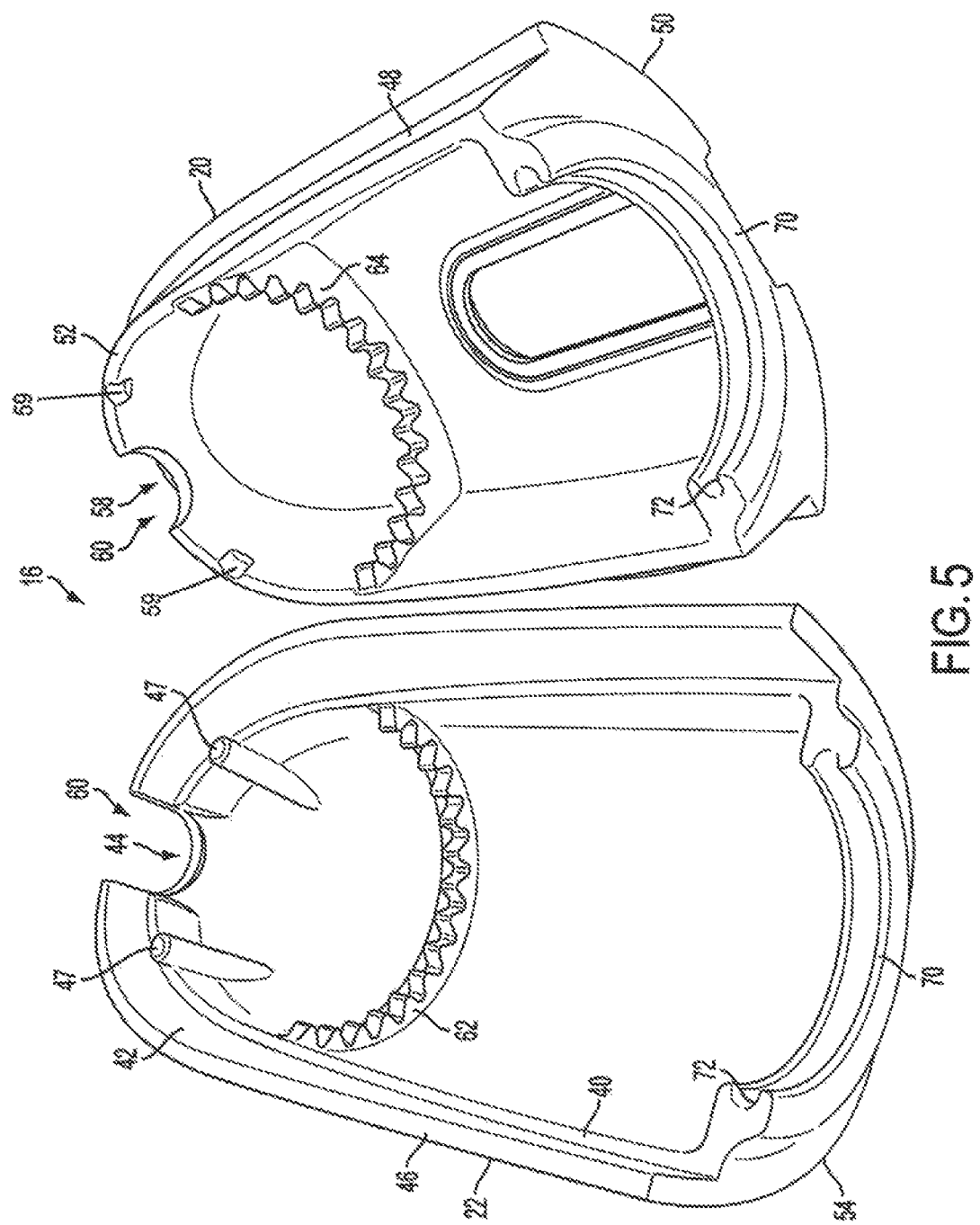
FIG. 5 shows a disassembled view of an alternate example of a handle proximal section of an endoscope.

FIG. 4 and FIG. 5 show example embodiments of a handle top section 20 and handle bottom section 22 of the handle proximal section 16 shown in FIG. 3A. The handle top section 20 and handle bottom section 22 are shown in an uncoupled or disassembled view. The handle proximal section 16 forms a shell-like structure when assembled. The handle bottom section 22 may include a ledge 40 that wraps around a bottom section inner wall 42 at a distance from the top face 46 of the handle bottom section 22. As shown, there is a curved or U-shaped cutout 44 in the handle bottom section 22 disposed at an angle substantially perpendicular to the top face 46 of the handle bottom section 22. Two peg projections 47 may be included near the rear of the handle bottom section 22. The peg projections 47 may extend slightly above the ledge 40 and be angled approximately perpendicular to the top face of the ledge 40.

As shown in FIGS. 4 and 5, a portion of the handle top section 20 may be dimensioned so that it may be overlapped by the handle bottom section 22 when the handle proximal section 16 is assembled. The overlapped section 48 may be stepped in from the handle top section outer surface 50 as shown in FIGS. 4 and 5. The height of the overlapped section 48 may be selected so that it is approximately equal to or slightly greater than the distance between the top of the ledge 40 of the handle bottom section 22 and the top face 46 of the handle bottom section 22. In such embodiments, when fully assembled, the bottom face 52 (refers to orientation when assembled) of the handle top section 20 abuts the top of the ledge 40 of the handle bottom section 22. Additionally in such embodiments, the handle top section outer surface 50 and handle bottom section outer surface 54 may be flush with each other and form a nearly continuous surface with little gap between the two. In some embodiments, there may be a small gap between the handle top section outer surface 50 and handle bottom section outer surface 54 (small gap shown in FIG. 3).

As shown, the handle top section 20 may include peg cutouts 59 which are shaped and disposed such that they may accept the peg projections 47 in the handle bottom section 22. The handle top section 20 may include a curved cutout 58 at the butt or proximal portion of the handle top section 20. As shown the curved cutout 58 may be recessed into the handle top section 20 at an angle substantially perpendicular to the bottom face 52 (refers to orientation when assembled) of the handle top section 20. When the handle proximal section 16 is assembled, the curved or U-shaped cutout 44 of the handle bottom section 22 and the curved cutout 58 of the handle top section 20 together may form a substantially circular or ovoid handle void or opening 60 which will be further described below. It should be appreciated that the use of the terms "cutout", "cut", etc. herein should not be construed to imply material must be physically removed by a cutting or material removal process. In some embodiments, the curved or U-shaped cutout 44 and the curved cutout 58 may be formed during manufacture without physically removing material.

As shown in FIG. 4 the handle bottom section 22 may include a shaft support member 63. The shaft support member 63 in FIG. 4 has a curved or semi-circular portion which roughly corresponds to the location of the toothed projection 62 in FIG. 5. The shaft support member 63 also includes a post. The post projects perpendicularly from a mid-point of the semi-circular portion, leaving approximately 90° of the semi-circular portion on each side of the post. Projecting perpendicularly from the top of the post of the shaft support member 63 toward the distal end of handle proximal section 16 is a shaft supporting section 65. The shaft supporting section 65 may include a depression in which a portion of a sensor gear shaft 120 (see FIG. 8) may be seated. The post of the shaft support member 63 may be approximately the length of the radius of the semi-circular portion when the handle proximal section 16 is fully assembled. The shaft support member 63, toothed projection 62, and toothed projection 64 will be further described below.

As shown in FIG. 5, the handle bottom section 22 may instead or optionally include a curved toothed projection 62. The curved toothed projection 62 is complemented by a similar toothed projection 64 included on the handle top section 20. The toothed projection 62 and toothed projection 64 may be disposed so that they are in line with one another and form an annulus or internal ring gear when the handle proximal section 16 is fully assembled.

As shown in FIGS. 4 and 5, the face of the handle bottom section 22 opposite the curved or U-shaped cutout 44 and face of the handle distal section 20 opposite the curved cutout 58 may include semi-circular openings or voids 70. A curved or U-shaped track 72 may be recessed into the edges of the semi-circular voids 70 along the entire arc of each semi-circular void 70 as shown in FIGS. 4 and 5.

Figure 6:
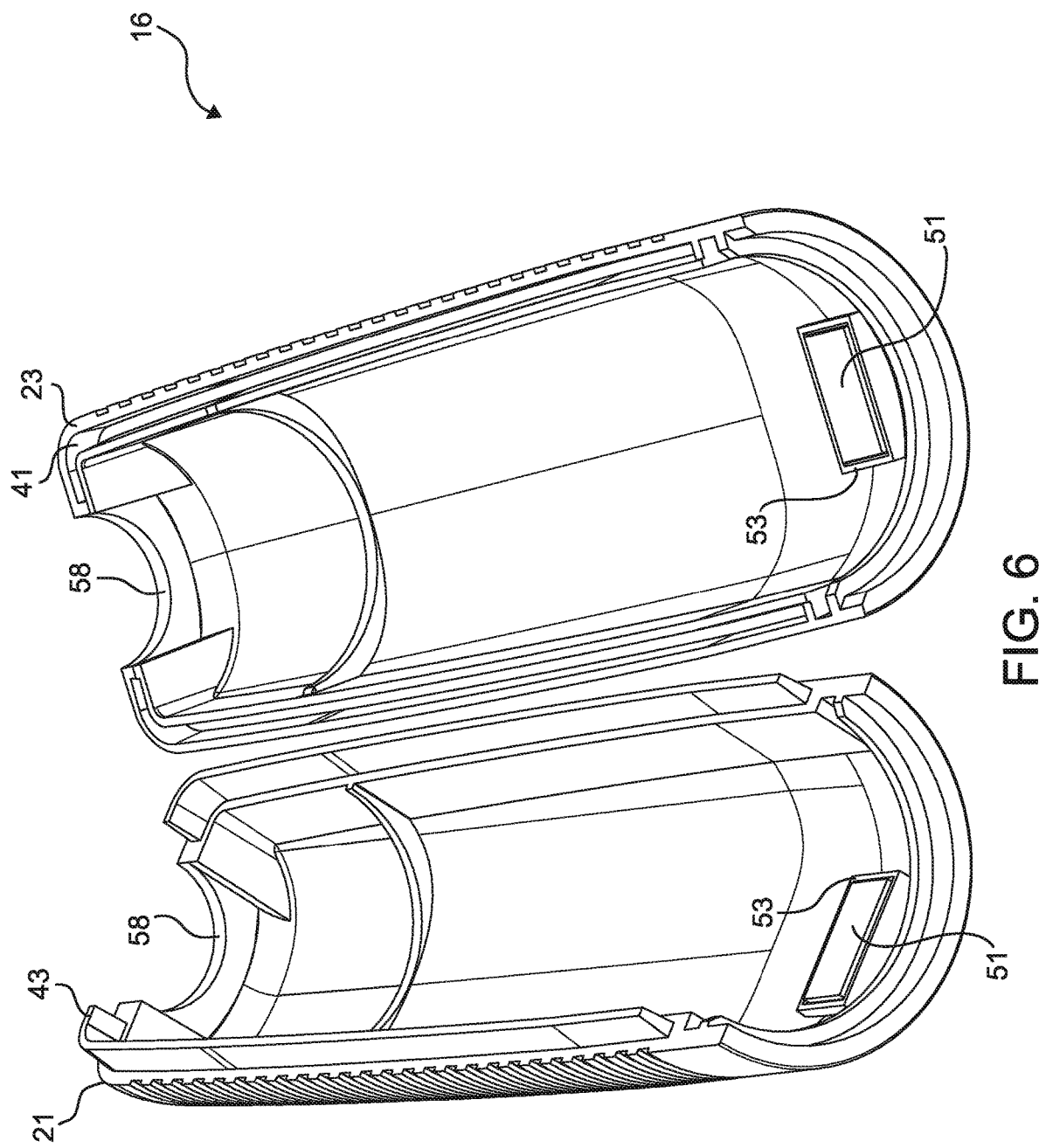
FIG. 6 shows a disassembled view of an alternate example of a handle proximal section of an endoscope.

FIG. 6 shows an example embodiment of a handle first half-shell 21 and handle second half-shell 23 of the handle proximal section 16 shown in FIG. 3B. The handle first half-shell 21 and handle second half-shell 23 are shown in an uncoupled or disassembled view. The handle proximal section 16 forms a shell-like structure when assembled. One of the first or second handle half-shells 21, 23 may include a slot 41 which is sized to fit a cooperating wall extension 43 in the other of the first and second handle half-shells 21, 23 to facilitate assembly. Similar to FIGS. 4 and 5, the example embodiment in FIG. 6 includes curved cutouts 58. These cutouts 58 allow access into the interior volume of the proximal handle section 16 when the proximal handle section 16 is assembled.

It may be useful to be able to track the rotational orientation of the handle proximal section 16 in relation to the handle distal section 30, shaft 14, and the sensor or camera at the distal end of the shaft. In an embodiment, this can be accomplished through the interaction between a Hall effect sensor and an associated magnet. The Hall sensor may be positioned on the handle proximal section 16, with a magnet located on an internal component within the handle proximal section 16, or one or more magnets may be positioned in the handle proximal section 16 with one or more associated Hall effect sensors mounted on a PCB within the handle proximal section 16. In some embodiments, one or more magnets 51 may be embedded in or attached to a part of the handle 12. In the example embodiment shown in FIG. 6 the proximal handle section 16 includes two magnets 51 situated generally opposite each other. A different number of magnets 51 may be used in other embodiments. As shown, in this case, each of the first and second handle half-shells 21, 23 includes a magnet 51 inserted in an interior wall of each half-section. In the example embodiment, the magnets 51 are coupled to a retaining structure 53 which holds the magnet 51 in place in the proximal handle section 16. The magnets optionally may be constructed of any appropriate rare earth or transition metal, or alloy thereof.

Figure 7A:
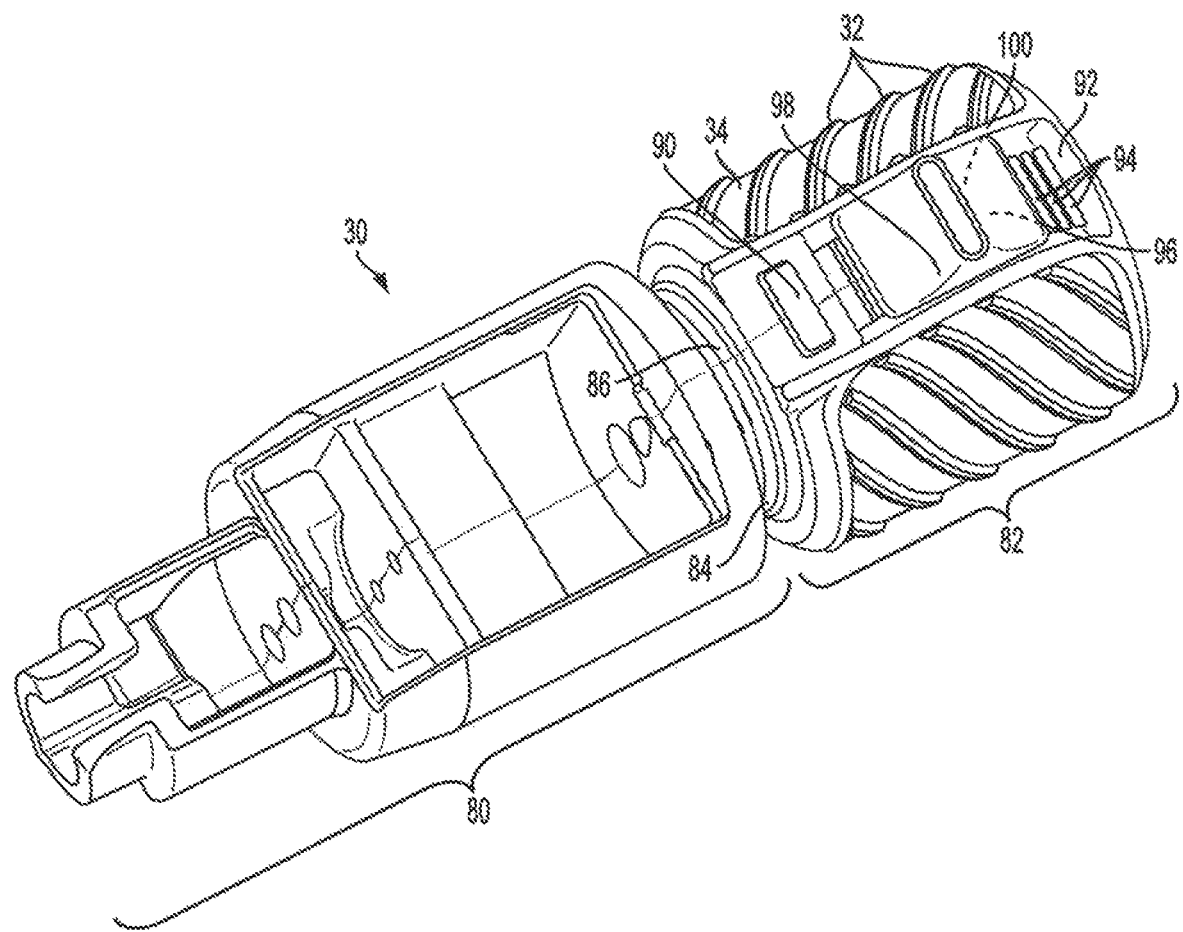
FIG. 7A shows a top perspective view of an example of a handle distal section of an endoscope.

The example handle distal section 30 of FIG. 3A is shown in FIG. 7A isolated from the rest of the handle 12. FIG. 7A shows the handle distal section 30 from a substantially top perspective view. As shown, the spiraling ribs 32 and front handle raised section 34 detailed above are visible on handle distal section 30. As indicated by the seam running down the vertical center plane of the handle distal section 30, the handle distal section 30 may be constructed as two or more separate parts (30a and 30b in the example embodiment) which are coupled together by any suitable means or combination of suitable means, such as, e.g., snap fit, adhesive and/or screws.

The handle distal section 30 in FIG. 7A additionally includes a section not shown in FIG. 3A. When the endoscope 10 is assembled, as it is in FIG. 3A, part of the handle distal section 30 may be housed inside the handle proximal section 16. For example, a housed handle electronics section 80 projects proximally from the external handle distal section 82 (which is visible in both FIG. 3A and FIG. 7A). The housed handle electronics section 80 will be further described below.

Between the housed handle electronics section 80 and the external handle distal section 82 is a small diameter span 84. As shown, the small diameter span 84 may include a rounded groove 86 which is recessed into the outer surface of the small diameter span 84. In some embodiments, when fully assembled, the small diameter span 84 of the handle distal section 30 may be disposed within the semi-circular openings 70 of the handle proximal section 16. The rounded groove 86 in the small diameter span 84 and the curved or U-shaped track 72 in the semi-circular openings 70 may be in line with one another. This may allow the handle distal section 30 and handle proximal section 16 to be rotated relative to one another as the endoscope 10 is used. Optionally, ball bearings (not shown) or other types of bearings may track along the rounded groove 86 in the small diameter span 84 of the handle distal section 30 and the U-shaped track 72 in the semi-circular openings 70 of the handle proximal section 16. In a preferred embodiment, an o-ring (not shown) may be placed in the rounded groove 86 of the small diameter span 84 of the handle distal section 30. The o-ring (not shown) may function as a dynamic seal between the handle proximal section 16 and handle distal section 30. In such embodiments, the handle proximal section 16 and handle distal section 30 may be rotated relative to one another while sealing the interior of the handle proximal section 16 from liquid.

A handle fin or paddle 36 or other protuberance may serve as an orientation marker for the user as the handle proximal portion 16 and handle distal section 30 are rotated relative to one another. Orientation may be checked either visually or by feel. In some embodiments, the gripping texture on the handle fin/paddle 36 may be different than spiraling ribs 32 on the rest of the handle distal section 30 to facilitate orientation-checking by feel.

As shown in FIG. 7A, the handle raised section 34 may include a button 90. In some embodiments, the handle raised section 34 may include more than one button 90, or no button at all. The button 90 may be located elsewhere on the handle distal section 30 or elsewhere on the handle 12. In some embodiments, the handle raised section 34 may include a button 90 and one or more additional buttons 90 may be located elsewhere on the handle 12. In some embodiments, a button 90 may be a mechanically actuated switch including a depressible member which when depressed completes or breaks a circuit. The button 90 may comprise a magnetic or Hall effect based switch by embedding a magnet into a portion of the button near a Hall effect sensor within the handle distal section 30. Other types of buttons or switches may be used. The button 90 may be assigned multiple functions that may be activated by various user manipulations. In some embodiments one or more of the buttons 90 may be sealed with respect to the external handle section 82 to inhibit liquid infiltration.

The button 90 may be an image capture button. In such embodiments, depressing the button 90 may cause a photograph to be recorded of a display imaged generated by the endoscope 10. In some embodiments, a user may double tap the button 90, long-press the button 90, or hold down the button 90 to cause the display equipment connected to the endoscope 10 to start recording video. To stop recording video, a user may double tap the button 90, long-press the button 90, or release the button 90. In some embodiments, a user may only be required to depress and release the button 90 to stop recording video. In some embodiments, a single depression of the button 90 by a user while the endoscope 10 is recording video may cause a still image to be recorded without the need to pause video recording. In other arrangements, a quick press-and-release of the button 90 may trigger the recording of a still image, while a more prolonged press-and-release, or a press-and-hold may trigger the recording of a video segment.

The handle raised section 34 may additionally include a slide button recess 92. As shown in FIG. 7A, the slide button recess 92 is arranged to permit fore and aft movement of a slide button or finger contact 98 (see FIG. 14) while constraining lateral movement. The slide button may be part of a pivot control or pivot control structure 100 (see, for example, FIG. 14) in some embodiments. In some embodiments, including the example embodiment shown in FIG. 7A, the slide button recess 92 may be slightly curved to conform to the shape of the portion of the handle within which it resides.

As shown in FIG. 7A, the slide button recess 92 may include a number of ridges or detents 94 that can engage with a corresponding element on the slide button to provide a series of discrete, positive stops when a user moves the slide button fore and aft. Some embodiments may not include the ridges 94. In some embodiments, the portion of a pivot control structure 100 (see FIG. 12) with which a user may interface may project through a pivot control structure notch 96 (see FIG. 14) located in the slide button recess 92 of the handle raised section 34. In the example embodiment in FIG. 7A, such a portion of the pivot control structure 100 includes a finger contact 98. As shown, the finger contact 98 may have sloped contours for ergonomic reasons. The pivot control structure 100 will be further described below.

Figure 7B:
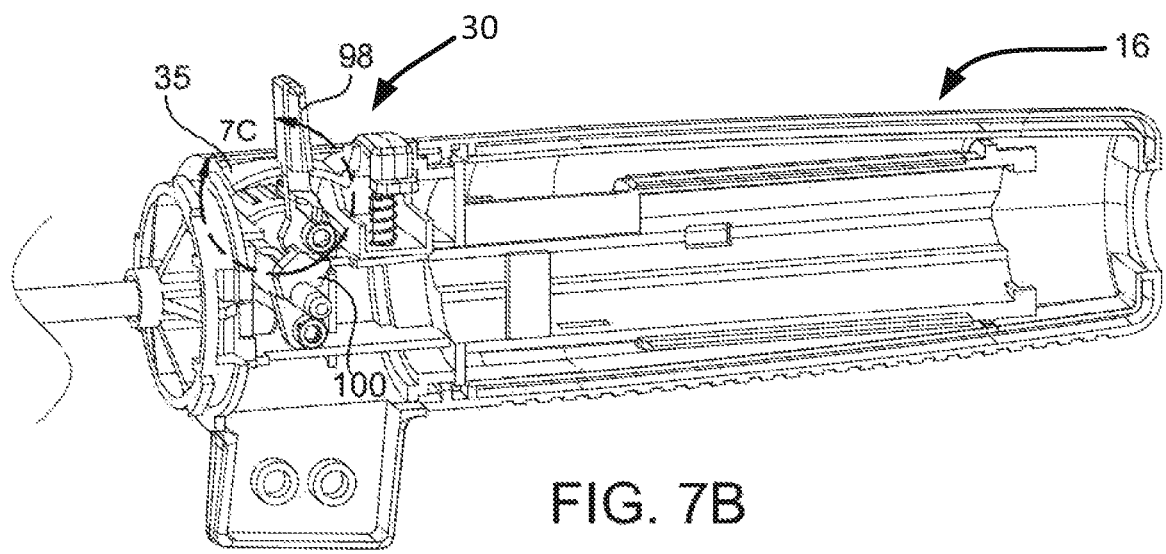
FIG. 7B shows a side view of an example endoscope with a portion of the handle removed.
Figure 7C:
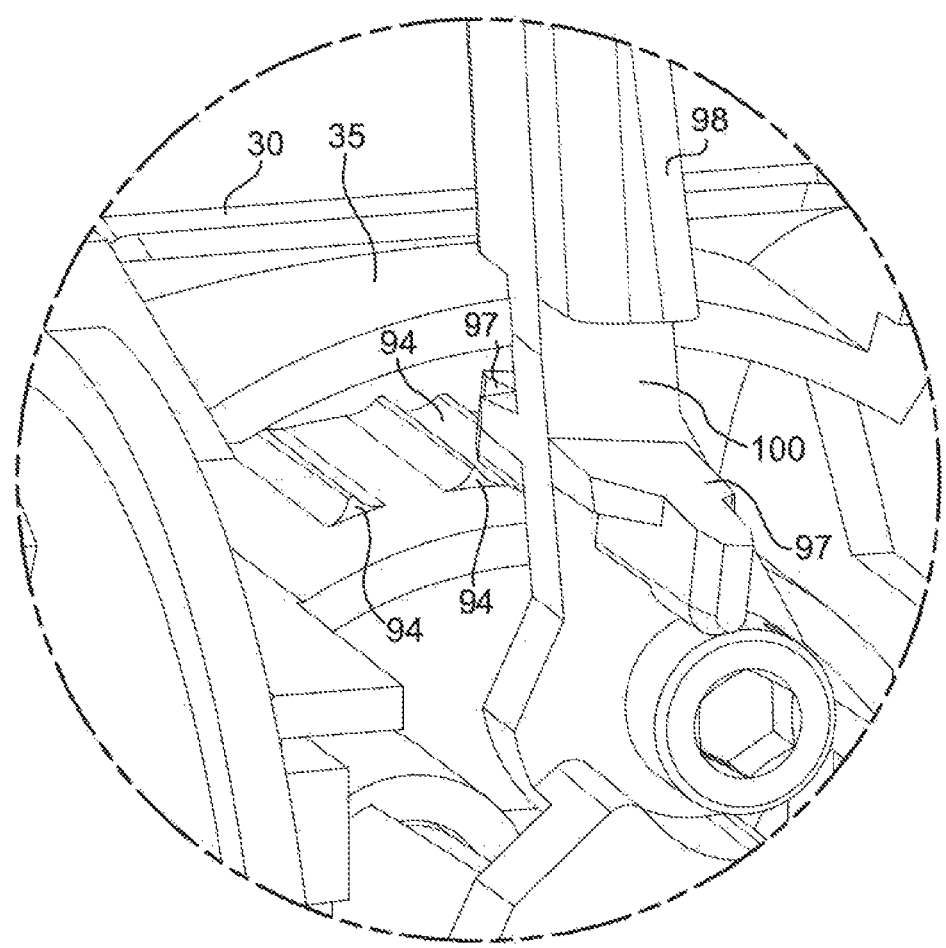
FIG. 7C shows a detailed view of a portion of an example handle distal section of an endoscope.

FIG. 7B and FIG. 7C depict an alternate embodiment of a recess 35 which may be used to accommodate a finger contact 98 of a pivot control structure 100. A portion of the handle proximal section 16 and handle distal section 30 has been removed for clarity. FIG. 7C depicts a detail view of region 7C of FIG. 7B. As best shown in FIG. 7C, in some embodiments, the recess 35 includes ridges 94 for stepwise movement of the pivot control structure similar to those of the slide button recess 96 shown in FIG. 7A. Alternatively, the recess 35 may be generally smooth and may be curved to accommodate the travel path of a pivot control structure 100.

The interior of the distal handle section 30 may include a shelf 95 which is located beneath the recess 35. The shelf 95 may have a surface whose contour mimics the contour of the recess 35. The shelf 95 may include one or more ridge(s) or detent(s) 94 to provide a series of discrete, positive stops when a user moves the pivot control structure 100 fore and aft. These ridges 94 may interact with one or more arms 97 extending from the pivot control structure 100. The arms 97 may move freely over portions of the shelf 95 which are smooth and devoid of ridges or ribs 94. When one of the arms 97 encounters a ridge 94, the ridge may abut the respective arm of the arms 97 and impede further displacement of the pivot control structure 100 until a force sufficient to overcome the mechanical interference presented by the ridge 94 is applied. That is, the ridges 94 may form force barriers that impede the actuation of the finger contact 98 out of a dwell position. Depending on the embodiment, the ridges 94 may be placed in pairs along a face of the shelf 95. The each rib or ridge 94 of the pair of ridges 94 may be placed apart by about the width of the arm 97 of the pivot control structure 100.

Figure 8:
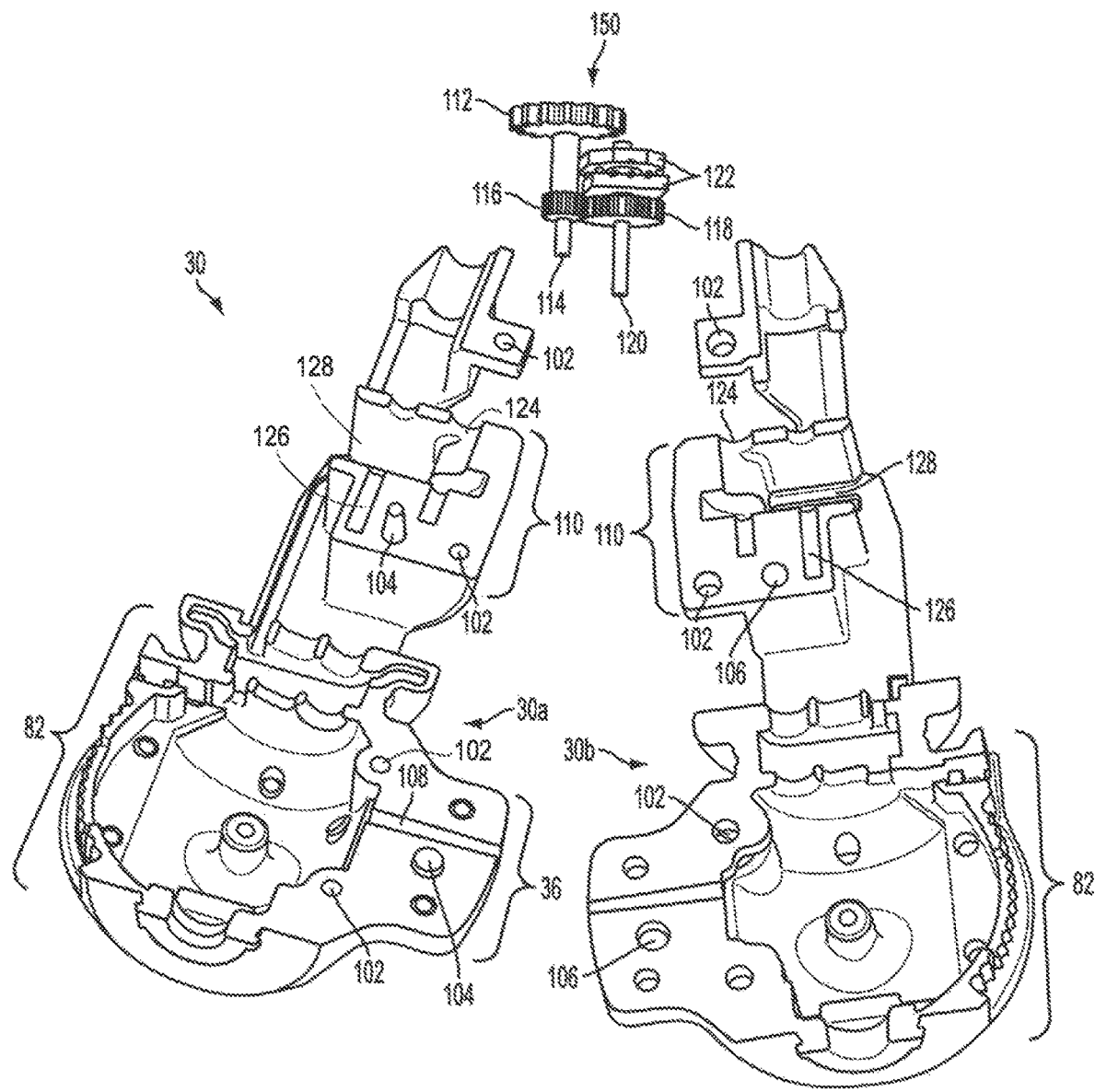
FIG. 8 shows an exploded view of a handle distal section and an example of a rotation sensing assembly of an endoscope.

FIG. 8 shows a more detailed illustration of an exemplary handle distal section 30 without an attached insertion section 14. An example rotation sensing assembly 150 is also shown in FIG. 8. As shown, the handle distal section 30 is manufactured as two separate parts 30a and 30b. In the example embodiment, the two separate parts 30a and 30b of the handle distal section 30 include a number of screw holes 102, which may be threaded. Screws (not shown) or other suitable fasteners may be used to couple the two separate parts 30a and 30b of the handle distal section 30 together. In some embodiments, the two separate parts 30a and 30b may be coupled together via a snap fit, ultrasonic weld, adhesive, etc.

In some embodiments one of the two separate parts 30a and 30b of the handle distal section 30 may include peg-like projections 104 which fit into complimentary peg accepting cavities 106 on the other of the two separate parts 30a and 30b. This may help to align and/or couple the two separate parts 30a and 30b together. In some embodiments, including the embodiment shown in FIG. 8, the external handle distal section 82 may be substantially hollow. In some embodiments, the hollow of the external handle distal section 82 may not be sealed against fluid. In the example embodiment shown in FIG. 8, a drain channel 108 may be included, for example, in the handle fin 36. The drain channel 108 may allow any fluid which enters the hollow of the external handle distal section 82 to easily drain out. Alternate embodiments may include additional and/or different drain arrangements.

The handle distal section 30 may also include a rotation sensor holder 110 as shown in FIG. 8. The rotation sensor holder 110 may retain the rotation sensing assembly 150 when the endoscope 10 is fully assembled. As shown, the rotation sensing assembly 150 may include a forward gear 112. The forward gear 112 is disposed about a forward gear shaft 114. As shown in FIG. 8, a transfer gear 116 is also placed on the forward gear shaft 114, such that rotation of the forward gear 112 causes the transfer gear 116 to rotate as well. The transfer gear 116 may mesh with a sensor shaft gear 118, disposed on a sensor gear shaft 120. As the forward gear 112 rotates, so will the sensor shaft gear 118 and the sensor gear shaft 120. Use of a gear assembly may allow for placement of an attached potentiometer 122 in a location that is off-center from the central rotational axis of the handle distal section 30, which may advantageously allow for a central placement of other internal structures (e.g., irrigation conduit, optical fiber bundle, electronic flex cable, or other electronic components).

As in the example embodiment in FIG. 8, the sensor gear shaft 120 may include a splined, or keyed (e.g., a D-shaped) portion. The keyed portion may operatively engage with one or more rotational potentiometers 122. In the example embodiment in FIG. 8, there are two rotational potentiometers 122. The potentiometers 122 may be mounted on or otherwise attached to a mounting element, or a part of a printed circuit board in the handle as described in reference to FIG. 61. The potentiometers 122 each include a keyed (e.g. D-shaped) void with which the corresponding keyed portion of the sensor gear shaft 120 mates. As the sensor gear shaft 120 rotates, the electrical resistance of the potentiometer(s) 122 will vary proportionately. Since the resistance will predictably change with the amount of rotation of the sensor gear shaft 120 the measured resistance of the potentiometer(s) 122 may be used to determine the amount of rotation that has taken place between the handle proximal section 16 and the handle distal section 30 (and by extension, the insertion section 14).

In some embodiments, the housing of each potentiometer 122 may be mounted to elements of the housed handle electronics section 80 (or other elements attached to the handle distal section 30), and thus immobilized relative to the handle distal section 30 (and by extension the insertion section 14), while the shaft or rotating hub of the potentiometer 122 is connected to the handle proximal section 16. In other embodiments, the housing of the potentiometer 122 may be immobilized relative to the handle proximal section 16, while its shaft or rotating hub may be connected to elements of the handle distal section 30 or the handle electronics section 80.

The example embodiment in FIG. 8 includes two rotational potentiometers 122 stacked together, and offset rotationally from one another. In an alternate embodiment, the potentiometers 122 may be spaced apart from each other, but share a common rotational axis (e.g., the wipers of both potentiometers 122 are caused to move by a common shaft). This arrangement permits a controller receiving electrical resistance values from both potentiometers 122 to compute the degree of rotation of a sensor shaft (and ultimately of components at the distal end of the endoscope) with a desired accuracy through 360 degrees of rotation, thus helping to eliminate computational "blind spots" in measuring the rotation of the components at the distal shaft (e.g., a camera) of the endoscope. Any blind spot created by the position of a wiper of one potentiometer 122 at the end of its range of motion may be compensated for by a wiper of a second potentiometer 122 whose position is not at the end of its range of motion. In alternative embodiments, more than two rotationally offset potentiometers 122 may be used. The rotational offset between the potentiometers 122 may be 180 degrees for computational simplicity, but other angular offsets may be used to achieve the same result, as long as the rotational offset allows any blind spot created by one potentiometer 122 to be overlapped by a functional range of another potentiometer 122. In alternative embodiments, the gearing ratios between the forward, transfer, and sensor shaft gears 112, 116, 118 may vary, depending on the degree of precision desired in measuring rotation, the sensitivity of the potentiometers 122, and other factors. In alternative embodiments, the rotation sensing assembly 150 may use belts rather than one or more of the gear assemblies. For example, the transfer gear 116 and sensor shaft gear 118 may be replaced by a belt. Other rotation to rotation arrangements known in the art may also be used. In some embodiments, the forward gear shaft 114 may include a keying feature (e.g., a D-shaped portion) which operatively engages the potentiometers 122 directly. Rotation sensors other than potentiometers 122 may also be used. Alternative embodiments may include rotation sensors such as, a rotary encoder, a rotary variable differential transformer, or other encoding devices. In embodiments using a rotary encoder, the encoder may be a gray encoder, magnetic encoder (see e.g., FIG. 9B), optical encoder, etc.

In an embodiment, the sensor gear shaft 120 may not extend to the shaft bearing section of a shaft support member 63. Rather, the rotation sensing assembly 150 may be supported by the rotation sensor holder 110. Among other benefits, this arrangement allows for an unlimited degree of rotation of the handle distal section 30 relative to the handle proximal section 16. Additionally, as would be appreciated by one of skill in the art, it allows for components a of rotation sensing assembly 150 to be located in an off-center position. This may provide benefits during assembly. For example, it may simplify routing of an irrigation line 434 (see FIG. 61), power cable 432 (see FIG. 61), etc.

In other embodiments, the shaft support member 63 and potentiometers 122 may be directly connected by a shaft. A shaft splined or keyed on a distal end may extend from the shaft bearing section of the shaft support member 63 and extend through a corresponding splined or keyed (e.g., D-shaped) void in the potentiometers 122. Since the shaft support member 63 may be fixed relative to the handle proximal section 16, rotation of the distal handle section 30 relative to the handle proximal section 16 will vary the resistance measured by the potentiometers 122. As mentioned above, since the resistance will predictably change with rotation of one handle section relative to the other, the resistance measurement may be used to determine the amount of rotation achieved by the handle distal section (and ultimately, the distal end of the endoscope or camera assembly 350 shown, for example, in FIG. 21).

In other embodiments, the rotation sensing assembly 150 may include a range finder which may be disposed on the housed handle electronics section 80 (see FIG. 7A). The interior walls of the handle proximal section 16 (see FIG. 4) may include a variable-thickness or variable-height raised surface that wraps around most or all of the 360° of the interior wall of the handle proximal section 16, and varies in thickness or height in a pre-determined manner along its circumferential path. As the handle proximal section 16 and handle distal section 30 rotate relative to one another, the range finder may provide a controller with a signal that varies according to the distance read by the range finder to the varying surface (either its varying thickness or height). The signal may be correlated to the thickness/height or distance measured by the range finder relative to a pre-determined base position in which the surface has a specified thickness or height and is correlated to a specified angular rotation of the handle distal section 30 relative to the handle proximal section 16. This distance may be compared to a previous distance to thereby determine the amount of rotation that has occurred. The range finder may be any type of range finder (e.g. a mechanical position sensor, a sonic range finder, laser or other optical range finder, etc.).

In yet another alternative embodiment, an optical mouse like sensor arrangement may be used. The sensor may be mounted on one of the housed handle electronics section 80 or handle proximal section 16 and may be configured to track movement of the other of the housed handle electronics section 80 or handle proximal section 16. In such embodiments, the amount and direction of movement sensed by the sensor may be used to determine the amount and direction of rotational displacement that has occurred. In some embodiments, the surface tracked by the sensor may have a reference grid, number of unique indicators, pattern, markings, or other differentiating features, which allow sensor determination of rotational orientation upon start up. Other varieties of rotation sensing assemblies 150 known to those skilled in the art may also be used in various embodiments.

As shown in FIG. 8, the rotation sensor holder 110 of the handle distal section 30 may be shaped such that when the two separate parts 30a and 30b of the handle distal section 30 are coupled together, the rotation sensing assembly 150 may be captured between the two separate parts 30a and 30b. Each side of the rotation sensor holder 110 may include a forward gear shaft trough 124 and a sensor gear shaft trough 126. When assembled the forward gear shaft trough 124 and the sensor gear shaft trough 126 may act as bearing surfaces respectively for the forward gear shaft 114 and the sensor gear shaft 120. Each side of the rotation sensor holder 110 may also include a holder void 128. The holder void 128 may be sized and shaped such that the transfer gear 116, sensor shaft gear 118, and potentiometers 122 may fit within the rotation sensor holder 110 when the handle distal section 30 is fully assembled.

Figure 9A:
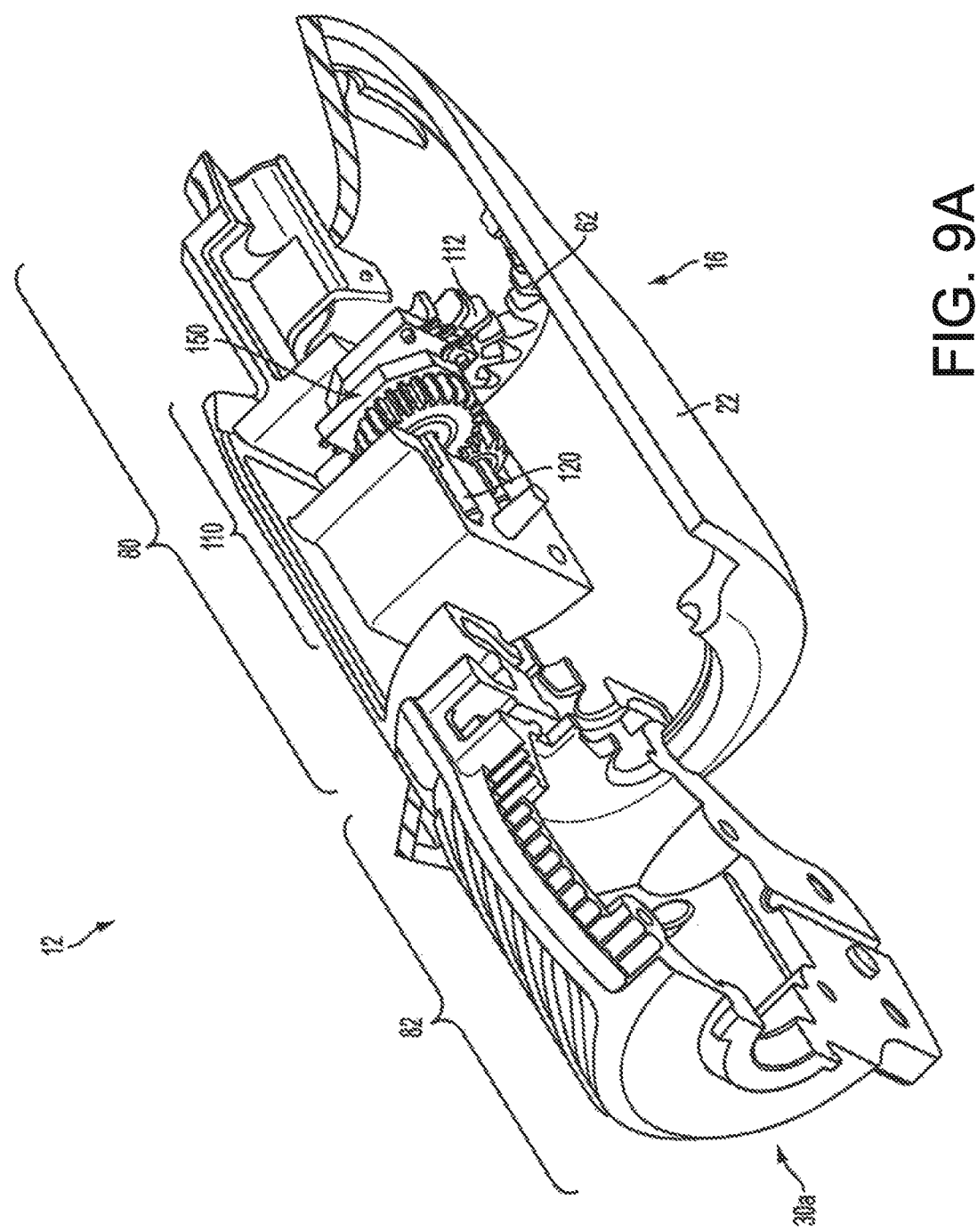
FIG. 9A shows a partially assembled view of an exemplary endoscope handle.

FIG. 9A shows a partially assembled view of the handle 12 of the endoscope 10. Only the handle bottom section 22 of the handle proximal section 16 is shown in FIG. 9A. As shown, a part of the handle bottom section 22 of the handle proximal section 16 has been cut away. Additionally, in the embodiment shown in FIG. 9A, the handle distal section 30 is assembled from two separate parts 30a and 30b (see FIG. 8). One of the halves (30b) of the handle distal section 30 has been removed in FIG. 9A for clarity. (In the embodiment shown in FIG. 9A, the handle distal section 30 is assembled from two separate parts 30a and 30b (see, e.g. FIG. 8). One of the halves (30a) of the handle distal section 30 has been removed in FIG. 9A for clarity). The housed handle electronics section 80 may be located inside the handle proximal section 16. The external handle distal section 82 extends beyond the handle proximal section 16 and is exposed to the environment.

As described above, the rotation sensing assembly 150 is disposed within the rotation sensor holder 110. As shown, the forward gear 112 of the rotation sensing assembly 150 may mesh with the annulus gear formed by the toothed projection 62 and toothed projection 64 (best shown in FIG. 5). In such embodiments, when the handle 12 is fully assembled, any rotation of the handle distal section 30 in relation to handle proximal section 16 causes the forward gear 112 to rotate since it meshes with the annulus gear formed by the toothed projection 62 and the toothed projection 64. This rotation may then be translated through the rest of the rotation sensing assembly 150 allowing the rotation to be measured by the rotation sensing assembly 150. In a preferred embodiment, the overall gear ratio may be approximately 1:1.

Alternatively, rather than gear elements, the handle proximal section 16, similar to that shown in FIG. 4, may comprise a keyed shaft or partially keyed shaft, affixed to the shaft support section 65 of the shaft support member 63. The keyed portion of the shaft may be arranged to mate with the hub of one or more potentiometers 122, which are held in rotation sensor holder 110. Thus as the handle distal section 30 is rotated relative to the handle proximal section 16, the wiper of the one or more potentiometers 122 is able to convert the relative positions of the handle distal section 30 and proximal section 16 into an electrical resistance value usable to determine rotational orientation.

Figure 9B:
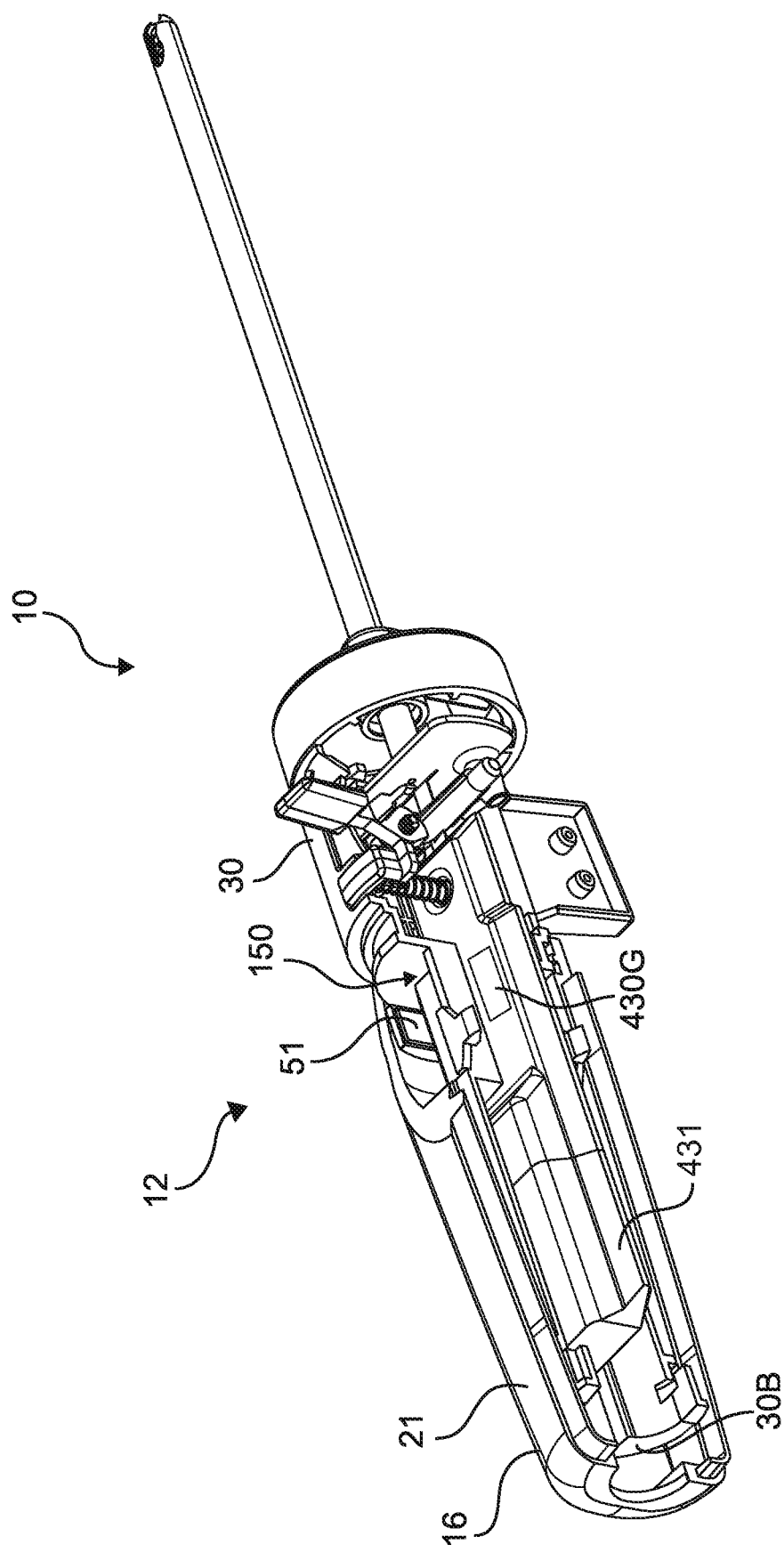
FIG. 9B shows a partial cutaway view of a handle of an endoscope including an example rotation sensing arrangement.

Referring now to FIG. 9B, an alternative embodiment of an example handle 12 of an endoscope 10 including a rotation sensing assembly 150 is depicted. Only the handle first half-shell 21 is shown in FIG. 9B to make the interior of the handle 12 visible. Additionally, a portion of the handle first half-shell 21 has been cut away.

Shown in FIG. 9B is an enclosure 431 for a printed circuit board (PCB) that comprises electronic components for processing image data from the image sensor at the distal end of the shaft, and optionally for providing power to light sources (e.g. LED's) at the distal end of the endoscope shaft. The enclosure 431 is an optional structure, because the PCB may also or additionally be encased in a water resistant material. The water resistant material may be any suitable potting material, such as, for example, Parylene, or other chemical vapor deposited polymer to coat and protect the individual electronic components mounted on the PCB. Also shown is a magnet 51 which is included in the handle first half-shell 21. The printed circuit board within enclosure 431 may include one or more magnetic position sensors 430g such as a Hall effect sensor or sensor array. As mentioned above in relation to FIG. 6, each of the handle first half-shell 21 and handle second half-shell 23 may include a magnet 51 or multiple magnets 51 in some embodiments. In an embodiment, two magnets 51 are positioned opposite each other in each half of the handle 16. As handle proximal section 16 is rotated relative to the handle distal section 30 the magnet(s) 51 move relative to the enclosure 431 and the enclosed printed circuit board. The magnetic sensor(s) 430g on the printed circuit board can detect the relative positions of the magnet(s) 51 through variations in magnetic field strength and location as the magnets move relative to the printed circuit board. In an embodiment, a single tri-axis position sensor is used for sensing the magnets 51. Data from the one or more sensors can be transmitted to a controller or processor for conversion of the sensor data into rotational position of the handle proximal portion 16 relative to the handle distal section 30 (and relative to the position of the optical sensor or camera at the distal end of the endoscope shaft). Thus, a displayed image of the field of view of the camera can be rotated to any desired orientation without actually moving the camera at the distal end of the endoscope shaft.

Figure 10A:
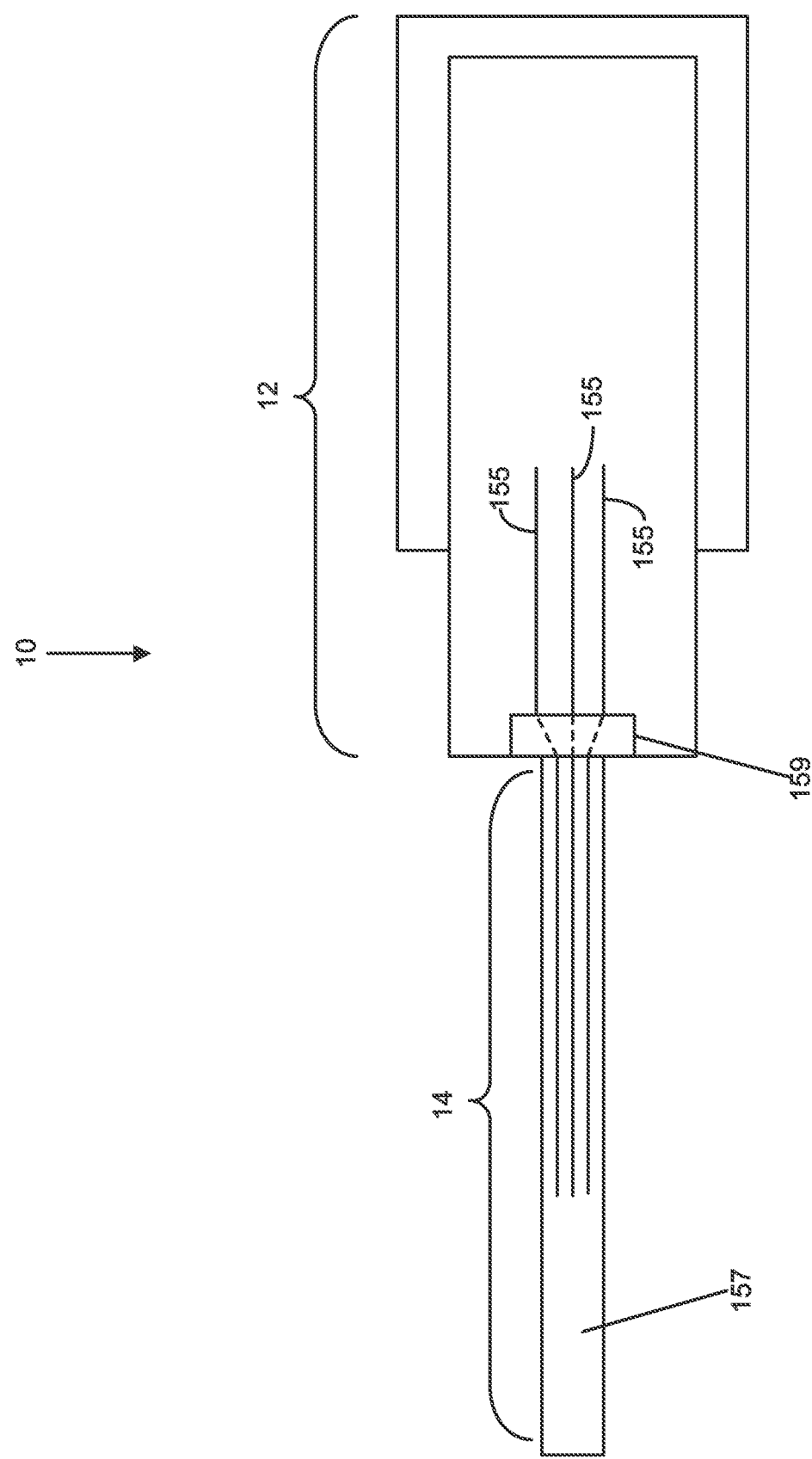
FIG. 10A is a representational illustration of a pass-through fluid barrier allowing utility components to pass from the handle to a conduit of an endoscope.

Referring now to FIG. 10A, in an embodiment, the insertion section 14 of an endoscope 10 includes a conduit 157 through which operations or functions may be performed. In industrial or medical applications, this conduit 157 may be used to pass instruments to manipulate objects at the end of the insertion section 14 (instruments such as graspers, forceps, clamps, wire baskets, dilators, knives, scissors, magnetic pickups, etc.). Fluid (gas or liquid) may also be passed to/from an external source from/to the space within which the insertion section 14 is placed. In medical applications, such a conduit 157 may be used to insufflate a body cavity with a gas, evacuate gas from a body cavity, irrigate a space with liquid, or aspirate liquid and/or suspended particulates from a space. The conduit 157 optionally may carry utility components such as light transmission, information transmission, power transmission, and mechanical control components, saving space within the insertion section 14 and helping to reduce the overall diameter of the insertion section 14. A light transmission component may include, for example, a fiberoptic bundle, ribbon, light pipe, light projection element, and/or the like. An information transmission component may include, for example, an electrical cable bundle or ribbon connecting an imager or image sensor at the end of the insertion section 14 to an image processing unit situated in the handle 12 or external to the endoscope 10. Such a cable may also provide power to the image sensor. Mechanical control components may include, for example, pushrods, pull wires, etc. to control the movement of an element near the end of the insertion section 14. This may include, for example, an actively flexible distal segment of the insertion section 14 that can be actively flexed by the use of the mechanical control component(s) extending from the handle 12. It may also include, for example, a rotatable camera or camera mount at the end of insertion section 14 that can be actively moved by the use of the mechanical control component (s) extending from the handle 12.

In an embodiment, a fluid carrying conduit 157 within the insertion shaft or section 14 is configured to enclose utility components of the endoscope 10, such as, for example, fiberoptic bundles, communication cables and mechanical actuators. In a further embodiment, the conduit 157 may be in fluid communication with a camera assembly 350 (see, for example, FIG. 21) at the distal end of insertion shaft 14. The camera assembly 350 may include a camera sensor or imager having connections to a communications cable. In this case, the camera sensor and communications cable connections, and the internal components of any associated lens assembly may be sealed against exposure to liquids present within the conduit 157. Allowing a camera assembly 350, lens assembly, communications cable, mechanical actuators (e.g. pull-wires) and fiberoptic cables or bundles to be exposed to a 'wet' conduit may be feasible if at least a portion of the endoscope 10 is configured to be a single use device, i.e., disposable after use in a medical procedure. Any technical challenges in adequately sterilizing intra-conduit components are thus obviated.

Some components of the endoscope 10, particularly electronic components located within the handle section 12, preferably should be kept dry. A bulkhead or barrier element 159 between the conduit 157 of the insertion section 14 and the interior of the handle 12 may allow passage of components from the handle 12 to the insertion section 14 conduit 157 (represented in FIG. 10A by line segments 155 and referred to as pass-through components), while also inhibiting infiltration of fluid from the conduit 157 into the interior space of the handle 12. The barrier 159 may comprise passageways (holes, slits, etc.) through which pass-through components 155, such as the utility components described supra, may pass from the handle 12 to the conduit 157 of the insertion section 14. The passageways may be formed to provide a relatively tight fit around the outside surface of the pass-through components 155. In some embodiments, elastomeric gaskets, O-rings, or other similar elements may further aid in inhibiting fluid infiltration from the conduit 157 of the insertion section 14 to the interior spaces of the handle 12. The barrier 159 may comprise a wall separating a junction region between the handle 12 and a proximal end of the insertion section 14. The junction region may be near an area where the conduit 157 connects to a conduit port providing an external fluid connection for the conduit 157. The barrier 159 may alternatively comprise a block through which a routing channel connects a utility hole communicating with the conduit 157 on a first side of the block with one or more features (e.g. a conduit port) on a second side of the block opposite the first side of the block, or on a third side of the block (which in some embodiments, may be roughly perpendicular to the first side of the block). Passageways for cables, ribbons, wires, pushrods or other components from the handle 12 may be formed on the second side of the block, opposite the first side of the block and may be aligned with the utility hole of the block. The conduit 157 may be formed from a sheath (such as inner sheath 312 of FIG. 17) connected or attached to the handle 12 of the instrument. In some embodiments, the pass-through barrier 159 between the handle 12 and a sheath of the insertion section 14 may comprise a sheath mount, which serves to support the sheath of the insertion section 14 near its origin proximally at the handle 12, and to attach or connect it to the handle 12. In some embodiments, the insertion section 14 may comprise a cannula within which the sheath may be positioned. The cannula may be mounted to the handle 12 via a disconnect feature, allowing the cannula to remain in situ while the endoscope 10—including handle 12 and sheath—can be withdrawn from a site.

Referring now to FIG. 10B, in some embodiments, the barrier 159 may include a flexible or elastomeric member 153. One or more pass-through components 155 may extend through the flexible member 153 of the barrier 159 to the conduit 157 of the insertion section 14. In some embodiments, one or both of the entry and exit points of the pass-through component 155 in the flexible member 153 may be sealed with a sealing member or agent 151. The sealing member or agent 151 may prevent the flow of fluid between the conduit 157 and the handle 12. The sealing member or agent 151 may also hold the pass-through component 155 such that it is prevented from moving relative to its entry and/or exit point in the flexible member 153. Any suitable sealing member or agent 151 may be used, such as, for example, a glue, epoxy, or other adhesive. In other embodiments, the pass-through components may be solvent bonded, heat bonded, etc. to the flexible member 153. In yet other embodiments, the flexible member 153 may be formed in place around the pass-through components 155 during manufacture such that a seal is created between the pass-through components 155 and the flexible member 153.

As the pass-though components 155 move (e.g. actuating pull wires for rotation of a camera assembly) the flexible member 153 may stretch or flex since the pass-through components 155 are fixed and prevented from displacing relative to their entry and exit point in the flexible member 153 due to the sealing member or agent 151. Thus, ingress or leakage of fluid into the handle from the conduit 157 may be substantially or totally inhibited while allowing the pass-through components 155 to move back and forth. Pass-though components 155 which remain in fixed position and do not displace need not necessarily pass though the flexible member 153. Instead, these components may pass through a rigid portion of a barrier 159 which may or may not be coupled to the flexible member 153. The flexible member 153 may be constructed, for example, as an elastomeric member, a flexible membrane, flaccid wall, a bellows-like arrangement, diaphragm, etc.

Figure 11A:
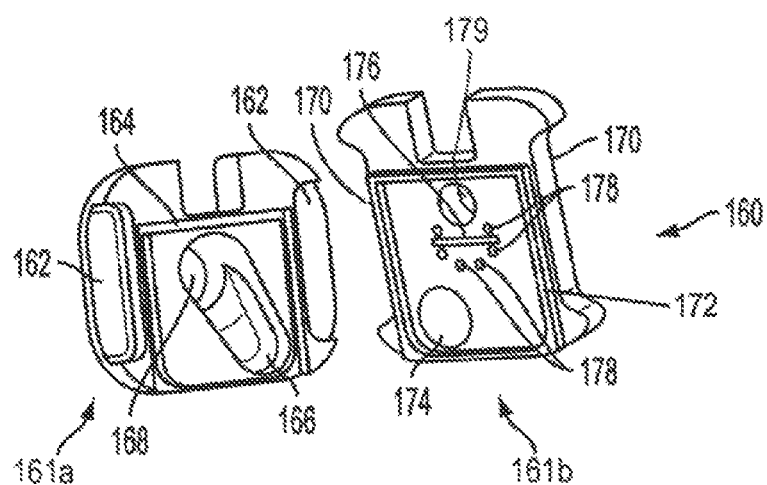
FIG. 11A shows an exploded view of an example of an inner sheath mount serving as a pass-through fluid barrier.

A barrier 159 described in relation to FIG. 10A is shown in FIG. 11A and can also be referred to as an inner sheath mount 160. As shown, the inner sheath mount 160 includes a distal section 161a and a proximal section 161b, separated in FIG. 11A from one another to reveal the interior of the inner sheath mount 160. As shown the distal section 161a may include notches 162 on each side of the distal section 161a. As shown in the example embodiment in FIG. 11A, a portion of an interior face 164 (when assembled) of the distal section 161a may be recessed. An irrigation or suction routing channel 166 may also be recessed into the distal section 161a of the inner sheath mount 160. As shown, the irrigation routing channel 166 is located within the recessed face 164. The irrigation routing channel 166 may be in communication on a first end with a utility hole 168. In the example embodiment, the utility hole 168 may be located substantially near the center of the distal section 161a, within the recessed face 164 (although in other embodiments, the utility hole 168 need not be centered).

The proximal section 161b of the inner sheath mount 160 may also include notches 170 in its right and left sides similar to the notches 162 recessed into distal section 161a. The notches 170 may extend all the way through the proximal section 161b. The notches 162 and 170 of the inner sheath mount 160 may be sized to accept a projection of the handle distal section 30, which may help to hold the inner sheath mount 160 in place when the endoscope 10 is fully assembled.

The proximal section 161b may also include a raised portion 172 of an interior face (when assembled). As shown, the raised portion 172 is of similar outer dimensions as the recessed face 164 in the distal section 161a. When assembled, the raised portion 172 may be pressed into the recessed face 164 to couple the distal section 161a and proximal section 161b together. In some embodiments, glue or another suitable adhesive between the recessed face 164 and raised portion 172 may be used to bind the proximal section 161b to the distal section 161a. This may also serve to create a hydraulic seal between the two components.

The proximal section 161b may include a number of other features. As shown, the proximal section 161b includes an irrigation or suction passage 174. The irrigation or suction passage 174 may be situated to align with a second end of the irrigation routing channel 166 when the proximal section 161b is mated to the distal section 161a. When the endoscope 10 is in use, irrigation or suctioned fluid may flow between the utility hole 168 and irrigation passage 174 via the irrigation routing channel 166.

As shown in the example embodiment in FIG. 11A, the proximal section 161b of the inner sheath mount 160 may include a sheath mount slit 176. As shown, the sheath mount slit 176 may be oriented horizontally (orientation refers to that shown in FIG. 11A) and located in the proximal section 161b of the inner sheath mount 160, roughly aligned with the utility hole 168. The sheath mount slit 176 may be oriented differently in alternate embodiments. In the example embodiment in FIG. 11A, the sheath mount slit 176 extends through the entire proximal section 161b at an angle substantially perpendicular to the plane of the interior face (when assembled) of the proximal section 161b.

The proximal section 161b of the inner sheath mount 160 may also include a number of orifices 178. In the example embodiment in FIG. 11A, the orifices 178 are small diameter holes which extend through the entire proximal section 161b, and can be used to allow passage of pull or push cables or wires from within the handle to the distal end of the endoscope 10. The proximal section 161b may also include a fiber optics passageway 179. In the example embodiment, the orifices 178 and fiber optics passageway 179 are angled perpendicular to the interior face (when assembled) of the proximal section 161b. In alternate embodiments, the orifices 178 and fiber optics passageway 179 may be angled differently or may have a different diameter. As shown, the orifices 178 are arranged around the sheath mount slit 176. When the inner sheath mount 160 is fully assembled, the sheath mount slit 176 and orifices 178 are aligned with the utility hole 168 of the distal section 161a.

In alternative embodiments, the shape, location, dimensions, etc. of some features of a bulkhead, pass-through barrier or inner sheath mount 160 may differ. A pass-through barrier or inner sheath mount 160 may include additional features or may omit certain features. In some embodiments, there may be a larger or smaller number of orifices 178. In some embodiments, the orifices 178 may not be arranged in the spatial arrangement shown in FIG. 11A. There may be more than one irrigation passage 174. In some embodiments, the inner sheath mount 160 may be associated with or include a gasket to further inhibit fluid infiltration into sensitive areas within the handle of the endoscope.

The handle electronics section 80 (see, e.g., FIG. 7A) is configured to enclose mechanical and electronic components that are preferably protected against excessive amounts of fluid infiltration. (Small amounts of fluid or moisture need not inhibit proper mechanical or electrical operation of the endoscope, particularly if the electronic components are coated with a moisture resistant film). The handle distal external section 82 (the pivot control housing), is configured to house the pivot control structures and actuation cables for controlling movement of a camera assembly in the distal end of the endoscope shaft or insertion shaft, and may be exposed to liquid with relatively minimal effect on the operation of the endoscope. Therefore, it is more important to maintain a liquid seal between the handle electronics section 80 and the handle distal external section 82. A bulkhead or pass-through barrier such as sealing member 210, shown in FIGS. 13 and 14 may be constructed to provide a tight seal (e.g. elastomeric seal) around an electronic flex cable, an optical fiber bundle, or other structures that must pass from the distal end of the endoscope to its proximal end before exiting. On the other hand, a pass-through barrier such as inner sheath mount 160, shown in FIGS. 11A and 14, may allow for a lesser seal, particularly as it may apply to any pull wires or cables that pass from the pivot control structure to the distal end of the endoscope shaft. Any fluid infiltration into the handle distal section 82 may be allowed to exit the housing through one or more drain holes or passages built into a dependent part of the housing, such as for example, passage 108 shown in FIG. 8.

In an alternate embodiment, a pass-through barrier 159 (see FIG. 10B) between the handle distal section or pivot control housing 82 and the shaft of the endoscope may comprise a fully sealed structure that yet permits movement of the pull cables or actuation cables that extend from the pivot control housing to the distal end of the endoscope shaft. For example, the pass-through barrier may comprise a flexible (or floppy) diaphragm, a pleated elastomeric diaphragm, accordion-structured rubber boot, bellows structure, or otherwise displaceable diaphragm that is attached at its periphery to the housing, that forms a fluid-tight seal around any structures passing through it near its central region, and whose central region may freely move back and forth distally and proximally to permit free movement of any pivot control cables passing therethrough. With a more complete seal at this portion of the endoscope, the need for a secondary seal between the pivot control housing and the handle electronics section 80 may be reduced or eliminated.

Figure 11B:
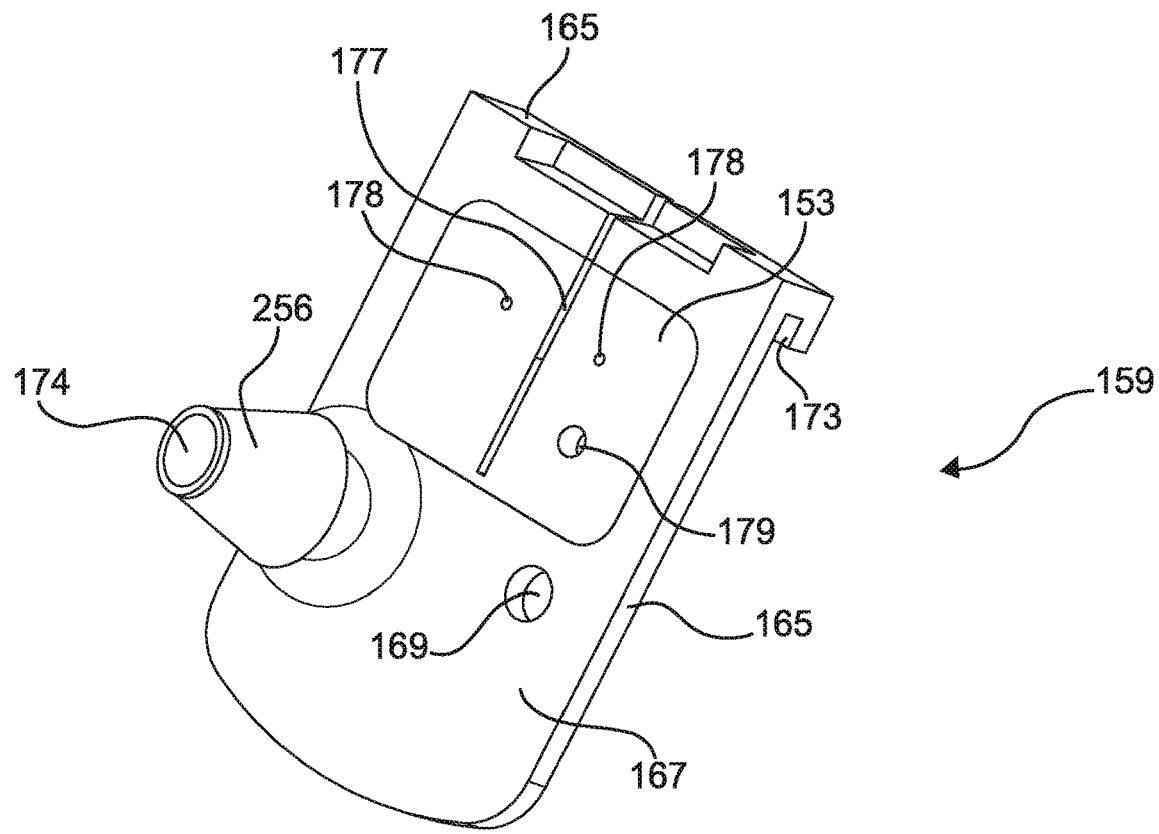
FIG. 11B shows an example embodiment of a bulkhead or pass-through fluid barrier.

FIG. 11B depicts an alternative embodiment of a bulkhead or pass-through barrier 159 which comprises a flexible member 153. As shown, the pass-through barrier 159 includes a rigid structure 167 and a flexible member 153. A rigid portion or structure 167 may act as a frame to which the flexible member 153 is attached or fused. In some embodiments, a dual molding process may be used to couple the flexible member 153 and the rigid portion or structure 167 together during manufacture. The rigid structure 167 may include one or more mating features 173 which may be sized to mate with a cooperating mating feature of the handle distal section 30 (see, e.g. FIG. 15). In some embodiments, the interaction of the mating feature(s) 173 with the cooperating portion of the handle distal section 30 (see, e.g. FIG. 15) may create a seal between the pass-through barrier 159 and the handle distal section (see, e.g., FIG. 15).

Figure 11C:
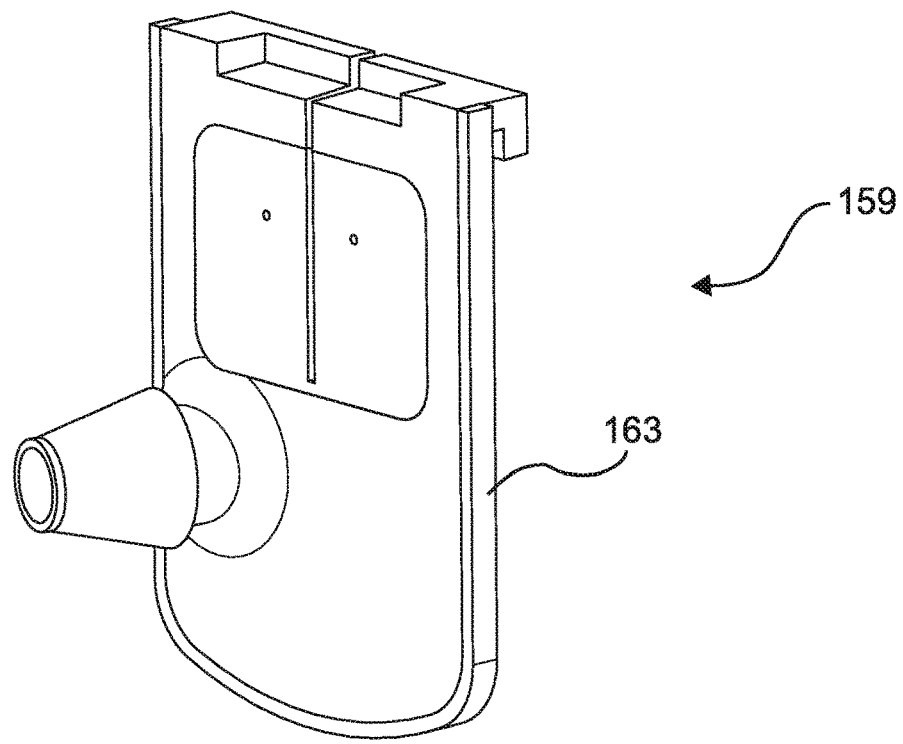
FIG. 11C shows another example embodiment of a bulkhead or pass-through fluid barrier.

Referring now also to FIG. 11C, to facilitate the creation of such a seal, a gasket member 163 may be included around the periphery of the pass-through barrier 159. Such a gasket member 163 may be placed along the outer edges 165 (FIG. 11B) of the pass-through barrier 159. Alternatively, a dual molding process may be used to attach the gasket member 163 to the pass-through barrier 159 during manufacture. The gasket member 163 may completely encircle the rigid structure 167, and may be formed from a compressible or elastomeric material, such as, e.g., Metaprene®.

Still referring to FIG. 11B and FIG. 11C, the flexible member 153 includes a number of pass-through elements. A number of orifices 178 are included in the example flexible member 153. Additionally, the flexible member 153 may include an optional illumination or fiber optic passage 179. Such an illumination passage 179 may not be needed in embodiments in which illumination is provided by one or more LEDs at the distal end of the endoscope shaft, for example. Additionally, a slit or slot 177 may be included in the flexible member 153. In the example embodiment, the slit 177 extends from the flexible member 153 through the rigid structure 167 to the edge of the pass-through barrier 159.

Pass-through elements and passages in the pass-through barrier 159 may also be disposed in the rigid frame structure 167 of the pass-through barrier 159 as well. It may be desirable, for example, that pass-through elements or passages associated with fixed or non-displacing components be disposed in the rigid structure 167 of the pass-through barrier 159. In the example embodiment a rigid structure passage 169 is shown providing a passageway through the rigid structure 167.

A conduit attachment site or port 256 may also be included on a pass-through barrier 159. As shown, the conduit attachment port 256 projects from the rigid structure 167 and optionally includes a barbed fitting over which a flexible tube or conduit may be secured. A conduit attachment site 256 may include an interior lumen which extends through the pass-through barrier 159. In the example embodiment shown in FIG. 11B the interior lumen is an irrigation or suction passage way 174 through which fluid may be transferred from one side of the pass-through barrier 159 to the other.

Figure 11D:
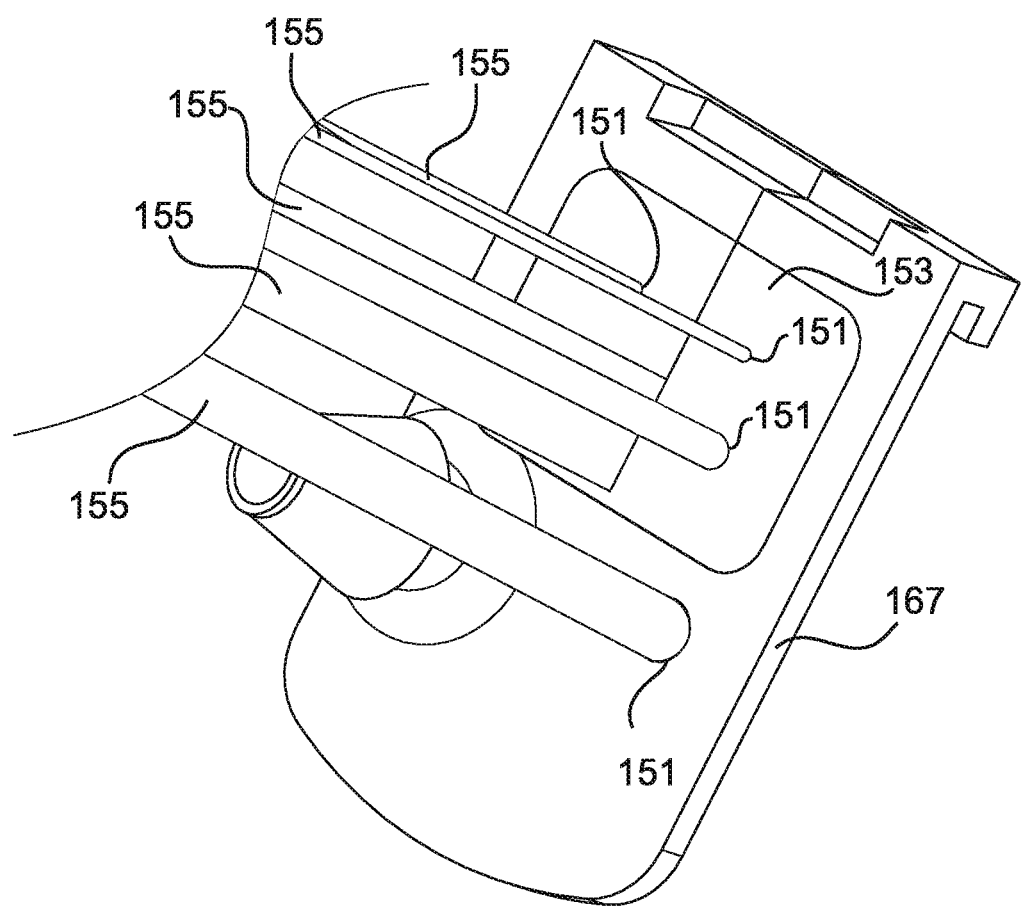
FIG. 11D shows an embodiment of a pass-through barrier through which a number of utility components extend.

Referring now also to FIG. 11D, when assembled, various pass through components 155 may be passed through the orifices 178, passage 179 and slit 177 in the pass-through barrier 159. Once these pass through components 155 have situated in the pass-through barrier 159, a sealing member or agent 151 optionally may be applied to one or both of the entry and/or exit points of the pass through components 155 in the pass-through barrier 159. In the example embodiment, the sealing member or agent 151 is fixative such as adhesive though in other embodiments any suitable sealing member or agent may be used. The sealing member or agent 151 may prevent fluid communication through the pass-through elements in the pass-through barrier 159. Additionally, when applied on the flexible member 153 it may fix pass through components 155 such that may not displace relative to their entry and exit point in the flexible member 153. As a result, in this case displacement of the pass-through components 155 will cause the flexible member 153 to move back and forth as well.

Figure 12:
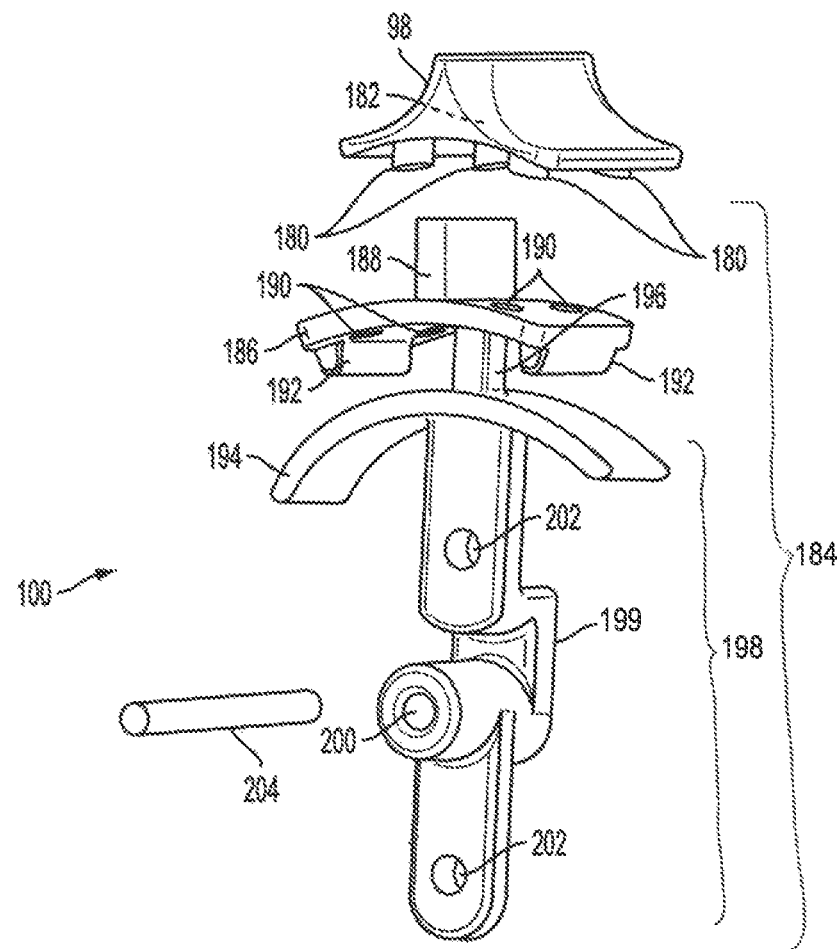
FIG. 12 shows an exploded view of an example of a pivot control assembly.

FIG. 12 shows an example exploded view of an embodiment of a pivot control structure 100. The pivot control structure 100 may control pivoting of a structure. The structure may for example be a camera assembly 350 (see FIG. 21) at a distal end of the insertion section 14 (see FIG. 3A). In alternate embodiments, the pivot control structure 100 may be used to instead or additionally control the flexing of a flexible section of the insertion section 14. Some embodiments of the pivot control structure 100 may include gearing, a motor, multi-bar linkage, dials, etc. that differ from the embodiment disclosed below.

The example pivot control structure 100 in FIG. 12 is shown in an exploded view. The finger contact 98 detailed above is shown separated from the pivot control structure 100. As shown, the bottom face of the finger contact 98 optionally may include a number of peg projections 180. In the example embodiment shown in FIG. 12, there are four peg projections 180 which are generally cylindrical in shape (number and shape of peg projections may differ). The finger contact 98 additionally includes a finger contact slot 182 situated in the under-surface of the finger contact 98.

Below the finger contact 98, an example embodiment of a pivoting portion 184 of the pivot control structure 100 is shown. The top of the pivoting member 184 of the pivot control structure 100 may include a slider 186. Projecting from the center of the slider 186 is a finger contact post 188 arranged to mate with finger contact slot 182. Optionally, finger contact peg holes 190 flank the finger contact post 188 on each side of the finger contact post 188. When the finger contact 98 is attached to the pivot control structure 100 the finger contact slot 182 may be slid onto the finger contact post 188 on the slider 186. Additionally, when assembled, the peg projections 180 of the finger contact 98, if present, may be seated in the finger contact peg holes 190 of the slider 186.

A pivot control structure 100 may interact with one or more feature of the endoscope allowing it to be locked or held in a desired orientation. As shown, the bottom face of the slider 186 of the pivoting member 184 optionally may include one or more catch bars or detent elements 192. In other embodiments, multiple catch bars 192 may be disposed along the bottom of the slider 186, arranged to engage with opposing raised features or ridges 94 on the handle 12.

The catch bars or detent elements 192 may interact with the raised features or ridges 94 of the slide button recess 92 of the handle raised portion 32 described above (best shown in FIG. 7A). As the pivot control structure 100 is displaced by the user, the spaces between ridges 94 may act as detents in which the catch bars 192 of the slider 186 may be "parked". This helps to prevent drifting or movement of the pivot control structure 100 once a user moves it to a desired position and releases it. It may also help to ensure that the pivot control structure 100 is not accidentally displaced during use of the instrument. In alternative embodiments, and as mentioned above in relation to FIG. 7C, in some embodiments, the pivot control structure 100 may include arms 97 which act as catch bars or detent elements 192.

As shown, the pivoting member 184 of the pivot control structure 100 includes a curved inner shield 194. The inner shield 194 is tiered below the slider 186, and under the handle housing when assembled. A post 196 may span the distance between the top face of the inner shield 194 and the bottom face of the slider 186. In some embodiments, the catch bars 192 may be located on the top of the inner shield 194. In such embodiments, the ridges 94 described above may be located on the interior wall of the housing of the handle distal section 30 such that the ridges 94 may form detents for the catch bars 192 on the inner shield 194. As described above, this allows the pivot control structure 100 to be "parked" in a desired position.

Extending from the bottom face of the inner shield 194 may be a pivot arm 198. In the example embodiment, the pivot arm 198 includes two mechanical cable attachment points or holes 202. One hole 202 is situated on one side of a pivoting shaft 204, while the second hole 202 is situated on the other side of pivoting shaft 204. In the illustrated embodiment, forward movement of slider 186 causes a mechanical cable connected to the lower hole 202 to be retracted proximally, while aft movement of slider 186 causes a mechanical cable connected to the upper hole 202 to be retracted proximally. In order to accommodate a relatively unimpeded passage of a fiberoptic or electrical cable from the proximal end of the handle to the distal end of the handle, the pivot arm 198 may be, for example, notched over its pivot shaft 204, so that a passing cable may rest freely on the pivot shaft 204 (or a concentric sleeve or hub surrounding the shaft 204). Such an arrangement would allow passage with minimal displacement laterally or vertically.

Figure 14:
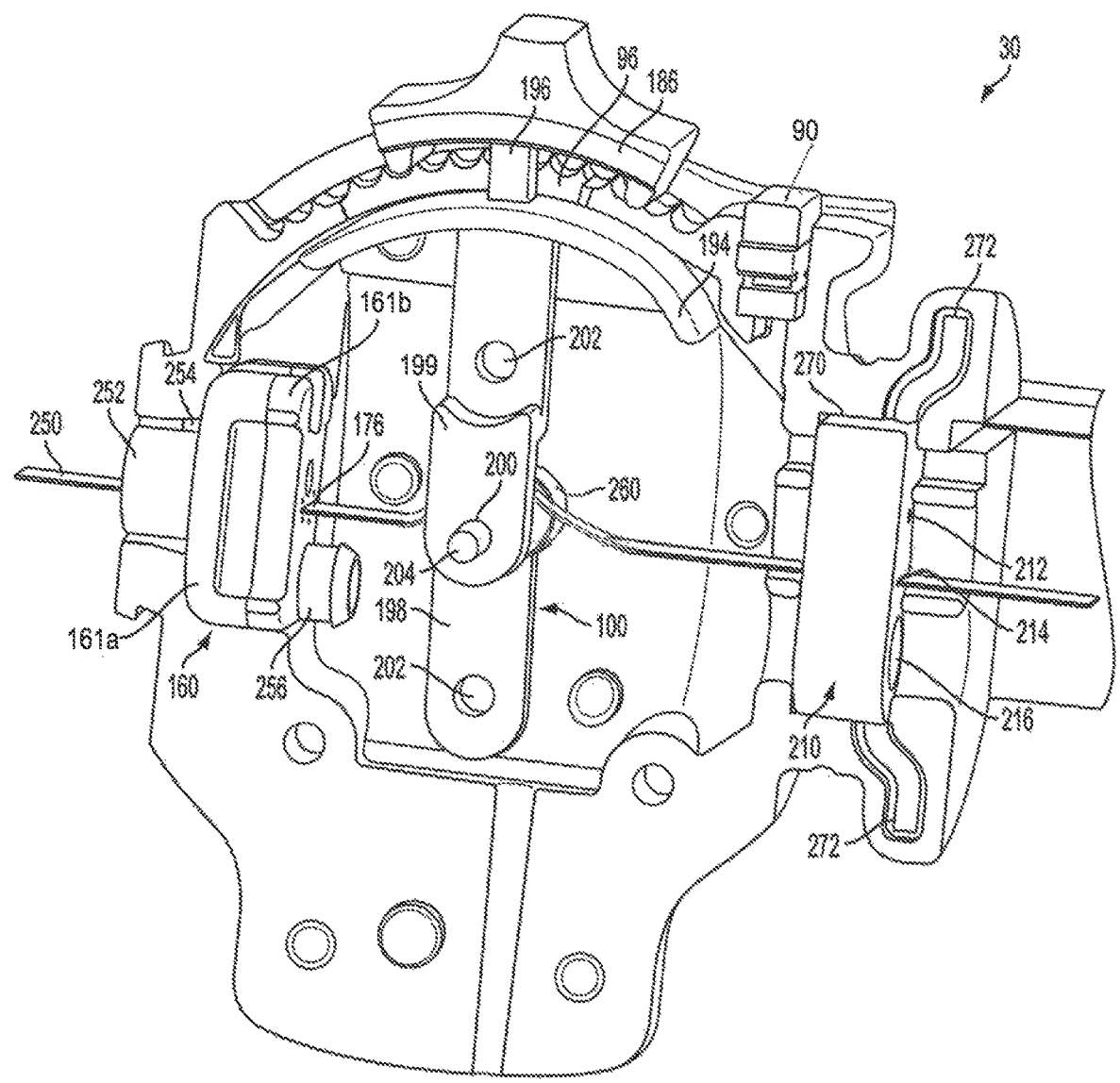
FIG. 14 shows a partially assembled view of an exemplary endoscope with an inner sheath mount, a pivot control structure or assembly, and sealing member in their assembled locations.

Referring now to both FIGS. 12 and 14, the pivot arm 198 is constructed to have a laterally displaced section 199 encompassing pivoting region 200 and pivot shaft 204. Thus a hub or sleeve encompassing pivot shaft 204 (when assembled) is shown to serve as a bearing surface upon which a passing cable 250 may rest. A lower portion of pivot arm 198 extends downward from a location beneath the hub or sleeve of pivot shaft 204. In some embodiments, the lower portion of pivot arm 198 optionally may be vertically aligned with the upper portion of pivot arm 198, so that mechanical cables connected to points or holes 202 are also aligned vertically. In other embodiments, one or more cables (e.g., cable 250) may travel around (or through) a hub of pivot shaft 204 in a variety of other ways, so that its path is minimally obstructed by the pivot arm 198 of the pivot control structure 100.

Optionally, a secondary pass-through seal provides an additional barrier between fluid that may infiltrate into the housing of the handle distal section 30 and the housing of handle proximal section 16, in which electronics section 80 may be housed. The seal may include orifices, holes or slits through which components such as though not limited to, fiberoptic bundle, electronic cable and/or fluid conduit tubing may pass. The holes or slits may be sized to provide a snug fit over these components as they pass through the seal. In an embodiment, the secondary pass-through seal is formed from a rubber or other elastomeric material to enhance its fluid sealing characteristics. In some embodiments, for example, those which include a pass through barrier 159 which includes a flexible member 153, no secondary pass-through seal may be included. In such embodiments, the electronics section 80 and the external handle section 82 may be the same volume or connected volumes.

Figure 13:
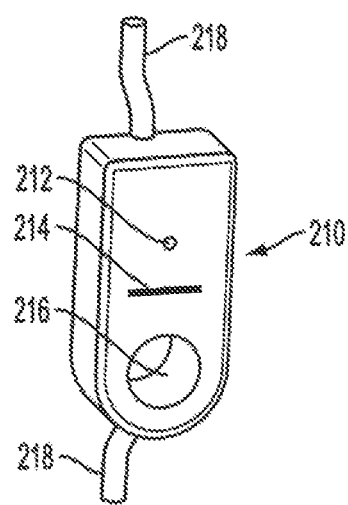
FIG. 13 shows a perspective view of an example of a sealing member.

FIG. 13 shows an example embodiment of a secondary seal, i.e. sealing member 210. The sealing member 210 may be roughly rectangular in shape as shown in FIG. 13. As shown in FIG. 13, one end of sealing member 210 may be of a first (e.g. a rectangular) shape, while a second end of sealing member 210 may be of a second shape (e.g. have rounded edges or be rounded). This may provide an advantage during assembly to ensure that the sealing member 210 is mounted in the proper orientation. The sealing member 210 may include a number of orifices. In the example embodiment, the sealing member 210 includes a fiberoptic bundle (e.g., an illumination fiber) orifice 212, a flex cable (i.e., electronic cable) orifice 214, and a fluid tubing (e.g., an irrigation line) orifice 216. In the example embodiment shown in FIG. 13 the illumination fiber orifice 212, flex cable orifice 214, and irrigation line orifice 216 extend through the entire sealing member 210. The illumination fiber orifice 212 has a relatively small diameter to match the diameter of a fiber bundle or light pipe. The flex cable orifice 214 is a slit, matching the size and shape of an electronic flex cable. The irrigation line orifice 216 is cylindrical and has a diameter larger than that of the illumination fiber orifice 212. The illumination fiber orifice 212, flex cable orifice 214, and irrigation line orifice 216 extend through the sealing member 210 at an angle that is substantially perpendicular to the front face (relative to FIG. 13) of the sealing member 210. In alternative embodiments, the orifices in the sealing member 210 may differ in number, size or shape. In some embodiments, the sealing member 210 may include an additional hole for wiring to the button 90, for example.

As shown in the example embodiment in FIG. 13, the sealing member 210 may also include a number of gasket arms 218. In the example embodiment in FIG. 13, the gasket arms 218 project away from the top and bottom faces of the sealing member 210 near the back edge of the sealing member 210. As shown, there may be two gasket arms 218. In some embodiments, the gasket arms 218 may be straight. In the example embodiment, the gasket arms 218 include two straight sections connected by an arcuate section which bends the gasket arms 218 away from the sealing member 210.

FIG. 14 shows an example embodiment of one half (30*a*) of the handle distal section 30. As shown, the inner sheath mount 160, pivot control structure 100 and the sealing member 210 are assembled and placed within the shown half (30*a*) of the handle distal section 30. A flex cable 250 (e.g., flexible electronic communications/power cable) is also shown. In the example embodiment shown in FIG. 14, the distal section 161*a* of the inner sheath mount 160 includes a sheath mounting hub 252. The sheath mounting hub 252 extends distally along the same axis as the utility hole 168 (see FIG. 11A). In the example embodiment, the sheath mounting hub 252 may be hollow and substantially cylindrical. The inner diameter of the sheath mounting hub 252 optionally may be approximately equal to or somewhat larger than the diameter of the utility hole 168. In the example embodiment, a sheath mount mounting tab 254 projects superiorly from the outer surface of the sheath mounting hub 252. The sheath mount mounting tab 254 is located next to the face of the insertion side piece 160*a* from which the sheath mounting hub 252 projects. The mounting tab 254 may serve to properly orient a sheath (e.g. inner sheath 312 shown in FIG. 17) as it is mounted onto the sheath mounting hub 252, and optionally may also serve as a locking member to secure a sheath to the sheath mounting hub 252 and sheath mount 160.

In other embodiments, the sheath mount tab 254 may be disposed on the inside surface of the sheath mount hub 252. This may be desirable because it obviates the need to nest the inner sheath mount hub 252 inside of a sheath removing a restriction in the diameter of the conduit of the sheath. Consequentially, a higher flow rate through such a conduit may be achieved. Alternatively, a sheath mount nub 254 may not be included in some embodiments. The sheath may instead be oriented and secured to a sheath mount hub 252 in any suitable fixture (not shown).

As shown the flex cable 250 extends through the inner sheath mount 160. The flex cable 250 passes through the sheath mounting hub 252 into the distal section 161a of the inner sheath mount 160. The flex cable 250 is also routed through the sheath mount slit 176 of the proximal section 161b.

The proximal section 161b of the inner sheath mount 160 includes a fluid conduit attachment site or port 256. The fluid conduit attachment site 256 may be a hollow, roughly cylindrical projection which extends toward the right of the page (in relation to FIG. 14) from the proximal section 161b of the inner sheath mount 160. Tubing of an irrigation line 434 (see FIG. 61) may be slid over the outer surface of the fluid conduit port 256, which optionally may be barbed to aid in retaining an installed section of tubing. As shown, the right edge of the fluid conduit port 256 may be chamfered in a manner to also facilitate ease of installation of a tubing segment to the port 256. Additionally, as shown in FIG. 14, the proximal end of the fluid conduit port 256 tapers to a slightly larger diameter than the rest of the port 256 surface. This may act as a barb and help ensure that once attached, the tubing of an irrigation line 434 (see FIG. 61) is not easily dislodged. In an alternative embodiment, the conduit port 256 may extend and be fitted into an irrigation line orifice 216 of a sealing member 210. The barbed portion/attachment site for an irrigation line 434 may then be placed on the sealing member 210.

The pivot control structure 100 may be pivotally coupled into the handle distal section 30 as shown in FIG. 14. As shown, the pivot shaft 204 extends through the pivot shaft hole 200 in the pivot arm 198 of the pivot control structure 100. The end of the pivot shaft 204 (or of a surrounding hub) inserted into the far wall of the handle distal section 30 may be seated in a pivot bearing 260 projecting from the inner wall of the handle distal section 30. When fully assembled, the opposite end of the pivot shaft 204 may similarly be seated in a pivot bearing 260 projecting from the inner wall of the other half (30b) of the handle distal section 30.

As shown in FIG. 14, the slider 186 and inner shield 194 of the pivot control structure 100 may be offset from each other by the post 196 a distance slightly larger than the thickness of the walls of the handle distal section 30. The post 196 may extend through the pivot control structure notch 96 described above. The curvature of the slider 186 and inner shield 194 may be selected such that the slider 186 and inner shield 194 may freely move fore and aft with input from a user without interfering with the walls of the handle distal section 30 housing. The length of the pivot control structure notch 96 may determine the amount of pivotal displacement a user may create with input to the pivot control structure 100.

In some embodiments, the walls of pivot control structure notch 96 may exert a frictional force against the post 196. In such embodiments, this frictional force may allow the pivot control structure 100 to be "parked" in a position. In such embodiments, the walls of the pivot control structure notch 96 may be made of a high friction material such as rubber or other elastomeric material. In such embodiments, the pivot control structure 100 may not need to include the catch bars 192 or the ridges 94 described above.

The endoscope 10 may also include mechanical pivot actuators in the form of pull cables or wires, belts, or pushrods. An actuator may be any elongate member, solid, braided, or otherwise extending from the handle of the endoscope 10 to a movable element at the distal end of the insertion section. The elongate member may be flexible or substantially rigid. The elongate member may be round (as in the example of a cable), ovoid, relatively flat, or may have any other shape or cross section. In some embodiments, the actuator may be a belt.

In an endoscope having a pannable camera or camera mount at or near the distal end of the shaft or insertion section, the pannable camera or camera mount may be rotated using pull wires or pushrods. In a pull wire embodiment, panning cables may be attached or connected to, or looped through the cable attachment holes 202. In some embodiments, two panning cables may be attached to each cable attachment hole 202. In a preferred embodiment both ends of a single panning cable are attached to each cable attachment hole 202 creating a loop. Alternatively, a single cable may be looped through the cable attachment hole 202 at about its midpoint, the ends of the cable then being connected distally to the rotatable camera or camera mount. The panning cables may extend from the cable attachment holes 202 in the pivot arm 198 and be routed through one or more orifices 178 in the proximal section 160b of the inner sheath mount 160. The panning cables may then extend through the utility hole 168 and through the conduit formed by the inner sheath, optionally alongside the length of an electronic flex cable 250 and/or fiberoptic bundle. By pivoting the pivot control structure 100, the panning cable or cables connected to one of the cable attachment holes 202 will be pulled, while the cable(s) connected to the other attachment hole 202 will slacken. By attaching the panning cable or cables associated with one cable attachment hole 202 to one side of a pivot point and attaching the panning cable or cables associated with the other cable attachment hole 202 to the opposite side of the pivot point, the pivot control structure 100 may be used to selectively rotate a pivoting object distally in the insertion section of the endoscope. In other embodiments, a similar cabling mechanism may be used to actively flex a flexible distal segment of the insertion section.

In some embodiments, the pivot arm 198 of the pivot control structure 100 may be pivoted via gearing. In such embodiments, the finger contact 98, finger contact post 188 (see FIG. 12), slider 186, vertical post 196, and inner shield 194 may not be needed. At least a portion of a user input gear contained in the handle distal section 30 may project out of the handle raised section 34. The user input gear may be rotated about a pivot axis disposed within the handle distal section 30. This rotation may be user-initiated via, for example, a user's finger or thumb. The user input gear may mesh with a pivot shaft gear disposed about the pivot shaft 204 for the pivot arm 198 of the pivot control structure 100. In such embodiments, as the user input gear is rotated, the pivot shaft gear and pivot arm 198 are also caused to rotate, acting on the pivot actuators (e.g. panning, actuating or pull wires) as described above. In some embodiments, there may be an intermediary gear or any number of intermediary gears between the user input gear and the pivot shaft gear to provide any desired gear reduction to meet precision-of-movement and ergonomic requirements.

In other embodiments, the pivot arm 198 may be caused to rotate via an electric motor (e.g., brushless motor, stepper motor, etc.). Rotation via the motor may be controlled by one or more user input means such as a button 90. In embodiments including at least one button 90, the button 90 or buttons 90 may control the speed and direction of movement of the pivot arm 198.

In some embodiments, the pivot shaft 204 may project to the outside of the handle distal section 30. In such embodiments, the pivot shaft 204 (or an overlying hub or sleeve) may be directly rotated by the user. In some embodiments, the portion of the pivot shaft 204 projecting out of the handle distal section 30 may include a knob, dial, crank, etc. so that a user may easily rotate the pivot shaft 204 by grasping and rotating the knob, dial, crank, etc.

As shown in FIG. 14, the sealing member 210 is positioned in a gasket recess 270. The gasket recess 270 may include gasket arm recesses 272. Various components may pass through the sealing member 210 as mentioned above. As shown, a flex cable 250, connected to a printed circuit board 430a (see, for example, FIG. 61) in the electronics section 80 housed in the handle proximal section 16 may pass through the flex cable orifice 214 of the sealing member 210 and extend beyond the sealing member 210 through the housing of the handle distal section 30 and sheath mount 160, ultimately to travel distally in the insertion section of the endoscope. The irrigation line 434 (see FIG. 61) and fiberoptic bundle (e.g., illumination fibers 364, see FIG. 61) may pass through their respective irrigation line orifice 216 and fiberoptic bundle orifice 212 and extend through the housing of the handle distal section 30 similar to the flex cable 250. In some embodiments, a sealing member 210 may not be included. Instead the electronics section 80 may not be partitioned from the rest of the handle 12. In such embodiments, the enclosed printed circuit board 431 (see, e.g. FIG. 15) may be coated or encased in a protective coating or layer, such as potting. In embodiments including a sealing member 210 a printed circuit board (see, e.g. FIG. 15) may still be encased in a protective coating or layer. Additionally or alternatively, the inner sheath mount 160 may include a flexible member 153 similar to that shown in FIG. 11B-C which forms a seal around and displaces as any pass-through components (e.g. flex cable 250, actuators/cables, illumination fibers, etc.) running through the inner sheath mount 160 are displaced.

Only one half of the gasket recess 270 is shown in FIG. 14. The other half of the gasket recess 270 may be located on the other, not shown half (30b, see FIG. 8, for example) of the handle distal section 30. When fully assembled, the sealing member 210 is captured between the two halves of the gasket recesses 270. When fully assembled the sealing member 210 may ensure that fluid which may be present in the handle distal section 30 may be inhibited from infiltrating into the handle proximal section 16, which contains electronics components comprising electronics section 80. The sealing member 210 may be made of suitably compliant (e.g., elastomeric) material or other suitable gasket material and may be pressed into the gasket recesses 270 to ensure a tight seal. In some embodiments, the sealing member 210 may be held in place using an adhesive.

Figure 15:
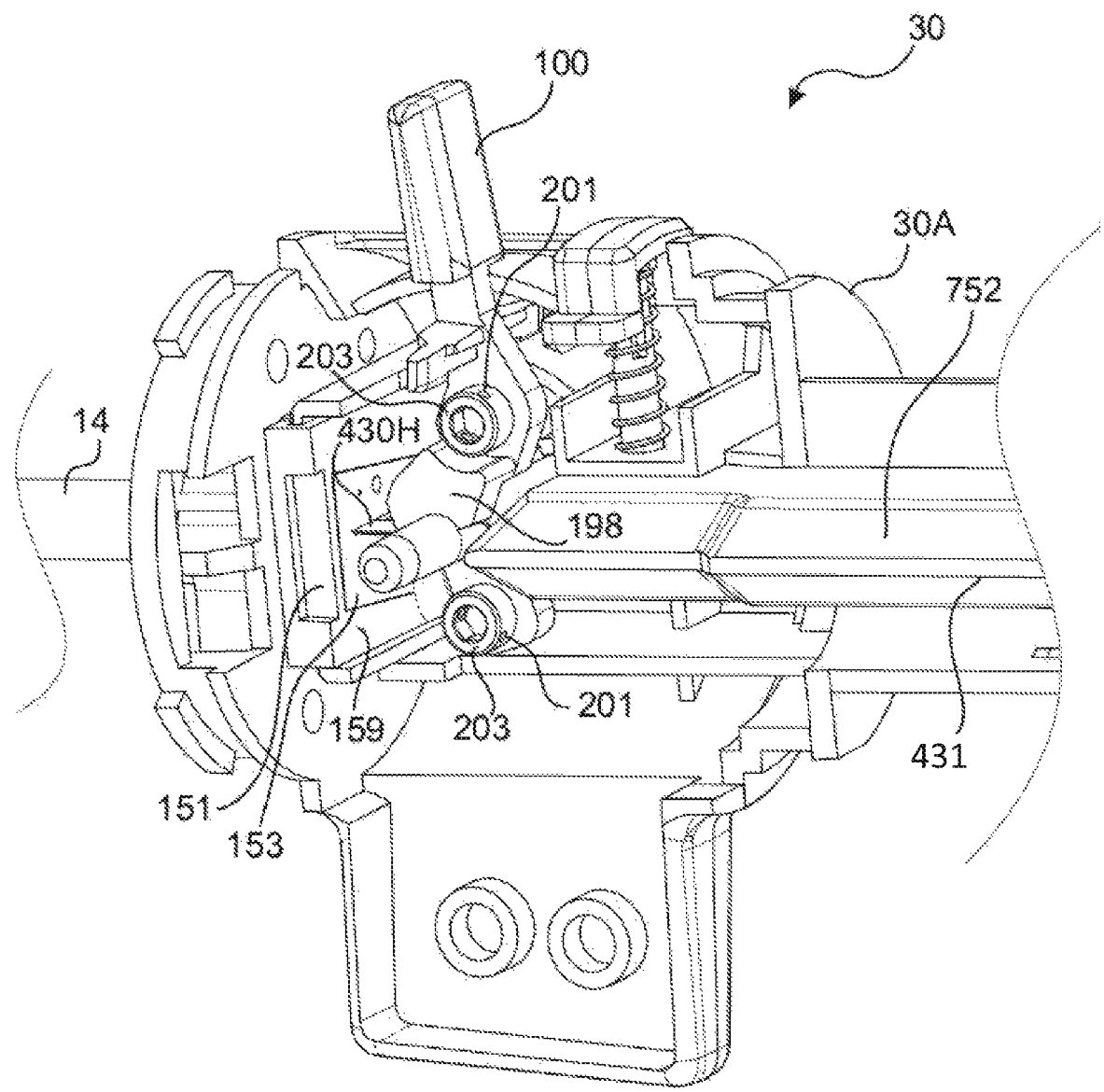
FIG. 15 shows another partially assembled view of an example endoscope with a pass-through barrier, pivot control structure, and printed circuit board encased in a protective material or housing.

FIG. 15 shows another example embodiment of one half (30a) of the handle distal section 30. As shown, a pass-through barrier 159 and a pivot control structure 100 are assembled and placed within the shown half (30a) of the handle distal section 30. An enclosure 431 of a printed circuit board which has been encased in a protective material 752 is also shown in place within part 30a of the handle distal section 30. In some embodiments, a projecting portion 430h may be a ribbon or flex cable 250 (see, e.g., FIG. 14). The printed circuit board may communicate with components at the distal end of the shaft 14 through one or more ribbon cables that pass through the bulkhead or pass-through barrier 159. These cables may or may not need to slide somewhat back and forth through the bulkhead, to accommodate rotational movement of the sensor or camera housing at the distal end of the endoscope shaft, or to accommodate flexion and extension of the shaft 14 if it is a flexible shaft. Alternatively, the PCB may include an extension 430h of the PCB itself which extends into the shaft or insertion section 14 through the pass-through barrier 159. In some specific embodiments the printed circuit board and its extension 430h may be similar to that shown and described in relation to FIGS. 33B and 33C, or FIG. 53. A sealing agent 151 is shown in place around the projecting portion 430h. The pass-though barrier 159 may include a peripheral gasket 163 (see, e.g. FIG. 11D) in some embodiments. The pass-though barrier 159 may be coupled to the handle distal section 30 in any number of ways, including but not limited to, adhesive, epoxy, glue, solvent bonding, press fit, etc.

The pivot control structure 100 of FIG. 15 is similar to that shown in FIG. 12 and FIG. 14. However, the pivot control structure 100 may include arms 97 which interface with ridges 94 described above in relation to FIG. 7C. Additionally, in this particular embodiment, the pivot arm 198 of the pivot control structure 100 does not include pull-wire attachment holes 202 (see, e.g. FIG. 14). Instead, fasteners 203 or a similar structure including eyelets 201 may be attached to or provided as part of the pivot arm 198. Pull-wires may be attached to the pivot arm through the eyelets 201 and the pivot control structure 100 may be used to actuate the pull-wires, e.g. to bend a flexible shaft or insertion section 14 or to rotate a camera assembly in an insertion section 14. The pull-wires may pass through the flexible member 153 of the pass-though barrier 159 to actuate components in the insertion section 14.

As shown in FIG. 15, the pass-through barrier 159 may be the only barrier separating the insertion section 14 from electronic components housed in the handle distal section 30 and proximal section 16. A sealing member 210 (see, e.g. FIG. 14) may not be included. In some embodiments, an electronics section 80 may not be partitioned from or fluidically isolated from the rest of the handle 12. As mentioned above in relation to FIG. 11C, a pass-through barrier 159 may include a peripheral gasket member 163 in some embodiments to provide an additional seal.

Figure 16:
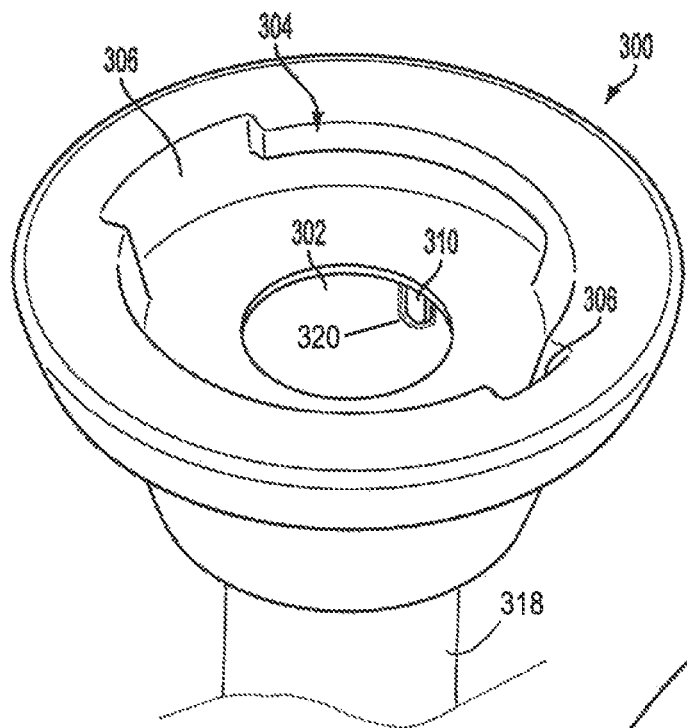
FIG. 16 shows a perspective view of an outer sheath mount.

FIG. 16 shows an example embodiment of an outer sheath or cannula mount 300.

Figure 16A:
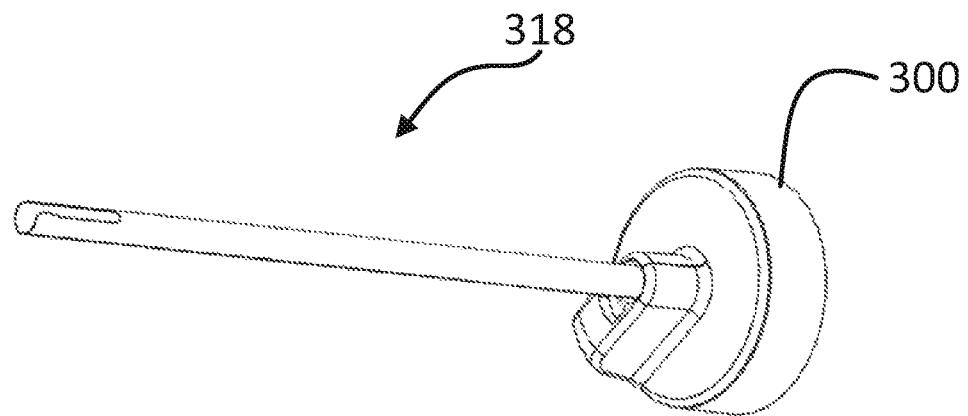
FIG. 16A shows a perspective view of an outer sheath and mount of an endoscope.
Figure 16B:
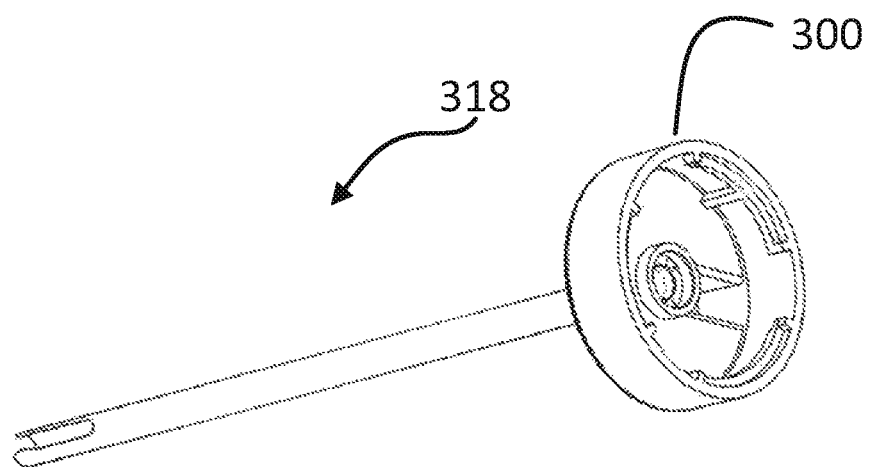
FIG. 16B is a rear perspective view of the outer sheath and mount of FIG. 16A.

As shown in FIG. 16A and FIG. 16B, an outer sheath or cannula 318 may be employed to provide additional protection to components in the distal end of the insertion section, or to allow a user to withdraw the insertion section of the endoscope while leaving the cannula 318 in situ, to allow later re-insertion of an insertion section of the endoscope. As shown, the cannula mount 300 may have a frustoconical shape, with the larger diameter section proximally forming a connector (e.g. bayonet mount) for the mounting of a cannula 318 over an inner sheath 312 (see, for example, FIG. 17). A cannula mount hole 302 may extend through the cannula mount 300 to merge with a cannula channel. The cannula or outer sheath mount hole 302 may be configured to accept and retain a cannula 318. The cannula 318 may be configured to act as a sleeve over an inner sheath 312 of the insertion section.

As shown, the female bayonet mount portion 304 includes two slots 306. The slots 306 optionally may have different dimensions to ensure proper orientation of the cannula 318 with respect to a mating (male) connector on a distal portion of the handle distal section 30. In some embodiments, the slots 306 of the female bayonet mount portion 304 may include a serif into which the male bayonet mount portion 308 may be spring loaded using, for example, a Belleville washer. In such embodiments, a spring-loaded connection may help ensure the two pieces (cannula 318 and handle distal section 30) are more securely locked together.

In some embodiments, an alignment feature may be included on the cannula mount 300 in order to properly orient the cannula 318 with the cannula mount 300 during assembly, and ultimately with the inner sheath 312 (see, for example, FIG. 17) when installed over the inner sheath 312 of the insertion section. In the example embodiment in FIG. 16, an outer sheath mount tab 310 may project from the inner wall of the outer sheath mount hole 302. The outer sheath mount tab 310 may extend from a distal face of the female bayonet mount portion 304, which may then be used to align the bayonet mount 300 with a cannula 318 having a mating slot during assembly. Alternatively, the need for such a feature may be removed by coupling the outer sheath or cannula 318 and cannula mount 300 in a suitable fixture.

Figure 17:
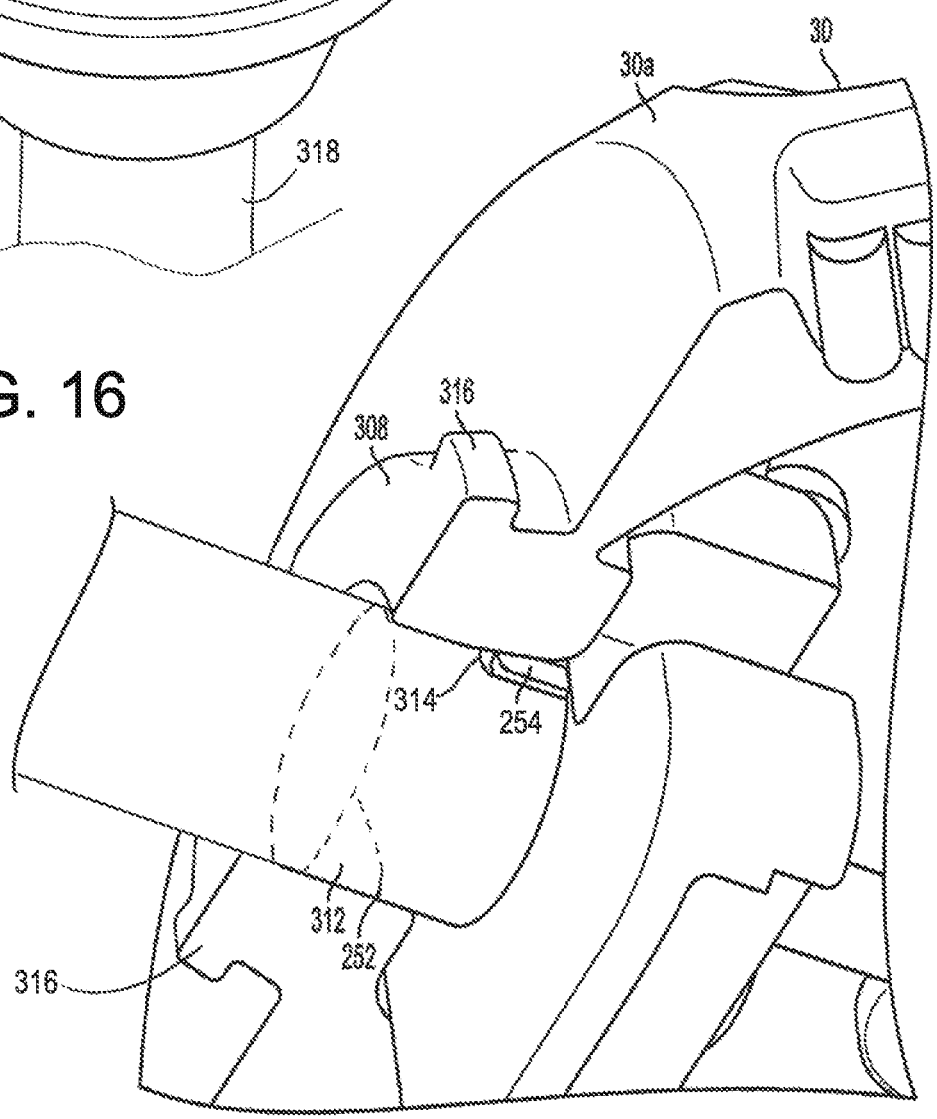
FIG. 17 shows a close up partial view of an endoscope in which an inner sheath mount, inner sheath, and outer sheath are in their assembled locations.

FIG. 17 shows a partial cutaway view of an example embodiment of the distal face of the handle distal section 30. An inner sheath 312 is mounted on the sheath mounting hub 252 of the inner sheath mount 160. The inner sheath 312 includes a sheath mount notch 314. The inner sheath mount notch 314 may be dimensioned to accept the sheath mounting tab 254 on the sheath mounting hub 252. In such embodiments, the sheath mounting tab 254 and inner sheath mount notch 314 may ensure that the inner sheath 312 is correctly oriented on the endoscope 10.

The inner sheath 312 (and/or the outer sheath or cannula 318, see FIG. 16) may be formed from steel, any of a number of hardened plastics or other rigid, durable material. Alternatively, the inner sheath 312 or a portion thereof may be flexible, allowing the insertion section of the endoscope to bend as needed for insertion into a non-line-of-site target area. In these embodiments, a user may forgo the use of an outer sheath or cannula 318, or the cannula 318 itself may also be constructed of a similarly flexible material.

The male bayonet mount portion 308 is also visible in the example embodiment shown in FIG. 17. The male bayonet mount portion 308 may include two prongs 316. The prongs 316 may be sized to fit in the legs of the L-shape slots 306 of the female bayonet mount portion 304 referring now also to FIG. 16. The outer sheath 318 and cannula mount 300 may be coupled to the handle distal section 30 by aligning the prongs 316 with the slots 306, pressing the bayonet mount over prongs 316, and then turning the bayonet mount to lock it into position. As shown, optionally the two prongs 316 are dimensioned differently such that the outer sheath mount 300 may only have one possible orientation when coupled onto the handle distal section 30.

Still referring now to both FIGS. 16-17, an outer sheath or cannula 318 may be slid over the inner sheath 312, forming a sleeve. The inner diameter of the outer sheath 318 may be only slightly larger than the outer diameter of the inner sheath 312 to ensure a snug fit. The outer sheath 318 may include an outer sheath notch 320. The outer sheath notch 320 may be dimensioned to accept the outer sheath mount tab 310 when the endoscope 10 is fully assembled. In some embodiments, the outer sheath 318 may be friction fit, glued or otherwise fused or attached to the wall surrounding the outer sheath mount hole 302. The outer sheath mount tab 310 may help to ensure correct orientation of the outer sheath 318 when the endoscope 10 is fully assembled.

When the shaft or insertion section 14 (see FIG. 3) of the endoscope 10 is inserted into a target region, the outer sheath 318 and outer sheath mount 300 may be uncoupled from the rest of the endoscope 10 as mentioned above. This may allow the outer sheath 318 to be used as a cannula, remaining in situ to permit the endoscope 10 to be re-introduced into the target region.

Figure 17A:
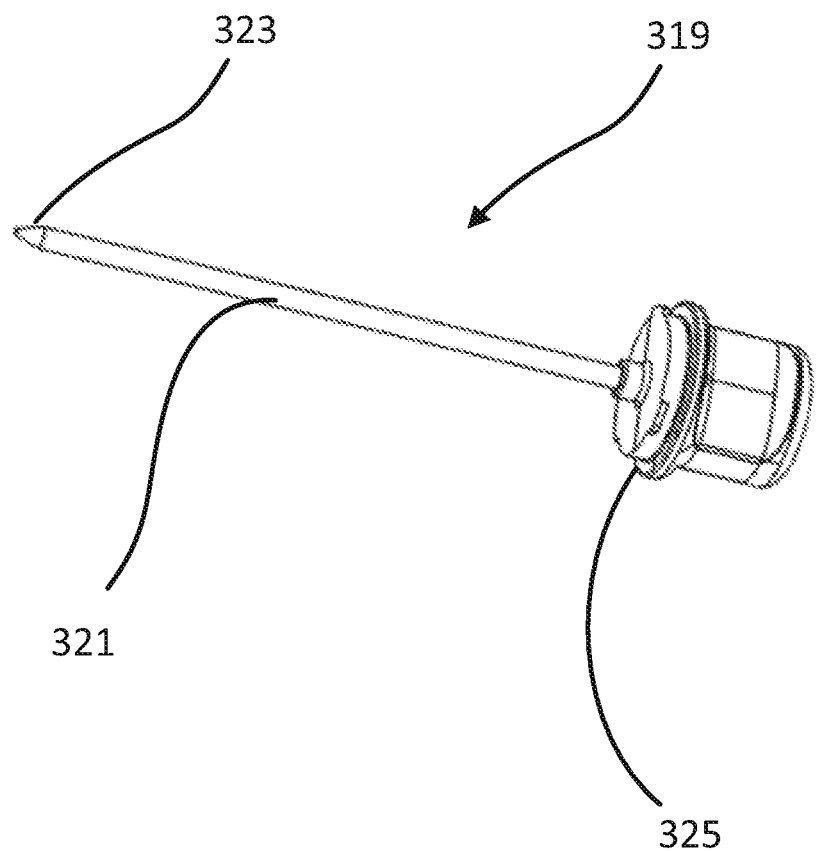
FIG. 17A shows an exemplary trocar or obturator for insertion into an outer sheath of an endoscope.

Shown in FIG. 17A is a trocar or obturator 319 adapted for use with the outer sheath 318. During introduction of the endoscope into the surgical field, the trocar may be inserted into an outer sheath 318 to facilitate entry of the outer sheath 318 into the desired location, after which the trocar can be withdrawn and the inner sheath 312 of the shaft 14 can be inserted. If the shaft 14 needs to be substantially repositioned within the surgical field during an operation, the endoscope shaft 14 can be withdrawn from the patient while keeping the outer sheath 318 in place, the trocar can be introduced into the outer sheath 318, and the trocar/outer sheath assembly can be repositioned as needed. Once in the proper location, the trocar can be withdrawn from the outer sheath 318, and the endoscope shaft with inner sheath 312 can then be re-inserted into the outer sheath 318. In the example shown, the trocar 319 includes a solid shaft portion 321 with pointed or blunted end 323, and a base portion 325. The base portion 325 is optionally equipped with a locking mount that matches that of the distal handle section 30 of the endoscope handle, so that the trocar can be secured to the outer sheath 318 when in use. If desired, the outer sheath or cannula 318 may be used as a conduit through which other instruments may be introduced into the target region. The outer sheath 318 may also function as a conduit through which fluid may be introduced or withdrawn from the target region.

Figure 18:
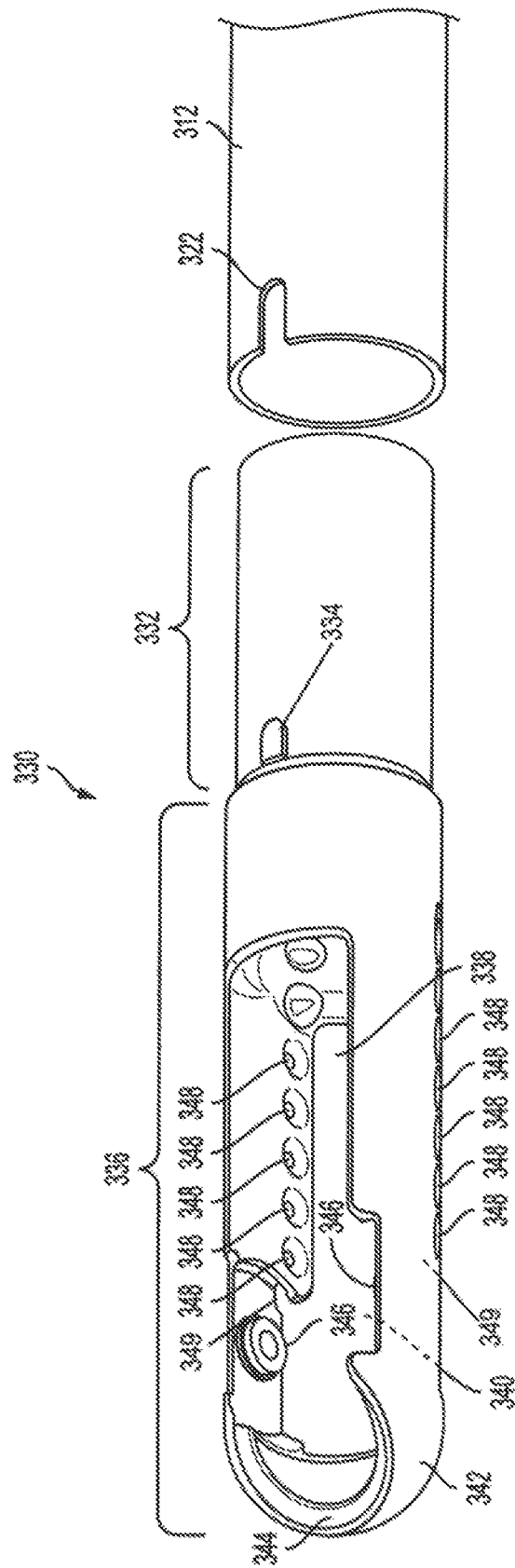
FIG. 18 shows an example of a camera assembly mount separated from an inner sheath.

A camera assembly housing 330 or distal working section is shown in FIG. 18, separated from a distal end of an inner sheath 312. In this embodiment, the distal working section of an insertion section of an endoscope may be constructed separately from the inner sheath 312, and subsequently mated to a distal end of the inner sheath 312 during assembly. In other embodiments the inner sheath 312 may be constructed as a single piece, incorporating a distal working section. In embodiments where the distal working section is constructed separately, the distal working section may be made from a material different from that of the inner sheath 312. Additionally, it may be constructed from a number of assembled parts.

In the example embodiment in FIG. 18, the distal edge of the inner sheath 312 includes an inner sheath distal notch 322. The camera assembly housing 330 may include a nested segment 332, shaped and having an outer diameter suitable for insertion into the distal end of inner sheath 312 during assembly of the endoscope 10. The nested segment 332 may include a nested segment tab 334 or other alignment feature. The nested segment tab 334 may be dimensioned so that it may be mated to the inner sheath distal notch 322 when the endoscope 10 is assembled. The nested segment tab 334 and inner sheath distal notch 322 may help ensure that the camera assembly housing 330 is properly oriented and aligned when the endoscope 10 is assembled.

The camera assembly housing 330 may additionally include a working segment 336. As shown, the working segment 336 in FIG. 18 may include a top void 338 with or without a bottom void 340. The top void 338 and bottom void 340 may extend along most of the working segment 336 of the camera assembly mount 330. A rounded tip 342 may be included at the distal end of the working segment 336 of the camera assembly mount 330. As shown, the rounded tip 342 may optionally include an embrasured opening 344. The edges of the embrasured opening 344 may be beveled, chamfered or rounded. In the example embodiment, the embrasured opening 344 is continuous with the top void 338. In some embodiments, the top void 338 and bottom void 340 may be similarly embrasured.

A rounded tip 342, such as the rounded tip 342 shown in FIG. 18 may provide a number of benefits. A rounded tip 342 may facilitate the insertion of the insertion section 14 into a target region of a patient. In some cases, this may eliminate the need for a trocar. In arthroscopic applications, the contours of the rounded tip 342 allow the endoscope 10 to be maneuvered into tight spaces within a joint. A rounded tip 342 additionally may allow a surgeon to exert pressure atraumatically on tissues within a target region. The rounded tip 342 may also serve as a guard feature for a camera assembly 350.

As shown in FIG. 18, the interior walls of the working segment 336 of the camera assembly housing 330 include two camera mount pivot bearings 346. In the example embodiment shown in FIG. 18, the camera pivot bearings 346 project substantially perpendicularly from the inner side walls of the camera assembly mount 330. The camera assembly housing 330 may be made of steel, any number of hardened plastics, or any other suitably strong, rigid material.

In the example embodiment shown in FIG. 18, the interior walls of the working segment 336 of the camera assembly housing 330 include a number of cable guide holes 348. In a preferred embodiment, there may only be two cable guide holes 348. One cable guide hole 348 may be located on one side wall while another cable guide hole 348 may be located on an opposing side wall. Preferably, the cable guide holes 348 may be disposed below the camera mount pivot bearings 346, so that the distal end of a control cable may form an angle with respect to a camera, camera mount, or camera assembly 350 (see, for example, FIG. 23) to which it is connected. The camera assembly housing 330 may also include one or a number of constraining features. In the example embodiment shown in FIG. 16, there are two restraining notches 349. One restraining notch 349 is located on one side wall and the other restraining notch 349 is located on an opposing side wall. As shown in FIG. 16, the restraining notches 349 are roughly in line with the cable guide holes 348. The cable guide holes 348 and restraining notches 349 will be described further below.

Figure 19:
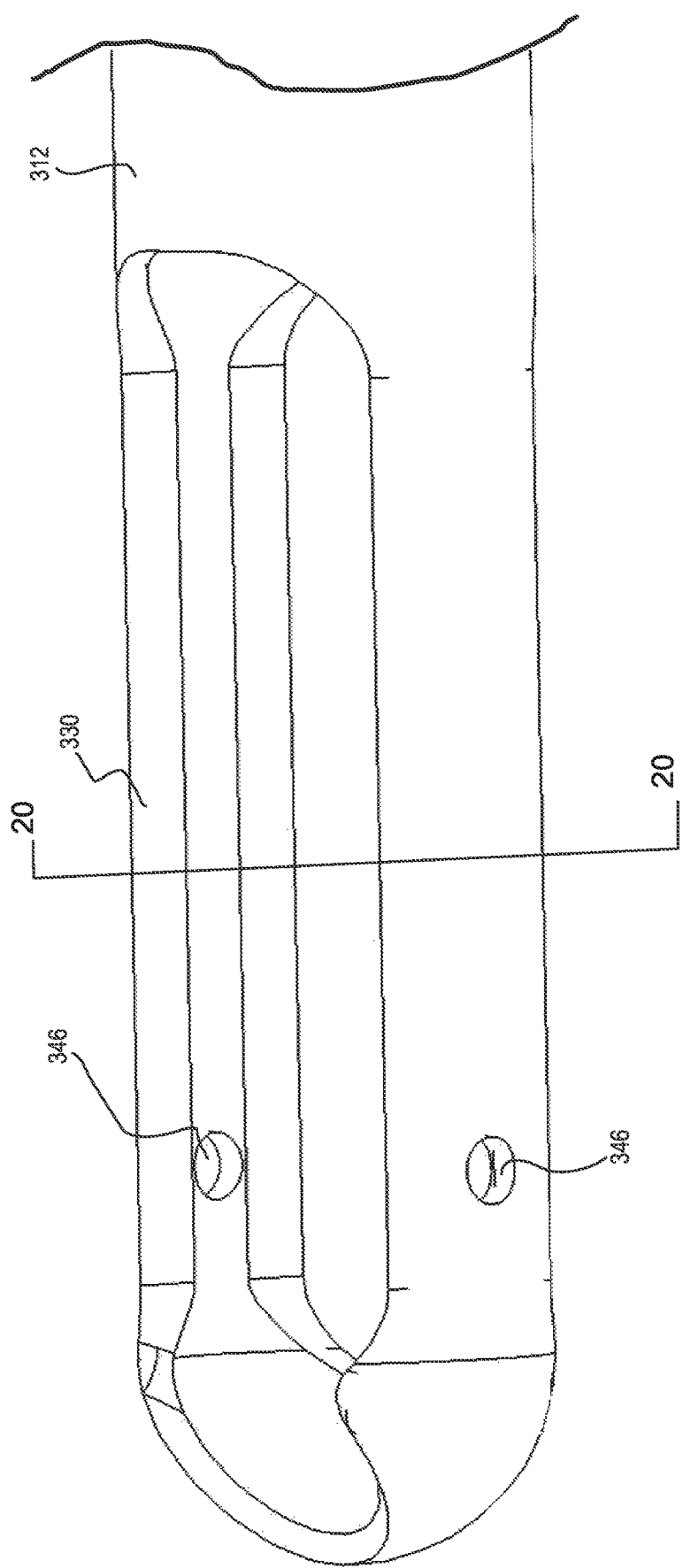
FIG. 19 shows an alternate example of a camera assembly mount as part of an inner sheath.

FIG. 19 depicts an embodiment of a distal working section or camera assembly housing 330 and inner sheath 312 which are constructed as a single part. Referring also to FIG. 20, a cross section taken at line 20-20 of the camera assembly housing 330 in FIG. 19 is shown. In embodiments where the distal working section or camera assembly housing 330 and the inner sheath 312 are constructed as a single part, they may be made from steel. In such instances the tip shape of the inner sheath 312 and camera assembly housing 330 may be created via a rolling process. Various voids, openings, and other features, for example those described above, may then be post machined into the part. In the example embodiment in FIG. 19, the camera assembly housing 330 includes only the camera mount pivot bearings 346.

It may be advantageous to create the inner sheath 312 and the camera assembly housing 330 as a single part. Among the advantages, the part may be stronger. Another advantage is that the need for a nested portion is removed. Consequently, a "choke point" in cross-sectional area at the junction of the inner sheath 312 and camera assembly housing 330 is removed. This may provide a number of benefits. Removing such a choke point allows more room for various components, such as utility components within the inner sheath 312 and camera assembly housing 330. Moreover, removal of such a choke point allows for increased flow of irrigation fluid within the inner sheath 312 and camera assembly housing 330. Alternatively or additionally, the overall diameter of the inner sheath 312 and camera assembly housing 330 may be decreased. The inner sheath 312 and camera assembly housing 330 may also be thickened. This helps to strengthen the part. Since thickening will strengthen the part, it may also allow an outer sheath or cannula 318 to be made thinner. A thinner outer sheath or cannula 318 in turn may allow for a larger diameter inner sheath 312 and camera assembly housing 330. That is, without increasing the overall diameter of an insertion section 14 (comprised of an outer sheath 318, inner sheath 312 and camera assembly housing 330), the cross-sectional area of a conduit within the insertion section 14 may be made larger. Thickening furthermore enables the camera mount pivot bearings 346 to have a larger bearing surface allowing pressure exerted against the bearing to be spread over a larger area.

Figure 21:
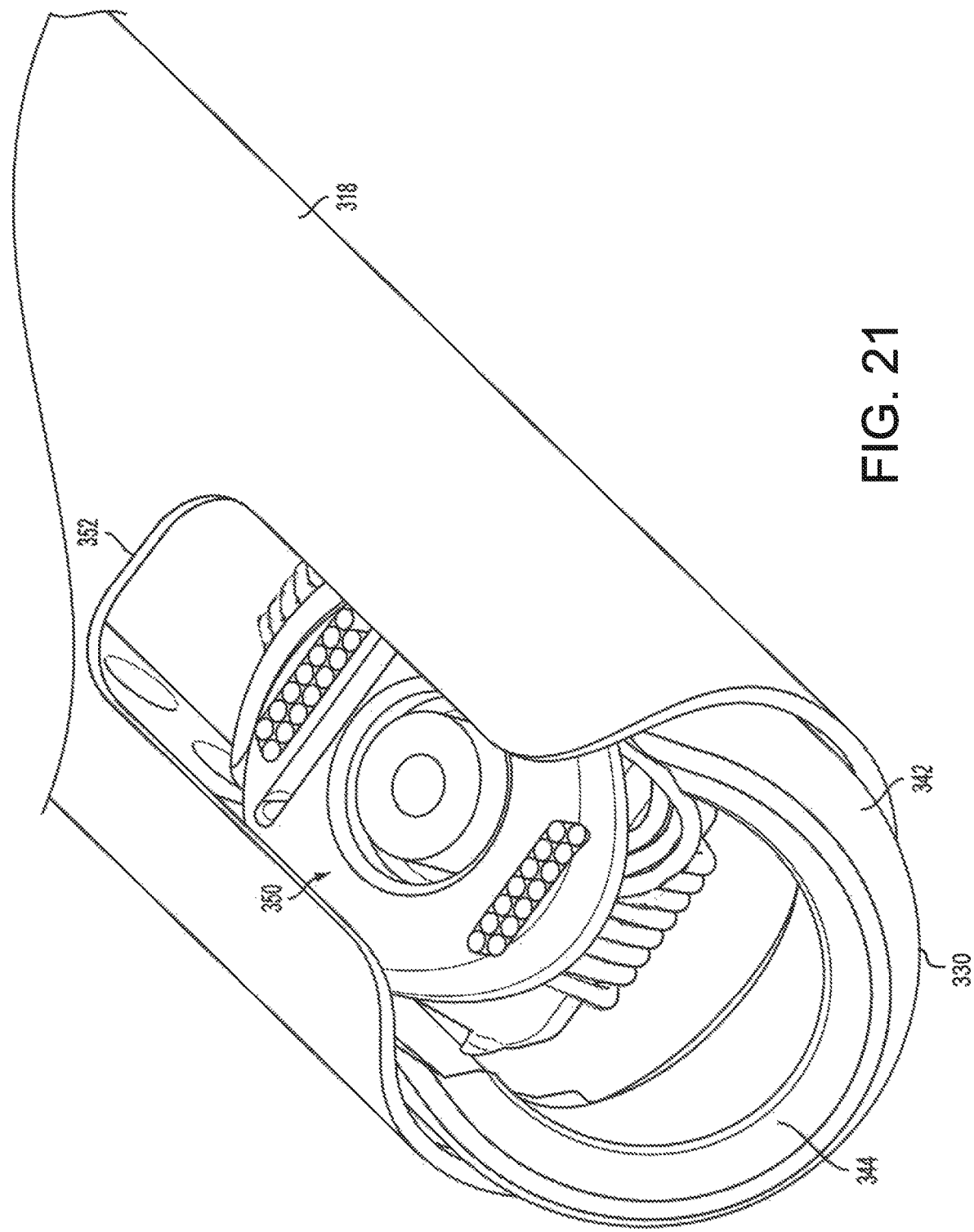
FIG. 21 shows an example of a camera assembly, part of an outer sheath, and part of a camera assembly mount.

FIG. 21 shows an assembled view of the tip of the insertion section 14 (best shown in FIG. 3A). The camera assembly housing 330, camera assembly 350, and outer sheath or cannula 318 are visible in FIG. 21. As shown, the rounded tip 342 of the camera assembly housing 330 projects past the distal end of the outer sheath or cannula 318. A viewing notch 352 is recessed into the top of the outer sheath 318. The camera assembly 350 may be pannable throughout the viewable range as defined by the opening created by the combination of the embrasured opening 344 and the viewing notch 352. In some embodiments the pannable range may be approximately 180°. When panning, the camera assembly 350 may pivot on the camera pivot bearings 346 (see, for example, FIG. 18). Panning actuation will be described further below.

In some embodiments, the outer sheath 318 may be rotated to an insertion position (not shown) when the insertion section 14 (see FIG. 3) of the endoscope 10 is being inserted into the target region. In the insertion position, the viewing notch 352 may not be aligned with the embrasured opening 344 and top void 338. This may help protect the camera assembly 350 during insertion, and in medical applications may reduce the risk of damage to tissue upon insertion of the insertion section 14. After insertion, the outer sheath 318 may be rotated back to a position in which the viewing notch 352 is aligned with the embrasured opening 344 and top void 338 so that the full viewable range is again available.

In some embodiments, a cap or window material may cover or be placed in the openings defining the viewing notch 352 and embrasured opening 344 to protect the camera assembly 350. In some embodiments, the distal edge of the outer sheath 318 and the viewing notch 352 may be embrasured, rounded, beveled, etc. to help prevent damage that might result from having sharp edges.

In the example embodiment, a cap or window is not used. Such an arrangement provides a number of benefits. For example, by not using a cap or window at the tip of the insertion section 14, the cost of the endoscope may be reduced because no expensive scratch and wear resistant materials such as sapphire, specialized glass, etc. are used. Not having a cap or window may also eliminate any undesirable reflections from the surface of the cap or window, which could otherwise affect the clarity of any image captured by a camera. Moreover, by not using a cap or window, irrigation of the target area may be conducted through the conduit of the inner sheath 312 (see FIG. 15) of the endoscope 10. This enables the total diameter of the insertion section 14 to be kept small while retaining irrigation capabilities. Furthermore, irrigation flow within the inner sheath 312 may help to clear/clean any debris or material away from the camera assembly 350 and any associated lens or lenses. In one example, a user may be able to effectively irrigate the camera assembly 350 by panning the camera assembly 350 during irrigation so that the irrigation flow washes over a lens assembly 354 (see, for example, FIG. 24) of the camera assembly 350 and carries away the debris or unwanted material. As an added benefit, the irrigation flow may also help to cool an image sensor 380 (see, for example, FIG. 49) associated with the camera assembly 350.

As shown, the embrasured opening 344 and viewing notch 352 may be dimensioned in order to protect the camera assembly 350 without the need for a cap or window. In the example embodiment in FIG. 21, the embrasured opening 344 and viewing notch 352 partially envelop the camera assembly 350, which is recessed from the outer surfaces formed by the embrasured opening 344 and viewing notch 352. Thus the embrasured opening 344 and viewing notch 352 define the edges of a guard for the camera assembly 350. The partial envelopment helps to protect movable components of the camera assembly 350 and any associated components (e.g. control, electric, information cables, etc.) from contact with external objects either during insertion of the insertion section into the target region, or during use of the instrument once in the target region. The embrasured opening 344 and viewing notch 352 provide the camera assembly 350 an unrestricted view while exposing only a small part of the camera assembly 350 to possible damage from objects external to the insertion section (such as, e.g., a medical instrument such as a shaver). This helps to ensure that the camera assembly 350 is not damaged during insertion or during a procedure.

As the camera assembly 350 rotates, the distance between the camera assembly 350 and the outer sheath 318 will change. As a consequence, the amount of the outer sheath 318 which falls into the field view of the camera assembly 350 will also change. The greater the distance from the camera assembly 350 to the inner sheath 318, the greater the amount of the outer sheath 318 which will be in the field of view of the camera assembly 350. Thus, an optimized amount of protection while still affording the camera assembly 350 and unrestricted view may be achieved by varying the width of a viewing notch 352.

Figure 22:
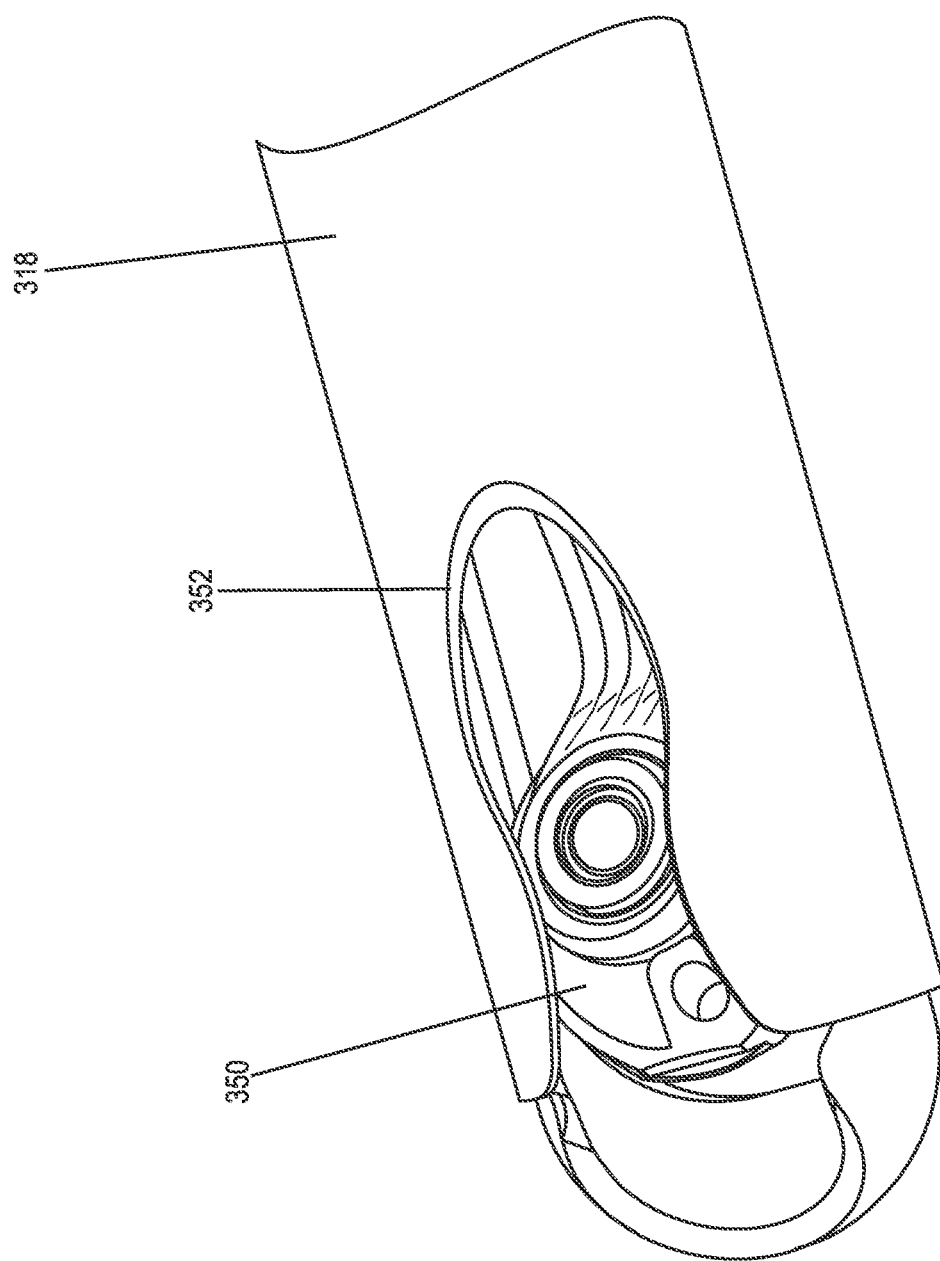
FIG. 22 shows an alternate example of a camera assembly, part of an outer sheath, and part of a camera assembly mount.

FIG. 22 depicts an alternate assembled view of the tip of an insertion section 14 (best shown in FIG. 3A) in which the viewing notch 352 has a varying width. The width of the viewing notch 352 varies such that the viewing notch 352 is just outside of the field of view of the camera assembly 350 in any angular orientation of the camera assembly 350. This allows for a greater degree of envelopment of a camera assembly 350 by an outer sheath 318.

FIG. 23 depicts another alternate embodiment of a tip of an insertion section 14 (best shown in FIG. 3A) in which a number of openings 353 separated by bars 351 are included in place of a viewing notch 352 like that shown in FIG. 20. Such an arrangement may provide additional protection to a camera assembly 350. To minimize the amount that the bars 351 obscure the field of view of the camera assembly 350, the bars 351 may be made of a transparent material. In other embodiments the bars 351 may be made of an opaque material, for example, the same material as the outer sheath 318.

Alternatively a cover member (not shown) which partially covers a viewing notch 352 (see FIG. 22) or one or more openings 353 (see FIG. 23) may be mounted to the distal tip of a shaft or an insertion section 14 (see, for example, FIG. 1) Such a cover member may for example be a cage which allows a substantially clear field of view for the camera assembly 350 while providing additional protection for the camera assembly 350. In some embodiments, the cover member may include an optically clear partial covering.

Figure 23A:
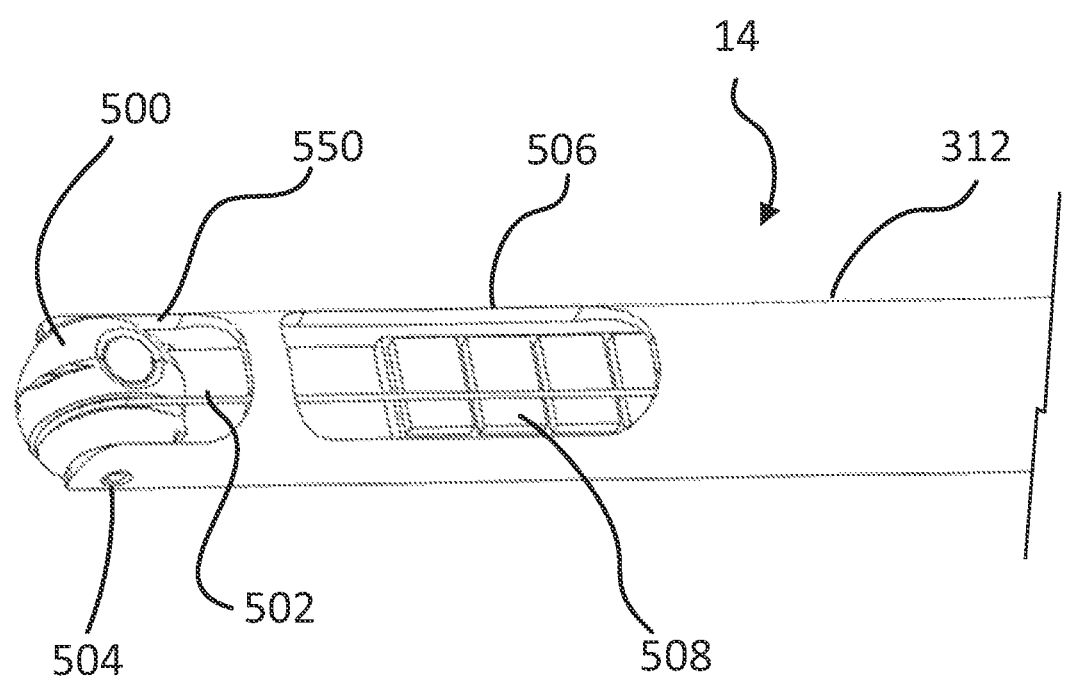
FIG. 23A shows a perspective view of the distal end of an endoscope shaft in which the camera assembly is mounted at the tip of the shaft without a protective guard, shield or tip structure.

In another embodiment, the camera assembly may be mounted at the distal end of an endoscope shaft without a protective tip structure 342. Although a tip structure 342 may provide some protection to a camera assembly, it may also inhibit a full field of view of the camera in all positions within its range of motion. An example of an alternative arrangement is shown in FIG. 23A. In this example, the sensor or camera housing 500 itself is constructed to provide adequate protection to an enclosed camera assembly (e.g., lens and sensor assembly). For example, the camera housing 500 may be at least partially constructed of steel or similarly strong material; at least an outer shell of the housing can be so constructed to withstand physical abuse when the insertion end of the endoscope is introduced or repositioned. The exposed portion of the housing 500 preferably has an outer spherical, spheroid (oblate, prolate, etc.) or dome shape—or an otherwise rounded shape providing rounded edges to help prevent damage to tissues as the endoscope shaft is inserted or moved within the operative field. Placing the camera assembly in a reinforced and at least partially rounded housing 500 at the distal end or tip 550 of the endoscope shaft 14 provides an unobstructed view of a greater portion of the surgical field, without placing the camera assembly or nearby tissues at risk of damage. In this example, the sensor or camera housing 500 can be rotated using pull wires 502, cables or bands about an axis 504 so that an optical axis of the camera assembly (lens and sensor assembly) can be aimed from less than zero degrees to more than ninety degrees with respect to the long axis of the distal end 550 of the endoscope shaft 14. If the sensor or camera assembly is arranged to have a wide field of view, then the range of motion of the camera housing can be arranged to provide an optical axis range of motion of between about 35 degrees and about 115 degrees with respect to the long axis of the endoscope shaft at its distal or insertion end. In this arrangement, the operator can still view the operative field directly opposite the distal end of the endoscope shaft, yet be able to view a region of the surgical field behind the tip of the endoscope. This arrangement may also allow the operator to irrigate the surface of the camera assembly to remove any accumulated surface debris by rotating it to a position equal to or greater than 90 degrees.

Figure 23B:
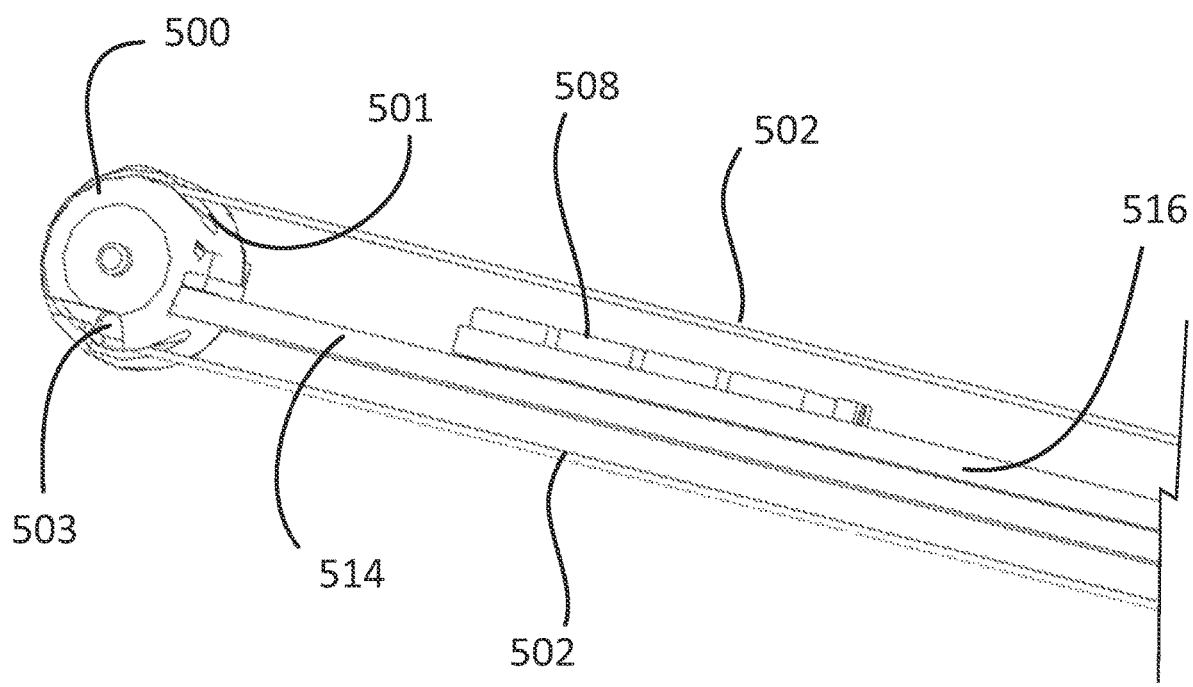
FIG. 23B shows a rotatable camera housing with pull wire, and a bank of LED's at an exposed end of an endoscope shaft (surrounding sheath removed)
Figure 23C:
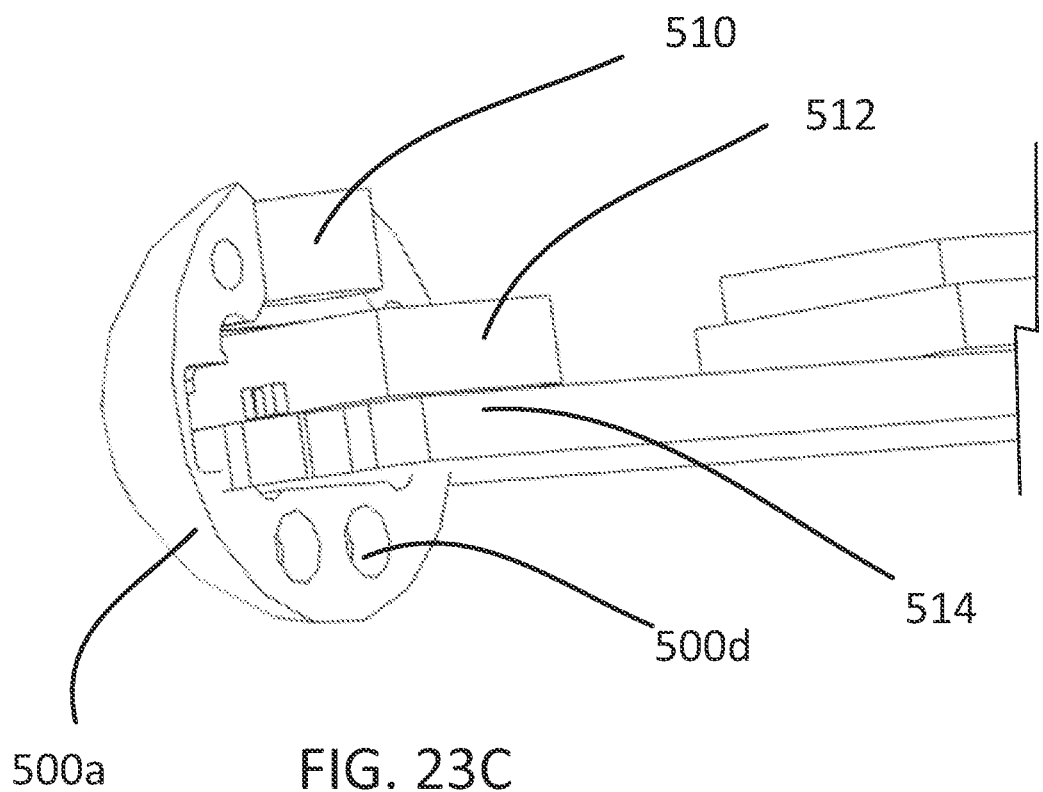
FIGS. 23C and 23D show each half of a spheroid rotatable housing for a camera assembly.
Figure 23D:
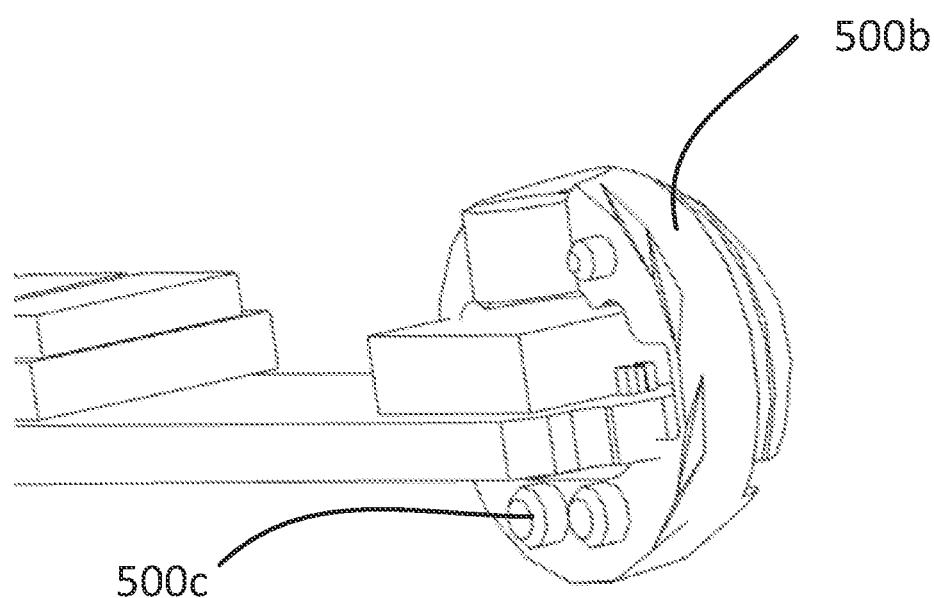
Figure 23E:
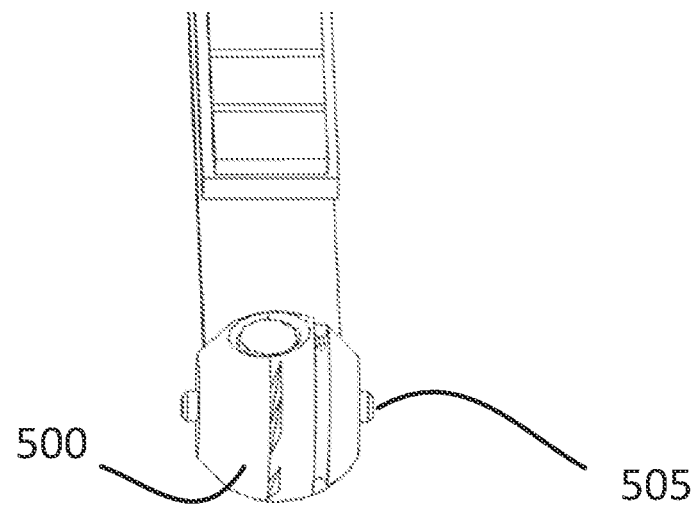
FIGS. 23E and 23F show the pivoting and bearing elements allowing for rotation of a housing for a camera assembly.
Figure 23F:
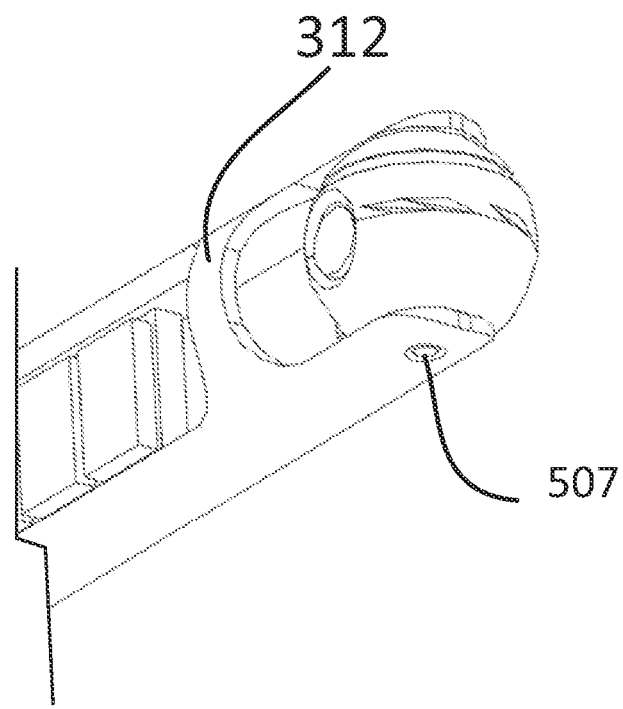
Figure 24:
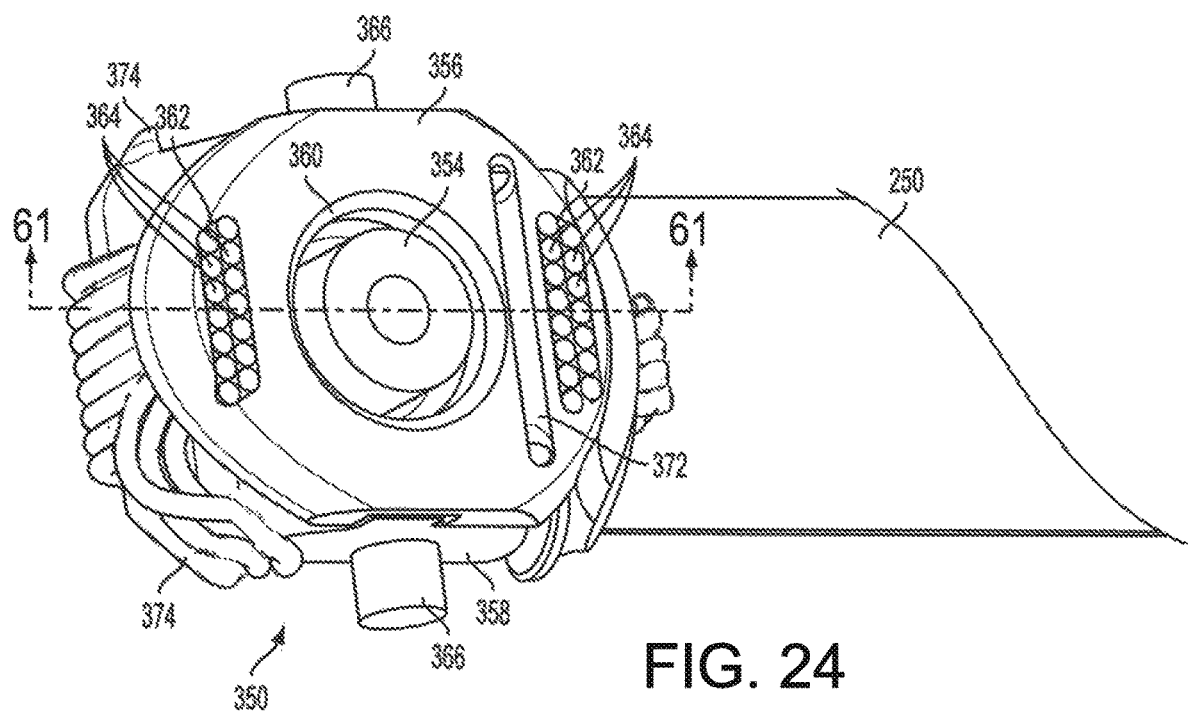
FIG. 24 shows a perspective view of a camera assembly.

A camera assembly 350 is shown in isolation in FIG. 24. This arrangement is more suited to the insertion section or shaft shown in FIG. 23, because of the physical protection offered by the rounded tip 342 of the working end of the distal endoscope shaft shown in FIGS. 18-23. As shown, a ribbon or flex cable 250 is coupled into the camera assembly 350 and may provide power and data communication paths to and from the camera assembly 350. The camera assembly 350 may be any suitable structure configured to support the camera of the endoscope 10. In embodiments where the camera assembly 350 may be panned, the camera assembly 350 may include pivot actuator attachment features.

As shown, the camera assembly 350 may include a lens assembly 354. As shown, the lens assembly 354 may be held in place between a camera housing top 356 and a camera housing bottom 358. When assembled, the camera housing top 356 and camera housing bottom 358 may be coupled together by any suitable means, such as, but not limited to glue, adhesive, ultrasonic welds, press fit of cooperating features, etc. In the example embodiment in FIG. 24, the lens assembly 354 projects through a lens opening 360 in the camera housing top 356 such that it may have a clear view of the target anatomical area. In some embodiments, at least a portion of the lens assembly 354 may be proud of the camera housing top 356.

The camera housing top 356 may include a number of other voids. In the exemplary embodiment shown in FIG. 24, the camera housing top 356 includes two elongate light projection voids 362 disposed on the right and left (relative to FIG. 24) flanks of the lens opening 360, the voids 362 being designed to accommodate terminal elements of optical fibers (or optionally other light sources such as LEDs) to project light onto a target area coinciding with the direction at which a camera lens or lens assembly 354 may be aimed. In the example shown, the right elongate void 362 is trapezoidal in shape while the left elongate void 362 is rhomboid in shape. In alternative embodiments, the shape of the voids 362 may differ, for example, both may be ovoid. In alternative embodiments, there may be additional voids 362. For example, in some embodiments, there may be three voids 362 arranged in a triangular configuration around the lens opening 360. In some embodiments there may be four voids 362 arranged in a rectangular, square, circular, or ovoid configuration around the lens opening 360.

One or more illumination sources for the endoscope 10 may be included at least partially within the endoscope 10. The illumination source or sources may illuminate the field of view of the camera of the camera assembly 350 regardless of its panned position. In some embodiments, the illumination source may be in the camera assembly 350. In the example embodiment in FIG. 24, the illumination source is a number of optical fibers (e.g. fiberoptic fibers) 364 which may transmit light from a lighting element (not shown) external to the endoscope 10. The optical fibers 364 may be routed and coupled into the voids 362 in the camera housing top 356. In the example embodiment, 28 optical fibers 364 are routed into the voids 362 of the camera housing top 356. The number of optical fibers 364 may differ in alternate embodiments. The light emitting ends of the optical fibers 364 may be roughly flush with the top face of the camera housing top 356. In some embodiments, other illumination sources, for example LEDs, may be used. The optical fibers 364 or other illumination source may be configured to supply any desired color or intensity of light at a predetermined light projection angle.

As shown in the example embodiment in FIG. 24, the camera assembly 350 may include pivot pins 366. The pivot pins 366 may be pivotally coupled into the pivot pin bearings 346 in the camera assembly housing 330 (see FIG. 18). The pivot pins 366 may project substantially perpendicularly from the long axis of the insertion section. The pivot pins 366 may allow the camera assembly 350 and optical fibers 364 (or other illumination source) to pivot in tandem with one another.

The camera assembly 350 may also include a pivot actuator attachment feature as mentioned above. In the example embodiment in FIG. 24, the camera assembly 350 includes a top cable attachment feature or anchor point 372 and a bottom cable attachment feature or anchor point 374. The top cable attachment feature 372 and bottom cable attachment feature 374 will be further discussed below.

As mentioned above, the endoscope 10 may also include a pivot actuator or actuators. A pivot actuator may be an elongate member used to pull on or push the camera assembly 350 via a pivot attachment feature. In the illustrated examples, the pivot actuators are mostly pull cables or wires, but these examples should not be construed as strictly limiting pivot actuators to a cable-like structure. The elongate member may be flexible or substantially rigid. The elongate member may be round (as in the example of a cable), flat, or may have any other shape or cross section. In some embodiments, the pivot actuator may be a belt routed around a cooperating attachment feature frictional engaged or otherwise meshed with features on the inner circumference of the belt. In a preferred embodiment, the pivot actuator may be used to only supply a pulling force. Such an arrangement allows for a smaller diameter insertion section 14 (see FIG. 3A) because the pivot actuator does not have to be sufficiently thick or cross-sectionally strengthened, or confined within a supporting track to prevent substantial lateral displacement within the insertion section 14 in response to a pushing force against the pivot actuator. A pull-wire or pull-cable arrangement also allows a greater range of materials to be used in constructing the pivot actuator because the material only needs to have tensile strength, rather than compressive stiffness.

Figure 25:
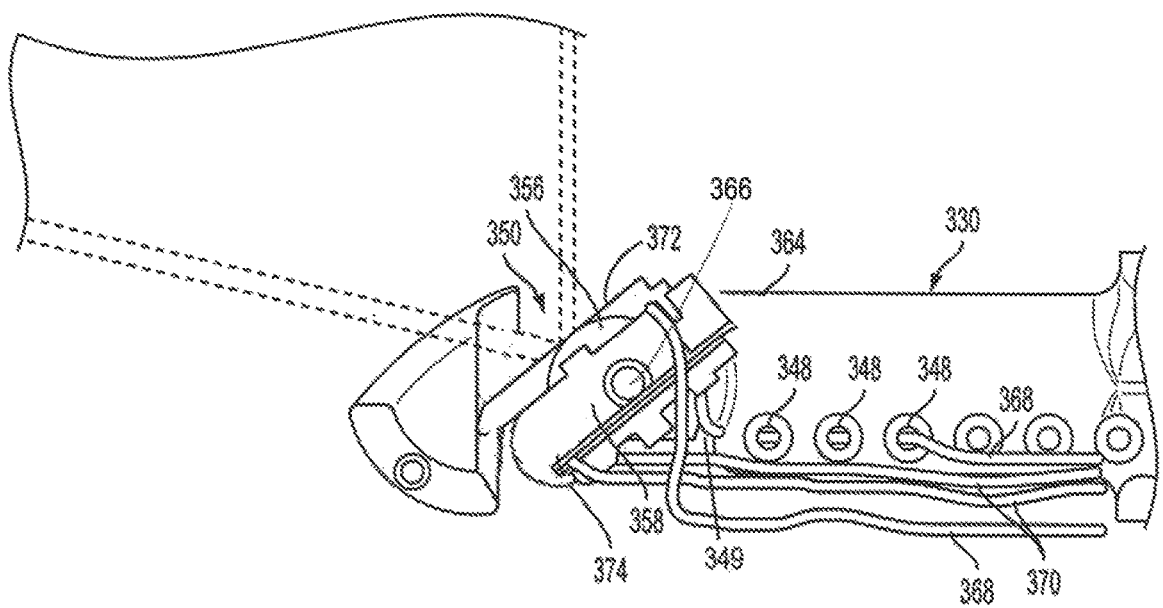
FIG. 25 shows a side view of a camera assembly and a camera assembly mount with a wall of the camera assembly mount removed for clarity.

As shown in FIG. 25, panning cables may be attached to the camera assembly 350 above and below the pivot pins 366. In the example embodiment, the panning cables are shown as relatively slack for ease of illustration. In operation one or more panning cables on one side of the pivot pins 366 would be under tension, while one or more panning cables on the other side of the pivot pins 366 would be slack. As detailed above and referring now also to FIG. 14, the panning cables may be attached proximally to the cable attachment holes 202 of the pivot control structure 100 (see FIG. 14). In some embodiments, two panning cables may be attached to each cable attachment hole 202. The panning cables may extend from the cable attachment holes 202 in the pivot arm 198 and be routed through one or more orifices 178 in the proximal section 161b of the inner sheath mount 160 (see FIG. 11A). The panning cables may then extend through the utility hole 168 alongside the flex cable 250. Since the cable attachment holes 202 are located on opposite sides of the pivot point of the pivot arm 198, pivoting the pivot control structure 100 may cause the panning cables attached to one of the cable attachment holes 202 to slacken and panning cables attached to the other to become taut. By attaching the panning cables associated with one cable attachment hole 202 to the camera assembly 350 on one side of the pivot pins 366 and attaching the panning cables associated with the other cable attachment hole 202 to the opposite side of the pivot pins 366, the pivot control structure 100 may be used to selectively rotate the camera assembly 350. In some embodiments, pushing the pivot control structure 100 forward may pan the camera assembly 350 forward while pulling the pivot control structure 100 aft may pan the camera assembly 350 backward. In some embodiments, when assembled, all of the panning cables may be under tension.

In a preferred embodiment, only a single panning cable may be attached to each cable attachment hole 202 on the pivot control structure 100 pivot arm 198 (see FIG. 14). In such embodiments, there may be a top panning cable 368 and a bottom panning cable 370. The top panning cable 368 and bottom panning cable 370 may extend as described above to the camera assembly 350. The top panning cable 368 may wrap around a top cable attachment feature 372 on the camera assembly 350 and return back to the same cable attachment hole 202 on the pivot arm 198 from which it originates. The bottom panning cable 370 may wrap around a bottom cable attachment feature 374 on the camera assembly 350 and return back to the same cable attachment hole 202 from which it originates. Alternatively, the panning cable may be looped through attachment hole 202, with both ends of the cable terminating on the cable attachment feature distally.

In the example embodiment, the top cable attachment feature 372 (best shown in FIG. 24) includes two holes in the camera housing top 356. The top cable attachment feature 372 additionally includes a recess that connects the two holes. The top panning cable 368 may enter one of the holes, follow the recess, and exit the other of the two holes to return to the cable attachment hole 202 (see FIG. 14) in the handle. The bottom cable attachment feature 374 (best shown in FIG. 24) includes two attachment points or hooks which project off opposite sides of the camera housing bottom 358. The bottom cable attachment feature 374 is on the opposite side of the pivot pins 366 than the top cable attachment feature 372. The bottom panning cable 370 may be wrapped around one attachment point or hook of the bottom cable attachment feature 374, strung over to the second attachment point or hook of the bottom cable attachment feature 374 and from there return to its cable attachment hole 202 on the pivot arm 198 of the handle. In alternate embodiments, the top cable attachment feature 372 and/or bottom cable attachment feature 374 may comprise, for example, eyelets, prongs, pegs, etc.

The top panning cable 368 and bottom panning cable 370 may be made from any suitable cable or wire-like material, either metallic or synthetic polymer, either braided or monofilament. The top panning cable 368 and bottom panning cable 370 may, for example, be metal or plastic strips or bands that are laterally flexible. In a preferred embodiment, the top panning cable 368 and bottom panning cable 370 are made from a material which is resistant to stretching under tension. Wrapping a single panning cable from each cable attachment hole 202 on the pivot arm 198 (see FIG. 14) around a pivot actuator attachment feature on the camera assembly 350 may be desirable because it ensures that the side of the panning cable running to the camera assembly 350 is under the same tension as the side of the panning cable returning from the camera assembly 350; any stretching of some portion of the cable over time or use will have an equal effect on both halves of the cable.

In a preferred embodiment, the top panning cable 368 may be run through one of the cable guide holes 348 on each interior wall of the camera assembly mount 330. As shown in FIG. 25, the top panning cable 368 is threaded through one of the cable guide holes 348 and continues extending toward the camera assembly 350 along the exterior of the camera assembly housing 330. In some embodiments, there may be a depression or trough recessed into the exterior of the camera assembly housing 330 along the path taken by the top panning cable 368. In such embodiments, the depression or trough may serve as a guide. The depression or trough may also help to ensure that the top panning cable 368 is roughly flush to exterior surface of the camera assembly housing 330. This may help to ensure that the outer sheath 318 (see FIG. 21) does not impinge on the top panning cable 368 to impair its movement during the use of a fully assembled endoscope 10.

As shown in FIG. 25, the top panning cable 368 is strung through the constraining notch 349 as it re-enters the interior of the camera assembly housing 330. The top panning cable 368 then runs to the top cable attachment feature 372 as describe above. On return to the cable attachment hole 202 (see FIG. 14), the top panning cable 368 runs from the top cable attachment feature 372 to the constraining notch 349 on the opposite wall (see FIG. 18) of the camera assembly housing 330. The top panning cable 368 then runs along the exterior surface of the front wall of the camera assembly housing 330 and optionally along a depression or trough in the wall. The top panning cable 368 then re-enters the interior volume of the camera assembly housing 330 and travels back to the cable attachment hole 202 in the handle as described previously.

A terminal segment of a pivot actuator (such as a wire or cable) proximal to its connection to a pivoting assembly at the distal end of the insertion section may be constrained at a fulcrum or support point to re-direct the actuator so as to form an angle with respect to the long axis of the insertion section or shaft. For example, by running the top panning cable 368 through the cable guide holes 348 and the constraining or re-directing notches 349, and then angling it up to the top cable attachment feature 372 on the other side of pivot pin 366, an increased pivotal range for the pivoting camera assembly 350 may be achieved. Thus an image sensor having a pre-determined or fixed angular field of view may be rotated to allow for a rotatable field of view, so that the viewable area can be increased to a range of up to 180 degrees. In other embodiments, an image sensor may be rotated so as to achieve a viewable area that exceeds 180 degrees. As shown in FIG. 25, having the cable routed as described places the cable at a more acute angle of incidence to its attachment point 372, and thus permits a greater degree of back-rotation of the camera assembly 350.

Figure 26:
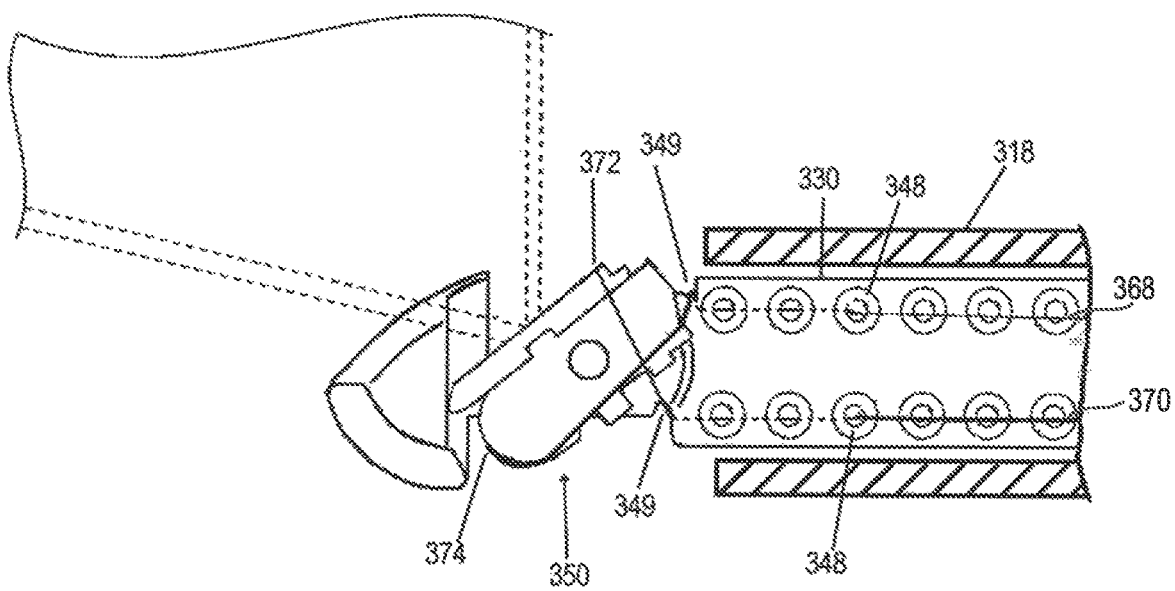
FIG. 26 shows a side view of an alternate exemplary camera assembly and camera assembly mount with a wall of the camera assembly mount removed for clarity.

In some embodiments, and referring now also to FIG. 26, the camera assembly 350 may be capable of rotating a full 180 degrees or more, because of the presence of two sets of cable guide holes 348: a lower set of guide holes 348 to control the camera housing top section, and an upper set of guide holes 348 to control the camera housing bottom section. The degree to which the camera assembly 350 can be rotated is a function of the angle that the terminal portion of the panning cable makes with respect to the proximal portion of the panning cable or the longitudinal axis of insertion section (or endoscope shaft) 14 (see FIG. 1). The greater the angle the terminal portion of the panning cable makes as it re-enters the exterior of the camera assembly housing 330 in relation to the longitudinal axis of the insertion section 14, the greater the range of motion it can induce in the camera assembly 350. In a preferred embodiment, the re-entry surface or re-directing guide of the camera assembly housing 330 is positioned to provide for an angle of the terminal portion of the panning cable to be within a range of about 30-90 degrees with respect to the long axis of insertion section 14. In other embodiments, the rotational range of motion of the camera assembly 350 may be improved while limiting the frictional resistance of the panning cable by positioning the cable re-entry surface or guide to achieve an angle of the terminal portion of the panning cable to be within a range of about 45-80 degrees. Such an embodiment, as described above, only requires a pulling force on either of a pair of complementary cables 368, 370 one angled up at a distal or terminal location in insertion section 14 to attach to the top cable attachment feature 372, and one angled down at a distal or terminal location in insertion section 14 to a corresponding bottom cable attachment feature 374. With this arrangement, neither actuating cable is required to move laterally or transversely within most of the length of insertion section 14, which allows the internal space within insertion section 14 to be narrower, helping to minimize its overall diameter.

In some embodiments, a constraining or re-directing notch 349 may not be used. Some embodiments may use a different type of constraint or re-directing element incorporated into a wall at the distal end of the insertion section. In some embodiments, a pulley or an eyelet may be used as a constraint. A pin, peg, post, etc. may also be used as a constraint or re-directing element. In some embodiments, a curved finger or prong may be formed in the side walls of the camera assembly housing 330. The curved finger may extend into the interior volume of the camera assembly housing 330 such that there is a space between the interior wall of the camera assembly housing 330 and the curved finger. The top panning cable 368 may be run through this space so that it is constrained by the curved finger. In most embodiments, it may be desirable that the point of contact between the constraint and the cable has a smoothness or radius of curvature sufficient to minimize the potential for frictional damage to the panning cable during operation of the endoscope. In some cases, the constraint may be coated with a material having a low coefficient of friction such as Teflon.

In some embodiments, the bottom panning cable 370 instead of the top panning cable 368 may be constrained similarly to the preceding description to enable a greater pivotal range of the camera assembly 350 in one direction of rotation over another. As shown in FIG. 26, in some embodiments, both the bottom panning cable 370 and top panning cable 368 may be constrained or redirected, allowing for even greater pivotal ranges.

In FIG. 26, the outer sheath 318, camera assembly housing 330, and camera assembly 350 are shown. There are two sets of cable guide holes 348. One set is above the longitudinal axis of the camera assembly housing 330 and the other is below the longitudinal axis of the camera assembly housing 330. There are also two constraining notches 349. One of the constraining notches 349 is located above the longitudinal axis of the camera assembly housing 330 and the other is located below the longitudinal axis of the camera assembly housing 330.

An improved mechanical advantage of the panning cables may be obtained by positioning the re-directing element (e.g. notch) on one side of (e.g., below) the pivoting axis of the camera assembly 350, while attaching the terminal end of the panning cable to a point on the camera assembly 350 located on the opposing side of (e.g. above) the pivoting axis of the camera assembly 350.

As shown, the top panning cable 368 is run through one of the cable guide holes 348 below the longitudinal axis, and re-enters the camera assembly housing 330 at the constraining notch 349 below the longitudinal axis. The top panning cable 368 then redirects up to the top cable attachment feature 372 on the camera assembly 350. In FIG. 26, the bottom panning cable 370 is run through a cable guide hole 348 above the longitudinal axis of the camera assembly housing 330. The bottom panning cable 370 then re-enters the camera assembly housing 330 through the constraining notch 349 above the longitudinal axis of the camera assembly housing 330. The bottom panning cable 370 then redirects down to the bottom cable attachment feature 374. The top panning cable 368 and bottom panning cable 370 may wrap around a portion of the camera assembly 350 depending on where the camera assembly 350 has been pivoted to. In FIG. 26 the bottom panning cable 370 is shown wrapping around a portion of the camera assembly 350.

Figure 27:
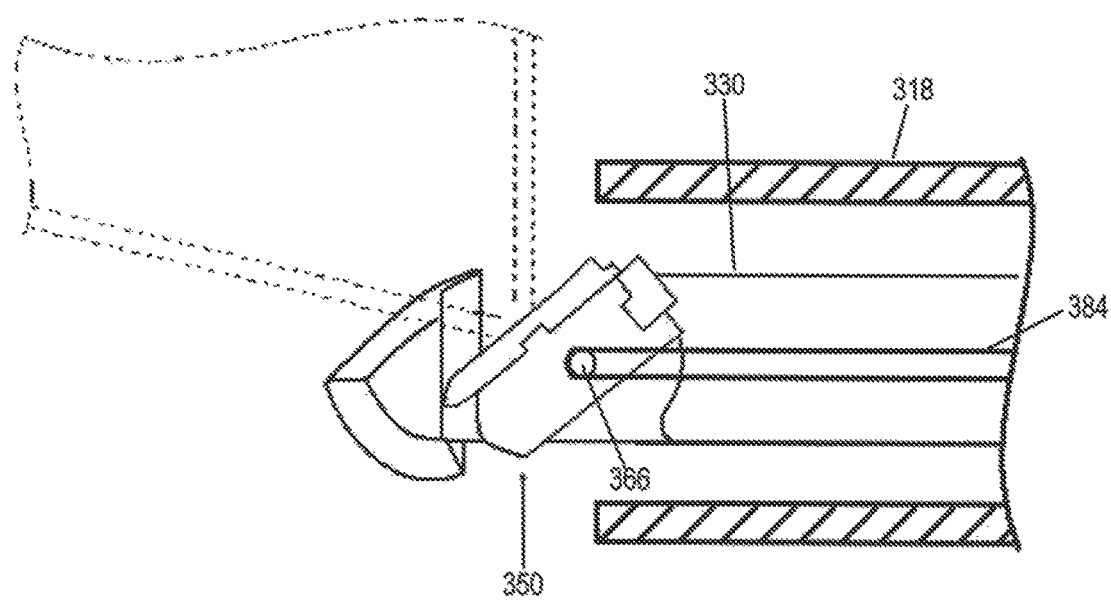
FIG. 27 shows a side view of an alternate exemplary camera assembly and camera assembly mount with a wall of the camera assembly mount removed for clarity.

Some embodiments may make use of a belt 384 as a pivot actuator. An embodiment which includes a belt 384 as a pivot actuator is shown in FIG. 27. As shown, the belt 384 wraps around one of the pivot pins 366 of the camera assembly 350. In some embodiments, the pivot pins 366 may be elongated such that a portion of at least one of the pivot pins 366 extends from the pivot bearings 346. In such embodiments, the belt 384 may be wrapped around this portion of the pivot pins 366 as shown in FIG. 27. In some embodiments, the shape of the camera assembly 350 may differ such that the belt 384 may wrap around the camera assembly 350. For example, the camera assembly 350 may be a substantially cylindrical shape. The substantially cylindrical shape of the camera assembly 350 may be coaxial with the pivot pins 366. In such embodiments, the belt 384 may be wrapped around the circumference of camera assembly 350.

In some embodiments, the surface over which a belt 384 is wrapped may be recessed (e.g., V-shaped) in relation to the surfaces which flank it. This may help to keep the belt 384 in place during operation. In other embodiments, any other type of guide may be used. For example, the surface over which a belt 384 is wrapped may be flanked by two walls which keep the belt 384 in place during operation.

A belt 384 may be made of a high friction material so that the belt 384 does not slip over the surface which it wraps around as the belt 384 is driven. In some embodiments, the belt 384 may have a coarse surface, or may be toothed to aid in its ability to grip or positively engage a camera assembly pivot pin 366 (which may be geared). Use of a belt 384 may allow for a wide range of pivoting of the camera assembly 350 without the need for a pull-cable pivot actuator to be redirected laterally within the insertion section 14 to achieve an equivalent range of motion of the camera assembly 350. This allows the insertion section 14 to be made with a smaller diameter.

In embodiments using a belt 384, the belt 384 may be configured to be driven by displacement of the pivot control structure 100 (see FIG. 14). In some embodiments, the opposite end of the belt 384 from that which wraps around the camera assembly 350 or pivot pins 366 may wrap around the pivot shaft 204 of the pivot control structure 100. In such embodiments, rotation of the pivot shaft 204 may drive the belt 384. The portion of the pivot shaft 204 which the belt 384 wraps around may have a relatively large diameter. This may be desirable so that only a small pivotal displacement of the pivot shaft 204 is needed to drive the belt 384 a relatively large amount. In embodiments where the belt 384 includes teeth, the teeth of the belt 384 may interdigitate with a gear located on the pivot shaft 204 of the pivot control structure 100. In such embodiments, rotation of the pivot shaft 204 and gear on the pivot shaft 204 may drive the belt 384. As the belt 384 is driven, the movement of the belt 384 will exert a driving force on the camera assembly 350 causing the camera assembly 350 to pivot.

In other embodiments, the pivot actuator may be the rack of a rack and pinion arrangement. In such embodiments, the pivot pins 366 of the camera assembly 350 may include a toothed portion. The toothed portion of the pivot pins 366 may be the pinion gear that interdigitates with the rack of the pivot actuator. As the rack displaces longitudinally within the insertion section 14, this motion is translated into rotation of the camera assembly 350 via the toothed, pinion portion of the pivot pins 366. While such an embodiment does not solely rely on a pulling force to rotate the camera assembly 350, the pivot actuator still does not require lateral displacement of the actuator within the insertion section 14. In some specific embodiments, a push-pull rack-type actuator may nevertheless require features (e.g., rigidity, thickness) or may otherwise be constrained within a track to prevent lateral or side-to-side flexion during the application of a compressive force on the rack In yet another arrangement using one or more panning cables, a similar pivotal range may be achieved without requiring any routing of a panning cable through various features included in a camera assembly mount 330. This may be desirable because it may allow the diameter of an insertion section 14 (see FIG. 1) to be made smaller. Additionally, a camera assembly mount 330 for such an embodiment would not require any fenestrations (e.g. the cable guide holes 348 of FIG. 18) or re-directing elements/constraints (e.g. the constraining notch 349 of FIG. 18) thus simplifying manufacture of a camera assembly mount. Such an embodiment may for example use the camera assembly mount 330 and inner sheath 312 shown in the example embodiment in FIG. 19.

In such an embodiment, a camera assembly 350 may include one or more spooling features or surfaces 1400. The spooling feature is configured to at least partially wind the terminal portion of a panning cable around the housing of the camera assembly 350. A connection or attachment point for the terminal end of the panning cable may be situated on the camera assembly housing distal to the spooling feature. The spooling feature preferably has a curved, somewhat recessed surface, which may partially or completely wrap around a portion of the camera assembly housing. Thus, in various embodiments, a panning cable may wind around the housing only partially, or in one or more complete loops around the housing. A longer spooling feature provides for a more extensive range of rotation of the camera assembly. During actuation, an associated panning cable may be wound or unwound from the spooling feature 1400. Spooling feature 1400 may increase the pivotal range of a camera assembly 350. Spooling feature 1400 may allow a more consistent torque to be applied to a camera assembly 350 during rotation. Spooling feature 1400 may be constructed to create a moment arm of desired or varying length. Additionally, positioning the spooling feature 1400 radially apart from the axis of rotation of the camera assembly may help a panning cable to generate rotational torque more efficiently.

The progression of FIGS. 28-32 conceptually illustrate a camera assembly 350 including a spooling feature 1400 in a number of rotational positions. As shown, the spooling feature 1400 may include an arcuate portion and a straight portion. The arcuate portion is shaped such it has a radius of curvature which extends from the pivot axis of the camera assembly 350. The straight portion of the spooling feature 1400 is angled such that is serves as a torque increasing feature. Additionally, the straight portion of the spooling feature 1400 allows the camera housing 355 to be made with more material (which would otherwise need to be removed to continue the arcuate section) and thus increases the structural integrity of the camera housing 355. This may be particularly important in embodiments where the camera assembly 350 is designed to fit in a very small space and thus must be made with a very small form factor.

As shown in FIG. 28 the top panning cable 368 may be wound around the spooling feature 1400. A pulling force exerted by the top panning cable 368 would create a torque about the pivot axis of the camera assembly 350 causing the camera assembly 350 to rotate in a clockwise direction. Additionally, the straight portion of the spooling feature 1400 creates a longer moment arm thus increasing the torque generated for a given amount of pulling force.

As the camera assembly 350 rotates to the position shown in FIG. 29, the top panning cable 368 begins to unwind from the spooling feature 1400. As force continues to be applied and the camera assembly continues to rotate, the top panning cable 368 will continue to unwind from the spooling feature as shown in FIG. 30. When sufficiently unwound, the point at which the top panning cable 368 leaves the spooling feature 1400 will be located on the arcuate section of the spooling feature 1400 (as shown in both FIG. 29 and FIG. 30). In an embodiment, all points on the arcuate section of the spooling feature 1400 may be located an equal distance from the pivot axis.

In an exemplary embodiment, as a pulling force continues to be exerted by the top panning cable 368, the camera assembly 350 will continue to rotate until the top panning cable 368 no longer contacts the surface of the spooling feature 1400 as shown in FIG. 31. The camera assembly 350 may then continue to rotate until the pulling force of the top panning cable 368 approaches coincidence with the axis of rotation of the camera assembly 350. This position is depicted in FIG. 32. As would be understood by one skilled in the art, a panning cable 368 may be wound around a spooling feature 1400 one or more times to increase the amount of rotation which may be created using the panning cable 368. The degree to which a panning cable 368 winds around a contact surface on the camera assembly 350 allows for a range of rotation of the camera assembly 350 that exceeds 90 degrees. The degree of rotation of the camera assembly 350 would then be limited only by the amount of slack and the flexibility of the attached electronic flex cable and/or the optical fiber bundle.

In an embodiment, the panning cable and spooling surface are arranged to permit the camera assembly 350 to rotate to a position between about 90 degrees to about 120 degrees of the long axis of the distal endoscope shaft, orienting the lens surface of the camera assembly at least partially in the direction of the proximal end of the endoscope shaft. In this position, any debris or other contamination of the lens surface may be washed away by irrigation fluid traveling distally in the endoscope shaft.

To rotate the camera assembly 350 from its position in FIG. 32 to the position shown in FIG. 30, a pulling force may be exerted via the bottom panning cable 370. In some embodiments, the bottom panning cable 370 may also be associated with a spooling feature. For example, the corners or edges of the camera assembly 350 around which the bottom panning cable 370 may wrap may be rounded.

FIG. 33-34 depicts a top perspective view of a specific example embodiment of a camera assembly 350 which includes a spooling feature 1400. The camera assembly 350 includes a lens assembly 354. The lens assembly 354 is disposed inside of a camera housing 355. The spooling feature 1400 may be recessed into a side of the camera housing 355 as shown. The spooling feature 1400 in the example embodiment includes an arcuate portion and a straight portion. The arcuate portion of the spooling feature 1400 is shaped such it has a radius of curvature which extends from the center of the pivot pins 366 or pivot axis.

As best shown in FIG. 33, the wall into which the spooling feature 1400 is recessed may include a first void 1402. The camera housing 355 may also include a second void 1404. The second void 1404 may pass through the top face of the camera housing 355 to the bottom face of the camera housing 355.

As shown, only a single panning cable 1406 may be used. The panning cable 1406 may extend through both the first void 1402 and the second void 1404 in the camera housing 355. One end of the panning cable 1406 may be attached to a cable attachment hole 202 on the pivot arm 198 (see FIG. 14). The other end of the panning cable 1406 may be attached to the other cable attachment hole 202 on the pivot arm 198. In some embodiments, the panning cable 1406 may be fixedly attached to the camera housing 355 at one or more points. For example, an adhesive of glue may be placed into one of the voids 1402 or 1404. This may ensure that the panning cable 1406 does not slip or move over the surface of the camera housing 355 during actuation. Additionally, in some embodiments, the panning cable 1406 may be knotted in one or more location. For example, the panning cable 1406 may be fed through one of the voids 1402 or 1404, knotted, and then fed through the other of the voids 1402 or 1404. Preferably, the width of the knot may be sufficiently wide so as to not fit through either of the voids 1402 or 1404. Such a knot may again help to keep the panning cable 1406 from slipping or moving over the surface of the camera housing 355 during actuation.

As would be appreciated by one skilled in the art, the embodiment shown in FIG. 33-34 may easily be modified to use two panning cables. One panning cable may terminate and be fixedly attached to the camera housing 355 in or at the location of the first void 1402. A second panning cable may terminate and be fixedly attached to the camera housing 355 in or at the location of the second void 1404.

In an alternative example, FIG. 23B shows how a pull wire 502 operated by the pivot control structure 100 may be wrapped around and/or attached to a rounded or dome-shaped sensor or camera housing 500 at the distal end of the endoscope shaft 14. The inner sheath 312 has been removed for clarity. In this example, camera housing 500 includes a nearly circumferential slot 501 offset to one side of the housing 500 so as not to interfere with the lens/camera assembly contained within the housing 500 (which is preferably positioned at about the center of two assembled halves of the housing). The pull wire 502 is retained within slot 501, and may be secured to the housing 500 at recess 503. A knot placed in the pull wire 502 may be embedded in recess 503 to act as an attachment point that causes the housing 500 to rotate when the pull wire 502 is moved back and forth along the endoscope shaft. Optionally, a small amount of adhesive may be used to provide added attachment security during assembly of the endoscope. In a preferred embodiment, the pull wire 502 comprises a Kevlar thread, which provides substantial longitudinal strength and resistance to stretching. Other wire types may include steel (braided or single-strand), nylon, or other materials of suitable strength and resistance to stretching.

The rounded sensor housing 500 shown in FIGS. 23A and 23B can enclose a more simply constructed lens 510 and image sensor 512, and the source of light for illumination of the operative field can be located near the sensor/camera housing 500 without having to be mounted to the housing itself. FIG. 23C and FIG. 23D show how a rounded or dome-shaped sensor/camera housing 500 can be constructed from two sections 500a and 500b. Each of these sections can be molded or machined to have internal cutouts for placement of the distal end of a PCB extension 514 or flex cable, its associated sensor 512 (e.g. CMOS or CCD) and a suitable lens 510. The two sections 500a and 500b can be joined over these components by a number of methods. In the example shown, one or more pins 500c of section 500b can be mated with a corresponding arrangement of matching recesses 500d of section 500a. As shown in FIG. 23E, a pivot shaft 505 on the outer side of each section can be inserted into corresponding holes, bearings or bushings 507 of the distal end of the inner sheath 312 of the endoscope shaft, which may be resiliently flexible to allow for assembly. An assembled housing 500 can be pressed or snap-fit into place within the holes 507, which may help to keep the two sections 500a and 500b joined together. Optionally, an adhesive may also be used to securely join the pins 500c to their corresponding recesses 500d. Although the illustrated sensor/camera housing 500 does not include a light source, this is an option; a suitably sized LED or group of LED's can be included around the periphery of the lens, or the terminus of a fiberoptic cable can be installed in a similar arrangement, as discussed below.

In an exemplary arrangement, one or more LED's 508 can be positioned along an open portion 506 of the inner sheath 312 of endoscope shaft 14. FIG. 33A shows a sensor 512 and lens 510 assembly within sensor housing 500 (half of the housing having been removed for clarity). Both the lens 510 and sensor 512 (e.g. a CMOS or CCD sensor) are suitably sealed to prevent liquid from entering between them. The sensor 512 may be connected to a ribbon or flex cable running through the endoscope shaft to the PCB in the endoscope handle. Similarly, the light source/LED's may be connected to the ribbon or flex cable to receive electrical power, or may be connected to a separate ribbon or flex cable adjacent to the sensor communications cable. In an alternative example, the main PCB in the endoscope handle can be manufactured with an elongate extension arranged to extend through the endoscope shaft to one or more components at the distal end of the shaft. The PCB may be constructed to have a flexible component sandwiched together with a rigid component. The flexible component may emerge from the main PCB to form a PCB extension for the endoscope shaft. The rigid component may similarly emerge from the main PCB to form a PCB extension for the endoscope shaft. Either or both of these extensions may alternatively be combined with a ribbon or flex cable coming from the main PCB to provide power or communications to components at the distal end of the endoscope shaft. For example, sensor 512 can be mounted to the distal end of a flexible PCB extension 514 from the main PCB in the endoscope handle 12. The sensor PCB extension 514 is flexible and has sufficient slack to permit rotation of the sensor 512 and lens 510 as the sensor housing 500 is rotated. Also, the light source in this example comprises one or more LED's 508 mounted to either the sensor PCB extension, or preferably mounted to a separate light source PCB extension 516. Because of the power requirements of the light source, mounting the power supply wires on a separate flex cable or PCB extension 516 may increase the reliability of the endoscope. Also, if the endoscope shaft 14 is rigid (e.g. as would be the case for most arthroscopes), the light source power wires can be mounted to a rigid PCB extension, further enhancing the overall robustness of the endoscope. In the example shown in FIG. 33A, a flexible sensor PCB extension 514 has been folded over at its base and placed against a rigid light source PCB extension 516, both extensions merging into the main PCB within the handle 12 of the endoscope (see below).

Figure 33B:
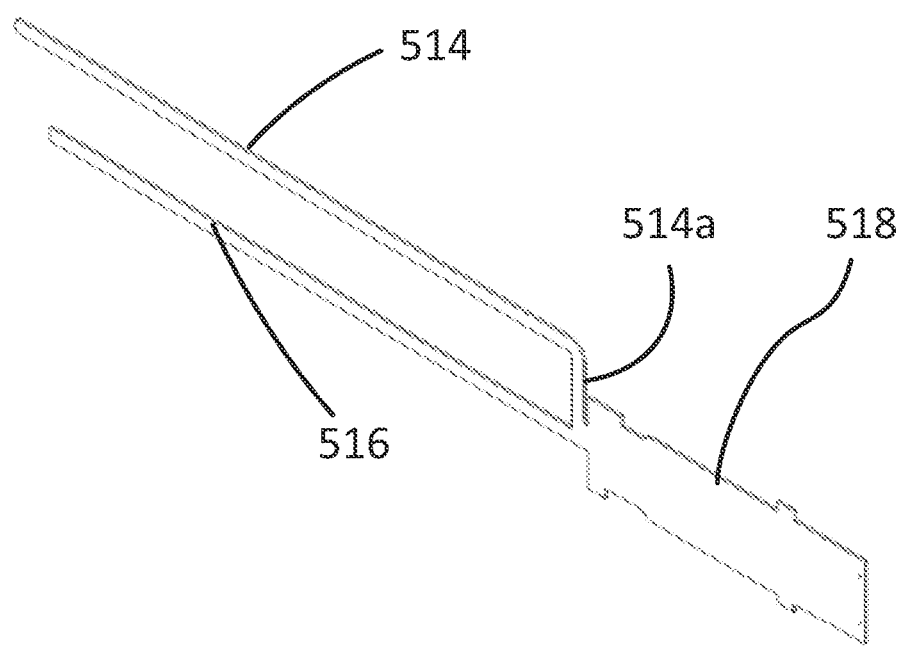
FIG. 33B shows a form factor for a PCB for an endoscope with extension components for the endoscope shaft.
Figure 33C:
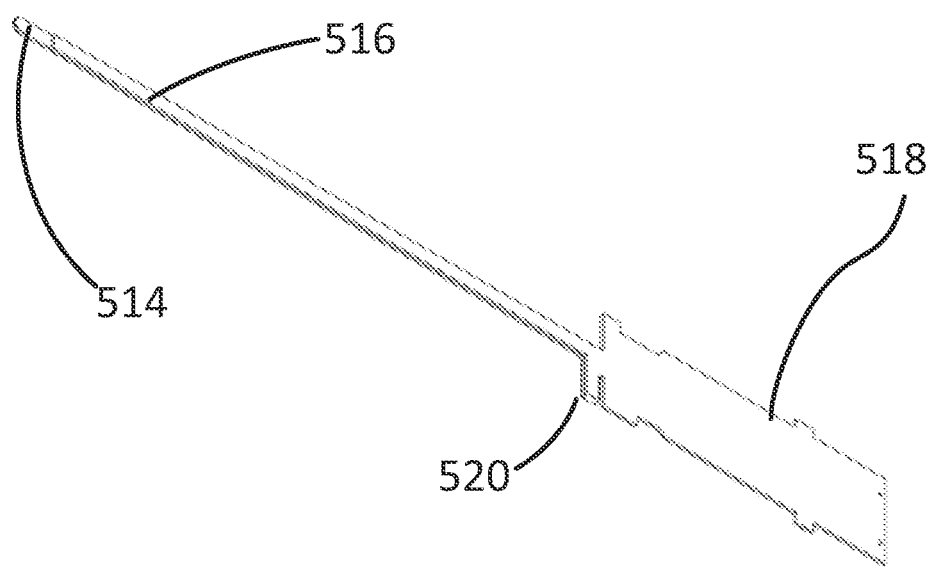
FIG. 33C shows the PCB of FIG. 33B with one flexible extension folded over another extension of the PCB.

The form factor for the printed circuit board (PCB) for the embodiment shown in FIGS. 23A and 33A is shown in FIG. 33B. Note that the form factor shown in FIGS. 33B and 33C may also be used to represent how a ribbon or flex cable can be folded over to run adjacent a companion ribbon or flex cable, or adjacent a companion PCB extension through the bulkhead and along the endoscope shaft to connected components at the distal end of the shaft. In one example, the rigid main PCB 518 (on which a number of electronic processing components are mounted) comprises a composite of both rigid and flexible components sandwiched together, the main PCB 518 being located within the endoscope handle. A flexible PCB extension portion 514 emerges from the composite main PCB 518 at an angle to the direction of a rigid extension portion 516, so that a proximal leg 514a of the flexible extension portion 514 can be folded over at point 520 (FIG. 33C) to run adjacent to the rigid portion 516, as shown in FIG. 33C. In the example shown, the proximal leg 514a of the flexible board extension is at an angle of approximately 90 degrees with respect to the rigid board extension. In some embodiments, the angle may be less than or more than 90 degrees, due to the flexibility of the flexible board extension permitting the proximal leg 514a to accommodate an imperfectly aligned fold. The flexible PCB extension 514 is shown running adjacent to the rigid PCB extension 516 in FIG. 33D along the endoscope shaft (inner sheath, sensor housing and lens removed for clarity). In this manner, both PCB extensions can pass through an elastomeric slot in a bulkhead or fluid barrier, such as the slot 177 shown in FIG. 11B or 11C.

Figure 33D:
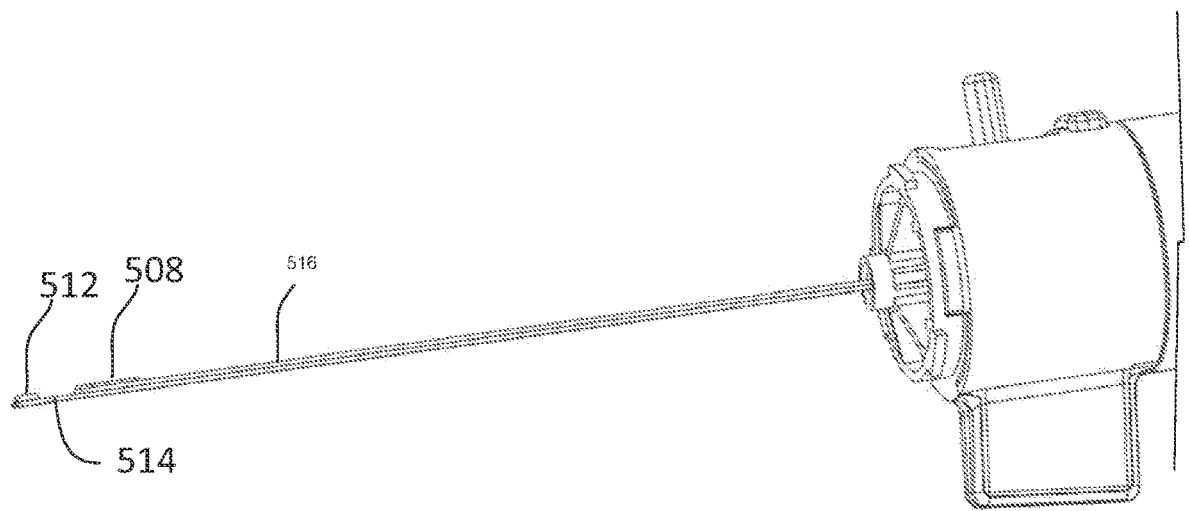
FIG. 33D shows how the PCB extensions are positioned in an endoscope shaft (sheath removed)
Figure 33E:
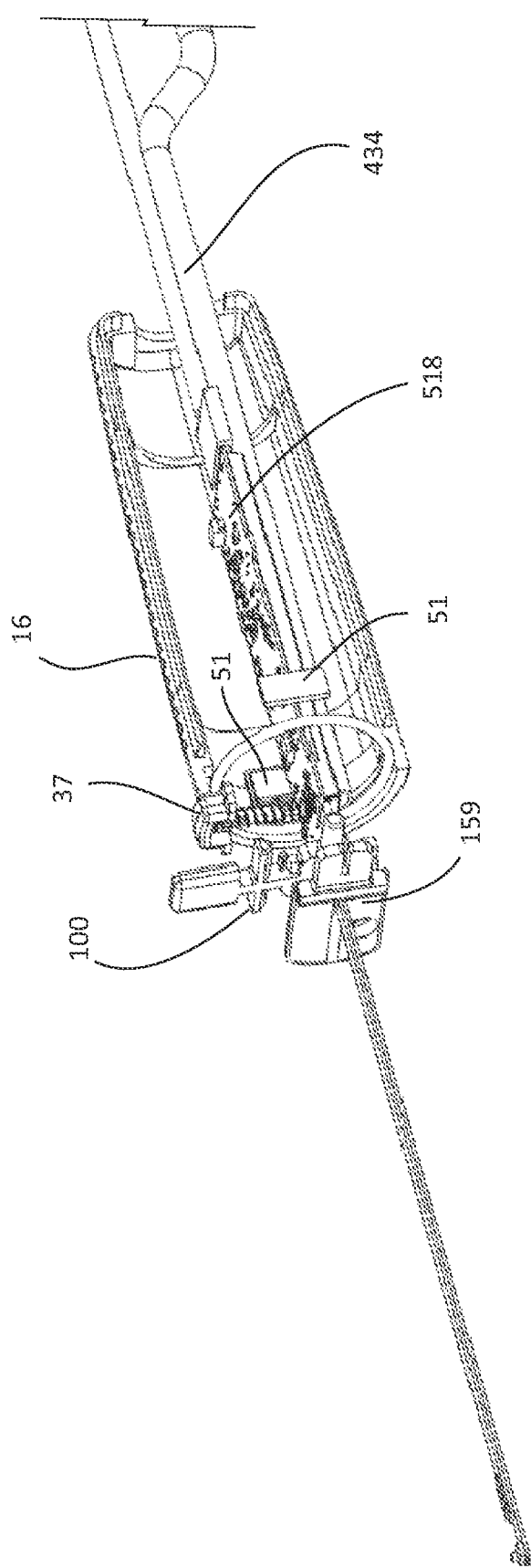
FIG. 33E shows a partially assembled endoscope showing a pass-through fluid barrier or bulkhead and PCB.
Figure 33F:
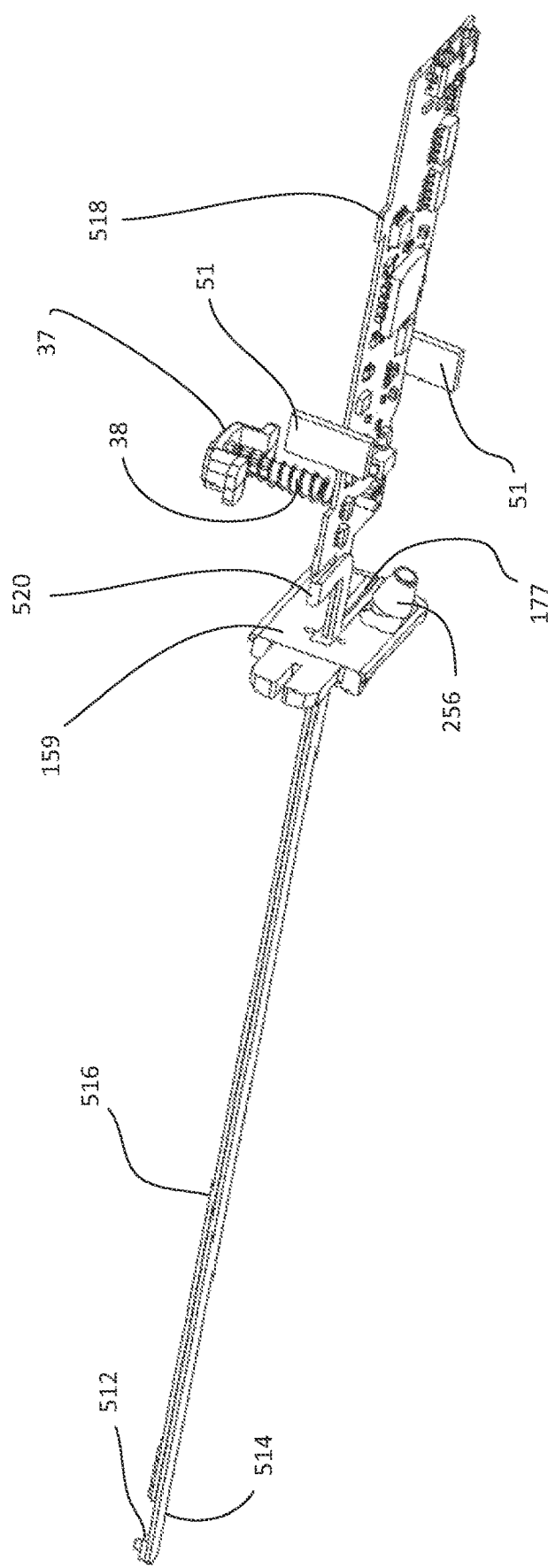
FIG. 33F shows a relationship between an endoscope PCB and other internal components of the endoscope handle.

FIG. 33D shows a cutaway view of an exemplary endoscope. The main PCB 518 is shown in relation to the handle proximal section 16, the camera control button 37 the bulkhead or pass-through barrier 159, and pivot control structure 100. Rotational position sensor magnets 51 are shown both in relation to the handle proximal section 16 and the main PCB 518. An exemplary fluid conduit 434 (for irrigation or suction) is shown approaching the bulkhead 159. It may be connected to bulkhead 159 through a barb fitting 256 as shown in FIG. 33F, or through any other suitable means of secure connection. In this case, the inner sheath 312 has been removed for clarity of the description.

FIG. 33F shows the PCB of the endoscope without the handle, inner sheath, pivot control structure and fluid conduit, as its extensions pass through the bulkhead or pass-through barrier 159. In addition, the rotation position sensing magnets 51 and the camera control button 37 and shaft 38 (with embedded magnet) are shown in relation to the main PCB 518 to provide an indication of where on the PCB 518 the respective Hall effect sensors for those magnets can be located. As shown, the fold point 520 of the flexible PCB extension is located proximal to the bulkhead 159, so that the combined adjacent flexible and rigid PCB extensions may pass through the bulkhead at slot 177. The slot in this case can be sealed securely against fluid infiltration, because a sufficient amount of slack in the flexible PCB extension 514 can be provided distally near its termination at the sensor 512.

Figure 33G:
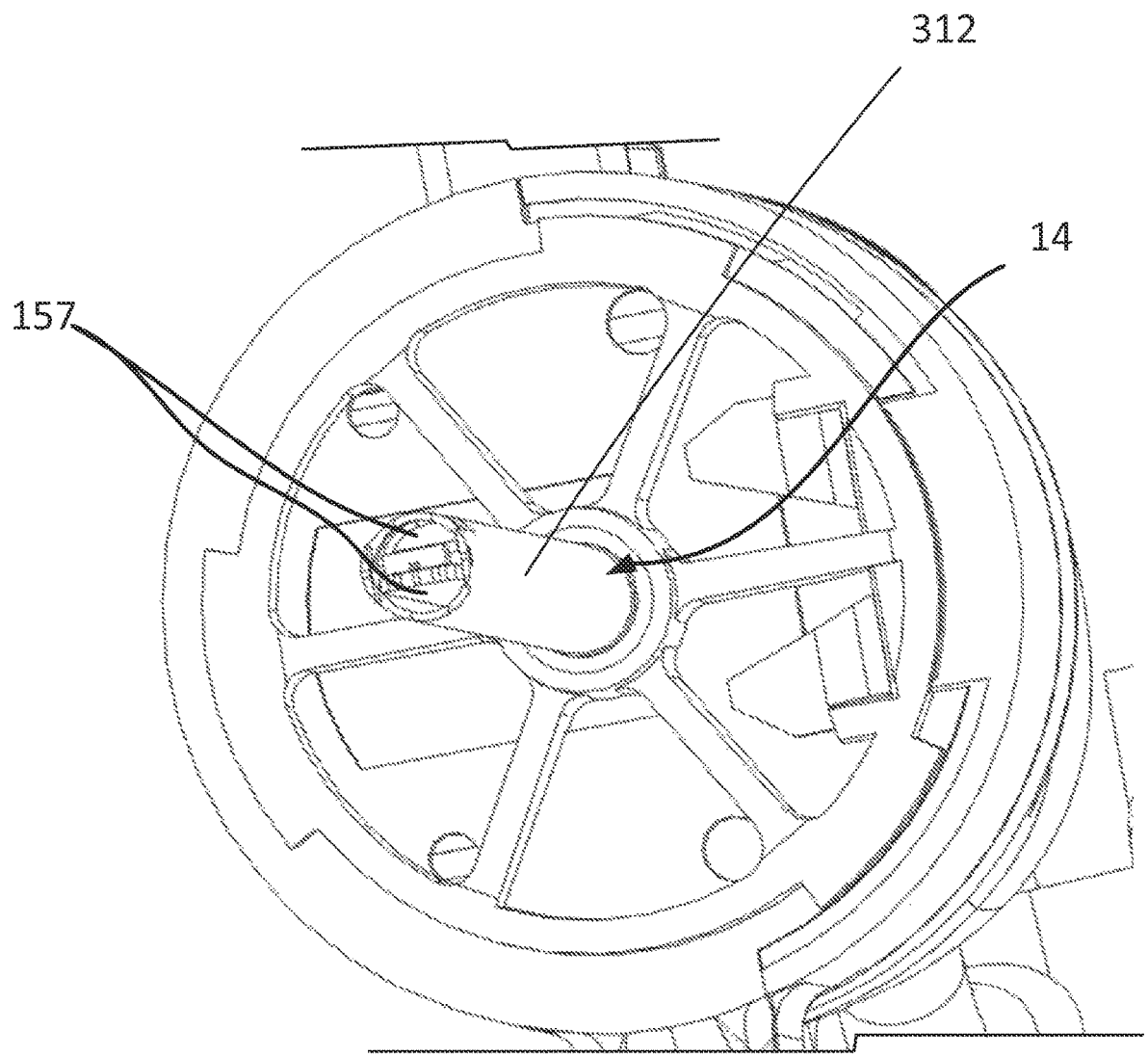
FIG. 33G shows a fluid carrying lumen and PCB extensions located within an inner sheath of an endoscope shaft.

As shown in FIG. 33G, a fluid or air carrying lumen 157 shares space within the endoscope shaft 14 with the PCB extensions 514, 516 (or alternatively with one or two ribbon or flex cables), which supply power to the light source and communications with the sensor/camera located at the distal end of the endoscope shaft 14. The sensor/camera housing has been removed for clarity. (Note that the inner sheath 312 of the shaft 14 has a cutout or opening proximal to the sensor/camera housing, above to provide illumination by the light source or LED's, and optionally below to improve fluid flow around the sensor/camera housing. This is shown, for example in FIGS. 23A and 23F).

Figure 33H:
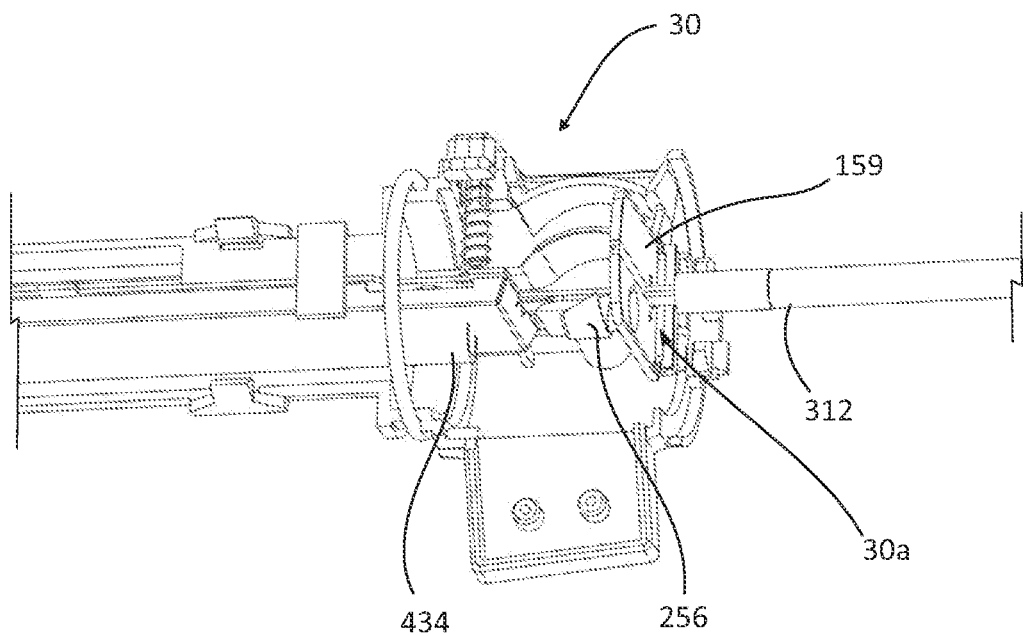
FIG. 33H shows an internal fluid path within the handle of an endoscope.

FIG. 33H shows a cutaway view of the interior of the handle distal section 30 of the above endoscope. The bulkhead or fluid barrier 159 separates a relatively dry region (in which the pivot control structure, camera control button, and distal end of the main PCB are located) from a wet section 30a. A fluid or air conduit 434 runs from the outside of the endoscope handle, through the handle proximal section 16, and connects to a port 256 of the bulkhead 159. In this example, fluid passing through the conduit 434 and port 256 communicates with the lumen 157 of the endoscope shaft 14 via the space occupied by the wet section 30a. Appropriate seals can be used to contain this fluid so that fluid or air does not leak out between the distal section housing and the proximal end of the endoscope inner sheath 312.

Referring now back to FIGS. 7C and 14, the pivot control structure 100 may be capable of being "parked" in detents defined by ridges 94 in the slide button recess 92 of the handle raised portion 34 or another portion of the handle 12. In some embodiments, the ridges 94 may be spaced such that the detents formed by the ridges 94 may correspond with specific angular orientations of the camera assembly 350. In some embodiments, the detents formed by the ridges 94 may be spaced such that their location corresponds to specific angular increments (e.g. 30°) of the camera assembly 350.

As mentioned above (see FIG. 7A), the handle distal section 30 may be rotatable relative to the handle proximal section 16. Such rotation would also cause the longitudinal axis of the insertion section 14 to rotate as well. In turn, the camera assembly 350 may rotate with the insertion section 14. This may allow a user to get a near-global view of the anatomical area in question with minimal to no angular repositioning of the endoscope 10. A user may need only to pan the camera assembly 350 and rotate the handle distal section 30 relative to the handle proximal section 16 to obtain a desired field of view within an anatomical area.

Repeated contortion and bending of optical fibers such as the optical fibers 364 may lead to fracturing or failure of one or more fibers. In the instance of the optical fibers 364, this leads to light and illumination loss which increases as more optical fibers 364 become compromised. Such bending may occur if the optical fibers 364 terminate and are attached or fused to a portion of a pivoting camera assembly 350 as described above. If the endoscope 10 is designed to be disposable, then any decrement in the integrity or performance of the optical fibers 364 may be within acceptable limits relative to the intended lifespan of the instrument. Consequently, in some embodiments the optical fibers 364 may be attached or fused to a pivotal camera assembly 350 with minimal concern for optical fiber 364 breakage and resultant light loss. A terminal illuminator, light projection element or light emitter associated with the optical fibers 364 may, in some embodiments, be advantageously mounted to the camera assembly 350 in order to project light at whatever target or field of view a lens assembly 354 of the camera assembly 350 has been rotated or panned to. Such an arrangement helps to ensure that the field of view (shown with dashed lines in FIG. 23-25) for the lens assembly 354 is always illuminated by the optical fibers 364 regardless of where the in the camera assembly's 350 pannable range the camera assembly 350 has been rotated to.

In some embodiments, the illumination system may include a light guide or light pipe 375. In some embodiments, the optical fibers 364 may comprise a light guide or light pipe 375 (see, for example, FIG. 35) along at least a part of the path of the illumination system. The terms "light guide" and "light pipe" are herein used interchangeably. When an optical fiber is relatively straight, light loss is relatively small because the angle of incidence of the light within the fiber is shallow enough to facilitate near total reflection within the optical fiber. Bending the optical fiber, however, may alter the angle of incidence to the point where some transmission of light out of the fiber is possible. Bends of a light pipe or guide may, however, be controlled. For this reason, use of a light guide 375 where feasible may help to minimize light loss in an illumination system comprising optical fibers 364 or may replace the optical fibers altogether. A light guide 375 may also provide a number of other benefits. For example, a light guide 375 may aid in assembly and shorten assembly time for a device. The light guide 375 may be of the types described herein or may be any suitable type light guide known to those skilled in the art.

Figure 35:
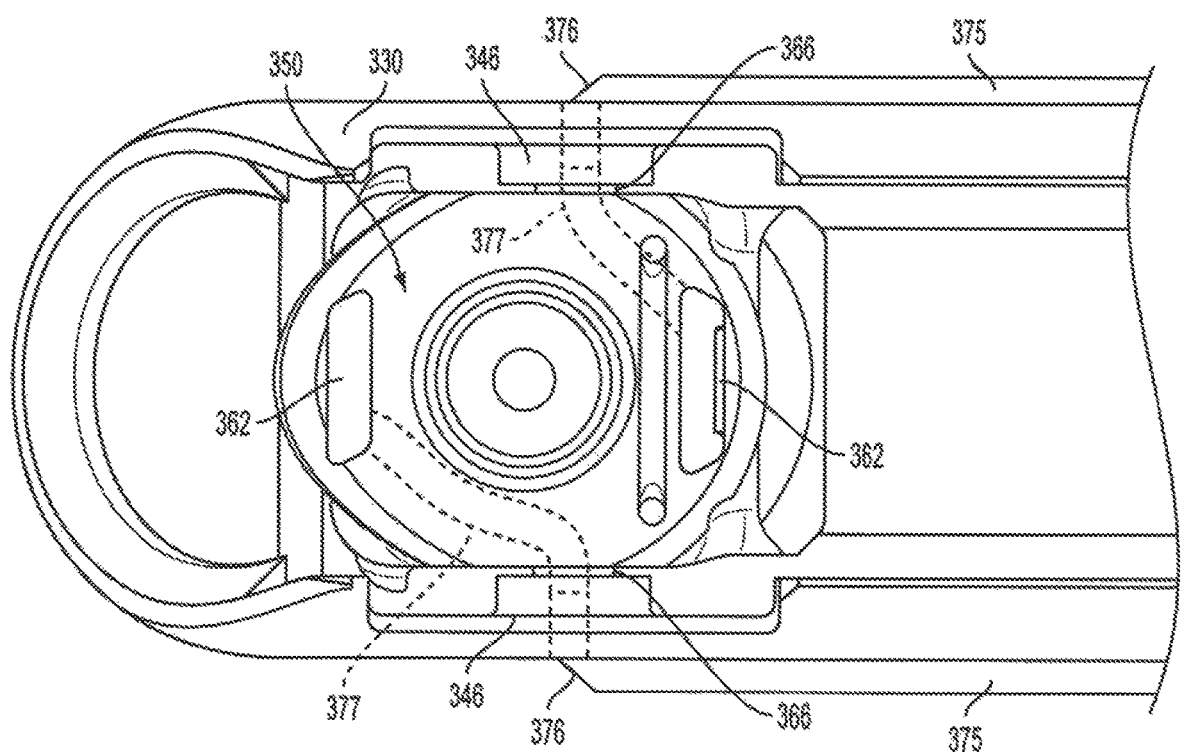
FIG. 35 shows a top view of an exemplary camera assembly and camera assembly mount.

FIG. 35 shows an example embodiment of an endoscope 10 utilizing light pipes 375. Two larger diameter light pipes 375 may extend along one or more sections of the wall of the inner sheath 312 (see FIG. 18) to the camera assembly housing 330 and then bend or curve into one of the camera assembly pivot bearings 346. The bent section of each light pipe 375 may be coated with a highly reflective material 376 in order to minimize loss of light out of the light pipe 375 as it changes direction. Any suitable highly reflective material 376 known to one skilled in the art may be used. In such embodiments, the camera assembly 350 may also have built-in camera assembly light pipes 377 that are formed in a junction with the light pipes 375 at the pivot bearings 346. The light carried by the light pipes 375 may be transferred to the camera assembly light pipes 377 at the junction. The camera assembly light pipes 377 may extend from each of the pivot pins 366 into the camera assembly 350. The camera assembly light pipes 377 terminate in the light projection voids 362 so that the field of view of the camera assembly 350 will be illuminated regardless of the rotational position of the camera and lens assemblies. In such an embodiment, any bends taken by the camera assembly light pipes 377 may be coated with a highly reflective material 376 as described above. In some embodiments, the highly reflective material 376 may be included on other portions of the light pipes 375 and camera assembly light pipes 377 in addition to the bends of the light pipes 375 and camera assembly light pipes 377.

Creating a light pipe junction coinciding with the pivoting region of the camera assembly 350 may be desirable because it avoids the bending or twisting of optical fibers 364 as the camera assembly 350 is rotated, removing the risk of damage to the optical fibers 364. Such a design can be adapted for use in either a reusable or disposable endoscope 10. This arrangement may also reduce the manufacturing or assembly costs of the endoscope 10.

In another example embodiment (not shown) which uses light pipes 375, a larger diameter light pipe 375 may extend substantially along the path of the flex cable 250. The end of the light pipe 375 nearest the inner sheath mount 160 may form a junction with the optical fibers 364 or be arranged to draw in light from another illumination source. The end of the light pipe 375 nearest the camera assembly 350 may also form a junction with illumination fibers 364 which extend to the camera assembly 350.

Figure 36:
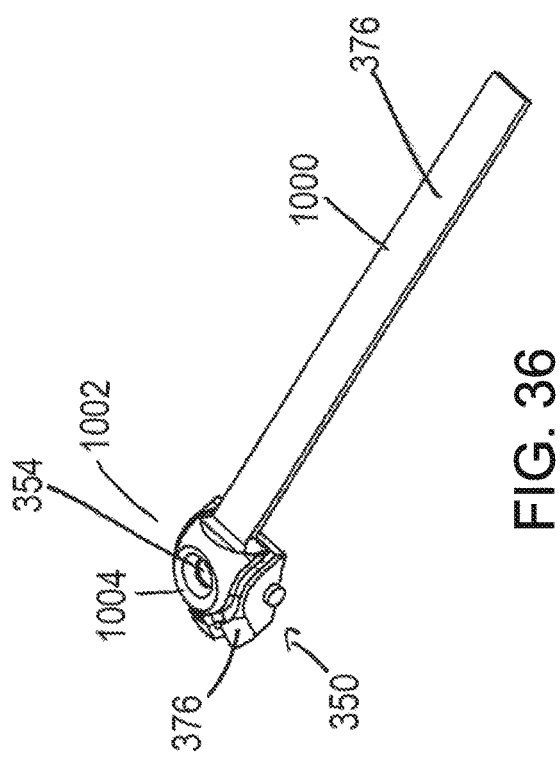
FIG. 36 shows a perspective view of a camera assembly and flexible optical fiber bundle or ribbon.

In some embodiments, the optical fibers 364 to the camera assembly 350 may be arranged to form a flexible ribbon 1000, creating a linear array of fibers that can be terminated into a light projection element with minimal bending or bending in only one dimension (see, e.g., FIG. 36). Alternatively, the flexible ribbon 1000 need not be a linear array of fibers and instead may, in some embodiments, be a single, ribbon-like, flexible piece of light guide material. In some embodiments there may be two flexible ribbons 1000 each extending to one of the light projection voids 362 in the camera assembly 350. In some embodiments, the flexible ribbons 1000 may be coated with a reflective material 376 to maximize the amount of light at the camera assembly 350. In some embodiments, a flexible ribbon 1000 may form a junction with a light pipe.

In some embodiments, a camera housing top 356 may comprise a light piping material to serve as a light projection element or illuminator. In this case, light may be emitted from most of the camera housing top 356 and into the viewing field of the camera assembly 350. In some embodiments, some areas of the camera housing top 356 may be blacked out or masked so that light is only emitted from a desired region or regions of the camera housing top 356. In some embodiments, some regions of the camera housing top 356 may be coated with a highly reflective material 376 to prevent the unwanted emission of light from those areas.

FIG. 36 shows an embodiment in which the optical fibers 364 are incorporated into a flexible ribbon 1000, which optionally may be coated in a highly reflective material 376. As shown, the flexible ribbon 1000 extends to the camera assembly 350. The flexible ribbon 1000 may be over-molded to, potted into, fused with or otherwise coupled to the camera assembly 350.

Figure 37:
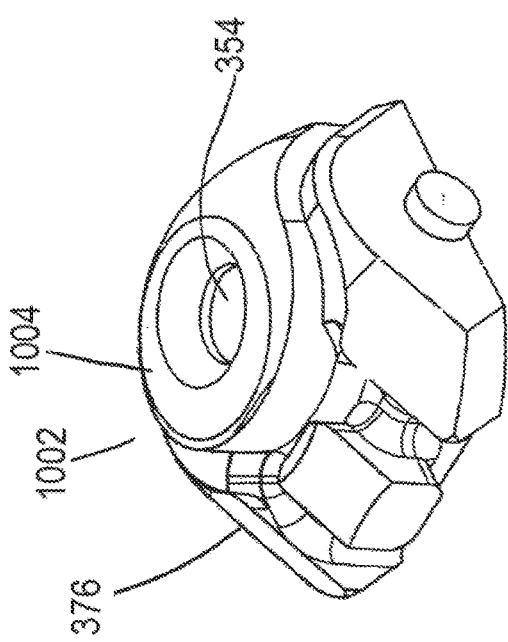
FIG. 37 shows a perspective view of a camera assembly having a monolithic camera housing and light emitting feature.

In the example embodiment in FIG. 36 the camera assembly 350 comprises a monolithic camera housing 1002. An example monolithic camera housing 1002 without an attached flexible ribbon 1000 is shown in greater detail in FIG. 37. In the example embodiment, the monolithic camera housing 1002 is made from a light piping or transmitting material and functions as a light projection element. The monolithic camera housing 1002 in the example embodiment may be nearly entirely coated with a highly reflective material 376 to maximize light output from the non-coated or non-masked regions of the monolithic camera housing 1002. A light projection or illumination surface 1004 having a shape suitable for placement adjacent a lens and image sensor assembly on the monolithic camera housing 1002 may be constructed by masking the area during application of a highly reflective material 376 (or alternatively a simple dark mask). In the example embodiment, the light projection surface 1004 has the shape of a ring. In other embodiments, the light projection surface 1004 may be crescent-shaped, semi-circular, or may have any other desired shape. Light may be emitted from the light projection surface 1004 of the monolithic camera housing 1002 to illuminate the field of view of the lens assembly 354. As in the above-described embodiments, the field of illumination preferably pivots with the camera assembly 350, ensuring that the field of view of the lens assembly 354 is always illuminated.

Figure 38:
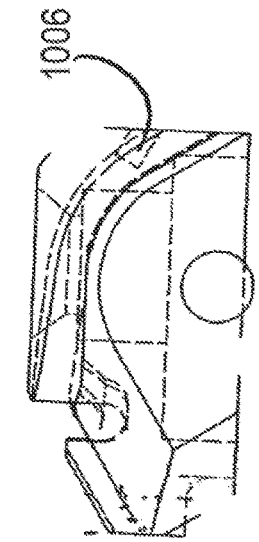
FIG. 38 shows a side view of the camera assembly of FIG. 37.

FIG. 38 shows another example embodiment of a monolithic camera housing 1002.

As shown in outline form, the monolithic camera housing 1002 includes a coupling recess 1006. The coupling recess 1006 may allow a flexible ribbon 1000 to be suitably coupled into the monolithic camera housing 1002. In some embodiments, the coupling recess 1006 may allow a flexible ribbon 1000 to be coupled, for example, via snap fit into the monolithic camera assembly 1002. In some embodiments, the coupling recess 1006 may accommodate optical fibers 364 not formed in a flexible ribbon 1000. Similar to FIG. 37, in FIG. 38, the monolithic camera housing 1002 may function as a light projecting element. The monolithic camera housing 1002 may also be similarly coated and/or masked as the monolithic camera housing 1002 described in relation to FIG. 37.

Figure 39:
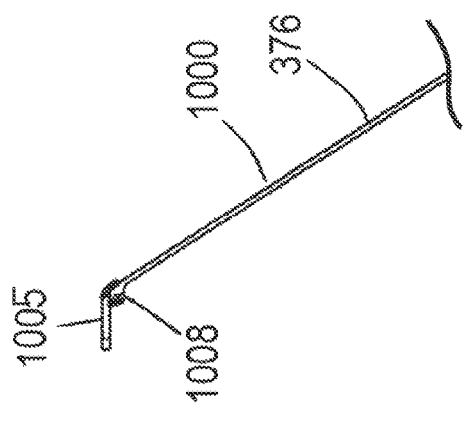
FIG. 39 shows an example of a flexible optical fiber bundle or ribbon.
Figure 40:
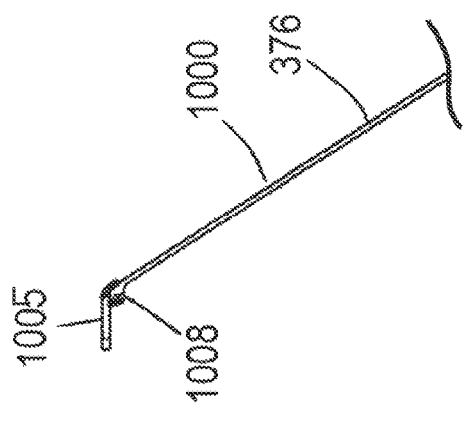
FIG. 40 shows a side view of the flexible optical fiber ribbon of FIG. 39.

FIG. 39 and FIG. 40 show an embodiment in which a light projection element 1005 is incorporated in an end of a flexible ribbon 1000. The light projection element 1005 may be formed from a light piping material, which in some embodiments may be a fusion of a group of fibers into a shape suitable for projecting light from a fiberoptic bundle or flexible ribbon 1000 in a desired manner. In some embodiments, the light projection element 1005 and flexible ribbon 1000 may be two separate parts fused together (e.g., by heating or by chemical means). In other embodiments the light projection element 1005 and flexible fiberoptic ribbon 1000 may be a single molded part. In some embodiments the light projection element 1005 may be created as described in relation to FIGS. 49-62.

Still referring to FIGS. 39 and 40, the flexible ribbon 1000 may be coated with a highly reflective material 376. The bottom and side walls of the light projection element 1005 may also be coated with a highly reflective material 376. This may ensure that light is only emitted from the non-coated top of the light projection element 1005 and into the field of view of the lens assembly 354. As show in FIG. 40, the light projection element 1005 or the flexible ribbon 1000 may include a coupling feature 1008. The coupling feature 1008 may allow the light projection element 1005 and flexible ribbon 1000 to be coupled onto or into a camera assembly 350. The coupling feature 1008 may be an integral part of the light projection element 1005.

Figure 41:
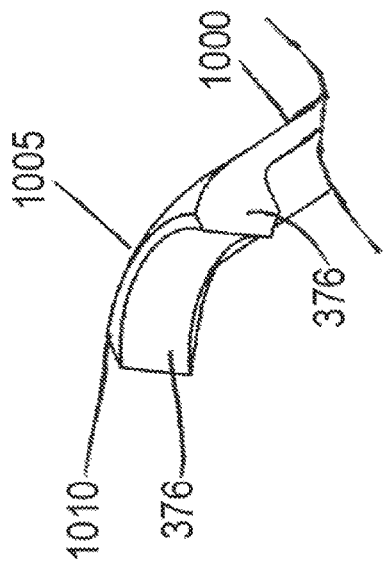
FIG. 41 shows a perspective view of an example of a light projection element.
Figure 42:
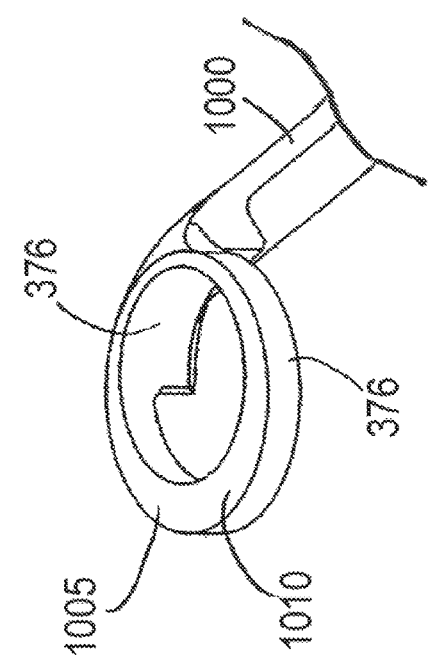
FIG. 42 shows a perspective view of another example of a light projection element.

FIG. 41 and FIG. 42 depict two example embodiments of a flexible ribbon 1000 which include light projection elements 1005, which may be formed from a light piping material. The light projection element 1005 in FIG. 41 has a generally ring-like shape while the light projection element 1005 in FIG. 42 is generally crescent shaped, although other shapes may be selected as desired. In the example embodiments in FIGS. 41 and 42 only the top surfaces of the light projection elements 1005 are left uncoated with a highly reflective material 376.

A light projection element 1005 may comprise one or a number of textures 1010 that help to direct the light emitted from the light projection elements 1005. In some embodiments, the texture 1010 or textures 1010 may be included to encourage light to be emitted in a diffuse manner. The texture 1010 or textures 1010 may be created, for example, during molding of the light projection element 1005, or alternatively, the light piping material forming the light projection element 1005 may include a fill material that encourages light to be emitted from the light projection element 1005 in a diffuse manner.

Figure 43:
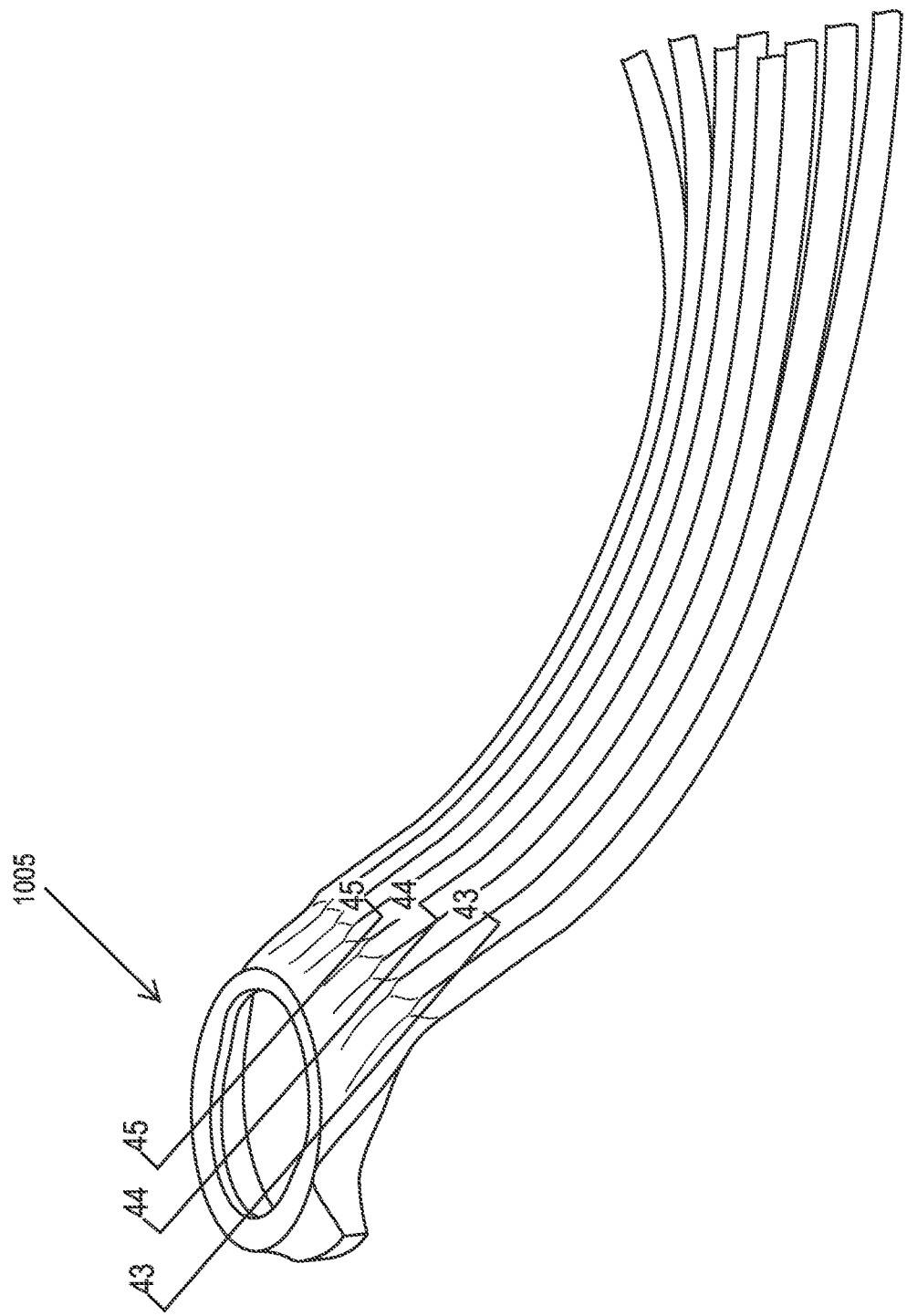
FIG. 43 shows a perspective view of another example of a light projection element.
Figure 44:
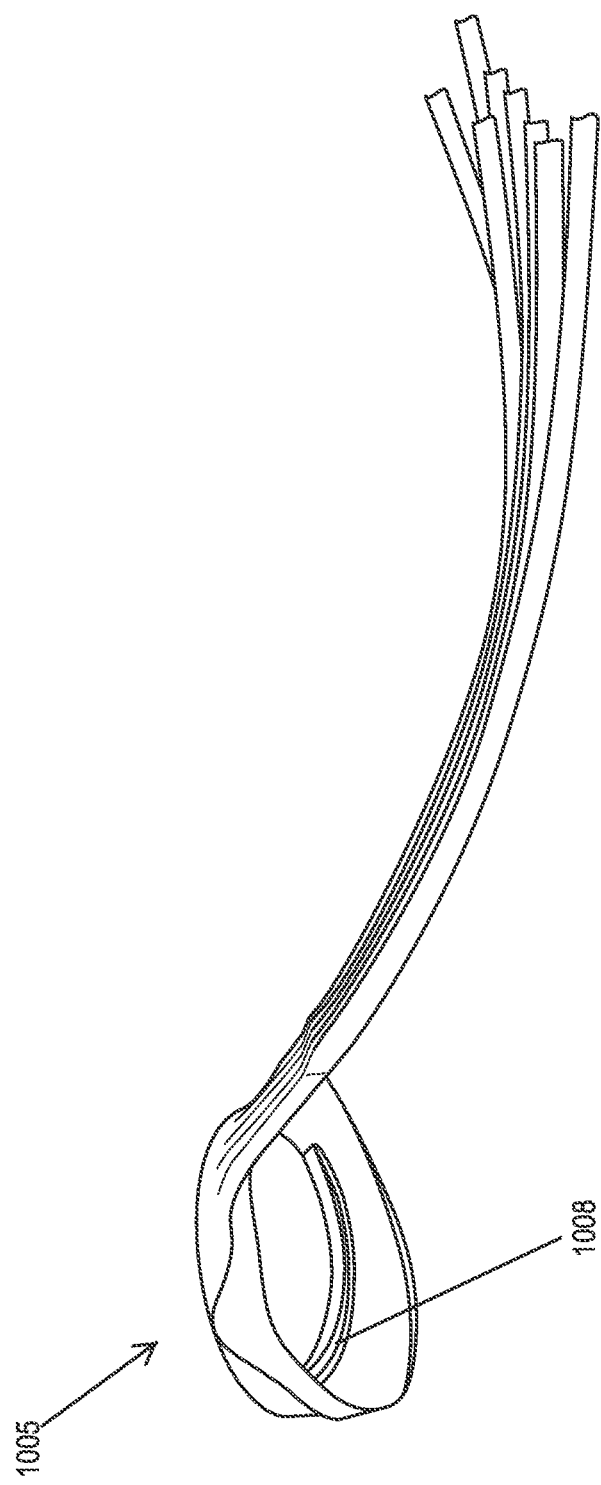
FIG. 44 shows a bottom perspective view of the light projection element shown in FIG. 43.

FIGS. 43 and 44 respectively depict top and bottom perspective views of another example embodiment of a light projection element 1005. As shown, the light projection element 1005 is ring-like in shape. The light projection element 1005 also includes a coupling feature 1008 as shown in bottom perspective view in FIG. 44. The coupling feature 1008 in FIG. 44 is an integral part of the light projection element 1005. In the example embodiment, the coupling feature 1008 is a ledge or shelf. The ledge coupling feature 1008 may help to locate and/or align the light projection element 1005 on another component such as a camera assembly 350. Additionally, in some embodiments, adhesive or glue may be placed along the ledge coupling feature 1008 to fix the light projection element 1005 to another component such as a camera assembly 350. The light projection element 1005 is shown attached to an example camera assembly 350 in FIG. 48.

The light projection element 1005 shown in FIGS. 43-44 does not include a highly reflective coating or material 376 (see, for example. FIG. 39). The need for such a highly reflective coating or material 376 may be minimized by dimensioning the light projection element 1005 to increase or maximize the total internal reflection of light entering and within the light projection element 1005 where the emission of light is not desired. This may be done by ensuring any bend or bends have a large radius in areas of the light projection element 1005 where the emission of light is undesired. Additionally, this may be done by dimensioning a light projection element 1005 such that thickness variations throughout the light projection element 1005 do not introduce changes in the angle of incidence of light within the light projection element 1005 which would make the angle of incidence less than the critical angle. It may be desirable that the thickness of the light projection element 1005 does not decrease to less than the thickness of the optical fibers or flexible ribbon to which the light projection element is attached 1005. It may also be desirable that the surface of the light projection element 1005 be smooth in areas where the emission of light is not desired.

Figure 45:
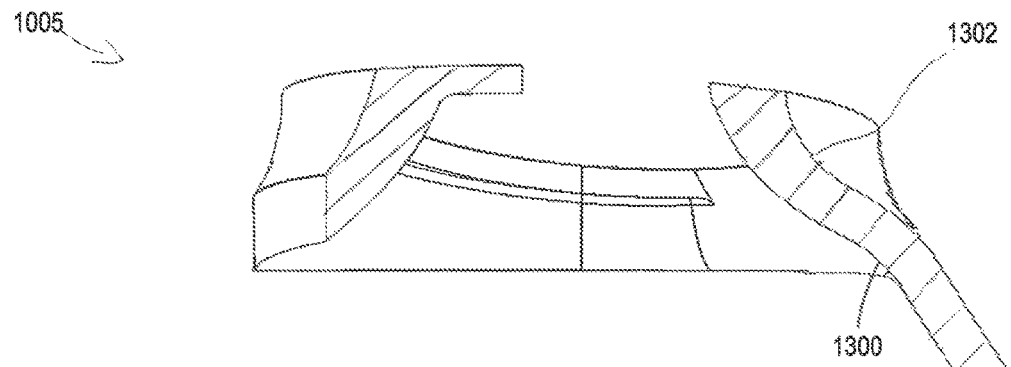
FIG. 45 shows a cross sectional view of the light projection element shown in FIGS. 43 & 44 taken at line 43-43 of FIG. 43.
Figure 46:
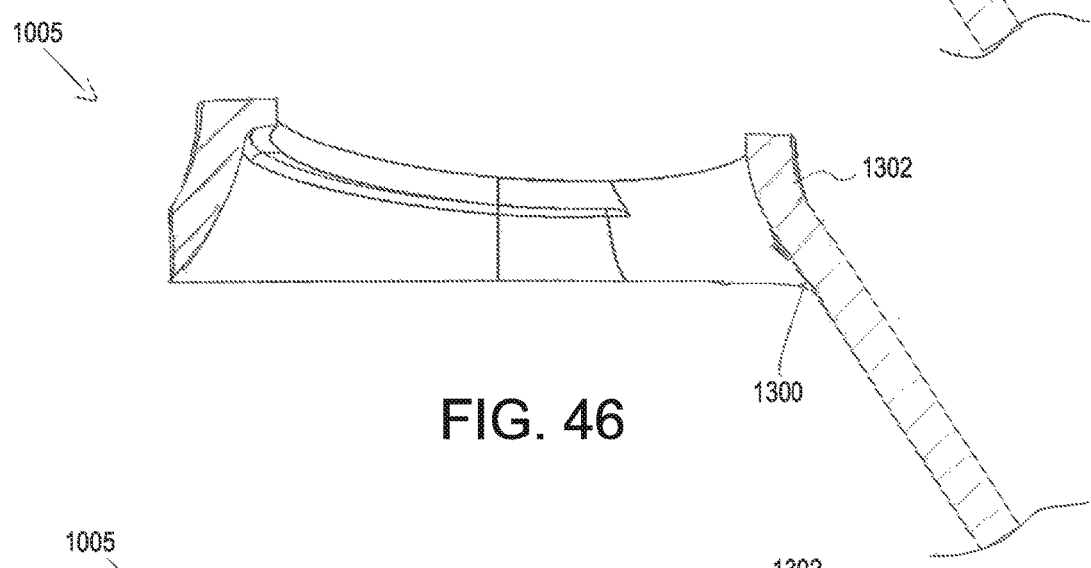
FIG. 46 shows a cross sectional view of the light projection element shown in FIGS. 43 & 44 taken at line 44-44 of FIG. 43.
Figure 47:
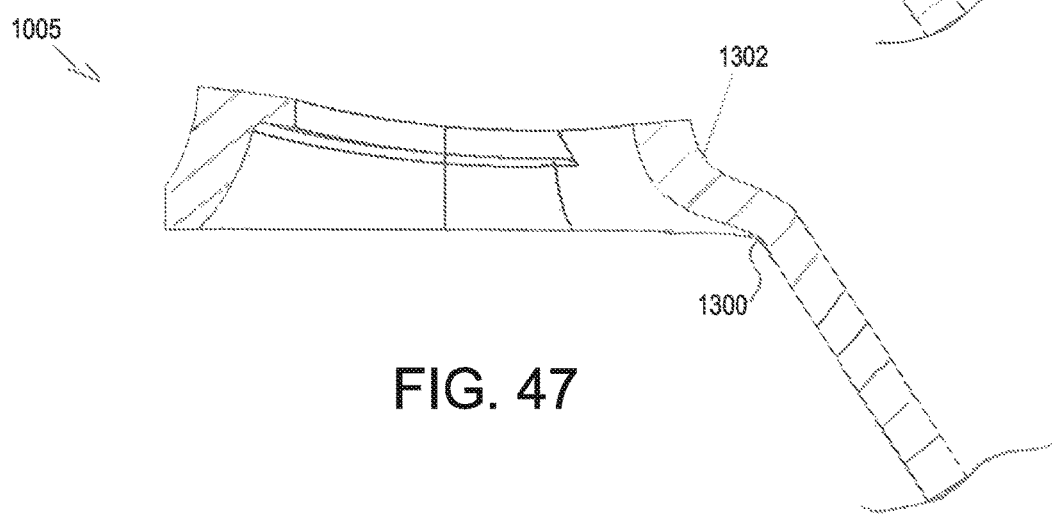
FIG. 47 shows a cross sectional view of the light projection element shown in FIGS. 43 & 44 taken at line 45-45 of FIG. 43.

FIGS. 45, 46, and 47 depict a number of cross sections of the light projection element 1005 depicted in FIGS. 43-44. The cross sections are respectively taken at lines 43-43, 44-44, and 45-45 of FIG. 43. As shown, light entering the light projection element 1005 must traverse a first bend 1300 and second bend 1302 before being emitted out of the top surface of the light projection element 1005. As shown in FIGS. 45-47, the light projection element 1005 may be shaped such that the radii of these bends vary depending on the plane of the light projection element 1005. The radius of each of these bends 1300 and 1302 may be chosen so as to be as gradual as possible in the available space in a given plane. Also as shown, the thickness of the light projection element 1005 is kept generally constant. This ensures that changes in angle incidence due to thickness variation are minimized.

Figure 48:
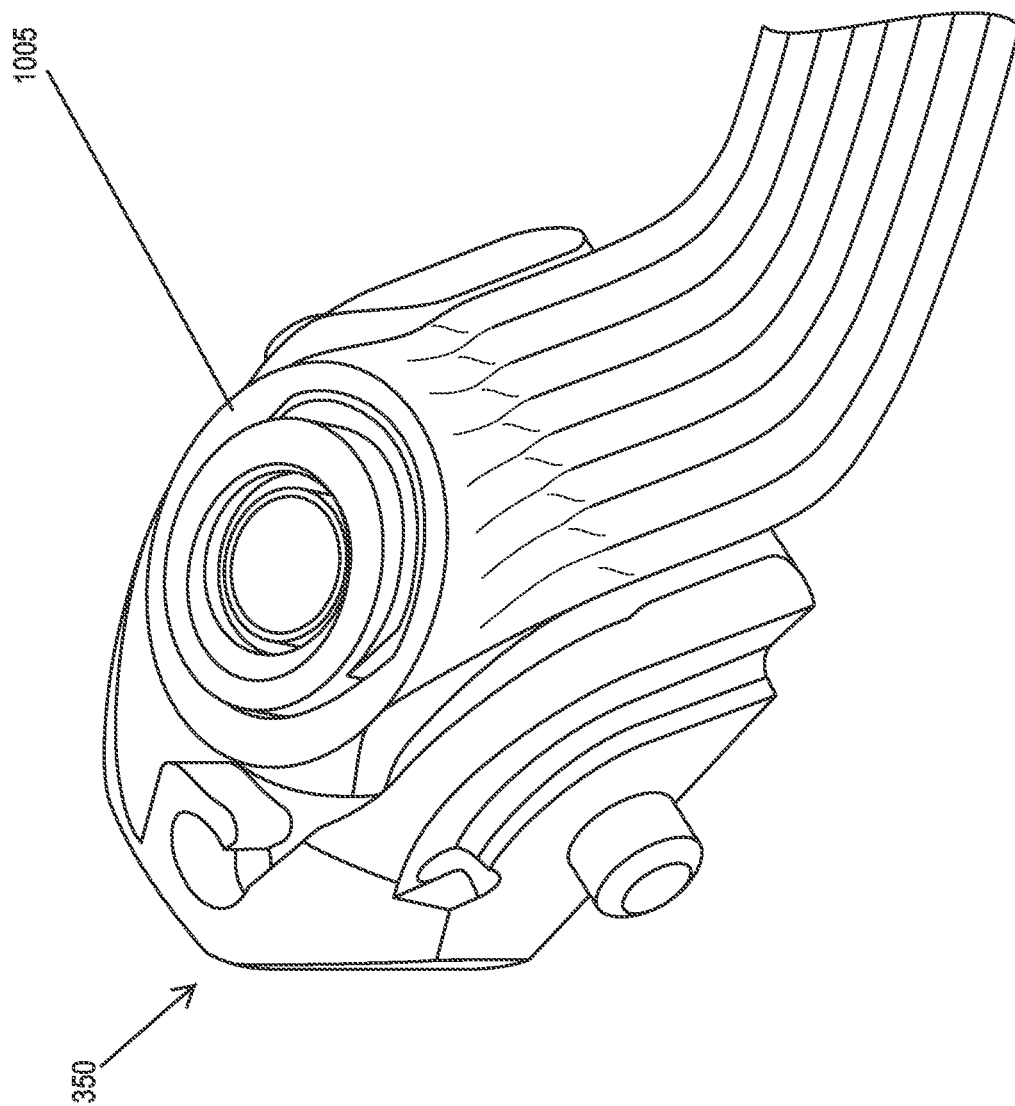
FIG. 48 shows a top perspective view of a camera assembly on which the light projection element of FIG. 43 is mounted.

The light projection element 1005 shown and described in relation to FIGS. 43-47 is attached to an example camera assembly 350 in FIG. 48. As shown the light projection element 1005 is arranged such that it projects light into a primary illumination field (the surrounding area around this primary illumination field also may be illuminated due to diffusion and reflection of the emitted light) which is substantially coincident with the field of view of the lens assembly 354.

Exemplary methods for constructing a fiberoptic light projecting element are disclosed in U.S. patent application Ser. No. 14/170,080 (US Application Publication No. 2014/0221749), filed Jan. 31, 2014, and incorporated herein by reference in its entirety.

Figure 49:
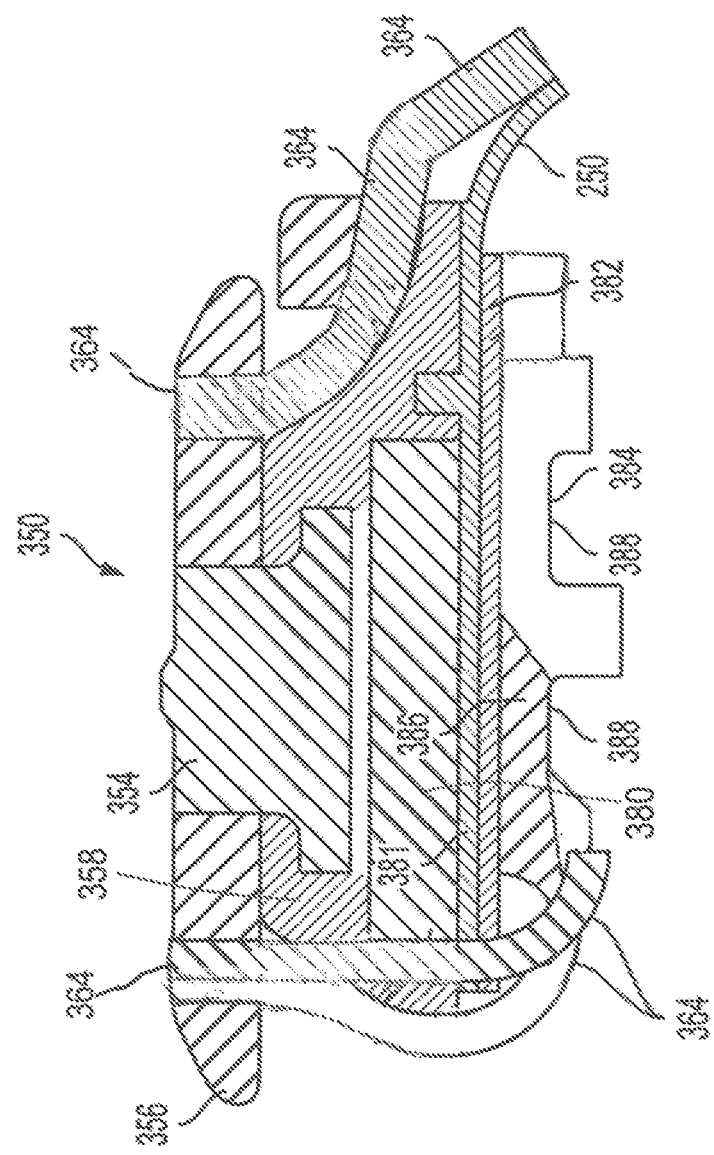
FIG. 49 shows a cross sectional view of an example camera assembly taken at line 61-61 of FIG. 24.

FIG. 49 shows a cross sectional view of an exemplary camera assembly including a lens assembly 354 taken at the cross-sectional plane represented by line 61-61 of FIG. 24. The lens assembly 354 is shown housed between the camera housing top 356 and camera housing bottom 358 as in FIG. 24. As shown, the lens assembly 354 is positioned to project an image onto the plane of an image sensor 380. The type of image sensor 380 may include, for example, a CCD image sensor, CMOS image sensor, etc. Preferably, the image sensor 380 may be housed in a sealed section of the camera assembly 350 to guard against fluid exposure. In a disposable endoscope, a less costly process may be used to seal the image sensor against fluid exposure (e.g., using a clear epoxy compound), because the assembly would not then be designed to withstand the rigors of sterilization and reuse.

As shown in FIG. 49 the image sensor 380 may be electrically coupled to a flex board 381 of the flex cable 250. In some embodiments, a conformal coating material may be used to give added protection against moisture, and optionally may be constructed to support the joints of a ball grid array mounting for the image sensor 380. The flex cable 250 may provide power to the image sensor 380, as well as the means of conveyance of data and/or commands from/to the image sensor 380. In some embodiments, a stiffener 382 may be included in the camera assembly 350. In the example embodiment shown in FIG. 49, a stiffener 382 is positioned to strengthen the structure on which the image sensor 380 is supported, which may help to protect the physical integrity of the image sensor 380. The stiffener 382 may comprise, for example, a thin aluminum backing (which in an exemplary embodiment may be about 0.002 inch thick).

The camera assembly 350 may also include one or a number of fiber guides 384. In the example shown in FIG. 49, a fiber guide 384 is coupled to the bottom face of the camera housing bottom 358. The example fiber guide 384 includes a guide trough 386. The back wall of the guide trough 386 of the fiber guide 384 may be seen projecting toward the bottom of the page in FIG. 49. The fiber guide 384 may also be or include a number of directing notches or channels 388 which in the example fiber guide 384 shown in FIG. 49 are recessed into the back wall of the guide trough 386. In some embodiments, including the exemplary embodiment in FIG. 49, directing notches or channels 388 may be formed in one or both of the camera housing top 356 and camera housing bottom 358. The fiber guide 384 may help to route the illumination fibers 364 during assembly of the endoscope 10. The fiber guide 384 may also act to keep the illumination fibers 364 in place during operation of the endoscope 10. The location, shape, number, size, etc. of the fiber guides 384 may vary depending on the specific configuration of the endoscope 10. In some embodiments, glue, epoxy or another suitable adhesive or agent may be used in addition to the fiber guides 384 to help keep the illumination fibers 364 in the desired location. In some cases, for example, in which light guides or light projection element (as shown, e.g., in FIG. 35-42 or as shown in FIG. 50) are used, fiber guides 384 may not be used in an assembly.

Figure 50:
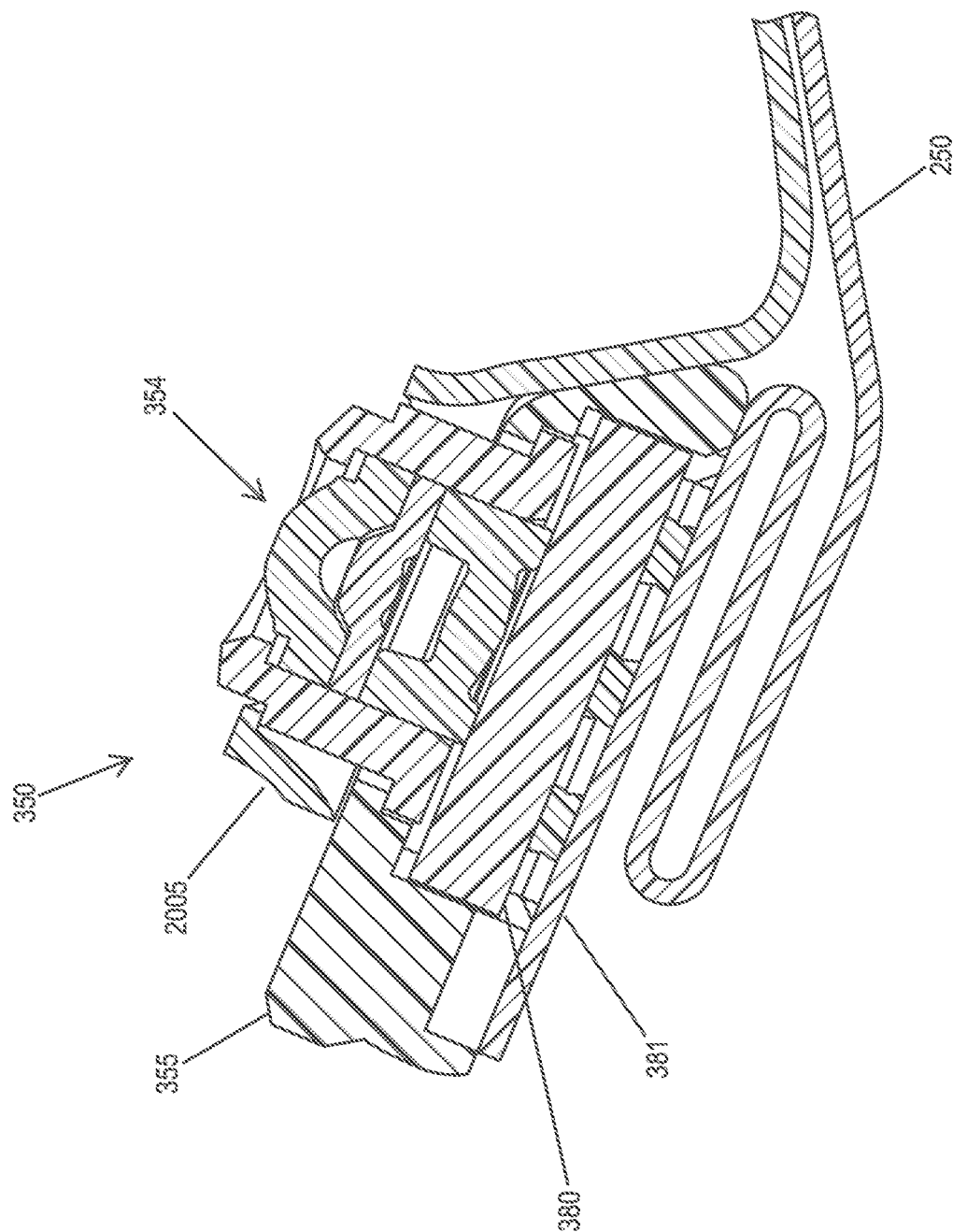
FIG. 50 shows a cross sectional view of an example camera assembly taken at line 62-62 of FIG. 34.

FIG. 50 depicts a cross section of the camera assembly 350 depicted in FIG. 34 taken at line 62-62 of FIG. 34. As shown, a lens assembly 354 is shown in place in the camera housing 355. An image sensor 380 is also shown in place within the camera housing 355. The lens assembly is positioned to project an image to the image sensor 380. As above, the image sensor 380 may be any type of image sensor (e.g. CCD, CMOS, etc.) and may be sealed against fluid exposure. Also as above, the image sensor 380 is coupled onto a flex board 381 attached to a flex cable 250. The camera assembly 350 shown in FIG. 50 does not include a fiber guide 384 (see FIG. 49). Instead a light projection element or light emitter 2005 is in place on the camera assembly 350 in FIG. 50.

As shown, the flex cable 250 is doubled back upon itself in the example embodiment. This may be accomplished by bending the flex cable 250 and then maintaining the bend by applying glue or another fixative to the affected areas of the flex cable 250. Double-looping the flex cable 250 below the camera assembly 350 may be advantageous in embodiments in which the camera assembly 350 is enclosed in a confined space. For example, confining the camera assembly 350 to the space within an inner sheath 312 as shown in FIG. 22 may limit the amount of flex cable 250 available for bending. The flex cable 250 may then have to bend over an undesirably small radius in certain rotation positions of the camera assembly 350. Such a small bend radius can be detrimental to a flex cable 250 especially if it occurs repeatedly. This problem becomes more of an issue as the diameter of the inner sheath 312 decreases. By arranging the flex cable 250 to double back upon itself, however, a greater length of flex cable 250 is available for repeated bending upon rotation of the camera assembly 350 and a larger minimum bend radius may be obtained. Thus, this may allow the inner sheath 312 to then be made with a smaller diameter without concern for the integrity of the flex cable 250 due to the repeated bending and unbending over a small radius.

Figure 51:
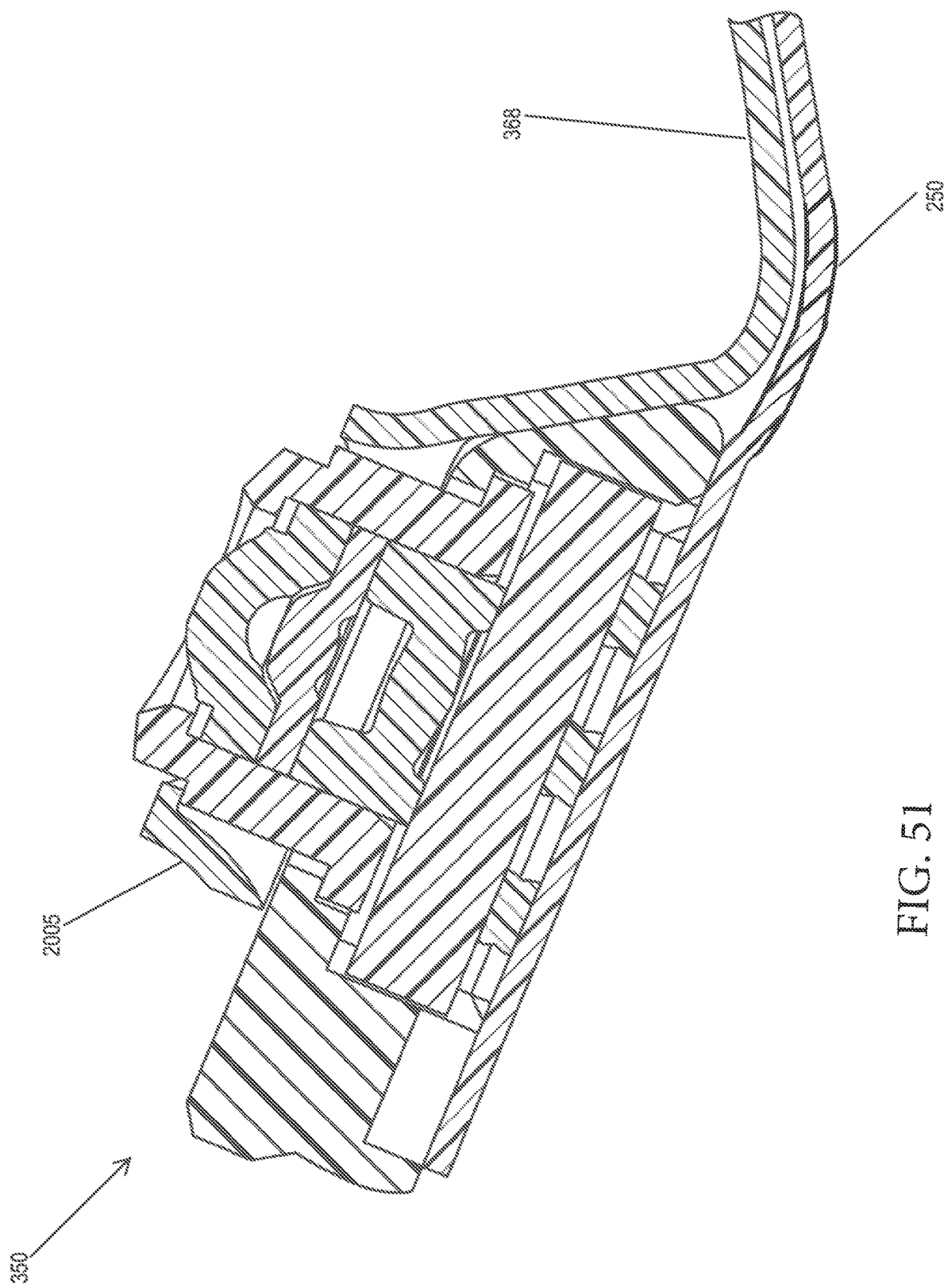
FIG. 51 shows a cross-section view of an example camera assembly taken at line 62-62 of FIG. 34.

Both the flex cable 250 and the optical fibers 364 leading the light projection element 2005 exhibit some resistance to bending. Additionally, both can exert a restoring spring force when bent. This resistance to bending may increase the camera assembly's 350 resistance to rotation. As shown in FIG. 51, the flex cable 250 and the optical fibers 364 may be angled toward one another. Such an arrangement may leverage the stiffness of the flex cable 250 against the optical fibers 364 or vice versa to assist in rotating camera assembly 350. To best illustrate this concept, the flex cable 250 is not doubled back upon itself in FIG. 51.

In some embodiments, at least one illumination source for a camera assembly 350 may be positioned to project light in a direction other than into the field of view of the camera assembly 350. That is, the direct illumination field of an illumination source may be oriented such that it is outside or not coincident with a field of view of a camera assembly. Such an illumination source may be referred to as an indirect lighting source whereas illumination sources which project light directly into a field of view of a camera assembly 350 may be referred to as direct lighting sources. An indirect lighting source may, for example, be oriented such that it emits light behind a camera assembly 350 or in a direction substantially opposite that of the field of view of the camera assembly 350. For example, instead or in addition to a light projecting element 2005 which couples around a lens assembly 354 or lens and projects light into a field of view of the lens assembly 354 or lens, a light projecting element 2005 may be attached to part of the camera assembly 350 opposite the lens assembly 354 or lens.

Though counter-intuitive, projecting light outside of the field of view of the camera assembly 350 (e.g. behind a camera assembly 350 in a direction opposite the field of view) provides increased image quality and reduces the need for image processing. For example, such an illumination arrangement may help to provide greater depth perception in endoscopic procedures as shadowing of areas which would otherwise be directly illuminated may be maintained. By emitting light from a light projecting element 2005 or other illumination source to points outside the field of view of a camera assembly 350, hot spots or areas which appear washed out and dark spots or areas which appear underexposed may be mitigated. Such an illumination arrangement may help to provide more uniform lighting within the field of view of the camera assembly 350.

Figure 52:
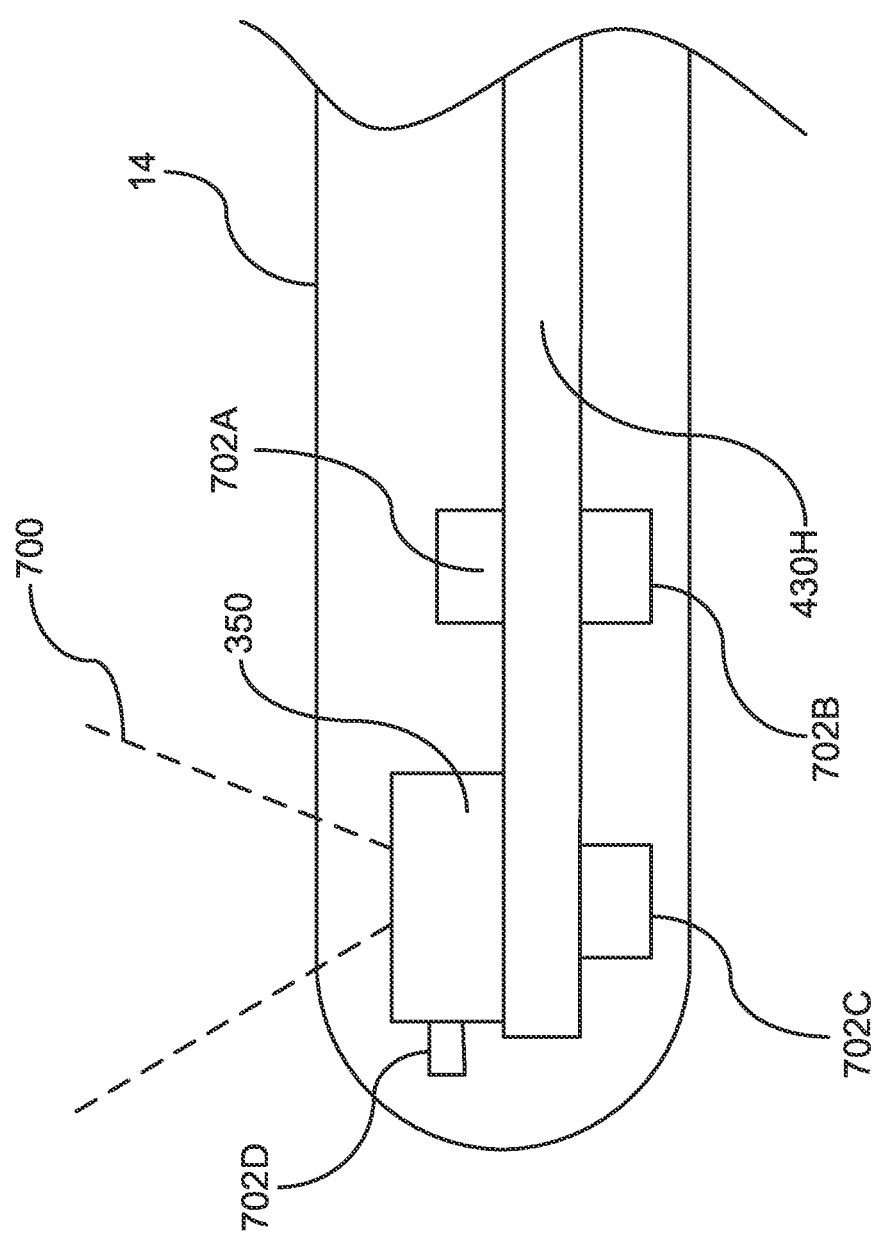
FIG. 52 depicts a representational illustration of a camera assembly at the distal tip of an endoscope in addition to an example sensor and number of example illumination sources.

A representational embodiment of an illumination arrangement in which light may be emitted from a number of light sources 702a-d to areas inside and outside of a field of view 700 of a camera assembly 350 is shown in FIG. 52. As shown, an extension 430h of a printed circuit board in the endoscope handle is shown extending to the camera assembly 350. The printed circuit board extension 430h may provide power and data communication pathways to various components in the insertion section 14. In some embodiments, a ribbon or flex cable 250 (see, e.g., FIG. 14) may be used instead of a printed circuit board extension 430h. A number of components are mounted to the printed circuit board extension 430h. These components may be any or a variety of different components such as a sensors, light emitters, etc. In the example embodiment, the components are described as light sources 702a-d. The light sources 702a-d may be any suitable light source, such as but not limited to, fiber optic cables, light projecting elements 2005 (see, e.g. FIG. 62), LEDs, or arrays of LEDs.

Use of LEDs may be desirable in some specific embodiments for a variety of reasons. For example, use of LEDs may obviate the need for a bundle/ribbon of illumination fibers, some specific embodiments. Some optical fibers may degrade when subjected to prolonged bending during usage and may be prone to light loss when bent. LEDs are long lasting and do not require a lengthy bundle of fibers which a subject to bending. Use of LEDs may also minimize the number of pass-through elements between a dry section (e.g. a handle 12) of an endoscope and a wet section of an endoscope (e.g. insertion section 14). Additionally, by omitting optical fibers less of the cross-sectional area of a fluid conduit in an insertion section 14 may be obstructed or filled. This may allow for increased flow rates of irrigation fluid through an insertion section 14. LEDs may also help to simplify or increase ease of manufacturing.

As shown, a first light source 702a is disposed such that it may project light generally toward the field of view 700 of the camera assembly 350. Such a light source 702a may generally provide direct lighting of the field of view 700. In some embodiments, a direct light source 702a may be omitted or may be accompanied by one or more other indirect lighting sources, such as, for example, any or a combination of light sources 702b-d. In embodiments where a direct lighting source 702a is included in conjunction with one or more indirect lighting source, the direct lighting source 702a may provide light at a lower intensity than one or more of the indirect lighting sources. In some embodiments, a direct lighting source 702a may provide light in a different spectrum or a subset of the spectrums emitted by an indirect lighting source(s). For example, a direct lighting source 702a may be a RBG LED array while indirect lighting sources may emit white light.

A number of other lighting sources 702b-d are also shown in FIG. 52. These lighting sources are shown together for illustrative purposes, and need not all be present in any given embodiment. Any number of lighting sources 702a-d may be included in various embodiments. Some of the lighting sources 702a-d may be omitted in various embodiments. Each of the light sources 702b-d is an indirect lighting source is arranged such that they do not emit light directly into the field of view 700 of the camera assembly 350. Light sources 702b-d are arranged to emit light in a direction substantially opposite the field of view 700 of the camera assembly 350. Light source 702d may be attached to the camera assembly 350 and may be arranged to emit light from a side of the camera assembly 350. In a preferred embodiment, backlighting provides the only source of illumination of the surgical field. In this case, an illumination source for the distal end of the endoscope may only comprise one or more LED's located at position 702B, for example; that is, projecting light from a side of the endoscope shaft that is away from the side from which most of the field of view of the camera assembly is directed. The light thus provided illuminates the space viewed by the camera assembly more indirectly and diffusely, preventing bright reflections of light aimed directly at the camera or reducing the casting of shadows, and improving the operator's view of the field. On the other hand, placing the LED's at position 702A may improve illumination of the area of the surgical field toward which the camera field of view 700 is directed.

The camera assembly 350 may include one or more optical filters to selectively use the wavelengths emitted from one or more of the light sources 702a-d. For example, a polarizing filter or band-gap filter may be used to enhance the imaging by the camera assembly 350.

Depending on the embodiment, the camera assembly 350 may be rotatable within the insertion section 14. In such embodiments, the lighting sources 702a-d may remain stationary as the camera assembly 350 is rotated. Alternatively, one or more lighting source 702a-d may rotate with the camera assembly 350 (e.g. a light source 702a-d may be attached to the camera assembly 350 and thus rotate with the camera assembly 350). A light source 702a-d may be positioned such that it does not emit light directly into the field of view 700 in any or a large percentage (e.g. from around 70% to 100%) of the possible rotational positions of the camera assembly 350. In some embodiments, the entire distal end of the shaft or insertion section 14 (or the entire insertion section 14) may be transparent such that the camera assembly 350 may be rotated therein to obtain many viewing angles through the transparent portion or portions; In this specific embodiment, the distal portion of the insertion section 14 optionally may be fluidly sealed from the surrounding space, the camera and light source relying on the transparency of the distal end of the shaft.

Additionally, in some embodiments, a controller monitoring the rotational position of the camera assembly 350 may increase or decrease the intensity of light emitted by various light sources 702a-d depending on the position of the field of view 700. For example, a controller may monitor displacement of a pivot control structure 100 (see, e.g. FIG. 14) via a sensor such as a rotational potentiometer attached to a pivot shaft 204 (see, e.g. FIG. 14). Based on data collected from the sensor, a controller may determine if a light source 702a-d has shifted from a direct light source to an indirect light source or vice versa. The controller may then adjust the intensity of light produced by that light source 702a-d accordingly. Based on the sensor reading, the controller may, for example, determine which light sources 702a-d are emitting light into the field of view 700 of the camera assembly 350 and decrease the intensity of light produced by those light sources 702a-d. A controller may use the sensor reading to determine if the camera assembly 350 has been rotated such that a light source 702a-d which was previously emitting light directly into the field of view 700 is now acting as an indirect light source. Upon determination that a light source 702a-d has shifted from a direct light source to an indirect light source the intensity of light produced by that light source 702a-d may be increased. The adjustment of the emitted light may be done in a continuous, gradual fashion, step wise fashion, or binary manner (e.g. switching between a preset direct and indirect intensity level).

An example of a printed circuit board 430a which includes a number of LED light sources 750 and a sensor 754 on an extension 430h of the printed circuit board 430a is shown in FIGS. 53-54. A sensor or camera assembly 350 is also shown at the end of the PCB extension 430h. FIG. 53 depicts a top down view of the printed circuit board 430a, while FIG. 54 depicts a side view of the printed circuit board 430a.

Figure 61:
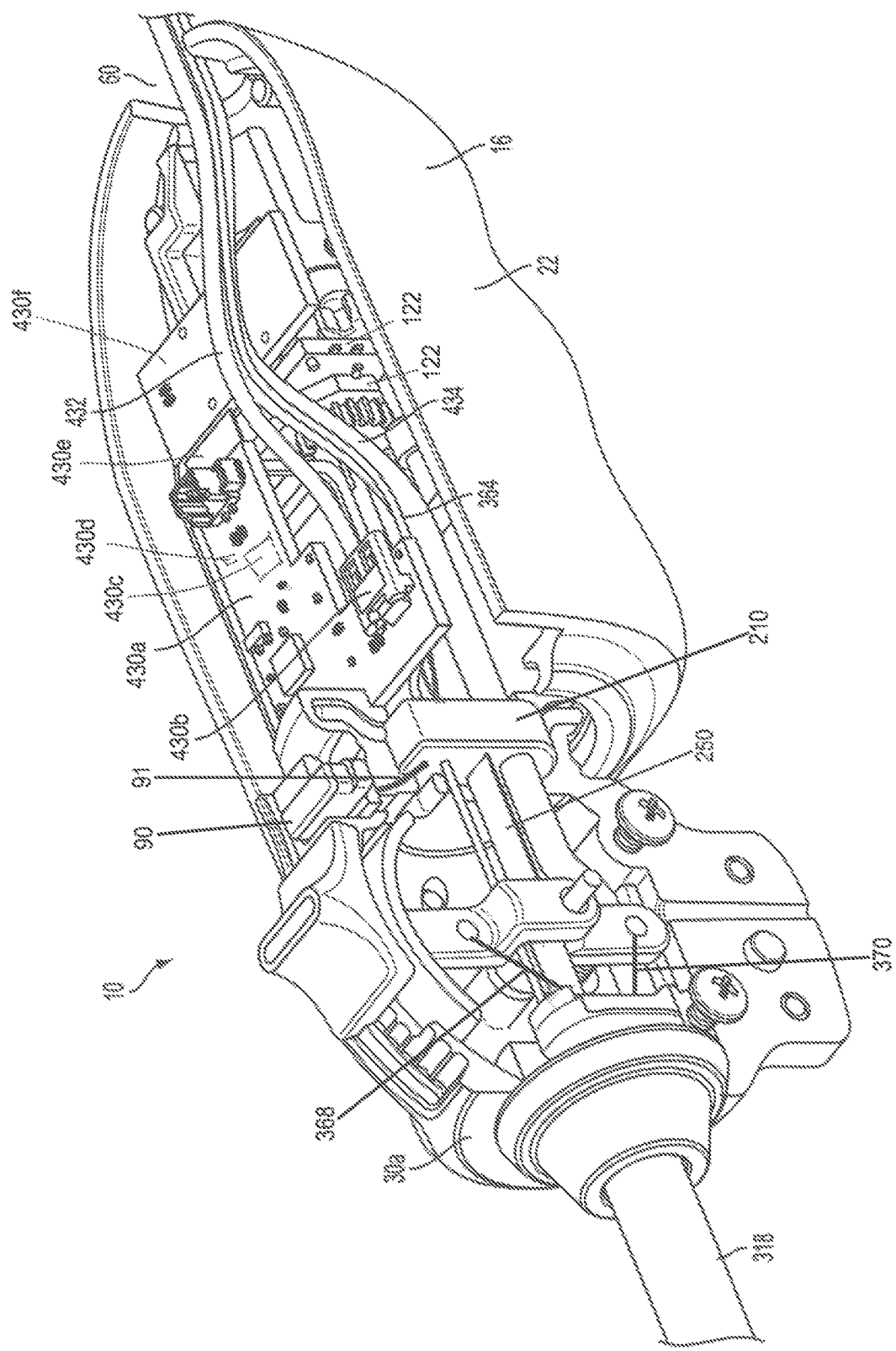
FIG. 61 shows a partially assembled view of an endoscope with a handle printed circuit board, power/HDMI cable, illumination fibers, and irrigation line in their assembled locations.

The printed circuit board 430a may include a main portion 430L from which a shaft portion 430H extends. The main portion 430l of the printed circuit board 430a may be housed in the handle 12 (see, e.g. FIG. 3A or 3B) of an endoscope 10. In the example embodiment shown in FIGS. 53-54, the main portion 430l is not shown populated with electronic components for sake of simplicity. An example printed circuit board 430a populated with exemplary components 430b-f is depicted in FIG. 61. In some embodiments, and as shown in FIG. 54, at least a portion of the main portion 430L of the printed circuit board 430a may be coated or encased in a protective coating or layer of material. The protective material may be any of a variety of potting material or conformal coating materials. Acrylic, epoxy, polyurethane, silicones, parylene, thermo-setting plastics, rubber, or any other potting material or conformal coating material may be used. Preferably, the protective material is biocompatible and provides waterproofing characteristics. A transparent protective coating may also be placed over the LEDs 750 and sensor 754 on the projecting portion 430h.

The PCB extension (or optionally ribbon cable) 430h may extend through a pass-through barrier 159 (see, e.g. FIG. 15) and along the axis of an insertion section 14 (see, e.g. FIG. 15) of an endoscope 10. The projecting portion 430h may provide power and data communication pathways to various components (e.g. a camera assembly 350 and/or LEDs 750) within the insertion section 14 (see, e.g., FIG. 15). The projecting portion 430h may be divided into a number of different parts. In the example shown, the projecting portion 430h includes a first portion 430i, second portion 430j, and a third portion 430k. (In other embodiments, the projecting portion 430h may be divided into a different number of components). Each part of the projecting portion 430h may possess different characteristics. For example, each part of the projecting portion 430h may have differing levels of flexibility. Certain parts may be rigid circuit board, while other parts are flex cable. Additionally, each part of the circuit board may have different number of layers, different widths, different numbers of traces on each layer, etc. It may be desirable that at least one part of the projecting portion 430h of the printed circuit board 430a be a flex cable or be otherwise flexible. This may help to facilitate rotation of the camera assembly 350.

In some embodiments, the first portion 430i may be a six layer rigid circuit board. The second portion 430j may be a 2 layer flex cable. The third portion 430k may be a 4 layer rigid circuit board. Each section may transition into the next section or connectors may be used between one or more section of the projecting portion 430h. To simplify manufacturing and to reduce costs, it may be preferable that the communications and power lines in the endoscope shaft comprise flexible and/or rigid extensions of the main PCB located in the endoscope handle. The entire PCB with extension(s) can be manufactured as shown in FIG. 33B, and any flexible PCB extension can be folded over as shown in FIG. 33C to run adjacent to a companion PCB extension (rigid or flexible) during assembly of the endoscope.

The sensor 754 may be any of a variety of sensors. In some embodiments, the sensor 754 may be a temperature sensor such as a thermistor, thermocouple, or resistance temperature detector. In some specific embodiments, the sensor 754 may be thermistor. A temperature sensor 754 may be used to monitor the temperature of the environment near or at the LEDs 750.

During an endoscopic procedure, irrigation fluid may flow over the LEDs 750. This fluid may help to cool the LEDs 750 keeping the temperature of the LEDs 750 within a desired temperature range. In the event that an endoscope 10 is outside of a patient and irrigation fluid is not running, a controller may monitor data from the sensor 754 to determine if the environment near the LEDs 750 is becoming hotter than a desired temperature range. In the event that temperature exceeds the temperature range, the controller may command current flow to the LEDs 750 to be lowered or the controller may command the LEDs 750 off. A temperature sensor may also be used as an irrigation fluid flow sensor. During an endoscopic procedure, the flow rate of irrigation fluid may be sufficient to dissipate heat produced by the LEDs 750 via convection such that the area surrounding the LEDs 750 is within a desired temperature range. In the event that the flow rate decreases beyond a certain amount, the temperature in the area proximal to the LEDs 750 may rise. This rise may, in some embodiments, be interpreted by a controller as a decrease in irrigation fluid flow rate. In response, the controller may generate a notification to user to this effect.

Figure 55:
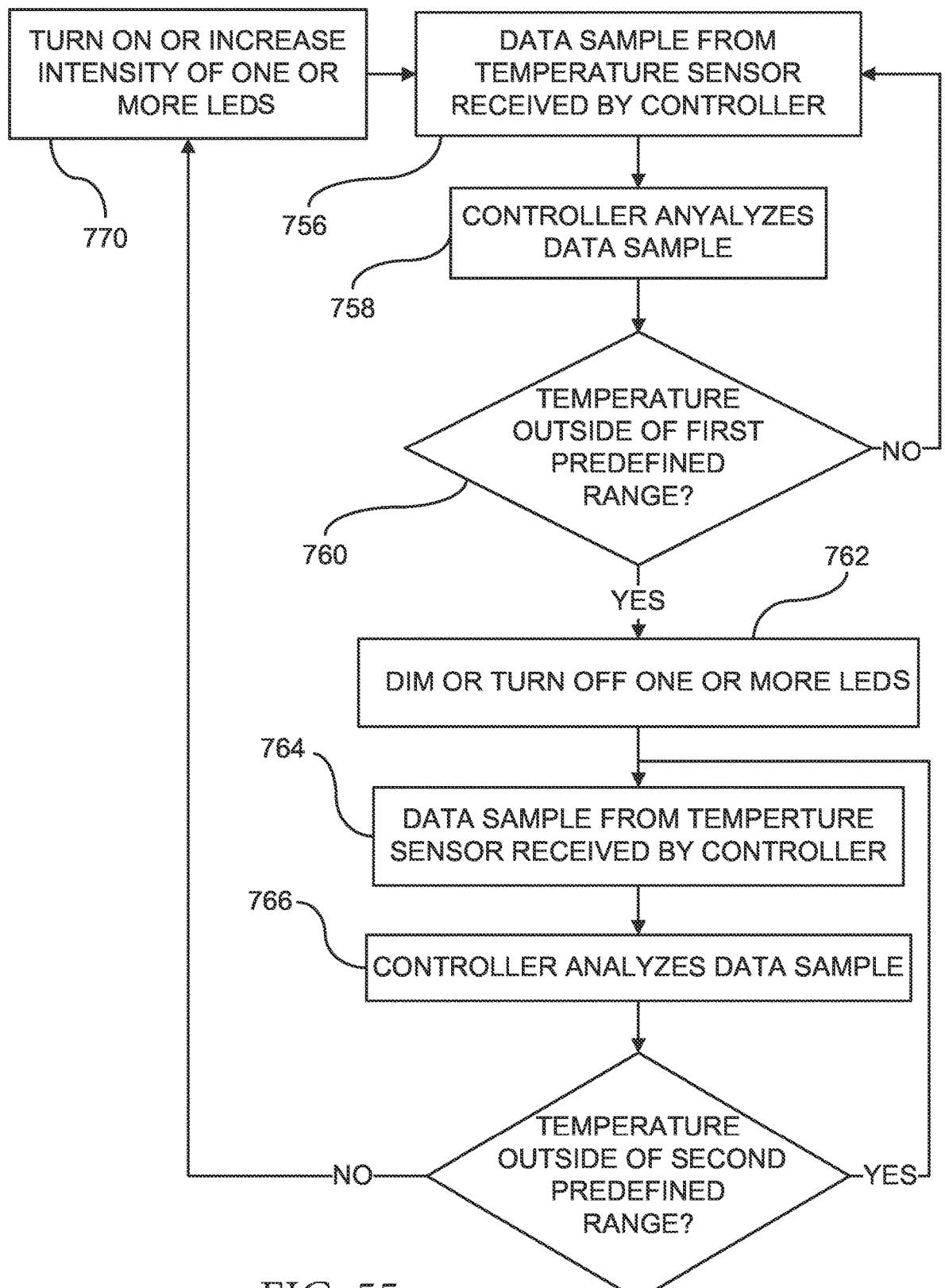
FIG. 55 depicts an example flowchart detailing a number of example steps which may be used to control, with a processor, at least one variable light source of an endoscope based on received sensor data.

FIG. 55 depicts a flowchart detailing a number of example steps which may be used by a controller to control LEDs in an insertion section 14 based on a sensed temperature. In step 756, a controller receives a data sample from a temperature sensor near the LEDs. The controller then analyzes the data sample in step 758. If 760 the temperature is not outside of a first predefined range, step 756 may be repeated. If 760 the temperature is outside of the first predefined range, the controller may transition one or more LED from a first state to a second state in step 762. The temperature range may have a high bound of between 40-50 degrees Celsius (e.g. 50 degrees Celsius). The first state may be a high light output intensity on-state and the second state may be an off-state. In the example flowchart, the second state is a dimmed or off-state. The controller receives a data sample from the temperature sensor in step 764 and analyzes the data sample in step 766. If 768 the data sample indicates the temperature is outside of a second predetermined range, step 764 may be repeated. If 768 the data sample indicates that the temperature is within the second predefined range, at least one LED may be turned on or commanded to increase the intensity of light it produces in step 770.

The first and second predefined ranges may be the same, or the first and second predefined ranges may differ, with the second predefined range being less than the first predefined range. This may ensure that the controller does not rapidly cycle between turn on/off or dimming and increasing the intensity of light from the LEDs. In some embodiments, after reaching step 762, a timer may be started. The timer may be a minimum dim or off time timer for the at least one LED whose brightness has been modified. In the event that the minimum off or dim timer has not elapsed, the at least one LED may not be turned back or commanded to increase light output intensity even if the temperature is within the second predefined range. This may again help to prevent rapid cycling between LED states.

Figure 56:
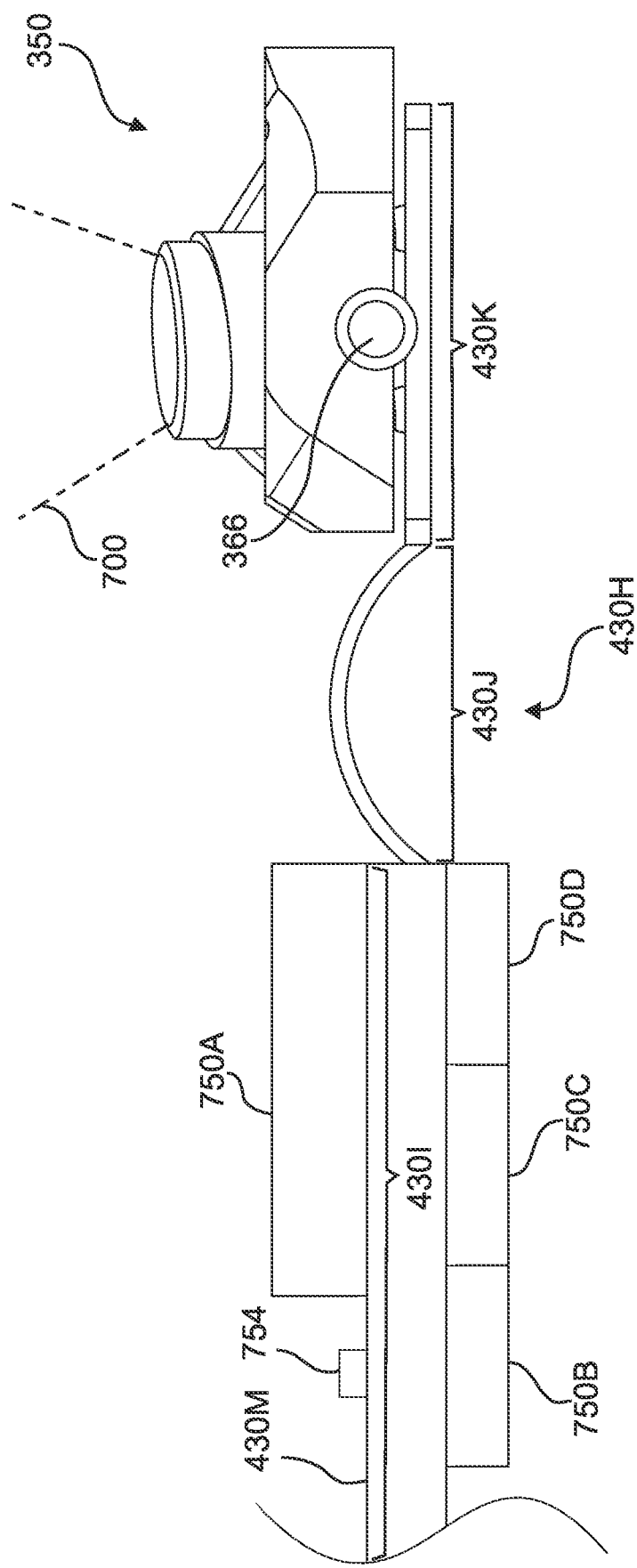
FIG. 56 shows a side view of a projecting portion of a printed circuit board having an example camera assembly, example sensor, and number of example light sources mounted thereto.

FIG. 56 depicts a close-up side view of an example of the end of the projecting portion 430h of the printed circuit board 430a. As shown, the projecting portion 430h includes a first portion 430i, second portion 430j, and third portion 430k. A camera assembly 350 is attached to the third portion 430k. A sensor 754 is mounted on the first portion 430i in the vicinity of a number of LEDs 750a-d. The sensor 754 may be a temperature sensor such as a thermistor and may be used to aid in control of the LEDs 750a-d. Sensors for detecting characteristics of a fluid environment other than temperature (e.g., conductivity, pH, etc.) may also be used.

LED 750a may be a direct lighting source and generally projects light into the field of view 700 of the camera assembly 350. LED 750a is mounted to a first side 430m of the first portion 430i of the projecting portion 430h. LEDs 750b-d are mounted on a second side 430n of the first portion 430i which is opposite the first side 430m. These LEDs 750b-d may be indirect light sources and in some embodiments may not project light directly into the field of view 700 of the camera assembly 350 in any rotational orientation of the camera assembly 350. In some embodiments, LED 750a may be a RBG LED array. LED 750a may be adjusted to provide light at a spectrum which may help to modify the color of the image produced by an image sensor of the camera assembly 350 in a desired manner. For example, LED 750a may be adjusted to correct a color bias of an image sensor of the camera assembly 750*a*. LEDs 750*b-d* may be white light LEDs. As shown, the first portion 430*i* of the projecting portion 430*h* may be a thicker portion of printed circuit board relative to other portions 430*j*, 430*k* of the projecting portion 430*h*. This may allow the power demands of the LEDs 750*a-d* to be easily accommodated.

The first portion 430*i* may transition into the second portion 430*j* of the projecting portion 430*h*. The second portion 430*j* may be a relatively thin flex cable. The second portion 430*j* may facilitate rotation of the camera assembly 350 about the axis of the pivot pins 366 of the camera assembly 350. As shown, the second portion 430*j* may be of a length such that when the first portion 430*i* and third portion 430*k* are parallel to one another, the second portion 430*j* is bowed or arched. This may help to allow for increased range of motion of the camera assembly 350.

Figure 57:
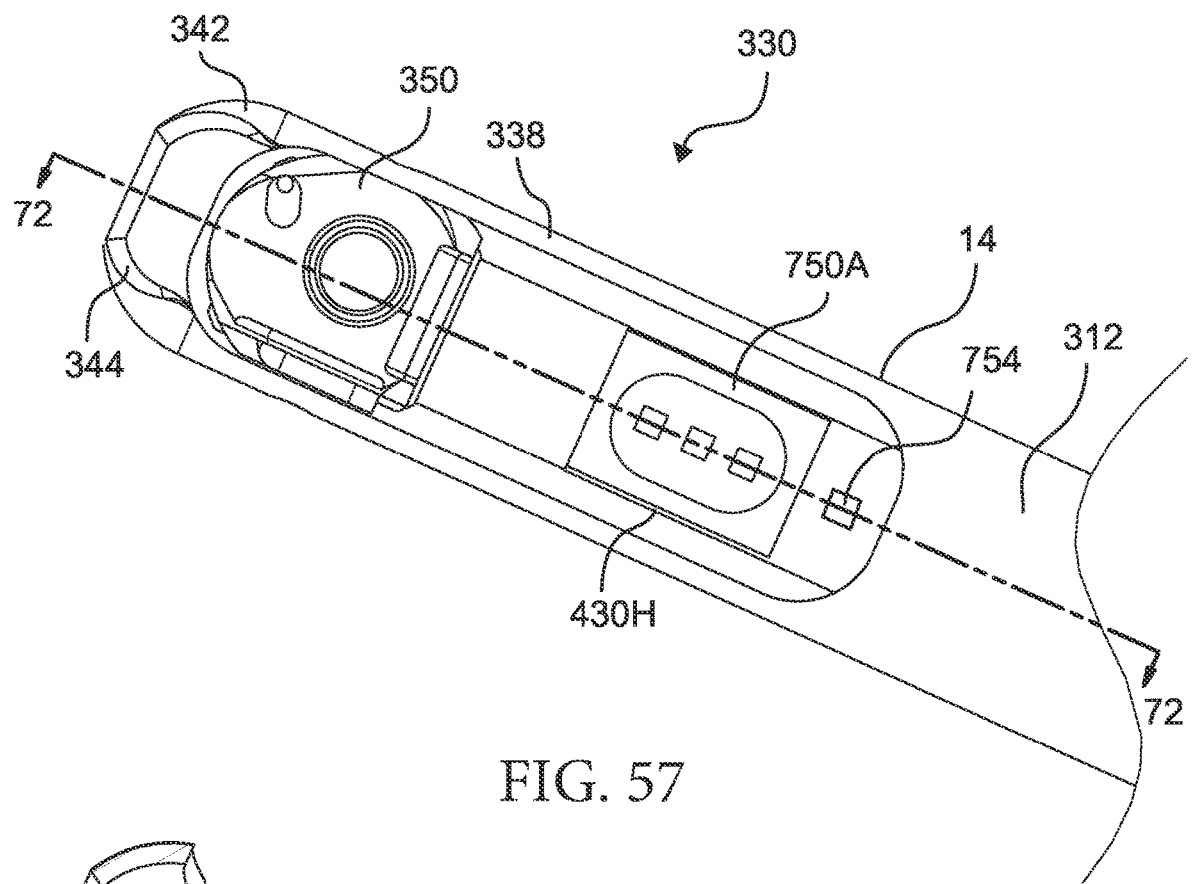
FIG. 57 shows a top down view of a distal tip of an example endoscope including the example projecting portion of a printed circuit board shown in FIG. 56.
Figure 58:
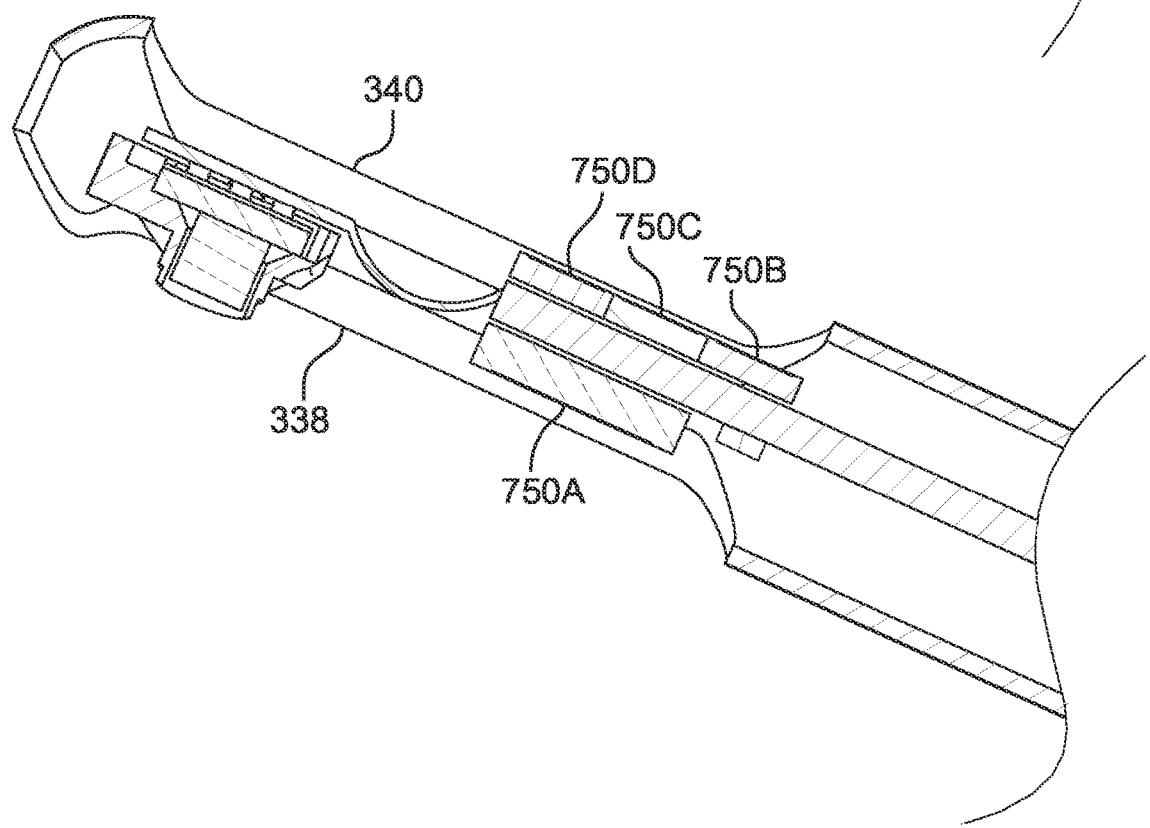
FIG. 58 shows a cross sectional view of the distal tip of an endoscope taken at line 72-72 of FIG. 57.

FIG. 57 depicts an example embodiment of a camera assembly housing 330 of an insertion section 14. FIG. 58 depicts a cross-sectional view of the camera assembly housing 330 taken at line 72-72 of FIG. 57. The camera assembly housing 330 is continuous with the inner sheath 312 and both can be formed as a single part. As shown in FIG. 57-58 a projecting portion 430*h* of a printed circuit board 430*a* (see, e.g., FIG. 54) is shown within the camera assembly housing 330. The projecting portion 430*h* is similar to that shown in FIG. 56 and includes a camera assembly 350, a number of LEDs 750*a-d* and, optionally, a sensor 754. As shown, the LEDs 750*a-d* are arranged such that they may emit light out of the top and bottom openings 338, 340 of the camera assembly housing 330. The camera assembly 350 may be panned such that its field of view can be swept from the embrasured opening 344 at the rounded tip 342 through the opening provided by the top void 338. When fully assembled an outer sheath 318 (see, e.g. FIG. 22) may be placed over the camera assembly housing 330 and inner sheath 312 to protect the camera assembly 350 while still providing an unobstructed field of view.

Figure 58A:
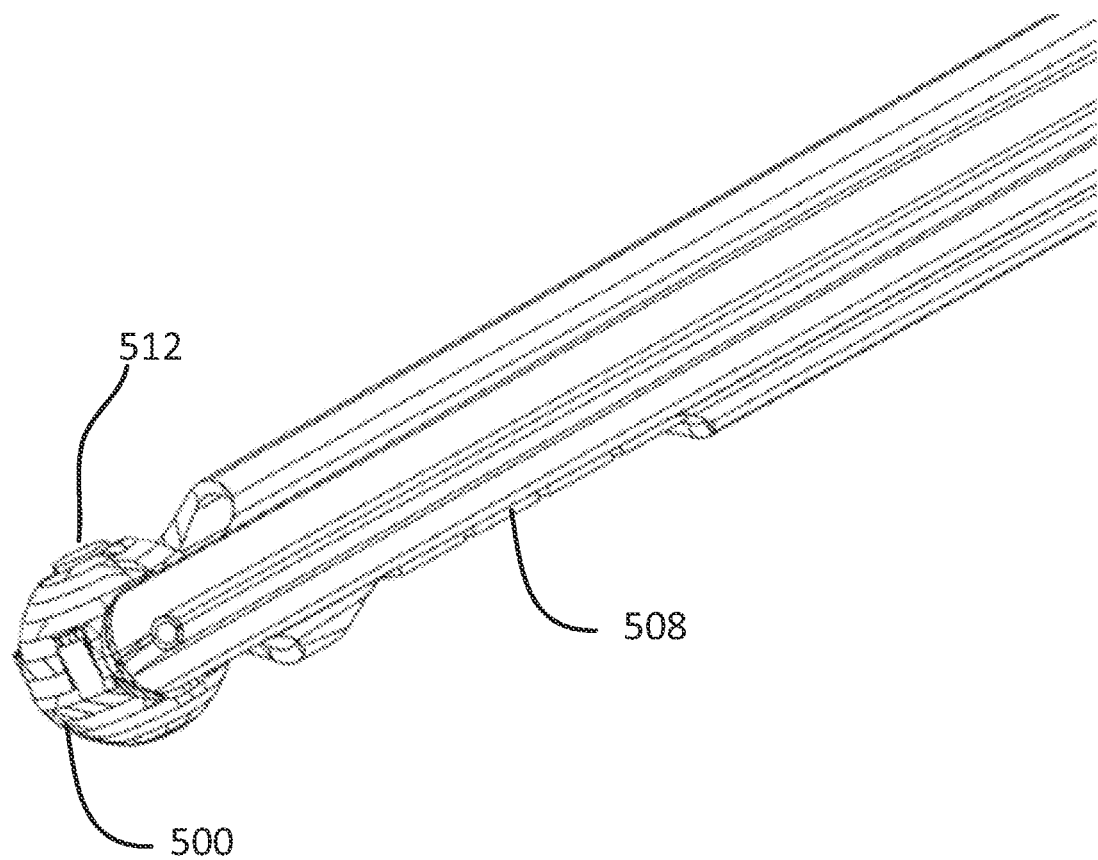
FIG. 58A shows a perspective view of the distal end of an endoscope shaft in which the light source is located on the shaft to project light in a direction generally away from the field of view of the camera assembly.

FIG. 23A shows a perspective view of the distal end of the shaft of an endoscope (or arthroscope) 14 in which the sensor or camera housing 500 is positioned at the tip of the shaft. In this case the inner sheath 312 has no distal-most protective guard, shield or tip structure. At least a portion of the rotatable sensor or camera housing 500 (i.e. the distal-most portion) forms the distal-most element of the endoscope insertion end. Thus the sensor housing 500 is preferably constructed to withstand repeated contact with anatomical structures including soft tissue, bone, cartilage or articular surfaces. In an embodiment, as described above for camera housing 350, the rounded or dome-shaped camera housing 500 may also include a light source, movable with the rotatable camera housing, and continuously directed toward the field of view of the camera housing 500. The light source may comprise, for example, one or more LED's, or the terminus of a fiberoptic bundle. In the example shown in FIG. 23.1, a light source 508 (in this case a bank of LED's) is positioned on a side of the shaft just proximal to the location of the rotatable sensor or camera housing 500. In the illustration, the light source 508 is on the side that directs illumination toward the general field of view of the camera/lens assembly 500 when rotated to approximately 90 degrees with respect to the long axis of the endoscope shaft 14. (Alternatively, the light source may be arranged to be opposite the side on which the camera assembly—lens and sensor—can be oriented). In the arrangement shown, the optical axis of the camera assembly can be directed generally toward the direction of light projected from a first side of the insertion end of the endoscope. In other arrangements, the light source is positioned on a second opposing side of the insertion end, projecting light away from the second side of the insertion end of the endoscope, while the optical axis of the camera assembly can be directed generally toward a field of view opposite the first side of the insertion end of the endoscope. FIG. 58A shows a perspective view of this latter arrangement, in which the light emitted by the light source 508 (LED's in this example) is directed to a region generally away from the field of view of the sensor and lens 512. The alternative second arrangement is intended to provide indirect illumination (or backlighting) of the field of view of the camera assembly, relying on the ambient light generated by the illumination source in the operative field of the endoscope. The illumination source or LED's are mounted to be flush with or recessed from the outer surface of the inner sheath or shaft of the insertion end. If recessed, there is less likelihood that heat generated by the LED's will directly touch or injure nearby tissues in the operative field.

Figure 59:
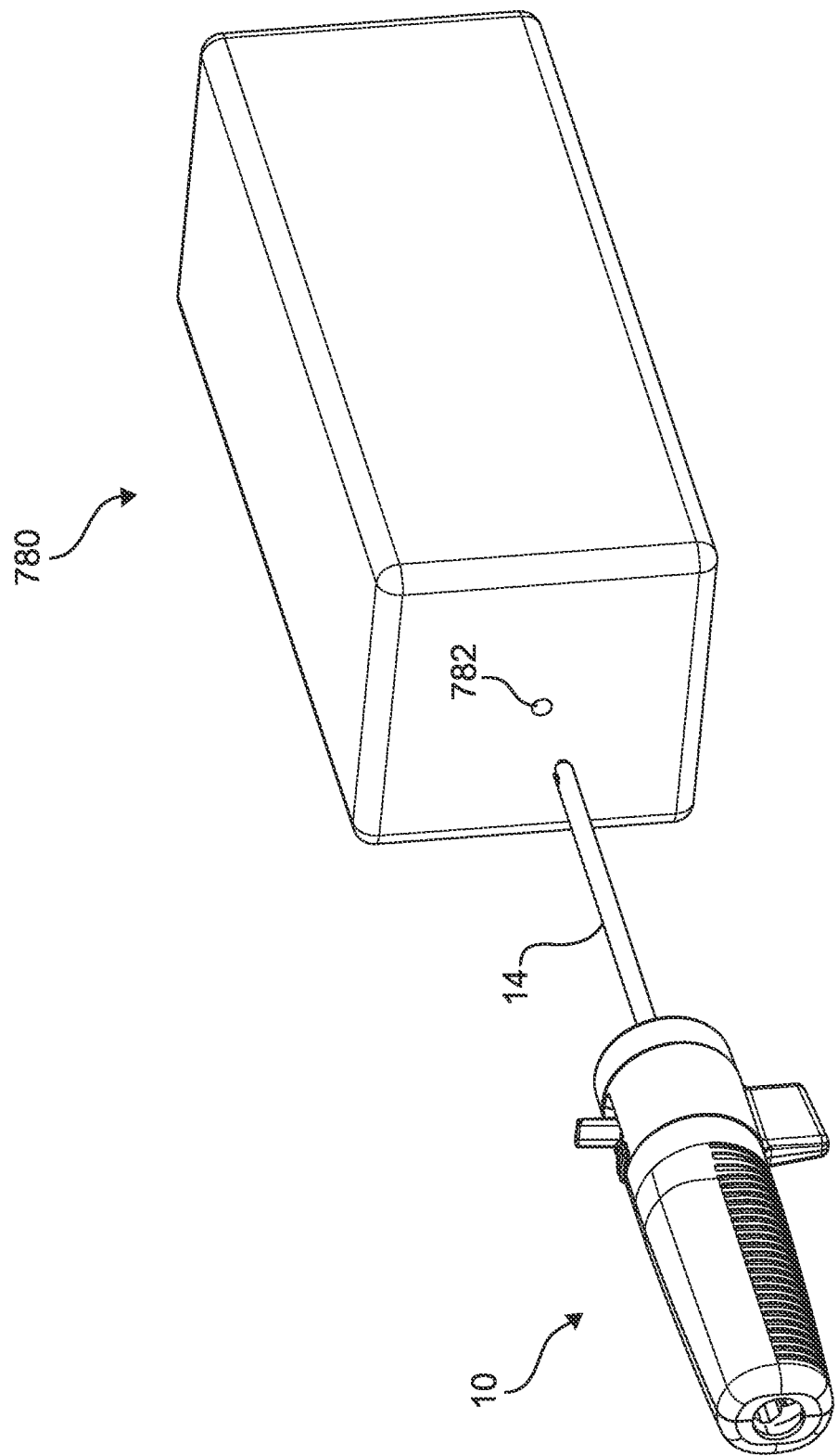
FIG. 59 depicts an example endoscope and example calibration fixture.

Referring now to FIG. 59, in embodiments which include at least one variable illumination source which may produce light at different intensities and/or spectrums, the endoscope 10 may be placed in a calibration fixture 780 to aid in setting various lighting parameters. An embodiment with one or more white LED and one or more colored LED (e.g. a RBG LED array) may for example be placed in a calibration fixture prior to usage to adjust light output intensity of its LEDs and adjust the color output of the one or more colored LED. This may help to ensure more uniform image quality and minimize differences between endoscopes 10 which may be attributable to variation between their LEDs and/or image sensors.

The calibration fixture 780 may be a light-tight box or other volume including an opening 782 sized to fit the insertion section 14 of the endoscope 10. This opening 782 may be gasketed such that a light-tight seal is formed against the insertion section 14 of the endoscope 10 when the endoscope 10 is installed in the calibration fixture 780. The interior of the calibration fixture 780 may include one or more target(s) with known characteristics placed within the field of view of a camera assembly 350 (see, e.g. FIG. 57) of the endoscope 10. For example targets with known color characteristics may be placed within the calibration fixture 780.

A controller may monitor characteristics of the one or more target(s) in the image captured by an image sensor of a camera assembly 350. Since the characteristics (e.g. color) of the targets is known, the controller may adjust the lighting provided by the variable light source(s) until the characteristics of the target(s) in the captured image match or are within a range of the target's or targets' known characteristics. For example, the intensity of light and/or spectrum of light produced by a number of LEDs 750*a-d* (see, e.g. FIG. 56) included in the insertion section 14 may be adjusted.

Figure 60:
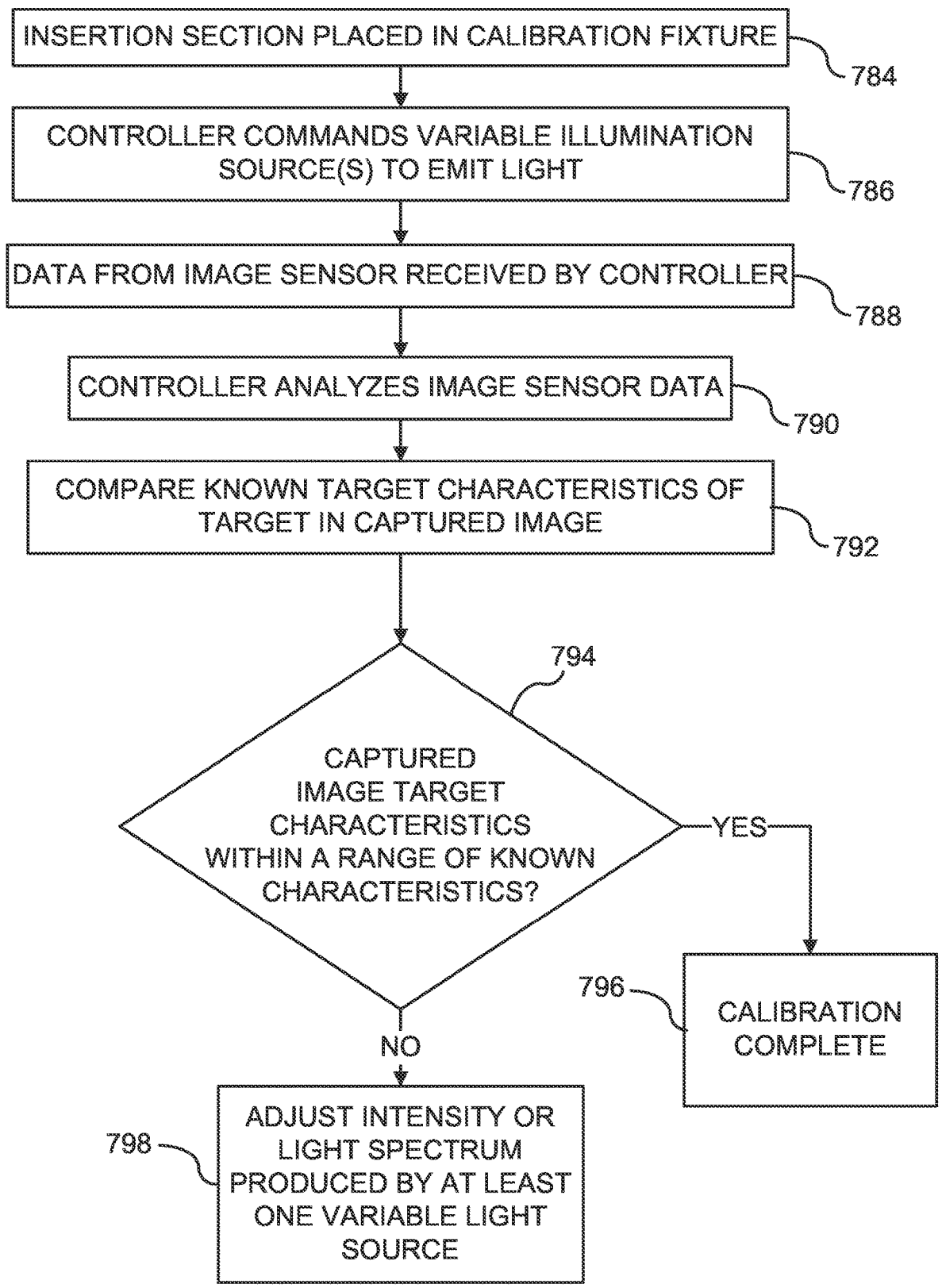
FIG. 60 depict flowchart including a number of example steps which may be used to calibrate lighting parameters values for variable illumination sources of an endoscope.

FIG. 60 depicts a flowchart detailing a number of example steps which may be used to calibrate one or more lighting parameter of at least one variable light source included in an endoscope. In step 784 a portion of the insertion section of an endoscope including a camera assembly may be placed in a calibration fixture. Once inserted, a controller may command variable illumination sources in the endoscope to emit light in step 786. The light may be emitted based on default parameters (e.g. light intensity and color parameters). In step 788, a controller may receive image date from an image sensor of an endoscope's camera assembly. This data may be analyzed by a controller in step 790. The image data may, for example, be analyzed to determine one or more characteristics of interest of a target or targets in the captured image.

These characteristics may be compared, in step 792, to the known or expected characteristics of the target or targets which have been imaged. If 794 the characteristics of the target in the captured image are within a range of the known or expected characteristics, the calibration may be considered complete in step 796. If 794 the characteristics of the target or targets in the captured image are not within a range of the known or expected characteristics, a controller may adjust one or more illumination parameter of at least one variable illumination source of the endoscope in step 798. In the example embodiment, the intensity and/or spectrum of light produced by at least one variable light source is adjusted in step 798. Step 788 may repeated after adjustment. Images may continue to be compared and analyzed and illumination parameters may be adjusted until the characteristics of targets in the captured image are within range of their known or expected values. Various methods may be used in the construction and assembly of a lens or group of lenses to focus images onto the sensor or camera at the distal end of the endoscope shaft. Examples of such methods and techniques are disclosed in U.S. patent application Ser. No. 14/170,080 (US Application Publication No. 2014/0221749), filed Jan. 31, 2014, and incorporated herein by reference in its entirety.

FIG. 61 shows another example embodiment of the endoscope 10. An outer sheath 318 is shown installed on the endoscope in FIG. 61. Additionally, only the bottom half-shell 22 of the handle proximal section 16, and half (30*a*) of the handle distal section 30 are visible for clarity of this description. As shown, the endoscope 10 includes a handle-enclosed printed circuit board 430*a* (also referred to herein as handle or main PCB 430*a*). An electronic cable (such as, e.g., a power/HDMI cable) 432, optical fibers 364, and irrigation/suction line 434 are also shown. FIG. 61 shows example routing pathways for the power/HDMI cable 432, optical fibers 364, and irrigation line 434. As shown, the electronic cable 432, optical fibers 364, and irrigation line 434 enter the endoscope 10 through an opening 60 at the rear or butt end of the handle proximal section 16. This entry point may be more advantageous than a handle side-entry point because it reduces the potential of various cords and cables to get tangled as the insertion section is rotated relative to the handle proximal section 16.

In some embodiments, the electronic cable 432, optical fibers 364 (if present), and irrigation line 434 may enter the endoscope 10 at an angle with respect to the rear handle opening 60. Such an arrangement would afford an ergonomic benefit to the user by allowing the user to grasp a greater portion of the rear portion of the handle proximal section 16.

As shown, the electronic cable 432, optical fibers 364 (if implemented in the endoscope), and irrigation line 434 extend over a portion of the handle PCB 430*a* after entering the handle proximal section 16. The electronic cable 432 plugs into a connector 430*b* (such as, e.g. a power/HDMI connector) on the handle PCB 430*a*. The electronic cable 432 may provide power to the endoscope 10. Image data may pass to the handle PCB 430*a* via the flex cable 250. The electronic cable 432 may transmit visual data collected by the endoscope 10 to an external graphical user interface display (not shown). The optical fibers 364 (if implemented in the endoscope) and irrigation line 434 extend under the handle PCB 430*a* and follow the pathways previously described. In embodiments in which the endoscope 10 is disposable, the electronic cable 432, optical fibers 364, and irrigation line 434 may all be included as disposable components to ensure sterility each time an endoscope is used, or to save on the costs of sterilization and packaging for re-use.

In this example, a control wire 91 for button 90 is also shown in FIG. 61. As shown, the control wire 91 passes through an orifice in the sealing member 210. The control wire 91 is in communication with the handle PCB 430*a*. Also as shown in FIG. 61 the handle PCB 430*a* includes a handle PCB flex cable 430*e*. The handle PCB flex cable 430*e* connects to a handle PCB portion 430*f*, permitting PCB portion 430*f* to be oriented at an angle (e.g., perpendicular) to the rest of the handle PCB 430*a*. When assembled, the flex attached handle PCB portion 430*f* may be disposed between the two potentiometers 122 of the example rotation sensing assembly 150 (see FIG. 8).

In some embodiments, the handle PCB 430*a* may include an image or graphic processing unit 430*c*. Preferably, however, the image processing unit 430*c* is located external to the endoscope 10. The image processing unit 430*b* may function as an electronic righting mechanism for the endoscope 10. The image processing unit 430*c* may receive the image captured by the image sensor 380 which is sent from the image sensor 380 to the handle PCB 430*a* via the flex cable 250. In a preferred embodiment, the image captured by the image sensor 380 is then transmitted to the image processing unit 430*c* external to the endoscope 10 via the electronic cable 432. The image processing unit 430*c* may also receive a signal from the rotation sensing assembly 150. In some embodiments, an analog to digital converter 430*d* may be included on the handle PCB 430*a* to convert the signal from the rotation sensing assembly 150. The image processing unit 430*c* may use the signal from the rotation sensing assembly 150 to electronically "right" the image to a desired orientation. In some embodiments, image may be rotated by the image processing unit 430*c* so that the image is displayed as if it were captured from the user's point of view. In some embodiments, the image processing unit 430*c* may also correct for the effects of lens distortion.

Unless the orientation of an image displayed on a graphical user interface is first corrected, the displayed image may be disorienting to the user. By defining a direction according to the user's point of view, the image processing unit 430*c* may use data from the rotation sensing assembly 150 to automatically rotate images so that images correspond with the user's point of view.

Figure 62:
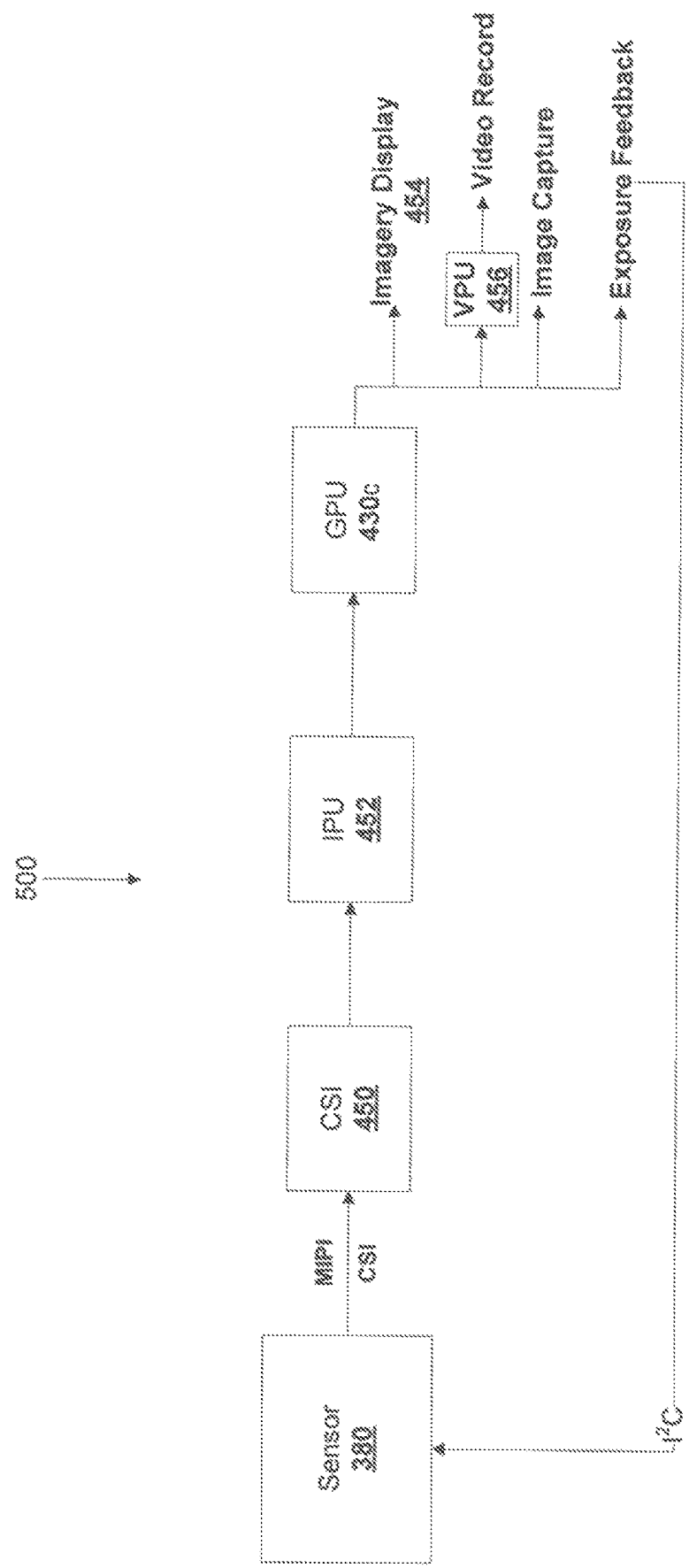
FIG. 62 shows a block diagram of an example image processing system.

FIG. 62 shows an example block diagram of an imaging system. As shown, the imaging system includes an image sensor 380 that captures an image. The image captured by the image sensor 380 may be passed via a camera serial interface 450 (for example a MIPI camera serial interface) to an image processing unit 452. The image processing unit 452 (IPU) may then move image frames to other hardware components in the imaging system. Other hardware components may include, but are not limited to, a memory device and a graphical processing unit 430*c* (GPU). The graphical processing unit 430*c* may correct any distortion caused by the lens assembly 354.

In some embodiments, the graphical processing unit 430*c* may correct this distortion by representing the image as a texture on a surface that has been loaded into the graphical processing unit 430*c*. This may cause the image to be adjusted or stretched in a manner which corrects and/or removes the distortion introduced by the lens assembly 354. In embodiments where the image is righted, the graphical processing unit 430*c* may then rotate the corrected image via input from a rotation sensing assembly 150 (see, for example, FIG. 8). For example, the measurement from a rotation sensing assembly 150 may be passed to the graphical processing unit 430c through an analog to digital converter 430d (see, for example, FIG. 61). The signal from the analog to digital converter 430d may then be used to rotate the image to its righted orientation. In some embodiments, a user may be able to toggle image righting, distortion correction, and/or various other image manipulations which may be performed on or off. Image righting will be further described later in the specification in relation to FIG. 63.

The processed image from the image processing unit 430c may then be displayed on a graphical user interface or display 454. In some embodiments, the processed image from the image processing unit 430c may be stored in memory. In such embodiments, a user may capture images to be stored in memory for later recall by triggering a button 90, for example. Some embodiments may include a video processing unit 456 which may encode the frames from the image sensor 380 into a recordable video format. In such embodiments, encoded video may then be stored in memory. A user may command the endoscope to initiate and stop video capture via interaction with a button such as button 90 as described above.

In some embodiments, the image processing unit 430c may also subject a captured image to exposure feedback analysis. In specific embodiments, an image histogram may be created from all the pixels of the image. The image histogram may then be used to tune the image or tune the exposure of subsequent images received by the image chip or sensor 380. Such further processing by the image processing unit 430c may help to reduce blown-out white areas of the image or underexposed dark areas of the image. Other means of tuning an image or images, such as, for example, tone mapping, etc. may also be used.

Figure 63:
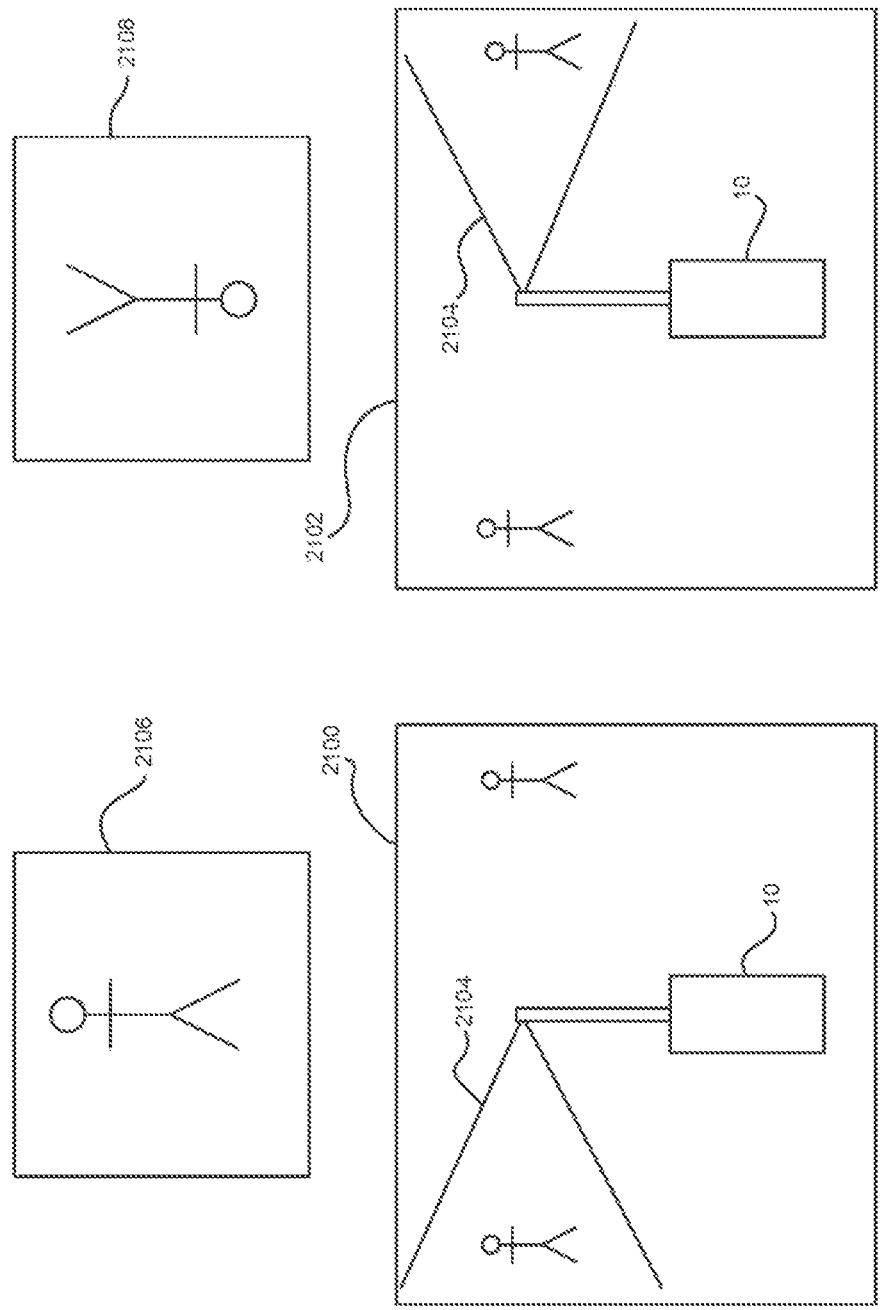
FIG. 63 depicts an example diagram illustrating how an image may be righted using input from a rotation sensing assembly.

FIG. 63 depicts an example diagram illustrating how an image may be righted using input from a rotation sensing assembly 150 (see, for example, FIG. 63). As shown, a first block 2100 and a second block 2102 are depicted. Within each block 2100, 2102 is an endoscope 10 having a field of view 2104 is depicted. The field of view 2104 of the endoscope 10 in the first block 2100 is oriented approximately 180 degrees from the endoscope 10 in the second block 2102. This may be accomplished by rotating the distal end of the endoscope 10 relative to the proximal end of the endoscope 10. In conventional endoscopes 10, during rotation of the distal section relative to the proximal section, the image sensor does not rotate because the image sensor is housed in the proximal section. Thus, the endoscopes 10 shown in the first block 2100 and second block would both capture image 2106.

This would not be the case In some embodiments described herein in which the image sensor 380 rotates with the distal end of the endoscope 2106. The endoscope 10 shown in the first block 2100 would capture image 2106, while the same endoscope 10 rotated to the position shown in the second block 2102 would capture image 2108. As the image sensor rotates with the distal end of the endoscope 10, the image sensor will invert the image. In this position, for example, the top of the image sensor will pick up what one accustomed to a conventional endoscope 10 would expect to be the bottom of the image.

Optionally, the image may be rotated in proportion to the degree of rotation of the distal end of the endoscope 10. Thus the image can always be displayed in a way which would be expected by a user accustomed to conventional endoscopes 10. This may help to alleviate problems associated with a rotating image sensor.

Various embodiments shown in the drawings are presented only to demonstrate certain examples of features of the disclosure. Not all features shown in any given drawing necessarily have to be included in a claimed device or feature. The drawings are to be interpreted only for illustrative purposes; as such, the size of some of the elements may be exaggerated and not drawn to a particular scale. Additionally, elements shown within the drawings that have the same reference numbers may be identical elements or may represent similar or analogous elements, depending on the context.

Any terms such as "first", "second", "third" and the like, whether used in the description or in the claims, are intended to distinguish between similar elements and not necessarily to describe a sequential or chronological order. It is to be understood that the terms so used are interchangeable under appropriate circumstances (unless clearly stated otherwise) and that the embodiments of the disclosure described herein are capable of operation in other sequences and/or arrangements than are described or illustrated herein.

The invention claimed is:

1. An endoscope comprising a handle comprising:
   a proximal handle housing configured to house an electronic processing board for processing signals from an image sensor located at a distal end of a shaft of the endoscope;
   a distal handle housing configured to hold the electronic processing board in a position fixed with respect to the distal handle housing;
   one or more rotation sensing magnets attached to an internal wall of the proximal handle housing, said rotation sensing magnets being located next to a first Hall effect sensor on the electronic processing board;
   an electronic control button on the handle comprising a member including an electronic control magnet located above or adjacent a second Hall effect sensor on the electronic processing board,
   wherein the proximal handle housing is rotatable with respect to the distal handle housing, and the first Hall effect sensor is configured to provide a rotational position signal representing the relative rotation of the proximal handle housing with respect to the distal handle housing, and
   wherein the second Hall effect sensor is configured to provide a button position signal corresponding to a position of the electronic control button member with respect to the second Hall effect sensor.

2. The endo scope of claim 1, wherein the electronic processor is connected to a user interface displaying an image generated by the image sensor, and wherein a rotational orientation of the image is altered by a change in the relative rotation of the proximal handle housing with respect to the distal handle housing.

3. The endoscope of claim 1, wherein the electronic control button is located on the distal handle housing.

4. The endoscope of claim 1, wherein the second Hall effect sensor is configured to provide a button duration signal corresponding to a duration that the electronic control button member remains in a pre-determined position.

5. The endoscope of claim 4, wherein the second Hall effect sensor is configured to provide a combination signal corresponding to a pre-determined series of two or more depressions and releases of the electronic control button, or to a release of the electronic control button between two depressions having two or more variable durations.

6. The endoscope of claim 4, wherein the position of the electronic control button comprises a position having a first duration or a longer second duration, a pre-determined series of two or more depressions and releases of the electronic control button, or a release of the electronic control button between two depressions having two or more variable durations.

7. The endoscope of claim 1, wherein the electronic control button is configured to cause an electronic controller communicating with the electronic processing board to start a recording of an image generated by the image sensor, to stop a recording of an image generated by the image sensor, or to take a photograph of an image generated by the image sensor, based on a movement or release of the button by a user.

8. The endoscope of claim 1, wherein the electronic control button is configured to cause an electronic controller communicating with the electronic processing board to turn on, turn off, or adjust a light source located at a distal insertion end of a shaft of the endo scope, based on a movement or release of the electronic control button by a user.

9. The endoscope of claim 1, wherein the position of the electronic control button comprises a position having a first duration or a longer second duration, a pre-determined series of two or more depressions and releases of the electronic control button, or a release of the electronic control button between two depressions having two or more variable durations.

* * * * *